(12) United States Patent
Bacon et al.

(10) Patent No.: US 8,765,779 B2
(45) Date of Patent: Jul. 1, 2014

(54) TRICYCLIC DERIVATIVES AND THEIR PHARMACEUTICAL USE AND COMPOSITIONS

(75) Inventors: Edward R. Bacon, Audubon, PA (US); Thomas R. Bailey, Phoenixville, PA (US); Derek D. Dunn, Coatesville, PA (US); Greg A. Hostetler, Newark, DE (US); Robert J. McHugh, Miramar, FL (US); George C. Morton, Collegeville, PA (US); Gerard C. Rosse, Poway, CA (US); Joseph M. Salvino, Chester Springs, PA (US); Babu G. Sundar, West Chester, PA (US); Rabindranath Tripathy, Churchville, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 13/529,378

(22) Filed: Jun. 21, 2012

(65) Prior Publication Data

US 2012/0295882 A1    Nov. 22, 2012

Related U.S. Application Data

(63) Continuation of application No. PCT/US2010/060937, filed on Dec. 17, 2010.

(60) Provisional application No. 61/289,090, filed on Dec. 22, 2009.

(51) Int. Cl.
*A61K 31/4355* (2006.01)
*C07D 491/048* (2006.01)

(52) U.S. Cl.
USPC ............................. 514/291; 546/89

(58) Field of Classification Search
USPC .............................. 546/89; 514/291
See application file for complete search history.

(56) References Cited

U.S. PATENT DOCUMENTS 5,854,245 A    12/1998    Duggan et al.

FOREIGN PATENT DOCUMENTS

| WO | WO 03/004501 A2 | 1/2003 |
| WO | WO 03/099821 A1 | 12/2003 |
| WO | WO 2004/096809 A1 | 11/2004 |
| WO | WO 2006/040180 A1 | 4/2006 |

OTHER PUBLICATIONS

Thomas Engler et al, lewis Acid- Directed Cyclocondensation of Piperidone Enol Ethers . . . 2000, pp. 2444-2457.*
Bentley et al., "Investigation of stretching behavior induced by the selective 5-HT$_6$ receptor antagonist, Ro 04-6790, in rats," *British Journal of Pharmacology* (1999), vol. 126, pp. 1537-1542.
Cain et al., "Novelty Seeking and Drug Use: Contribution of an Animal Model," *Experimental and Clinical Psychopharmacology* (2005), vol. 13, pp. 367-375.
Chiu et al., "Serotonin 6 Receptor Polymorphism in Schizophrenia: Frequency, Age at Onset and Cognitive Function", *Neuropsychobiology* (2001), vol. 43, pp. 113-116.
Dellu et al., "Novelty-Seeking in Rats—Biobehavioral Characteristics and Possible Relationship with the Sensation-Seeking Trait in Man," *Neuropsychobiology* (1996), vol. 34, pp. 136-145.
Duzic et al., "Factors Determining the Specificity of Signal Transduction by Guanine Nucleotide-Binding Protein-Coupled Receptors", *J. Biological Chemistry* (1992), vol. 267, pp. 9844-9851.
Engler et al., "Lewis Acid-Directed Cyclocondensation of Piperidone Enol Ethers with 2-Methoxy-4-(N-phenylsulfonyl)-1,4,-benzoquinoneimine: A New Regioselective Synthesis of Oxygenated Carbolines", *J. Org. Chem.* (2000), vol. 65, pp. 2444-2457.
Engler et al., "Lewis Acid-Directed Reactions of Benzoquinone Mono-/Bis-imines: Application to Syntheses of Substituted β- and γ-Tetrahydrocarbolines", *Tetrahedron Letters* (1997), vol. 38, pp. 6135-6138.
Finn et al., "The effects of pharmacological blockade of the 5-HT$_6$ receptor on formalin-evoked nociceptive behavior, locomotor activity and hypothalamo-pituitary-adrenal axis activity in rats", *European J. Pharmacology* (2007), vol. 569, pp. 59-63.
Geldenhuys et al., "Serotonin 5-HT$_6$ Receptor Antagonists for the Treatment of Alzheimer's Disease," *Curr. Topics in Med. Chem.* (2008), vol. 8, pp. 1035-1048.
Heal et al., "Selective 5-HT$_6$ receptor ligands: Progress in the development of a novel pharmacological approach to the treatment of obesity and related metabolic disorders," *Pharmacology & Therapeutics* (2008), vol. 117, pp. 207-231.
Holenz et al., "Medicinal chemistry strategies to 5-HT$_6$ receptor ligands as potential cognitive enhancers and antiobesity agents," *Drug Discovery* (2006), vol. 11, pp. 283-299.
Holenz et al., "Medicinal Chemistry Driven Approaches Toward Novel and Selective Serotonin 5-HT$_6$ Receptor Ligands," *J. Med. Chem.* . . . (2005), vol. 48, pp. 1781-1795.
Hutchison et al., "Benzofuro[2,3-c]pyridin-6-ols: Synthesis, Affinity for Opioid-Receptor Subtypes, and Antinociceptive Activity," *J. Med. Chem.* (1989), vol. 32, pp. 2221-2226.
Johnson et al., "5-HT$_6$ receptor antagonists: Prospects for the treatment of cognitive disorders including dementia", *Curr. Opin. Drug Discov. Development* (2008), vol. 11, pp. 642-654.

(Continued)

*Primary Examiner* — Rita Desai

(57) ABSTRACT

This application relates to tricyclic compounds of Formula I:

including all stereoisomers, mixtures of stereoisomers, and salts thereof. This application also relates to compositions comprising compounds of Formula I and uses therefore.

16 Claims, No Drawings

(56) References Cited

OTHER PUBLICATIONS

Kabalka et al., "The Conversion of Phenols to the Corresponding Aryl Halides Under Mild Conditions," *Synthesis* (2005), vol. 4, pp. 547-550.

Kohen et al., "Cloning, Characterization, and Chromosomal Localization of a Human 5-Ht$_6$ Serotonin Receptor", *J. Neurochemistry* (1996), vol. 66, pp. 47-56.

Kreis et al., "A General and Efficient Method for the Synthesis of Silyl-Protected Arenethiol from Aryl Halides or Triflates," *Adv. Synth. Catal.* (2005), vol. 47, pp. 313-319.

Macor et al., "A Simple Synthesis of 5-Amino-3-(2-Dimethylaminoethyl)indole [5-amino-n,n-dimethyltryptamine]", *Synthetic Comm.* (1993), vol. 23, pp. 65-72.

Mitchell et al., "5-HT$_6$ receptors: a novel target for cognitive enhancement", *Pharmacology & Therapeutics* (2005), vol. 108, pp. 320-333.

Monsma et al., "Cloning and Expression of a Novel Serotonin Receptor with High Affinity for Tricyclic Psychotropic Drugs," *Molecular Pharmacology* (1992), vol. 43, pp. 320-327.

Morairty et al., "Selective 5-HT$_{2A}$ and 5-HT$_6$ Receptor Antagonists Promote Sleep in Rats," *Sleep* (2008), vol. 31, pp. 34-44.

Morice et al., "Synthesis of constrained arylpiperidines using intramolecular Heck or radical reactions," *Tetrahedron Lett.* (2001), vol. 42, pp. 6499-6502.

Navari et al., "Treatment of cancer-related anorexia with olanzapine and megestrol acetate: a randomized trial," *Support Care Cancer* (2009).

Passik et al., "A Pilot Exploration of the Antiemetic Activity of Olanzapine for the Relief of Nausea in Patients with Advanced Cancer and Pain," *J. Pain Symptom Manage* (2002), vol. 23, pp. 526-532.

Perez-Garcia et al., "Oral administration of the 5-HT$_6$ receptor antagonists SB-357134 and SB-399885 improves memory formation in an autoshaping learning task," *Pharmacology, Biochem. & Behavior* (2005), vol. 81, pp. 673-682.

Srivastava et al., "Olanzapine as an Antiemetic in Refractory Nausea and Vomiting in Advanced Cancer," *J. Pain & Symptom Management* (2003), vol. 25, pp. 578-582.

Upton et al., "5-HT$_6$ Receptor Antagonists as Novel Cognitive Enhancing Agents for Alzheimer's Disease," *J. Amer. Soc. Exper. NeuroTherapeutics* (2008), vol. 5, pp. 458-469.

Vogt et al., "Investigation of the Human Serotonin 6 (5-HT$_6$) Receptor Gene in Bipolar Affective Disorder and Schizophrenia," *Amer. J. Med. Genetics (Neuropsychiatric Genetics)* (2000), vol. 96, pp. 217-221.

Wesolowska et al., "Effects of the brain-penetrant and selective 5-HT$_6$ receptor antagonist SB-399885 in animal models of anxiety and depression," *Neuropharmcology* (2007), vol. 52, pp. 1274-1283.

Wood et al., "Therapeutic potential of serotonin antagonists in depressive disorders," *Expert Opin. Investig. Drugs* (2002), vol. 11, pp. 457-467.

Woolley et al., "5-HT$_6$ Receptors," *Curr. Drug Targets—CNS & Neurological Disorders* (2004), vol. 3, pp. 59-79.

Yoshioka et al., "Central Distribution and Function of 5-HT$_6$ Receptor Subtype in the Rat Brain," *Life Sci.* (1998), vol. 62, pp. 1473-1477.

Zuckerman et al., "Sensation Seeking and Psychopathology," *Psychiatry Res.* (1979), vol. 1, pp. 255-264.

\* cited by examiner

TRICYCLIC DERIVATIVES AND THEIR PHARMACEUTICAL USE AND COMPOSITIONS

CROSS-REFERENCE TO RELATED APPLICATIONS

This application is a continuation of International Application No. PCT/US2010/060937, filed Dec. 17, 2010, which claims priority to U.S. Provisional Application Ser. No. 61/289,090, filed Dec. 22, 2009. The disclosures of the aforementioned applications are incorporated herein by reference in their entireties for all purposes.

SUMMARY

This application relates to tricyclic compounds of Formula I:

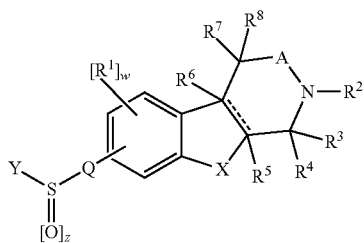

including all stereoisomeric forms and all mixtures of stereoisomeric forms of these compounds.

This application also relates to salts of the compounds of Formula I and compositions comprising compounds of Formula I or salts of compounds of Formula I.

This application further relates to pharmaceutically acceptable salts of the compounds of Formula I and pharmaceutical compositions comprising compounds of Formula I or pharmaceutically acceptable salts of the compounds of Formula I.

The compounds of Formula I and/or their pharmaceutically acceptable salts are useful for treating conditions, disorders and diseases mediated by one or more members of the serotonin receptor (5-HT) family, such as for example, $5\text{-HT}_6$ and $5\text{-HT}_7$ receptors.

Compounds of Formula I are $5\text{-HT}_6$ receptor ligands and are therefore useful in the treatment of various conditions, disorders or diseases such as those related to the central nervous system (CNS) and the gastrointestinal (GI) tract.

It should be understood that the section titles used in this application are for indexing and search purposes only and should not be construed as limiting in any way.

BACKGROUND

Serotonin has been implicated in a number of conditions, disorders and diseases that originate in the central nervous system. These include conditions, disorders and diseases related to mood, cognitive function, sleeping, eating, pain, depression, anxiety, schizophrenia, and other bodily states. Serotonin also plays an important role in peripheral systems, such as the gastrointestinal system where it has been found to mediate a variety of contractile, secretory, and electrophysiologic effects.

The superfamily of serotonin receptors (5-HT) includes 7 classes ($5\text{-HT}_1$-$5\text{-HT}_7$) encompassing 14 human subclasses which modulate the effects of the neurotransmitter 5-hydroxytryptamine (5-HT, serotonin). The $5\text{-HT}_6$ receptor is the latest serotonin receptor to be identified by molecular cloning both in rats and in humans. *Mol. Pharmacol.* 1993, 43, 320-327; *J Neurochem,* 1996, 66, 47-56. The human $5\text{-HT}_6$ receptor is a 440 amino acid polypeptide with seven transmembrane spanning domains which is consistent with the structure of a G protein-coupled receptor (GPCR). There is about 89% sequence homology between $5\text{-HT}_6$ receptors in human and rat and the relative distribution of $5\text{-HT}_6$ receptor mRNA in the brain also appears to be similar. Together, these observations suggest that the rat is an appropriate model for predicting the pharmacology of $5\text{-HT}_6$ receptor ligands in humans.

The $5\text{-HT}_6$ receptor is primarily present in the central nervous system and is involved in glutamatergic and cholinergic neuronal activity. *Curr Drug Targets CNS Neurol Disord,* 2004, 3, 59-79. Blocking the function of $5\text{-HT}_6$ receptors has been found to increase acetylcholine (ACh) and glutamate-mediated neurotransmission, and enhance cognitive processes. Several antidepressants and atypical antipsychotics have also been shown to bind to the $5\text{-HT}_6$ receptor with high affinity. This binding may be a contributing factor in the therapeutic profile of these drugs. $5\text{-HT}_6$ receptor activity has also been linked to generalized states of stress and anxiety. *Life Sciences,* 1998, 62, 1473-1477. Taken together, these studies and observations suggest that compounds with $5\text{-HT}_6$ receptor affinity may be useful for the treatment of various conditions, disorders or diseases related to the central nervous system (CNS) such as cognitive diseases, neurodegenerative diseases, schizophrenia, anxiety, and depression. Other CNS-related conditions, disorders or diseases that may be affected by modulating $5\text{-HT}_6$ receptor activity include sleep/wakefulness disorders as well as nociception, i.e., the neural processes of encoding and processing noxious stimuli.

The $5\text{-HT}_6$ receptor has also been shown to play a role in conditions, disorders or diseases that relate to food ingestion or food intake, such as, for example, anorexia, cachexia, and obesity. See, for example, *Drug Discovery Today,* 2006, 11, 283-299. The $5\text{-HT}_6$ receptor is also thought to be involved in conditions, disorders or diseases related to the gastrointestinal (GI) tract, such as irritable bowel syndrome and functional bowel disorder.

Given the broad spectrum of physiologic effects that are mediated by serotonin there is a tremendous amount of interest in identifying and developing compounds that affect serotonergic systems, including those conditions, disorders or diseases that are directly or indirectly mediated, effected, controlled, or influenced by the $5\text{-HT}_6$ receptor. Compounds that have affinity for, interact with, stimulate, or inhibit the $5\text{-HT}_6$ receptor are commonly referred to as $5\text{-HT}_6$ ligands.

This application relates to new compounds with affinity for the $5\text{-HT}_6$ receptor, i.e., $5\text{-HT}_6$ ligands, which may be useful as active ingredients in pharmaceutical preparations for the treatment of certain conditions, disorders or diseases related to the central nervous system (CNS) such as memory disorders, anxiety, epilepsy, migraine, panic attacks, depression, bipolar disorder, obsessive compulsive disorders, cognition/cognitive disorders, mild cognitive impairment (MCI), senile dementia, psychosis, schizophrenia, ADHD/ADD; or for the treatment of pain including neuropathic pain and chronic pain; head trauma or injury; or for the treatment of neurodegenerative conditions, disorders or diseases such as Alzheimer's disease, Parkinson's disease, Huntington's disease, amyotrophic lateral sclerosis (ALS) or multiple sclerosis; or for the treatment of conditions, disorders or diseases related to addiction and/or withdrawal from substances such as narcotics, ethanol (alcoholism), nicotine, and/or benzodiazepines; sleep/wakefulness disorders; or for the treatment of gastrointestinal (GI) conditions, disorders or diseases such as irritable bowel syndrome (IBS), functional bowel disorder; or for the treatment of conditions, disorders or diseases related to feeding behaviors or food intake such as anorexia, cachexia, and obesity.

These compounds may also be useful for the improvement of cognition (cognitive enhancement) and/or improvement of memory in otherwise healthy subjects.

DETAILED DESCRIPTION

The following provides additional non-limiting details of the compounds of Formula I, compounds of Formulae II through V, as well as various species and more specific embodiments of the same, intermediates, and other compounds of interest.

As used herein, the term "compound(s) of Formula I" should be understood as including compounds of Formulae II through V, unless expressly stated to the contrary.

As used herein, the term "compound(s)" whether used by itself or in combination with any Formula should be understood as including all stereoisomers, all mixtures of stereoisomers, and all salts of such compounds, stereoisomers, and mixtures of stereoisomers, unless expressly stated to the contrary. Accordingly, use of the phrase "compound(s) of Formula I or salts thereof" refers to and includes compounds of Formulae I through Formula V, all stereoisomers, all mixtures of stereoisomers, and all salts of such compounds, stereoisomers, and mixtures of stereoisomers. This understanding extends to pharmaceutical compositions and methods that employ or comprise one or more compounds of Formula I.

One aspect of this application is directed to compounds of Formula I

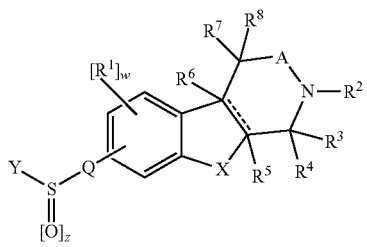

I or salts thereof wherein:

X is selected from S, O, or NH;

A is —$(CR^9R^{10})_n$— and n is 1, 2, or 3 and $R^9$ and $R^{10}$ at each occurrence are each independently selected from H or unsubstituted $(C_1-C_6)$alkyl, or $(C_1-C_6)$haloalkyl;

$R^1$ at each occurrence is independently selected from H, halogen, CN, $NO_2$, $NR^{11}R^{12}$, $COR^{13}$, $CO_2R^{13}$, $(C_1-C_6)$alkyl, $(C_1-C_6)$haloalkyl, $(C_1-C_6)$alkyl$(C_1-C_6)$alkoxy, $(C_1-C_6)$alkyl$(C_1-C_6)$haloalkoxy, $(C_3-C_{10})$cycloalkyl, $(C_1-C_6)$alkyl$(C_3-C_{10})$cycloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, and $(C_1-C_6)$alkyl$(C_5-C_9)$heteroaryl, and W is 0, 1, 2 or 3, wherein any of the foregoing, except for H, halogen, CN, and $NO_2$, is optionally substituted with one or more substituents;

$R^2$ is selected from H, $(C_1-C_6)$alkyl, $(C_1-C_6)$haloalkyl, $(C_1-C_6)$alkyl$(C_1-C_6)$alkoxy, $CO(C_1-C_6)$alkyl, $CO_2(C_1-C_6)$alkyl, $CO(C_6-C_{10})$aryl, $CO_2(C_6-C_{10})$aryl, $(C_6-C_{10})$aryl, $(C_1-C_6)$alkyl$(C_6-C_{10})$aryl, $(C_3-C_{10})$cycloalkyl, $CO(C_3-C_{10})$cycloalkyl, $CO_2(C_3-C_{10})$cycloalkyl, $(C_1-C_6)$alkyl$(C_3-C_{10})$cycloalkyl, $CO(C_1-C_6)$alkyl$(C_3-C_{10})$cycloalkyl, $CO_2(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $CO(C_1-C_6)$alkyl$(C_2-C_9)$heterocycloalkyl, $CO_2(C_1-C_6)$alkyl$(C_2-C_9)$heterocycloalkyl, $(C_5-C_9)$heteroaryl, $CO(C_5-C_9)$heteroaryl, $CO_2(C_5-C_9)$heteroaryl, $(C_1-C_6)$alkyl$(C_5-C_9)$heteroaryl, $CO(C_1-C_6)$alkyl$(C_5-C_9)$heteroaryl, and $CO_2(C_1-C_6)$alkyl$(C_5-C_9)$heteroaryl, wherein any of the foregoing, except for H, is optionally substituted with one or more substituents;

$R^3$ and $R^4$ are each independently selected from H, $(C_1-C_6)$alkyl, $(C_1-C_6)$haloalkyl, $(C_1-C_6)$alkoxy, $(C_1-C_6)$aminoalkyl, $(C_1-C_6)$haloalkoxy, $(C_1-C_6)$alkyl$(C_1-C_6)$alkoxy, $(C_1-C_6)$alkyl-$NR^{13}$CO—$(C_1-C_6)$alkyl, $(C_1-C_6)$alkyl-CON$(R^{13})_2$, $(C_6-C_{10})$aryl, $(C_6-C_{10})$aryloxy, $(C_1-C_6)$alkyl$(C_6-C_{10})$aryl, $(C_1-C_6)$alkyl$(C_6-C_{10})$aryloxy, $(C_3-C_{10})$cycloalkyl, $(C_3-C_{10})$cycloalkyloxy, $(C_1-C_6)$alkyl$(C_3-C_{10})$cycloalkyl, $(C_1-C_6)$alkyl$(C_3-C_{10})$cycloalkyloxy, $(C_5-C_9)$heteroaryl, $(C_5-C_9)$heteroaryloxy, $(C_2-C_9)$heterocycloalkyl, $(C_2-C_9)$heterocycloalkyloxy, $(C_1-C_6)$alkyl$(C_2-C_9)$heterocycloalkyl, $(C_1-C_6)$alkyl$(C_2-C_9)$heterocycloalkyloxy, $(C_1-C_6)$alkyl$(C_5-C_9)$heteroaryl, and $(C_1-C_6)$alkyl$(C_5-C_9)$heteroaryloxy, wherein any of the foregoing, except for H, is optionally substituted with one or more substituents; or $R^3$ and $R^4$ are taken together to form a $(C_4-C_{10})$cycloalkyl or $(C_4-C_9)$heterocycloalkyl spirocyclic ring wherein either of the foregoing is optionally substituted with one or more substituents selected from $(C_1-C_6)$alkyl, $(C_1-C_6)$haloalkyl, $(C_1-C_6)$hydroxyalkyl, $COR^{11}$, $CO_2R^{11}$, $CONR^{11}R^{13}$, halogen, $(C_1-C_6)$alkoxy, $(C_1-C_6)$haloalkoxy, $OR^{13}$, and oxo; or $R^2$ and one of $R^3$ or $R^4$ are taken together to form an optionally substituted $(C_3-C_9)$heterocycloalkyl ring and the other of $R^3$ or $R^4$ is selected from H, $(C_1-C_6)$alkyl, and $(C_1-C_6)$hydroxyalkyl;

"- - - -" is a bond or is absent;

$R^5$ and $R^6$ are each independently selected from H, $(C_1-C_6)$alkyl, $(C_1-C_6)$hydroxyalkyl, and OH provided that "- - - -" is absent;

$R^7$ and $R^8$ are each independently selected from H, $(C_1-C_6)$alkyl, or $(C_1-C_6)$haloalkyl; or $R^7$ and $R^8$ are taken together to form a $(C_4-C_{10})$cycloalkyl ring or a $(C_4-C_9)$heterocycloalkyl spirocyclic ring wherein either of the foregoing is optionally substituted with one or more substituents;

$R^{11}$ and $R^{12}$ at each occurrence are independently selected from H, $(C_1-C_6)$alkyl, $(C_1-C_6)$alkoxy, $(C_1-C_6)$alkyl$(C_1-C_6)$alkoxy, and $(C_1-C_6)$hydroxyalkyl;

$R^{13}$ at each occurrence is independently selected from H and $(C_1-C_6)$alkyl;

Q is absent, —O—, or —$NR^{13}$—;

Z is 1 or 2; and

Y is selected from $(C_3-C_{10})$cycloalkyl, $(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $(C_6-C_{10})$aryl, $(C_1-C_6)$alkyl$(C_6-C_{10})$aryl, $(C_5-C_9)$heteroaryl, and $(C_1-C_6)$alkyl$(C_5-C_9)$heteroaryl wherein any of the foregoing is optionally substituted with one or more substituents; or Y is $NR^{14}R^{15}$ wherein $R^{14}$ and $R^{15}$ are each independently selected from H, $(C_1-C_6)$alkyl, $(C_3-C_{10})$cycloalkyl, $(C_1-C_6)$alkyl$(C_3-C_{10})$cycloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, and $(C_1-C_6)$alkyl$(C_5-C_9)$heteroaryl, wherein any of the foregoing, with the exception of H may be optionally substituted with one or more substituents and provided that both $R^{14}$ and $R^{15}$ are not both H; or $R^{14}$ and $R^{15}$ are taken together to form a $(C_2-C_9)$heterocycloalkyl ring optionally substituted with one or more substituents.

Another aspect of this application is directed to compounds of Formula I having the structure of Formula II:

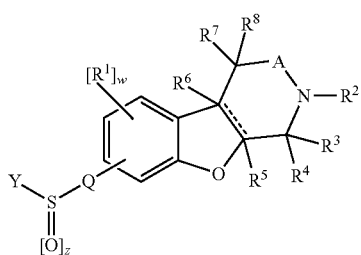

or salts thereof.

In some embodiments of compounds of Formula II:

A is —$(CR^9R^{10})_n$— and n is 1, 2, or 3 and $R^9$ and $R^{10}$ at each occurrence are independently selected from H or unsubstituted $(C_1-C_6)$alkyl, or $(C_1-C_6)$haloalkyl;

$R^1$ at each occurrence is independently selected from H, halogen, CN, $NO_2$, $NR^{11}R^{12}$, $COR^{13}$, $CO_2R^{13}$, $(C_1-C_6)$alkyl, $(C_1-C_6)$haloalkyl, $(C_1-C_6)$alkyl$(C_1-C_6)$alkoxy, $(C_1-C_6)$alkyl$(C_1-C_6)$haloalkoxy, $(C_3-C_{10})$cycloalkyl, $(C_1-C_6)$alkyl$(C_3-C_{10})$cycloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, and $(C_1-C_6)$alkyl$(C_5-C_9)$heteroaryl, and W is 0, 1, 2 or 3, wherein any of the foregoing, except for H, halogen, CN, and $NO_2$, is optionally substituted with one or more substituents;

$R^2$ is selected from H, $(C_1-C_6)$alkyl, $(C_1-C_6)$haloalkyl, $(C_1-C_6)$alkyl$(C_1-C_6)$alkoxy, $CO(C_1-C_6)$alkyl, $CO_2(C_1-C_6)$alkyl, $CO(C_6-C_{10})$aryl, $CO_2(C_6-C_{10})$aryl, $(C_6-C_{10})$aryl, $(C_1-C_6)$alkyl$(C_6-C_{10})$aryl, $(C_3-C_{10})$cycloalkyl, $CO(C_3-C_{10})$cycloalkyl, $CO_2(C_3-C_{10})$cycloalkyl, $(C_1-C_6)$alkyl$(C_3-C_{10})$cycloalkyl, $CO(C_1-C_6)$alkyl$(C_3-C_{10})$cycloalkyl, $CO_2(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $CO(C_1-C_6)$alkyl$(C_2-C_9)$heterocycloalkyl, $CO_2(C_1-C_6)$alkyl$(C_2-C_9)$heterocycloalkyl, $(C_5-C_9)$heteroaryl, $CO(C_5-C_9)$heteroaryl, $CO_2(C_5-C_9)$heteroaryl, $(C_1-C_6)$alkyl$(C_5-C_9)$heteroaryl, $CO(C_1-C_6)$alkyl$(C_5-C_9)$heteroaryl, and $CO_2(C_1-C_6)$alkyl$(C_5-C_9)$heteroaryl, wherein any of the foregoing, except for H, is optionally substituted with one or more substituents;

$R^3$ and $R^4$ are each independently selected from H, $(C_1-C_6)$alkyl, $(C_1-C_6)$haloalkyl, $(C_1-C_6)$alkoxy, $(C_1-C_6)$aminoalkyl, $(C_1-C_6)$haloalkoxy, $(C_1-C_6)$alkyl$(C_1-C_6)$alkoxy, $(C_1-C_6)$alkyl-$NR^{13}CO$—$(C_1-C_6)$alkyl, $(C_1-C_6)$alkyl-$CON(R^{13})_2$, $(C_6-C_{10})$aryl, $(C_6-C_{10})$aryloxy, $(C_1-C_6)$alkyl$(C_6-C_{10})$aryl, $(C_1-C_6)$alkyl$(C_6-C_{10})$aryloxy, $(C_3-C_{10})$cycloalkyl, $(C_3-C_{10})$cycloalkyloxy, $(C_1-C_6)$alkyl$(C_3-C_{10})$cycloalkyl, $(C_1-C_6)$alkyl$(C_3-C_{10})$cycloalkyloxy, $(C_5-C_9)$heteroaryl, $(C_5-C_9)$heteroaryloxy, $(C_2-C_9)$heterocycloalkyl, $(C_2-C_9)$heterocycloalkyloxy, $(C_1-C_6)$alkyl$(C_2-C_9)$heterocycloalkyl, $(C_1-C_6)$alkyl$(C_2-C_9)$heterocycloalkyloxy, $(C_1-C_6)$alkyl$(C_5-C_9)$heteroaryl, and $(C_1-C_6)$alkyl$(C_5-C_9)$heteroaryloxy, wherein any of the foregoing, except for H, is optionally substituted with one or more substituents; or $R^3$ and $R^4$ are taken together to form a $(C_4-C_{10})$cycloalkyl or $(C_4-C_9)$heterocycloalkyl spirocyclic ring wherein either of the foregoing is optionally substituted with one or more substituents selected from $(C_1-C_6)$alkyl, $(C_1-C_6)$haloalkyl, $(C_1-C_6)$hydroxyalkyl, $COR^{11}$, $CO_2R^{11}$, $CONR^{11}R^{13}$, halogen, $(C_1-C_6)$alkoxy, $(C_1-C_6)$haloalkoxy, $OR^{13}$, and oxo; or $R^2$ and one of $R^3$ or $R^4$ are taken together to form an optionally substituted $(C_3-C_9)$heterocycloalkyl ring and the other of $R^3$ or $R^4$ is selected from H, $(C_1-C_6)$alkyl, and $(C_1-C_6)$hydroxyalkyl;

"- - - -" is a bond or is absent;

$R^5$ and $R^6$ are each independently selected from H, $(C_1-C_6)$alkyl, $(C_1-C_6)$hydroxyalkyl, and OH provided that "- - - -" is absent;

$R^7$ and $R^8$ are each independently selected from H, $(C_1-C_6)$alkyl, or $(C_1-C_6)$haloalkyl; or $R^7$ and $R^8$ are taken together to form a $(C_4-C_{10})$cycloalkyl ring or a $(C_4-C_9)$heterocycloalkyl spirocyclic ring wherein either of the foregoing is optionally substituted with one or more substituents;

$R^{11}$ and $R^{12}$ at each occurrence are independently selected from H, $(C_1-C_6)$alkyl, $(C_1-C_6)$alkoxy, $(C_1-C_6)$alkyl$(C_1-C_6)$alkoxy, and $(C_1-C_6)$hydroxyalkyl;

$R^{13}$ at each occurrence is independently selected from H and $(C_1-C_6)$alkyl;

Q is absent, —O—, or —$NR^{13}$—;

Z is 1 or 2; and

Y is selected from $(C_3-C_{10})$cycloalkyl, $(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $(C_6-C_{10})$aryl, $(C_1-C_6)$alkyl$(C_6-C_{10})$aryl, $(C_5-C_9)$heteroaryl, and $(C_1-C_6)$alkyl$(C_5-C_9)$heteroaryl wherein any of the foregoing is optionally substituted with one or more substituents; or Y is $NR^{14}R^{15}$ wherein $R^{14}$ and $R^{15}$ are taken together to form a $(C_2-C_9)$heterocycloalkyl ring optionally substituted with one or more substituents.

In another aspect, this application is directed to compounds of Formula I having the structure of Formula IIa:

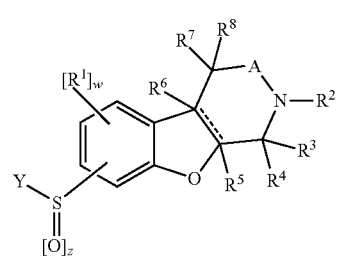

or salts thereof.

In certain embodiments of compounds of Formula IIa:

A is —$(CR^9R^{10})_n$— wherein n is 1, 2, or 3 and $R^9$ and $R^{10}$ at each occurrence are independently selected from H or unsubstituted $(C_1-C_6)$alkyl, or $(C_1-C_6)$haloalkyl;

$R^1$ at each occurrence is independently selected from H, halogen, CN, $NO_2$, $NR^{11}R^{12}$, $COR^{13}$, $CO_2R^{13}$, $(C_1-C_6)$alkyl, $(C_1-C_6)$haloalkyl, $(C_1-C_6)$alkyl$(C_1-C_6)$alkoxy, $(C_1-C_6)$alkyl$(C_1-C_6)$haloalkoxy, $(C_3-C_{10})$cycloalkyl, $(C_1-C_6)$alkyl$(C_3-C_{10})$cycloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, $(C_1-C_6)$alkyl$(C_5-C_9)$heteroaryl, and W is 0, 1, 2 or 3, wherein any of the foregoing, except for H, halogen, CN, and $NO_2$, is optionally substituted with one or more substituents;

$R^2$ is selected from H, $(C_1-C_6)$alkyl, $(C_1-C_6)$haloalkyl, $(C_1-C_6)$alkyl$(C_1-C_6)$alkoxy, $CO(C_1-C_6)$alkyl, $CO_2(C_1-C_6)$alkyl, $CO(C_6-C_9)$aryl, $CO_2(C_6-C_9)$aryl, $(C_6-C_9)$aryl, $(C_2-C_6)$alkyl$(C_6-C_{10})$aryl, $(C_3-C_{10})$cycloalkyl, $CO(C_3-C_{10})$cycloalkyl, $CO_2(C_3-C_{10})$cycloalkyl, $(C_1-C_6)$alkyl$(C_3-C_{10})$cycloalkyl, $CO(C_1-C_6)$alkyl$(C_3-C_{10})$cycloalkyl, $CO_2(C_1-C_6)$alkyl$(C_3-C_{10})$cycloalkyl, $(C_2-C_6)$alkyl$(C_2-C_9)$heterocycloalkyl, $CO(C_1-C_6)$alkyl$(C_2-C_9)$heterocycloalkyl, $CO_2(C_1-C_6)$alkyl$(C_2-C_9)$heterocycloalkyl, $(C_2-C_6)$alkyl$(C_5-C_9)$heteroaryl, $CO(C_1-C_6)$alkyl$(C_5-C_9)$heteroaryl, and $CO_2(C_1-C_6)$alkyl$(C_5-C_9)$heteroaryl wherein any of the foregoing, except for H, is optionally substituted with one or more substituents;

$R^3$ and $R^4$ are each independently selected from H, $(C_1-C_6)$alkyl, $(C_1-C_6)$haloalkyl, $(C_1-C_6)$alkoxy, $(C_1-C_6)$haloalkoxy, $(C_1-C_6)$aminoalkyl, $(C_1-C_6)$alkyl$(C_1-C_6)$alkoxy, $(C_1-C_6)$alkyl-$NR^{13}CO$—$(C_1-C_6)$alkyl, $(C_1-C_6)$alkyl-$CON(R^{13})_2$, $(C_6-C_{10})$aryl, $(C_6-C_{10})$aryloxy, $(C_1-C_6)$alkyl$(C_6-C_{10})$aryl, $(C_1-C_6)$alkyl$(C_6-C_{10})$aryloxy, $(C_3-C_{10})$cycloalkyl, $(C_3-C_{10})$cycloalkyloxy, $(C_1-C_6)$alkyl$(C_3-C_{10})$cycloalkyl, $(C_1-C_6)$alkyl$(C_3-C_{10})$cycloalkyloxy, $(C_5-C_9)$heteroaryl, $(C_5-C_9)$heteroaryloxy, $(C_2-C_9)$heterocycloalkyl, $(C_2-C_9)$heterocycloalkyloxy, $(C_1-C_6)$alkyl$(C_2-C_9)$heterocycloalkyl, $(C_1-C_6)$alkyl$(C_2-C_9)$heterocycloalkyloxy, $(C_1-C_6)$alkyl$(C_5-C_9)$heteroaryl, and $(C_1-C_6)$alkyl$(C_5-C_9)$heteroaryloxy, wherein any of the foregoing, except for H, is optionally substituted with one or more substituents; or $R^3$ and $R^4$ are taken together to form a $(C_4-C_{10})$cycloalkyl or $(C_4-C_9)$heterocycloalkyl spirocyclic ring wherein either of the foregoing is optionally substituted with one or more of $(C_1-C_6)$alkyl, $(C_1-C_6)$haloalkyl, $(C_1-C_6)$hydroxyalkyl, $COR^{11}$, $CO_2R^{11}$, $CONR^{11}R^{13}$, halogen, $(C_1-C_6)$alkoxy, $(C_1-C_6)$haloalkoxy, $OR^{13}$, and oxo; or $R^2$ and one of $R^3$ or $R^4$ are taken together to form an optionally substituted $(C_3-C_9)$heterocycloalkyl ring and the other of $R^3$ or $R^4$ is selected from H, $(C_1-C_6)$alkyl, and $(C_1-C_6)$hydroxyalkyl;

"- - - -" is a bond or is absent;

$R^5$ and $R^6$ are each independently selected from H, $(C_1-C_6)$alkyl, $(C_1-C_6)$hydroxyalkyl, and OH provided that "- - - -" is absent;

$R^7$ and $R^8$ are each independently selected from H, $(C_1-C_6)$alkyl, and $(C_1-C_6)$haloalkyl; or $R^7$ and $R^8$ are taken together to form a $(C_4-C_{10})$cycloalkyl ring or $(C_4-C_9)$heterocycloalkyl spirocyclic ring wherein either of the foregoing is optionally substituted with one or more substituents;

$R^{11}$ and $R^{12}$ at each occurrence are independently selected from H, $(C_1-C_6)$alkyl, $(C_1-C_6)$alkoxy, $(C_1-C_6)$alkyl$(C_1-C_6)$alkoxy, and $(C_1-C_6)$hydroxyalkyl;

$R^{13}$ at each occurrence is independently selected from H and $(C_1-C_6)$alkyl;

Z is 1 or 2; and

Y is $NR^{14}R^{15}$ where $R^{14}$ and $R^{15}$ are each independently selected from H, $(C_1-C_6)$alkyl, $(C_3-C_{10})$cycloalkyl, $(C_1-C_6)$alkyl$(C_3-C_{10})$cycloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, and $(C_1-C_6)$alkyl$(C_5-C_9)$heteroaryl, wherein any of the foregoing, with the exception of H may be optionally substituted with one or more substituents and provided that both $R^{14}$ and $R^{15}$ are not both H.

Another aspect of this application is directed to compounds of Formula I having the structure of Formula III:

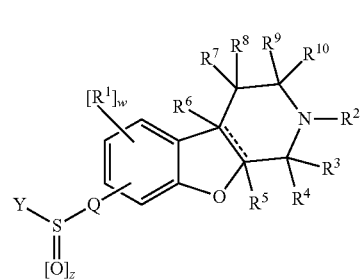

III or salts thereof.

Another aspect of this application is directed to compounds of Formula I having the structure of Formula III-A

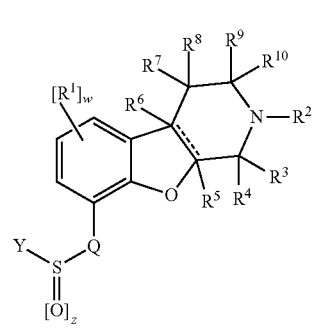

III-A or salts thereof.

In certain embodiments of compounds of Formula III-A:
W is 0; $R^2$ is H; $R^3$, $R^4$, $R^7$, $R^8$, $R^9$, and $R^{10}$ are each H; "- - - -" is absent; $R^5$ and $R^6$ are each selected from H and —$OR^{13}$; Q is absent; Z is 2; and Y is $(C_6-C_{10})$aryl optionally substituted with one or more substituents.

In certain more specific embodiments, Y is optionally substituted with at least one substituent selected from halogen, $(C_1-C_6)$alkoxy, $NO_2$, and $(C_6-C_{10})$aryl.

Another aspect of this application is directed to compounds of Formula I having the structure of Formula III-B:

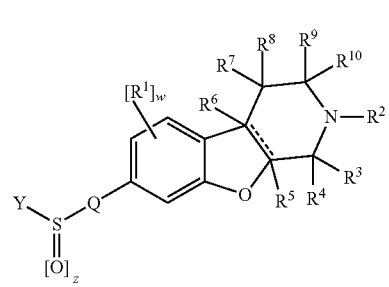

III-B or salts thereof.

In certain embodiments of compounds of Formula III-B:
$R^2$ is selected from H, $(C_1-C_6)$alkyl, $(C_1-C_6)$alkyl$(C_1-C_6)$alkoxy, $(C_1-C_6)$hydroxyalkyl, $(C_1-C_6)$alkyl$(C_6-C_{10})$aryl, $(C_3-C_{10})$cycloalkyl, $CO(C_1-C_6)$alkyl and $(C_1-C_6)$haloalkyl wherein any of the foregoing, with the exception of H, is optionally substituted with one or more substituents;

$R^3$, $R^4$, $R^7$, $R^8$, $R^9$, and $R^{10}$ are each H;
Q is absent; and
Y is selected from $(C_3-C_{10})$cycloalkyl, $(C_6-C_{10})$aryl, $(C_2-C_9)$heterocycloalkyl, and $(C_5-C_9)$heteroaryl wherein any of the foregoing is optionally substituted with one or more substituents selected from O—$(C_1-C_6)$alkyl-$OR^{13}$, O—$(C_1-C_6)$alkyl-$CO_2R^{13}$, O—$(C_1-C_6)$alkyl-CN, O—$(C_1-C_6)$alkyl-CON$(R^{13})_2$, O—$(C_1-C_6)$alkyl-CO$(C_2-C_9)$heterocycloalkyl, $(C_3-C_{10})$cycloalkyloxy, $(C_1-C_6)$alkoxy$(C_2-C_9)$heterocycloalkyl, $CO_2(C_1-C_6)$alkyl, $NR^{13}CO$—$(C_1-C_6)$alkyl, halogen, OH, CN, $NO_2$, $N(R^{13})_2$, $(C_1-C_6)$alkyl, $(C_1-C_6)$haloalkyl, $(C_6-C_{10})$aryl, $(C_6-C_{10})$aryloxy, $(C_1-C_6)$alkoxy$(C_6-C_{10})$aryl, $(C_1-C_6)$alkoxy, $(C_1-C_9)$heteroaryl, $(C_4-C_9)$heteroaryloxy, $(C_1-C_6)$alkoxy$(C_4-C_9)$heteroaryl, $(C_1-C_6)$haloalkoxy, $OCON(R^{13})_2$, $(C_2-C_9)$heterocycloalkyl, $CON(R^{13})_2$, and oxo, wherein any of the foregoing alkyl, alkoxy, cycloalkyl, heterocycloalkyl, aryl and heteroaryl substituents is optionally substituted with one or more substituents.

In certain embodiments of compounds of Formula III-B:
W is 0; $R^2$ is H; $R^3$, $R^4$, $R^7$, $R^8$, $R^9$, and $R^{10}$ are each H; "- - - -" is a bond; and Y is selected from $(C_3-C_{10})$cycloalkyl, $(C_6-C_{10})$aryl, $(C_2-C_9)$heterocycloalkyl, and $(C_5-C_9)$heteroaryl wherein any of the foregoing is optionally substituted with one or more substituents.

In certain more specific embodiments Y is optionally substituted with at least one substituent selected from halogen, OH, CN, $NO_2$, $N(R^{13})_2$, $(C_1-C_6)$alkyl, $(C_1-C_6)$haloalkyl, $(C_6-C_{10})$aryl, $(C_6-C_{10})$aryloxy, $(C_1-C_6)$alkoxy, $(C_1-C_6)$haloalkoxy, $(C_2-C_9)$heterocycloalkyl, and $CON(R^{13})_2$.

In other embodiments of compounds of Formula III-B:
W is 0; $R^2$ is H; $R^3$, $R^4$, $R^7$, $R^8$, $R^9$, and $R^{10}$ are each H; "- - - -" is absent; $R^5$ and $R^6$ are each independently selected from H and $(C_1-C_6)$alkyl; and Y is selected from $(C_3-C_{10})$cycloalkyl, $(C_6-C_{10})$aryl, $(C_2-C_9)$heterocycloalkyl, and $(C_4-C_9)$heteroaryl wherein any of the foregoing is optionally substituted with one or more substituents.

In certain more specific embodiments Y is optionally substituted with at least one substituent selected from O—$(C_1-C_6)$alkyl-$OR^{13}$, O—$(C_1-C_6)$alkyl-$CO_2R^{13}$, O—$(C_1-C_6)$alkyl-CN, O—$(C_1-C_6)$alkyl-CON$(R^{13})_2$, O—$(C_1-C_6)$alkyl-CO$(C_2-C_9)$heterocycloalkyl, $(C_3-C_{10})$cycloalkyloxy, $(C_1-C_6)$alkoxy$(C_2-C_9)$heterocycloalkyl, $CO_2(C_1-C_6)$alkyl, $NR^{13}CO$—$(C_1-C_6)$alkyl, halogen, OH, CN, $NO_2$, $N(R^{13})_2$, $(C_1-C_6)$alkyl, $(C_1-C_6)$alkoxy, $(C_1-C_6)$haloalkyl, $(C_6-C_{10})$aryl, $(C_6-C_{10})$aryloxy, $(C_1-C_6)$alkoxy$(C_6-C_{10})$aryl, $(C_1-C_9)$heteroaryl, $(C_4-C_9)$heteroaryloxy, $(C_1-C_6)$alkoxy$(C_4-C_9)$heteroaryl, $(C_1-C_6)$haloalkoxy, $OCON(R^{13})_2$, $(C_2-C_9)$heterocycloalkyl, $CON(R^{13})_2$, and oxo, wherein any of the foregoing alkyl, alkoxy, cycloalkyl, heterocycloalkyl, aryl and heteroaryl substituents is optionally substituted with one or more substituents selected from $(C_1-C_6)$alkyl, CN, halogen, OH, $(C_1-C_6)$alkoxy, $(C_1-C_6)$haloalkyl and $(C_1-C_6)$hydroxyalkyl.

In other embodiments of compounds of Formula III-B:
W is 0; $R^2$ is selected from $(C_1-C_6)$alkyl, $(C_1-C_6)$alkyl$(C_1-C_6)$alkoxy, $(C_1-C_6)$hydroxyalkyl, $(C_1-C_6)$alkyl$(C_6-C_{10})$aryl, CO$(C_1-C_6)$alkyl and $(C_1-C_6)$haloalkyl; $R^3$, $R^4$, $R^7$, $R^8$, $R^9$, and $R^{10}$ are each H; "- - - -" is a bond; Z is 2; and Y is $(C_6-C_{10})$aryl optionally substituted with one or more substituents.

In other embodiments of compounds of Formula III-B:
W is 0; $R^2$ is selected from $(C_1-C_6)$alkyl, $(C_3-C_{10})$cycloalkyl, $(C_1-C_6)$alkyl$(C_6-C_{10})$aryl, and CO$(C_1-C_6)$alkyl; $R^3$, $R^4$, $R^7$, $R^8$, $R^9$, and $R^{10}$ are each H; "- - - -" is absent; $R^5$ and $R^6$ are each independently selected from H and $(C_1-C_6)$alkyl; Z is 2; and Y is $(C_6-C_{10})$aryl optionally substituted with one or more substituents.

In other embodiments of compounds of Formula III-B:
$R^2$ is H; "- - - -" is a bond or is absent; $R^5$ and $R^6$ are each independently selected from H and $(C_1-C_6)$alkyl provided that "- - - -" is absent; $R^9$ and $R^{10}$ are H; Q is absent; and Y is selected from $(C_6-C_{10})$aryl, $(C_5-C_9)$heteroaryl, and $(C_3-C_9)$heterocycloalkyl wherein any of the foregoing is optionally substituted with one or more substituents.

In certain more specific embodiments Y is optionally substituted with at least one substituent selected from halogen, $N(R^{13})_2$, OH, $(C_1-C_6)$alkyl, $(C_1-C_6)$alkoxy, $(C_1-C_6)$haloalkyl, $(C_1-C_6)$haloalkoxy, $(C_3-C_9)$heterocycloalkyl, and oxo.

In certain embodiments of compounds of Formula III-B:
W is 0; $R^3$ and $R^4$ are each independently selected from H, $(C_1-C_6)$alkyl, $(C_1-C_6)$hydroxyalkyl, $(C_1-C_6)$aminoalkyl, $(C_1-C_6)$haloalkyl, $(C_3-C_9)$heterocycloalkyl, $(C_1-C_6)$alkyl$(C_1-C_6)$alkoxy, $(C_3-C_{10})$cycloalkyl, $(C_1-C_6)$alkyl-$NR^{13}$—CO$(C_1-C_6)$alkyl, and $(C_1-C_6)$alkyl-CON$(R^{13})_2$; or $R^3$ and $R^4$ are taken together to form a $(C_4-C_{10})$cycloalkyl or $(C_3-C_9)$heterocycloalkyl spirocyclic ring wherein any of the foregoing may be optionally substituted with one or more substituents selected from $COR^{13}$, oxo, $(C_1-C_6)$alkyl, $(C_1-C_6)$alkoxy, and halogen; "- - - -" is a bond; and Y is selected from $(C_6-C_{10})$aryl, $(C_5-C_9)$heteroaryl and $(C_3-C_9)$heterocycloalkyl wherein any of the foregoing is optionally substituted with one or more substituents.

In certain more specific embodiments, Y is optionally substituted with at least one substituent selected from halogen, $N(R^{13})_2$, OH, $(C_1-C_6)$alkyl, $(C_1-C_6)$alkoxy, $(C_1-C_6)$haloalkyl, $(C_1-C_6)$haloalkoxy, $(C_3-C_9)$heterocycloalkyl, and oxo.

In other embodiments of compounds of Formula III-B:
W is 0; $R^3$ and $R^4$ are each independently selected from H and $(C_1-C_6)$alkyl; or $R^3$ and $R^4$ are taken together to form a $(C_4-C_{10})$cycloalkyl or $(C_3-C_9)$heterocycloalkyl spirocyclic ring; "- - - -" is absent; $R^5$ and $R^6$ are each independently selected from H and $(C_1-C_6)$alkyl; $R^7$ and $R^8$ are H; Z is 2; and Y is $(C_6-C_{10})$aryl which is optionally substituted with one or more substituents.

In certain more specific embodiments, Y is optionally substituted with at least one substituent selected from halogen, $N(R^{13})_2$, OH, $(C_1-C_6)$alkyl, $(C_1-C_6)$alkoxy, $(C_1-C_6)$haloalkyl, and $(C_1-C_6)$haloalkoxy.

In other embodiments of compounds of Formula III-B:
W is 0; $R^3$ and $R^4$ are each independently selected from H and $(C_3-C_9)$heterocycloalkyl, or $R^3$ and $R^4$ are taken together to form a $(C_3-C_9)$heterocycloalkyl spirocyclic ring; "- - - -" is a bond; $R^7$ and $R^8$ are each independently selected from H and $(C_1-C_6)$alkyl; and Y is selected from $(C_6-C_{10})$aryl and $(C_5-C_9)$heteroaryl either of which is optionally substituted with one or more substituents.

In certain more specific embodiments, Y is optionally substituted with at least one substituent selected from halogen, oxo, $(C_1-C_6)$alkyl, $(C_1-C_6)$alkoxy, $(C_1-C_6)$haloalkyl, $(C_1-C_6)$haloalkoxy, $N(R^{13})_2$, and OH.

In further embodiments of compounds of Formula III-B:
$R^2$ is taken together with one of $R^3$ or $R^4$ to form an optionally substituted $(C_3-C_9)$heterocycloalkyl ring and the other of $R^3$ or $R^4$ is selected from H and $(C_1-C_6)$hydroxyalkyl; "- - - -" is a bond; $R^7$, $R^8$, $R^9$, and $R^{10}$ are each H; Q is absent; Z is 2; and Y is $(C_6-C_{10})$aryl optionally substituted with one or more substituents.

In additional embodiments of compounds of Formula III-B:

R² is selected from H, $(C_1$-$C_6)$alkyl, $(C_3$-$C_{10})$cycloalkyl, $(C_6$-$C_{10})$aryl, and $(C_1$-$C_6)$alkyl$(C_6$-$C_{10})$aryl; R³ and R⁴ are each H; "- - - -" is either a bond or is absent; R⁵ and R⁶ are each independently selected from H and $(C_1$-$C_6)$alkyl, provided that "- - - -" is absent; R⁷, R⁸, R⁹, and R¹⁰ are each H; Q is —O—; Z is 2; and Y is selected from $(C_6$-$C_{10})$aryl, $(C_1$-$C_6)$alkyl$(C_6$-$C_{10})$aryl, $(C_4$-$C_9)$heteroaryl and $C_1$-$C_6)$alkyl$(C_3$-$C_{10})$cycloalkyl wherein any of the foregoing is optionally substituted with one or more substituents.

In certain more specific embodiments, Y is optionally substituted with at least one substituent selected from $(C_1$-$C_6)$alkyl, halogen, $(C_1$-$C_6)$alkoxy, NR¹³CO—$(C_1$-$C_6)$alkyl, $(C_4$-$C_9)$heteroaryl, $(C_1$-$C_6)$haloalkyl, $(C_6$-$C_{10})$aryl, $(C_1$-$C_6)$haloalkoxy, $(C_2$-$C_9)$heterocycloalkyl, $(C_6$-$C_{10})$aryloxy, and NO₂.

In other embodiments of compounds of Formula III-B:
W is 0; R² is H; "- - - -" is absent; and R⁵ and R⁶ are each H.

In other embodiments of compounds of Formula III-B:
W is 0; R² is selected from $(C_1$-$C_6)$alkyl, $(C_3$-$C_{10})$cycloalkyl, and $(C_1$-$C_6)$alkyl$(C_6$-$C_{10})$aryl; "- - - -" is absent; R⁵ and R⁶ are each H; and Y is $(C_6$-$C_{10})$aryl optionally substituted with one or more substituents.

In additional embodiments of compounds of Formula III-B:
W is 0; "- - - -" is a bond; and Y is $(C_4$-$C_9)$heteroaryl optionally substituted with one or more substituents.

In still other embodiments of compounds of Formula III-B:
R² is H; "- - - -" is absent; R⁵ and R⁶ are each H; Q is NR¹³ and R¹³ is $(C_1$-$C_6)$alkyl; and Y is $(C_4$-$C_9)$heteroaryl optionally substituted with one or more substituents.

Yet another aspect of this application is directed to compounds of Formula I having a structure of Formula III-C:

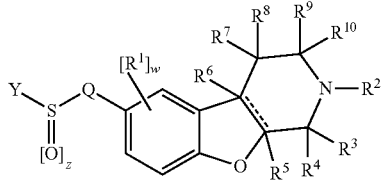

III-C or salts thereof.

In some embodiments of compounds of Formula III-C:
W is 0; R² is H; R³, R⁴, R⁷, R⁸, R⁹, and R¹⁰ are each H; "- - - -" is a bond; Q is absent; and Y is selected from $(C_6$-$C_{10})$aryl, $(C_5$-$C_9)$heteroaryl, and $(C_3$-$C_{10})$cycloalkyl wherein any of the foregoing is optionally substituted with one or more substituents.

In certain more specific embodiments, Y is optionally substituted with at least one substituent selected from halogen, $(C_1$-$C_6)$alkyl, $(C_1$-$C_6)$alkoxy, $(C_1$-$C_6)$haloalkyl, $(C_6$-$C_{10})$aryloxy, NO₂, CO₂$(C_1$-$C_6)$alkyl, CN, NR¹³CO—$(C_1$-$C_6)$alkyl, $(C_1$-$C_6)$haloalkoxy, $(C_6$-$C_{10})$aryl, N(R¹³)₂, and oxo.

In other embodiments of compounds of Formula III-C:
W is 0; R² is H; R³, R⁴, R⁷, R⁸, R⁹, and R¹⁰ are each H; "- - - -" is absent; R⁵ and R⁶ are each independently selected from H and $(C_1$-$C_6)$alkyl; Q is absent; and Y is selected from $(C_6$-$C_{10})$aryl and $(C_5$-$C_9)$heteroaryl wherein either of the foregoing is optionally substituted with one or more substituents.

In certain more specific embodiments, Y is optionally substituted with at least one substituent selected from halogen, $(C_1$-$C_6)$alkoxy, $(C_1$-$C_6)$alkyl, NO₂, $(C_6$-$C_{10})$aryloxy, oxo, NR¹³CO—$(C_1$-$C_6)$alkyl, and $(C_1$-$C_6)$hydroxyalkyl.

In additional embodiments of compounds of Formula III-C:
W is 0; R² is H; R³ and R⁴ are each independently selected from H, $(C_1$-$C_6)$alkyl, $(C_1$-$C_6)$haloalkyl, $(C_3$-$C_{10})$cycloalkyl, $(C_1$-$C_6)$alkyl$(C_1$-$C_6)$alkoxy, $(C_2$-$C_9)$heterocycloalkyl, and $(C_1$-$C_6)$alkyl-NR¹³CO—$(C_1$-$C_6)$alkyl; or R³ and R⁴ are taken together to form a $(C_3$-$C_9)$heterocycloalkyl spirocyclic ring; R⁷, R⁸, R⁹, and R¹⁰ are each H; "- - - -" is a bond; Z is 2; Q is absent; and Y is selected from $(C_6$-$C_{10})$aryl optionally substituted with one or more substituents.

In certain more specific embodiments, Y is optionally substituted with at least one substituent selected from halogen, $(C_1$-$C_6)$haloalkyl, and $(C_1$-$C_6)$alkoxy.

In still further embodiments of compounds of Formula III-C:
W is 0; R² and one of R³ and R⁴ are taken together to form a $(C_3$-$C_9)$heterocycloalkyl ring and the other of R³ and R⁴ is H; "- - - -" is a bond; Z is 2; Q is absent; and Y is $(C_6$-$C_{10})$aryl optionally substituted with one or more substituents.

In still further embodiments of compounds of Formula III-C:
R² is selected from H, $(C_1$-$C_6)$alkyl, $(C_3$-$C_{10})$cycloalkyl, and $(C_1$-$C_6)$alkyl$(C_6$-$C_{10})$aryl; R³, R⁴, R⁷, R⁸, R⁹, and R¹⁰ are each H; "- - - -" is absent; R⁵ and R⁶ are each independently selected from H and $(C_1$-$C_6)$alkyl; Q is —O—; Z is 2; and Y is selected from $(C_6$-$C_{10})$aryl, $(C_1$-$C_6)$alkyl$(C_6$-$C_{10})$aryl, and $(C_3$-$C_9)$heteroaryl wherein any of the foregoing is optionally substituted with one or more substituents.

In certain more specific embodiments, Y is optionally substituted with at least one substitutent selected from halogen, $(C_1$-$C_6)$alkoxy, $(C_1$-$C_6)$alkyl, $(C_1$-$C_6)$haloalkyl, $(C_1$-$C_6)$haloalkoxy, $(C_3$-$C_9)$heteroaryl, $(C_1$-$C_6)$haloalkyl, $(C_6$-$C_{10})$aryloxy, NR¹³CO—$(C_1$-$C_6)$alkyl, $(C_6$-$C_{10})$aryl, and NO₂.

In additional embodiments of compounds of Formula III-C:
W is 0; and R² is H.

In still additional embodiments of compounds of Formula III-C:
W is 0; and R² is selected from $(C_1$-$C_6)$alkyl, $(C_3$-$C_{10})$cycloalkyl, and $(C_1$-$C_6)$alkyl$(C_6$-$C_{10})$aryl.

In still further embodiments of compounds of Formula III-C:
R² is selected from H and CO$(C_1$-$C_6)$alkyl; R³, R⁴, R⁷, R⁸, R⁹, and R¹⁰ are each H; "- - - -" is absent; R⁵ and R⁶ are each H; Q is —NH—; Z is 2; and Y is selected from $(C_6$-$C_{10})$aryl, $(C_3$-$C_9)$heteroaryl, and $(C_1$-$C_6)$alkyl$(C_6$-$C_{10})$aryl wherein any of the foregoing may be optionally substituted with one or more substituents.

In yet further embodiments of compounds of Formula III-C: R² is H; and Y is selected from $(C_6$-$C_{10})$aryl, $(C_3$-$C_9)$heteroaryl, and $(C_1$-$C_6)$alkyl$(C_6$-$C_{10})$aryl wherein any of the foregoing may be optionally substituted with one or more substituents.

In certain more specific embodiments, Y is optionally substituted with at least one substitutent selected from $(C_1$-$C_6)$alkyl, halogen, and $(C_1$-$C_6)$alkoxy.

In still further embodiments of compounds of Formula III-C:
W is 0; R² is H; R³, R⁴, R⁷, R⁸, R⁹, R¹⁰ are each H; "- - - -" is absent; R⁵ and R⁶ are each H; R¹³ is H or methyl; Z is 2; and Y is selected from $(C_6$-$C_{10})$aryl, $(C_1$-$C_6)$alkyl$(C_6$-$C_{10})$aryl, or $(C_3$-$C_{10})$cycloalkyl wherein any of the foregoing is optionally substituted with one or more substituents.

In certain more specific embodiments, Y is optionally substituted with at least one substituent selected from $(C_1-C_6)$ alkyl, $(C_1-C_6)$alkoxy, and halogen.

In other embodiments of compounds of Formula III-C:

W is 0; $R^2$ is H; $R^3$, $R^4$, $R^7$, $R^8$, $R^9$, $R^{10}$ are each H; "- - - -" is absent; $R^5$ and $R^6$ are each H; Q is absent; Z is 2; and Y is $NR^{14}R^{15}$ wherein $R^{14}$ and $R^{15}$ are taken together to form a $(C_2-C_9)$heterocycloalkyl ring which is optionally substituted with one or more substituents selected from $(C_6-C_{10})$aryl or $(C_2-C_9)$heterocycloalkyl.

Additional aspects of this application are directed to compounds of Formula I having the structure of Formula III-D:

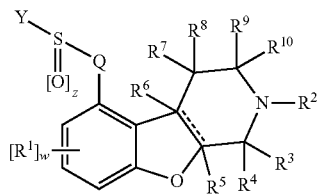

III-D or salts thereof.

Still additional aspects of this application are directed to compounds of Formula I having the structure of Formula IV:

IV or salts thereof.

In some embodiments of compounds of Formula IV:

A is $—(CR^9R^{10})_n—$ wherein n is 1, 2, or 3 and $R^9$ and $R^{10}$ at each occurrence are independently selected from H or unsubstituted $C_1-C_6$ alkyl, or $(C_1-C_6)$haloalkyl;

$R^1$ at each occurrence is independently selected from H, halogen, CN, $NO_2$, $NR^{11}R^{12}$, $COR^{13}$, $CO_2R^{13}$, $(C_1-C_6)$ alkyl, $(C_1-C_6)$haloalkyl, $(C_1-C_6)$alkyl$(C_1-C_6)$alkoxy, $(C_1-C_6)$alkyl$(C_1-C_6)$haloalkoxy, $(C_3-C_{10})$cycloalkyl, $(C_1-C_6)$alkyl$(C_3-C_{10})$cycloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, $(C_1-C_6)$alkyl$(C_5-C_9)$heteroaryl, and W is 0, 1, 2 or 3, wherein any of the foregoing, except for H, halogen, CN, and $NO_2$, may be optionally substituted with one or more substituents;

$R^2$ is selected from H, $(C_1-C_6)$alkyl, $(C_1-C_6)$haloalkyl, $(C_1-C_6)$alkyl$(C_1-C_6)$alkoxy, $CO(C_1-C_6)$alkyl, $CO_2(C_1-C_6)$alkyl, $CO(C_6-C_{10})$aryl, $CO_2(C_6-C_{10})$aryl, $(C_6-C_{10})$ aryl, $(C_1-C_6)$alkyl$(C_6-C_{10})$aryl, $(C_3-C_{10})$cycloalkyl, $CO(C_3-C_{10})$cycloalkyl, $CO_2(C_3-C_{10})$cycloalkyl, $(C_1-C_6)$alkyl$(C_3-C_{10})$cycloalkyl, $CO(C_1-C_6)$alkyl$(C_3-C_{10})$ cycloalkyl, $CO_2(C_1-C_6)$alkyl$(C_3-C_{10})$cycloalkyl, $(C_2-C_9)$heterocycloalkyl, $(C_1-C_6)$alkyl$(C_2-C_9)$ heterocycloalkyl, $CO(C_1-C_6)$alkyl$(C_2-C_9)$heterocycloalkyl, $CO_2(C_1-C_6)$alkyl$(C_2-C_9)$heterocycloalkyl, $(C_5-C_9)$heteroaryl, $CO(C_5-C_9)$heteroaryl, $—CO_2(C_5-C_9)$heteroaryl, $(C_1-C_6)$alkyl$(C_5-C_9)$heteroaryl, $CO(C_1-C_6)$alkyl$(C_5-C_9)$heteroaryl, and $CO_2(C_1-C_6)$alkyl$(C_5-C_9)$heteroaryl, wherein any of the foregoing, except for H, is optionally substituted with one or more substituents;

$R^3$ and $R^4$ are each independently selected from H, halogen, OH, $(C_1-C_6)$alkyl, $(C_1-C_6)$haloalkyl, $(C_1-C_6)$aminoalkyl, $(C_1-C_6)$alkoxy, $(C_1-C_6)$haloalkoxy, $(C_1-C_6)$alkyl$(C_1-C_6)$alkoxy, $(C_1-C_6)$alkyl-$NR^{13}CO—(C_1-C_6)$ alkyl, $(C_1-C_6)$alkyl-$CON(R^{13})_2$, $(C_6-C_{10})$aryl, $(C_6-C_{10})$ aryloxy, $(C_1-C_6)$alkyl$(C_6-C_{10})$aryl, $(C_1-C_6)$alkyl$(C_6-C_{10})$aryloxy, $(C_3-C_{10})$cycloalkyl, $(C_3-C_{10})$ cycloalkyloxy, $(C_1-C_6)$alkyl$(C_3-C_{10})$cycloalkyl, $(C_1-C_6)$alkyl$(C_3-C_{10})$cycloalkyloxy, $(C_5-C_9)$heteroaryl, $(C_5-C_9)$heteroaryloxy, $(C_2-C_9)$heterocycloalkyl, $(C_2-C_9)$heterocycloalkyloxy, $(C_1-C_6)$alkyl$(C_2-C_9)$heterocycloalkyl, $(C_1-C_6)$alkyl$(C_2-C_9)$heterocycloalkyloxy, $(C_1-C_6)$alkyl$(C_5-C_9)$heteroaryl, and $(C_1-C_6)$alkyl$(C_5-C_9)$ heteroaryloxy, wherein any of the foregoing, except for H, is optionally substituted with one or more substituents; or $R^3$ and $R^4$ are taken together to form a $(C_4-C_{10})$cycloalkyl or $(C_4-C_9)$heterocycloalkyl spirocyclic ring wherein either of the foregoing is optionally substituted with one or more of $(C_1-C_6)$alkyl, $(C_1-C_6)$haloalkyl, $(C_1-C_6)$hydroxyalkyl, $COR^{11}$, $CO_2R^{11}$, $CONR^{11}R^{13}$, halogen, $(C_1-C_6)$alkoxy, $(C_1-C_6)$haloalkoxy, $OR^{13}$, and oxo;

or $R^2$ and one of $R^3$ or $R^4$ are taken together to form an optionally substituted $(C_3-C_9)$heterocycloalkyl ring and the other of $R^3$ or $R^4$ is selected from H or $(C_1-C_6)$ hydroxyalkyl;

"- - - -" is a bond or is absent;

$R^5$ and $R^6$ are each independently selected from H, $(C_1-C_6)$ alkyl, $(C_1-C_6)$hydroxyalkyl, and OH provided that "- - - -" is absent;

$R^7$ and $R^8$ are each independently selected from H, $(C_1-C_6)$ alkyl, or $(C_1-C_6)$haloalkyl; or $R^7$ and $R^8$ are taken together to form a $(C_4-C_{10})$cycloalkyl ring or $(C_4-C_9)$heterocycloalkyl spirocyclic ring wherein either of the foregoing is optionally substituted with one or more substituents;

$R^{11}$ and $R^{12}$ at each occurrence are independently selected from H, $(C_1-C_6)$alkyl, $(C_1-C_6)$alkoxy, $(C_1-C_6)$alkyl$(C_1-C_6)$alkoxy, or $(C_1-C_6)$hydroxyalkyl;

$R^{13}$ at each occurrence is independently selected from H or $(C_1-C_6)$alkyl;

Q is absent, or $—O—$;

Z is 1 or 2; and

Y is selected from $(C_3-C_{10})$cycloalkyl, $(C_1-C_6)$alkyl$(C_3-C_{10})$cycloalkyl, $(C_2-C_9)$heterocycloalkyl, $(C_1-C_6)$alkyl $(C_2-C_9)$heterocycloalkyl, $(C_6-C_{10})$aryl, $(C_1-C_6)$alkyl $(C_6-C_{10})$aryl, $(C_5-C_9)$heteroaryl, and $(C_1-C_6)$alkyl$(C_5-C_9)$heteroaryl wherein any of the foregoing is optionally substituted with one or more substituents; or Y is $NR^{14}R^{15}$ wherein $R^{14}$ and $R^{15}$ are taken together to form a $(C_2-C_9)$heterocycloalkyl ring which is optionally substituted with one or more substituents.

Additional aspects of this application are directed to compounds of Formula I having a structure of Formula IVa:

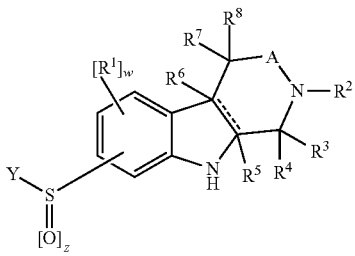

or salts thereof.

In some embodiments of compounds of Formula IVa:

A is —$(CR^9R^{10})_n$— wherein n is 1, 2, or 3 and $R^9$ and $R^{10}$ at each occurrence are independently selected from H or unsubstituted $C_1$-$C_6$ alkyl, and $(C_1$-$C_6)$haloalkyl;

$R^1$ at each occurrence is independently selected from H, halogen, CN, $NO_2$, $NR^{11}R^{12}$, $COR^{13}$, $CO_2R^{13}$, $(C_1$-$C_6)$ alkyl, $(C_1$-$C_6)$haloalkyl, $(C_1$-$C_6)$alkyl$(C_1$-$C_6)$alkoxy, $(C_1$-$C_6)$alkyl$(C_1$-$C_6)$haloalkoxy, $(C_3$-$C_{10})$cycloalkyl, $(C_1$-$C_6)$alkyl$(C_3$-$C_{10})$cycloalkyl, $(C_6$-$C_{10})$aryl, $(C_1$-$C_6)$ alkyl$(C_6$-$C_{10})$aryl, $(C_2$-$C_9)$heterocycloalkyl, $(C_1$-$C_6)$ alkyl$(C_2$-$C_9)$heterocycloalkyl, $(C_5$-$C_9)$heteroaryl, $(C_1$-$C_6)$alkyl$(C_5$-$C_9)$heteroaryl, and W is 0, 1, 2 or 3, wherein any of the foregoing, except for H, halogen, CN, and $NO_2$, is optionally substituted with one or more substituents;

$R^2$ is selected from H, $(C_1$-$C_6)$alkyl, $(C_1$-$C_6)$haloalkyl, $(C_1$-$C_6)$alkyl$(C_1$-$C_6)$alkoxy, $CO(C_1$-$C_6)$alkyl, $CO_2(C_1$-$C_6)$alkyl, $CO(C_6$-$C_9)$aryl, $CO_2(C_6$-$C_9)$aryl, $(C_6$-$C_9)$aryl, $(C_2$-$C_6)$alkyl$(C_6$-$C_{10})$aryl, $(C_3$-$C_{10})$cycloalkyl, $CO(C_3$-$C_{10})$cycloalkyl, $CO_2(C_3$-$C_{10})$cycloalkyl, $(C_1$-$C_6)$alkyl $(C_3$-$C_{10})$cycloalkyl, $CO(C_1$-$C_6)$alkyl$(C_3$-$C_{10})$cycloalkyl, $CO_2(C_1$-$C_6)$alkyl$(C_3$-$C_{10})$cycloalkyl, $(C_2$-$C_6)$ alkyl$(C_2$-$C_9)$heterocycloalkyl, $CO(C_1$-$C_6)$alkyl$(C_2$-$C_9)$ heterocycloalkyl, $CO_2(C_1$-$C_6)$alkyl$(C_2$-$C_9)$ heterocycloalkyl, $(C_2$-$C_6)$alkyl$(C_5$-$C_9)$heteroaryl, $CO(C_1$-$C_6)$alkyl$(C_5$-$C_9)$heteroaryl, and $CO_2(C_1$-$C_6)$ alkyl$(C_5$-$C_9)$heteroaryl wherein any of the foregoing, except for H, is optionally substituted with one or more substituents;

$R^3$ and $R^4$ are each independently selected from H, halogen, OH, $(C_1$-$C_6)$alkyl, $(C_1$-$C_6)$haloalkyl, $(C_1$-$C_6)$ alkoxy, $(C_1$-$C_6)$haloalkoxy, $(C_1$-$C_6)$alkyl$(C_1$-$C_6)$ alkoxy, $(C_1$-$C_6)$alkyl-$NR^{13}$CO—$(C_1$-$C_6)$alkyl, $(C_1$-$C_6)$ alkyl-$CON(R^{13})_2$, $(C_6$-$C_{10})$aryl, $(C_6$-$C_{10})$aryloxy, $(C_1$-$C_6)$alkyl$(C_6$-$C_{10})$aryl, $(C_1$-$C_6)$alkyl$(C_6$-$C_{10})$aryloxy, $(C_3$-$C_{10})$cycloalkyl, $(C_3$-$C_{10})$cycloalkyloxy, $(C_1$-$C_6)$ alkyl$(C_3$-$C_{10})$cycloalkyl, $(C_1$-$C_6)$alkyl$(C_3$-$C_{10})$cycloalkyloxy, $(C_5$-$C_9)$heteroaryl, $(C_5$-$C_9)$heteroaryloxy, $(C_2$-$C_9)$heterocycloalkyl, $(C_2$-$C_9)$heterocycloalkyloxy, $(C_1$-$C_6)$alkyl$(C_2$-$C_9)$heterocycloalkyl, $(C_1$-$C_6)$alkyl $(C_2$-$C_9)$heterocycloalkyloxy, $(C_1$-$C_6)$alkyl$(C_5$-$C_9)$heteroaryl, and $(C_1$-$C_6)$alkyl$(C_5$-$C_9)$heteroaryloxy, wherein any of the foregoing, except for H, is optionally substituted with one or more; or $R^3$ and $R^4$ are taken together to form a $(C_4$-$C_{10})$cycloalkyl or $(C_4$-$C_9)$heterocycloalkyl spirocyclic ring wherein either of the foregoing is optionally substituted with one or more of $(C_1$-$C_6)$alkyl, $(C_1$-$C_6)$haloalkyl, $(C_1$-$C_6)$hydroxyalkyl, $COR^{11}$, $CO_2R^{11}$, $CONR^{11}R^{13}$, halogen, $(C_1$-$C_6)$alkoxy, $(C_1$-$C_6)$haloalkoxy, $OR^{13}$, and oxo; or $R^2$ and one of $R^3$ or $R^4$ are taken together to form an optionally substituted $(C_3$-$C_9)$heterocycloalkyl ring and the other of $R^3$ or $R^4$ is selected from H, $(C_1$-$C_6)$alkyl, and $(C_1$-$C_6)$hydroxyalkyl;

"- - - -" is a bond or is absent;

$R^5$ and $R^6$ are each independently selected from H, $(C_1$-$C_6)$ alkyl, $(C_1$-$C_6)$hydroxyalkyl, and OH provided that "- - - -" is absent;

$R^7$ and $R^8$ are each independently selected from H, $(C_1$-$C_6)$ alkyl, or $(C_1$-$C_6)$haloalkyl; or $R^7$ and $R^8$ are taken together to form a $(C_4$-$C_{10})$cycloalkyl ring or $(C_4$-$C_9)$heterocycloalkyl spirocyclic ring wherein either of the foregoing is optionally substituted with one or more substituents;

$R^{11}$ and $R^{12}$ at each occurrence are each independently selected from H, $(C_1$-$C_6)$alkyl, $(C_1$-$C_6)$alkoxy, $(C_1$-$C_6)$ alkyl$(C_1$-$C_6)$alkoxy, and $(C_1$-$C_6)$hydroxyalkyl;

$R^{13}$ at each occurrence is independently selected from H and $(C_1$-$C_6)$alkyl;

Z is 1 or 2; and

Y is $NR^{14}R^{15}$ wherein $R^{14}$ and $R^{15}$ are each independently selected from H, $(C_1$-$C_6)$alkyl, $(C_3$-$C_{10})$cycloalkyl, $(C_1$-$C_6)$alkyl$(C_3$-$C_{10})$cycloalkyl, $(C_6$-$C_{10})$aryl, $(C_1$-$C_6)$alkyl $(C_6$-$C_{10})$aryl, $(C_2$-$C_9)$heterocycloalkyl, $(C_1$-$C_6)$alkyl $(C_2$-$C_9)$heterocycloalkyl, $(C_5$-$C_9)$heteroaryl, and $(C_1$-$C_6)$alkyl$(C_5$-$C_9)$heteroaryl, wherein any of the foregoing, with the exception of H, is optionally substituted with one or more substituents and provided that both $R^{14}$ and $R^{15}$ are not both H.

Additional aspects of this application are directed to compounds of Formula I having a structure of Formula V:

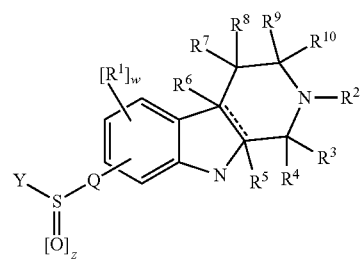

or salts thereof.

Additional aspects of this application are directed to compounds of Formula I having a structure of Formula V-A

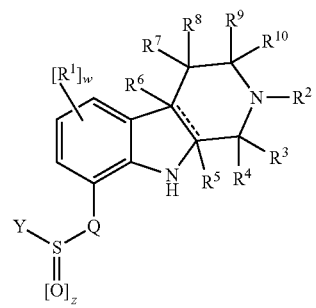

or salts thereof.

Further aspects of this application are directed to compounds of Formula I having a structure of Formula V-B:

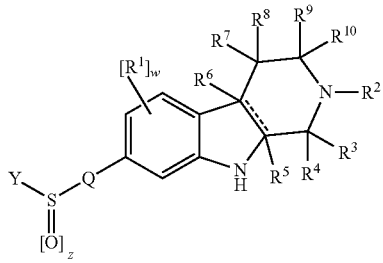

V-B or salts thereof.
In some embodiments of compounds of Formula V-B:
W is 0;
$R^2$ is H;
$R^3$ and $R^4$ are each independently selected from H, $(C_1-C_6)$ alkyl, and $(C_1-C_6)$haloalkyl; or
$R^3$ and $R^4$ are taken together to form an optionally substituted $(C_4-C_9)$heterocycloalkyl spirocyclic ring;
"- - - -" is a bond;
$R^7$, $R^8$, $R^9$, and $R^{10}$ are each H;
Q is absent;
Z is 2; and
Y is $(C_6-C_{10})$aryl optionally substituted with one or more substituents.
In certain more specific embodiments, Y is optionally substituted with at least one substituent selected from halogen, $(C_1-C_6)$haloalkyl, and $(C_1-C_6)$haloalkoxy.
Further aspects of this application are directed to compounds of Formula I having the structure of Formula V-C:

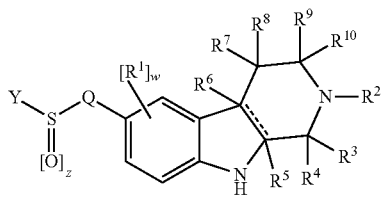

V-C or salts thereof.
Still additional aspects of this application are directed to compounds of Formula I having the structure of Formula V-D:

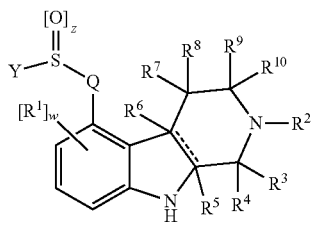

V-D or salts thereof.
In another aspect, this application relates to salts of the compounds of Formula I wherein the salts are pharmaceutically acceptable salts.

In another aspect, this application relates to compounds of Formula I specifically named herein.

In another aspect, this application relates to compositions comprising one or more compounds of Formula I or a salt thereof. In specific embodiments, the salt is a pharmaceutically acceptable salt. In additional specific embodiments, the composition comprises at least one pharmaceutically acceptable excipient. In other specific embodiments, the composition further comprises at least one additional therapeutically active agent.

In another aspect, this application relates to methods of treating conditions, disorders or diseases mediated, controlled, effected or influenced by a member of the serotonin receptor (5-HT) family. In some embodiments, the condition, disorder or disease is mediated, controlled, effected or influenced by at least one of the $5-HT_6$ or 5-HT, receptors. In some specific embodiments, the condition, disorder or disease is: related to the central nervous system (CNS) such as memory disorders, anxiety, epilepsy, migraine, panic attacks, depression, bipolar disorder, obsessive compulsive disorders, cognition/cognitive disorders, mild cognitive impairment (MCI), senile dementia, psychosis, schizophrenia, ADHD/ADD; or for the treatment of pain including neuropathic pain and chronic pain; head trauma or injury; or for the treatment of neurodegenerative conditions, disorders or diseases such as Alzheimer's disease, Parkinson's disease, Huntington's disease, amyotrophic lateral sclerosis (ALS) or multiple sclerosis; or for the treatment of conditions, disorders or diseases related to addiction and/or withdrawal from substances such as narcotics, ethanol (alcoholism), nicotine, and/or benzodiazepines; sleep/wakefulness disorders; or for the treatment of gastrointestinal (GI) conditions, disorders or diseases such as irritable bowel syndrome (IBS), functional bowel disorder; or for the treatment of conditions, disorders or diseases related to feeding behaviors or food intake such as anorexia, cachexia, and obesity.

In another aspect this application relates to methods for improving cognition (cognitive enhancement) and/or improving memory in otherwise healthy subjects.

In another aspect, this application relates to methods of treating conditions, disorders or diseases mediated, controlled, effected or influenced by the $5-HT_6$ receptor comprising administering a therapeutically effective amount of a compound of Formula I or a pharmaceutically acceptable salt thereof. In some specific embodiments, the method further comprises administration of at least one additional therapeutically active agent.

Definitions

The compounds and intermediates described herein may be named according to either the IUPAC (International Union for Pure and Applied Chemistry) or CAS (Chemical Abstracts Service) nomenclature systems.

The various hydrocarbon-containing moieties described herein may be described using a prefix designating the minimum and maximum number of carbon atoms in the moiety, i.e. "$(C_a-C_b)$". For example, $(C_a-C_b)$alkyl indicates an alkyl moiety of the integer "a" to the integer "b" carbon atoms, inclusive. Certain moieties may also be described according to the minimum and maximum number of members with or without specific reference to a particular atom or group of atoms. For example, the terms "a- to b-membered" or "having between a to b members" or "between a to b substituents" respectively refer to a moiety having the integer "a" to the integer "b" number of atoms or substituents, inclusive.

As used herein by themselves or in conjunction with another term or terms, "alkyl" and "$(C_1-C_6)$alkyl" refer to straight or branched hydrocarbon groups containing the requisite number of carbon atoms as described above. As used herein, alkyl groups may be optionally substituted with between one to four substituents. Representative examples of alkyl groups include, but are not limited to, e.g., methyl, ethyl, n-propyl, isopropyl, n-butyl, isobutyl, sec-butyl, t-butyl, etc.

As used herein by themselves or in conjunction with another term or terms, "alkoxy" and "($C_1$-$C_6$)alkoxy" refer to straight or branched hydrocarbon groups containing the requisite number of carbon atoms as described above, bonded to an oxygen atom. As used herein, all such alkoxy groups may be optionally substituted with between one to four substituents. Representative examples of alkoxy groups include, but are not limited to, e.g. methoxy, ethoxy, tert-butoxy, etc.

As used herein by themselves or in conjunction with another term or terms, "aminoalkyl" and "($C_1$-$C_6$)aminoalkyl" refer to alkyl groups, as described above, where at least one hydrogen atom, at any position, is replaced by an amino group, i.e., $NH_2$. As used herein, aminoalkyl groups may be optionally substituted with between one to four substituents.

As used herein by themselves or in conjunction with another term or terms, "alkenyl" and "($C_1$-$C_6$)alkenyl" refer to straight or branched hydrocarbon groups containing the requisite number of carbon atoms as described above, and at least one double bond. As used herein, alkenyl groups may be optionally substituted with between one to four substituents. Representative examples of alkenyl groups include, but are not limited to, e.g. ethenyl, 2-propenyl (allyl), iso-propenyl, 2-methyl-1-propenyl, etc.

As used herein by themselves or in conjunction with another term or terms, "alkynyl" and "($C_1$-$C_6$)alkynyl" refer to straight or branched hydrocarbon groups containing the requisite number of carbon atoms as described above, and at least one triple bond. As used herein, alkynyl groups may be optionally substituted with between one to four substituents. Representative examples of alkynyl groups include, but are not limited to, e.g. ethynyl, propynyl, butynyl, etc.

As used herein by itself or in conjunction with another term or terms, "aromatic" refers to monocyclic and polycyclic conjugated ring systems containing 4 n+2 pi electrons, where n is an integer. As used herein, aromatic refers to and includes ring systems that contain only carbon atoms (i.e. "aryl" or "aromatic carbocycle") as well as ring systems that contain at least one heteroatom selected from N, O or S (i.e. "heteroaromatic" or "heteroaryl"). As used herein, all such aromatic ring systems may be optionally substituted with between one to four substituents.

As used herein by itself or in conjunction with another term or terms, "non-aromatic" refers to a monocyclic or polycyclic ring system having at least one isolated, i.e. not part of a conjugated pi system, double bond. As used herein, non-aromatic refers to and includes ring systems that contain only carbon atoms as well as ring systems that contain at least one heteroatom selected from N, O or S, such as for example, 1,2,5,6-tetrahydropyridine. As used herein, all such non-aromatic ring systems may be optionally substituted with between one to four substituents.

As used herein by themselves or in conjunction with another term or terms, "aryl" and "($C_6$-$C_{10}$)aryl" refer to monocyclic and polycyclic hydrocarbon ring systems, i.e. carbocycles, having the requisite number of carbon atoms as described above, where at least one ring is aromatic, as described above. As used herein, aryl groups may be optionally substituted with between one to four substituents. Representative examples include, but are not limited to, e.g., phenyl (phenylenyl), napthyl (napthylenenyl), 1,2,3,4-tetrahydro-naphthalenyl, etc.

As used herein by themselves or in conjunction with another term or terms, "arylalkyl" and "($C_1$-$C_6$)alkyl($C_6$-$C_{10}$)aryl" refer to alkyl groups, as defined above, having an aryl group, as defined above, as a substituent. Arylalkyl groups may be optionally substituted with between one to four substituents. Representative examples include, but are not limited to, e.g., benzyl, phenylethyl, etc.

As used herein by themselves or in conjunction with another term or terms, "aryloxy", "($C_6$-$C_{10}$)aryloxy", "alkoxyaryl", and "($C_1$-$C_6$)alkoxy($C_6$-$C_{10}$)aryl" refer to aryl groups, as defined above, that are bonded directly to an oxygen atom or to an alkoxy group, as defined above, respectively. These groups may be optionally substituted with between one to four substituents. Representative examples include, but are not limited to, e.g., phenoxy, benzyloxy, phenylethoxy, napthyloxy, etc.

As used herein by themselves or in conjunction with another term or terms, "carbocyclic" and "carbocycle" refer to monocyclic and polycyclic ring systems that contain only carbon atoms in the ring(s),i.e. hydrocarbon ring systems, without regard to aromaticity. Thus, carbocyclic and carbocycle refer to and include ring systems that are saturated or unsaturated, aromatic or non-aromatic, as well as ring systems having fully saturated, aromatic and/or non-aromatic portions. The terms carbocyclic and carbocycle further include bridged, fused, and spirocyclic ring systems. Carbocycles may be optionally substituted with between one to four substituents. Representative examples include, but are not limited to, e.g., cyclopropyl, cyclobutyl, 1,3-dimethylcyclopentyl, cyclohexyl, phenyl, napthyl, cyclohexenyl, 2,3-dihydro-indenyl, 1,2,3,4-tetrahydro-naphthalene, spiro[3.4]octanyl, bicycle[2.2.1]hept-5-enyl, adamantanyl, norbornanyl, bicyclo[2.2.1]heptanyl, etc.

As used herein by themselves or in conjunction with another term or terms, "halo" and "halogen" include fluorine, chlorine, bromine, and iodine atoms and substituents. These groups may also be referred to as fluoro, chloro, bromo and iodo.

As used herein by themselves or in conjunction with another term, "haloalkyl" and "($C_1$-$C_6$) haloalkyl" refer to alkyl groups, as defined above, having one or more hydrogen atoms replaced by halogen atoms, as defined above. It should be understood that where there is more than one halogen atom present in a haloalkyl group, the halogen atoms may be the same or different and/or may be located on the same carbon atom or on different carbon atoms. Representative examples of haloalkyl groups include, but are not limited to, e.g., difluoromethyl, trifluoromethyl, chloromethyl, 3-bromo-2-chloro-propyl, 2,2-dibromoethyl, 2-bromo-2-chloro-ethyl, 1,1,2,2,3,3,4,4-octafluoro-butyl, etc.

As used herein by themselves or in conjunction with another term or terms, "haloalkoxy" and "($C_1$-$C_6$)haloalkoxy" refer to haloalkyl groups, as defined above, bonded to an oxygen atom. Representative examples of haloalkoxy groups include, but are not limited to, e.g., difluoromethoxy, trifluoromethoxy, chloromethoxy, 2,2-dibromoethoxy, 3-bromo-2-chloro-propoxy, 1,1,2,2,3,3,4,4-octafluoro-butoxy, etc.

As used herein by themselves or in conjunction with another term or terms, "cycloalkyl" and "($C_3$-$C_{10}$)cycloalkyl" refer to monocyclic and polycyclic hydrocarbon ring systems containing the requisite number of carbon atoms as described above, which may be optionally substituted with between one to four substituents. These terms refer to and include ring systems that are fully saturated or contain at least one double or triple bond, as well as ring systems with fully saturated or aromatic or non-aromatic portions, such as, for example, 1,2,3,4-tetrahydro-naphthalenyl. It should be understood that these terms further refer to and include bridged and/or fused polycyclic structures such as, for example, bicyclo[3.2.1]octanyl, bicyclo[5.2.0]nonanyl, bicyclo[2.2.1]hept-5-enyl and the like, as well as spirocyclic ring systems such as, for example, spiro[3.4]octanyl, spiro[3.5]nonyl and the like. Other representative examples of cycloalkyl groups include, but are not limited to, e.g., cyclopropyl, methylcyclopropyl, cyclobutyl, cyclobutenyl, isopropylcyclobutyl, cyclopentyl, 1,3-dimethylcyclopentyl, cyclohexyl, cyclohexenyl, cycloheptyl, 2,3-dihydro-1H-inden-2-yl, norbornyl, decahydronaphthalenyl, etc.

As used herein by themselves or in conjunction with another term or terms, "cycloalkyloxy", "$(C_3-C_{10})$cycloalkyloxy", "alkoxycycloalkyl", "alkoxy$(C_3-C_{10})$cycloalkyl", and "$(C_1-C_6)$alkoxy$(C_3-C_{10})$cycloalkyl" refer to a cycloalkyl group having the requisite number of carbon atoms as described above, bonded directly to an oxygen atom or an alkoxy group, respectively. As used herein, these groups may be optionally substituted with between one to four substituents. Representative examples include, but are not limited to, e.g., cyclopropyloxy, cyclobutyloxy, cyclopentyloxy, 2-cyclopentyl-ethoxy, cyclohexyl-methoxy, cyclohex-3-yloxy, etc.

As used herein by themselves or in conjunction with another term or terms, "heterocycloalkyl", "$(C_2-C_9)$heterocycloalkyl", "heterocycle", and "heterocyclic" refer to monocyclic and polycyclic ring systems containing the requisite number of carbon atoms as described above and at least one heteroatom selected from N, O, or S. These groups may be optionally substituted with between one to four substituents. These terms further refer to and include ring systems that are fully saturated or contain at least one double or triple bond, as well as ring systems with fully saturated or aromatic portions, such as for example, dihydrobenzo[1,4]-dioxinyl, and/or non-aromatic portions. It should be understood that polycyclic heterocycloalkyl groups further include fused, bridged and spirocyclic ring systems and ring systems in which the N or S is oxidized, i.e. 1,1-dioxide-thiomorpholinyl, 1-oxo-piperidinyl. Additional representative examples of heterocycloalkyl groups include, but are not limited to, e.g., oxiranyl, thiaranyl, aziridinyl, oxetanyl, thiatanyl, azetidinyl, tetrahydrofuranyl, tetrahydrothiophenyl, pyrrolidinyl, dihydrofuranyl, tetrahydropyranyl, pyranyl, tetrahydrothiopyranyl, thiopyranyl, piperidinyl, 1,4-dioxanyl, 1,4-oxathianyl, morpholinyl, thiomorpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, chromanyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, 7-oxa-1-aza-spiro[4.4]nonanyl, 3-azabicyclo[3.1.0]hexanyl, indolinyl, octahydro-1H-indolyl, octahydro-2H-pyrido[1,2-a]pyrazinyl, 3-azabicyclo[4.1.0]heptanyl, 3,4-dihydro-2H-pyranyl, 1,2,3,4-tetrahydropyridinyl, etc.

As used herein by themselves or in conjunction with another term or terms, "alkylheterocycloalkyl" and "$(C_1-C_6)$alkyl$(C_2-C_9)$heterocycloalkyll" refer to alkyl groups, as defined above, having a heterocycloalkyl group, as defined above, as a substituent. Alkylheterocycloalkyl groups may be optionally substituted with between one to four substituents. Representative examples include, but are not limited to, e.g., piperidinylmethyl, pyrrolidinylethyl, etc.

As used herein by themselves or in conjunction with another term or terms, "heterocycloalkyloxy", "$(C_2-C_9)$heterocycloalkyloxy", "alkoxy$(C_2-C_9)$heterocycloalkyl" and "$(C_1-C_6)$alkoxy$(C_2-C_9)$heterocycloalkyl" respectively refer to a heterocycloalkyl group, as defined above, bonded directly to an oxygen atom or to an alkoxy group, as defined above, and may be optionally substituted with between one to four substituents. Representative examples include, but are not limited to, e.g., pyrrolidin-3-yloxy, piperidin-4-yloxy, azepan-4-yloxy, pyrrolidin-1-yl-ethoxy, pyrrolidin-2-yl-methoxy, tetrahydro-pyran-3-ylpropyloxy, etc.

As used herein by themselves or in conjunction with another term or terms, "heteroaryl", "$(C_5-C_9)$heteroaryl", and "heteroaromatic", refer to monocyclic and polycyclic aromatic ring systems containing the requisite number of carbon atoms, as described above, and at least one heteroatom selected from N, O, or S. As used herein, a heteroaromatic ring system refers to and includes polycyclic ring systems that contain aromatic portions while other portions of the ring system may be fully saturated or non-aromatic such as, for example, dihydrobenzo[1,4]-dioxinyl. Heteroaromatic rings may be optionally substituted with between one to four substituents. Additional representative examples include, but are not limited to, e.g., pyrrolyl, furanyl, thiophenyl, thienyl, pyrazolyl, imidazolyl, isoxazolyl, oxazolyl, isothiazolyl, thiazolyl, 1,2,3-triazolyl, 1,2,4-triazolyl, tetrazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridinyl (pyridyl), pyridazinyl, pyrimidinyl, pyrazinyl, 1,2,3-triazinyl, 1,3,5-triazinyl, pyrazolo[3,4-b]pyridinyl, cinnolinyl, pteridinyl, purinyl, 6,7-dihydro-5H-[1]pyridinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, 1,2,3,4-tetrahydro-isoquinolinyl, 2,3-dihydro-1H-isoindolyl, 1,3,4,5-tetrahydro-benzo[b]azepin-2-one, 1,3,4,5-Tetrahydro-benzo[d]azepin-2-one, 2,3,4,5-Tetrahydro-benzo[c]azepin-1-one, 1,2,4,5-Tetrahydro-benzo[c]azepin-3-one, 2,3,4,5-Tetrahydro-1H-benzo[b]azepinyl, 2,3,4,5-Tetrahydro-1H-benzo[d]azepinyl, 2,3,4,5-Tetrahydro-1H-benzo[c]azepinyl, etc.

As used herein, "⁓" indicates a point of attachment.

As used herein by itself or in conjunction with another term or terms, "pharmaceutically acceptable" indicates that the designated entity such as for example, e.g. carrier, vehicle, diluent, excipient, salt or prodrug, is generally chemically and/or physically compatible with the other ingredients comprising a formulation, and/or is generally physiologically compatible with the recipient thereof.

As used herein by themselves or in conjunction with another term or terms, "subject(s)" and "patient(s)", refer to mammals, including humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s) when used in conjunction with the phrase " . . . optionally substituted by between one to four . . . " unless otherwise specified.

As used herein, representative examples of substituents include, but are not limited to, e.g., hydrogen (may be denoted as H), halogen (may be denoted as halo), $(C_1-C_6)$alkyl, $(C_1-C_6)$alkoxy, $(C_1-C_6)$alkoxy$(C_1-C_4)$alkyl, carboxylic acid (may be denoted as COOH), formyl, $(C_1-C_6)$acyl, $(C_1-C_6)$haloalkyl, $(C_1-C_6)$haloalkoxy, hydroxyl (may be denoted as OH), $(C_1-C_6)$aminoalkyl, $C_6)$hydroxyalkyl, nitro (may be denoted as $NO_2$), cyano (may be denoted as CN), amino (may be denoted as $NH_2$), mono- or di$(C_1-C_6)$alkylamino (may be denoted as $NHR^1$, $NR^1R^2$ or $N(R^1)_2$, oxo (may be denoted as $>=O$ or carbonyl), $(C_6-C_{10})$aryl, $(C_1-C_6)$alkyl$(C_6-C_{10})$aryl, $(C_6-C_{10})$aryloxy, $(C_6-C_{10})$aryl$(C_1-C_6)$alkoxy, $(C_5-C_9)$heteroaryl, $(C_5-C_9)$heteroaryloxy, $(C_1-C_6)$alkyl$(C_5-C_9)$heteroaryl, $(C_5-C_9)$heteroaryl$(C_1-C_6)$alkoxy, $(C_1-C_6)$alkoxycarbonyl (may be denoted as COOR or $CO_2R$), $(C_3-C_{10})$cycloalkyl, $(C_3-C_{10})$cycloalkyloxy, $(C_3-C_{10})$cycloalkyl$(C_1-C_6)$alkoxy, $(C_1-C_6)$alkyl$(C_3-C_{10})$cycloalkyl, $(C_2-C_9)$heterocycloalkyl, $(C_2-C_9)$heterocycloalkyloxy, $(C_1-C_6)$alkyl$(C_2-C_9)$heterocyclalkyl, $(C_2-C_9)$heterocycloalkyl$(C_1-C_6)$alkoxy, $(C_1-C_6)$alkyl$(C_1-C_6)$alkoxycarbonyl (may be denoted as RCOOR or $RCO_2R$), $(C_1-C_6)$alkylsulfinyl, $(C_1-C_6)$alkylsulfonyl, mono- and di-$(C_1-C_6)$alkylaminocarbonyl (may be denoted as $NH_2CO$, NHCO, $NR^1CO$, $N(R^1)_2CO$), $(C_1-C_6)$acylthio, and $(C_1-C_6)$acyloxy.

As used herein, "treating", "treated", and "treatment", whether used alone or in conjunction with another term or terms, include preventative (e.g., prophylactic), ameliorative, palliative, and curative uses and results, or any combination thereof. It should be understood that the terms "preventing" and "preventative" and "prophylactic" are not absolute but rather refer to uses and results where the administration of a compound or composition diminishes the likelihood or seriousness of a condition, symptom, or disease state, and/or delays the onset of a condition, symptom, or disease state for a period of time.

As used herein, the terms "therapeutic" and "therapeutically effective amount", whether used alone or in conjunction with another term or terms, denote an amount of a compound, composition or medicament that (a) treats or prevents a particular disease, condition or disorder; (b) attenuates, ameliorates or eliminates one or more symptoms of a particular disease, condition or disorder; (c) prevents or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c).

As used herein, a "therapeutically active agent", whether used alone or in conjunction with another term or terms, refers to any compound, i.e. a drug, that has been found to be useful in the treatment of a disease or disorder and is not described by Formula I.

The compounds (including final products and intermediates) described herein may be isolated and used per se or may be isolated in the form of a salt. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more. Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved (by a regulatory authority such as FDA) for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of Formula I may have two or more asymmetric centers and therefore can exist in a number of stereoisomeric configurations. Consequently, such compounds can be synthesized and/or isolated as mixtures of enantiomers and/or as individual (pure) enantiomers, as well as diastereomers and mixtures of different diastereomers. It should be understood that the present application includes all such enantiomers and diastereomers and mixtures thereof in all ratios.

In practice, resolution and isolation of pure enantiomers can be achieved using methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation or inversion.

For those compounds of Formula I that contain one or more additional stereogenic centers, those skilled in the art will appreciate that all diastereoisomers and mixtures diastereoisomers in any amount of the compounds illustrated and discussed herein are within the scope of the present application. Compounds of Formula I that exist as diastereoisomers may be isolated by methods known to those skilled in the art, for example, by crystallization, gas-liquid or liquid chromatography. Alternatively, intermediates in the course of a synthesis that exist as racemic mixtures may be subjected to resolution by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers may be synthesized by asymmetric synthesis using optically active reagents, substrates, catalysts or solvents, or by converting one stereoisomer into the other by asymmetric transformation or inversion.

Compounds of the application may be administered as prodrugs. The term "prodrug" refers to a compound that is transformed in vivo to yield a compound of Formula I. The in vivo transformation may occur by various mechanisms, such as hydrolysis, in the blood or other biological fluids.

A prodrug of a compound of Formula I may be formed in a conventional manner with one or more functional groups in the compound, such as an amino, hydroxyl or carboxyl group. For example, if a compound of Formula I contains a carboxylic acid functional group, a prodrug can comprise: (1) an ester formed by the replacement of a hydrogen of the acid group with a group such as $(C_1-C_6)$alkyl or $(C_6-C_{10})$ aryl; (2) an activated ester formed by the replacement of the hydrogen of the acid group with groups such as —$(CR_2)$COOR', where $CR_2$ is a spacer and R can be groups such as H or methyl and R' can be groups such as $(C_1-C_6)$alkyl or $(C_6-C_{10})$ aryl; and/or (3) a carbonate formed by the replacement of the hydrogen of the acid with groups such as CHROCOOR' where R can be groups such as H or methyl and R' can be groups such as $(C_1-C_6)$alkyl or $(C_6-C_{10})$aryl. Similarly, if a compound of Formula I contains an alcohol functional group, a prodrug can be formed via the replacement of the hydrogen of the alcohol with groups such as $(C_1-C_6)$alkanoyloxymethyl or $(C_1-C_6)$ alkanoyloxyaryl or by forming an ester via condensation with, for example, an amino acid. Where a compound of Formula I contains a primary or secondary amino group, a prodrug may comprise, for example, an amide formed by the replacement of one or both of the hydrogens of the amino group with $(C_1-C_{10})$alkanoyl or $(C_6-C_{10})$aroyl. Other prodrugs of amines are well known to those skilled in the art. Alternatively, certain compounds of Formula I may themselves act as prodrugs of other compounds of Formula I.

Discussions regarding prodrugs and their the use can be found in, for example, "Prodrugs as Novel Delivery Systems," T. Higuchi and W. Stella, Vol. 14 of the ACS Symposium Series, and *Bioreversible Carriers in Drug Design*, Pergamon Press, 1987 (ed. E B Roche, American Pharmaceutical Association). Further examples of replacement groups may be found in the aforementioned references.

This application also relates to all isotopically-labeled compounds of Formula I. As used herein, the term "isotopically-labeled compound" refers to a compound that has been prepared such that at least one atom has been replaced by an atom having the same atomic number, but a different atomic mass or mass number.

Examples of isotopes that may be incorporated into compounds of Formula I include isotopes of: hydrogen, such as $^{2}H$ and $^{3}H$; carbon, such as $^{11}C$, $^{13}C$, and $^{14}C$; chlorine, such as fluorine, such as $^{18}F$; iodine, such as $^{123}I$ and $^{125}I$; nitrogen, such as $^{13}N$ and $^{15}N$; oxygen, such as $^{15}O$, $^{17}O$ and $^{18}O$; phosphorus, such as $^{32}P$; and sulphur, such as $^{35}S$. It should be understood that a compound of Formula (I) may include isotopes of more than one element. For example, a compound of Formula (I) may include isotopes of both hydrogen and carbon.

Certain isotopically-labeled compounds of Formula I such as, for example, those incorporating a radioactive isotope, may be useful in drug and/or substrate tissue distribution or diagnostic studies. In particular, radioactive isotopes such as tritium, i.e. $^{3}H$, and carbon-14, i.e. $^{14}C$, are particularly useful for these purposes in view of their ease of incorporation and ready means of detection.

Other isotopically-labeled compounds of Formula I such as, for example, those incorporating deuterium, i.e. $^{2}H$, may have certain therapeutic advantages over unlabeled compounds of Formula (I). Under certain circumstances deuterium labeled compounds can exhibit greater metabolic stability, increased in vivo half-life and/or reduced dosage requirements as compared to the unlabeled version of the compound.

Incorporation of other isotopes, such as $^{11}C$, $^{18}F$, $^{15}O$ and $^{13}N$, can be useful in Positron Emission Topography (PET) studies for examining substrate receptor occupancy.

One of ordinary skill in the art will readily appreciate additional advantages and applications of isotopically-labeled compounds of Formula I as being within the scope of the present disclosure.

Isotopically-labeled compounds of Formula I can generally be prepared by conventional techniques known to those skilled in the art or by processes analogous to those described in the accompanying Examples and Preparations using an appropriate isotopically-labeled reagents in place of the non-labeled reagent previously employed.

Preparations and Examples

In general, compounds of Formula I may be prepared by the methods described in the Preparations, Schemes, and Experimental sections of the present application and/or by additional or alternative processes and procedures known in the chemical arts in combination with the knowledge of the skilled practitioner. It should be understood that the methods set forth in the following descriptions, reaction Schemes, Preparations and Experimental sections are intended for illustrative purposes and are not to be construed as limiting the scope of the disclosure.

Alternative reagents, intermediates, starting materials, synthetic routes and methods can be used or adapted in practice, particularly in light of the scope of the present disclosure in combination with the knowledge of one of ordinary skill in the art. Such alternatives and modifications should be understood as being within the spirit and scope of the present application and the claims.

Unless otherwise indicated, it should be understood that variables appearing in or referred to in the Schemes, and/or Preparations are defined as above or as defined in the Claims. In the reaction schemes below, it should be understood that for compounds where "- - - - - -" is a bond, $R^5$ and $R^6$ are absent.

Although specific embodiments and/or individual compounds will be described with reference to particular Schemes, Preparations, and/or Examples, it should be understood that these embodiments and/or compounds are illustrative of a small number (i.e. a subset) of the more general descriptions, genera, subgenera, formulae, species, embodiments and compounds that fall within the scope and spirit of the present application. Accordingly, these specific embodiments and/or compounds should not be interpreted as limiting the scope of the disclosure in any way.

General Synthesis

Schemes I and II depict generalized routes that may be used to prepare the compounds described herein. Methods A through J illustrate more particular aspects of the generalized routes. Preparations A through D describe particular reaction sequences that may be used to make various intermediates. The Examples provide additional detail regarding the synthesis of a number of intermediates and compounds of Formula I.

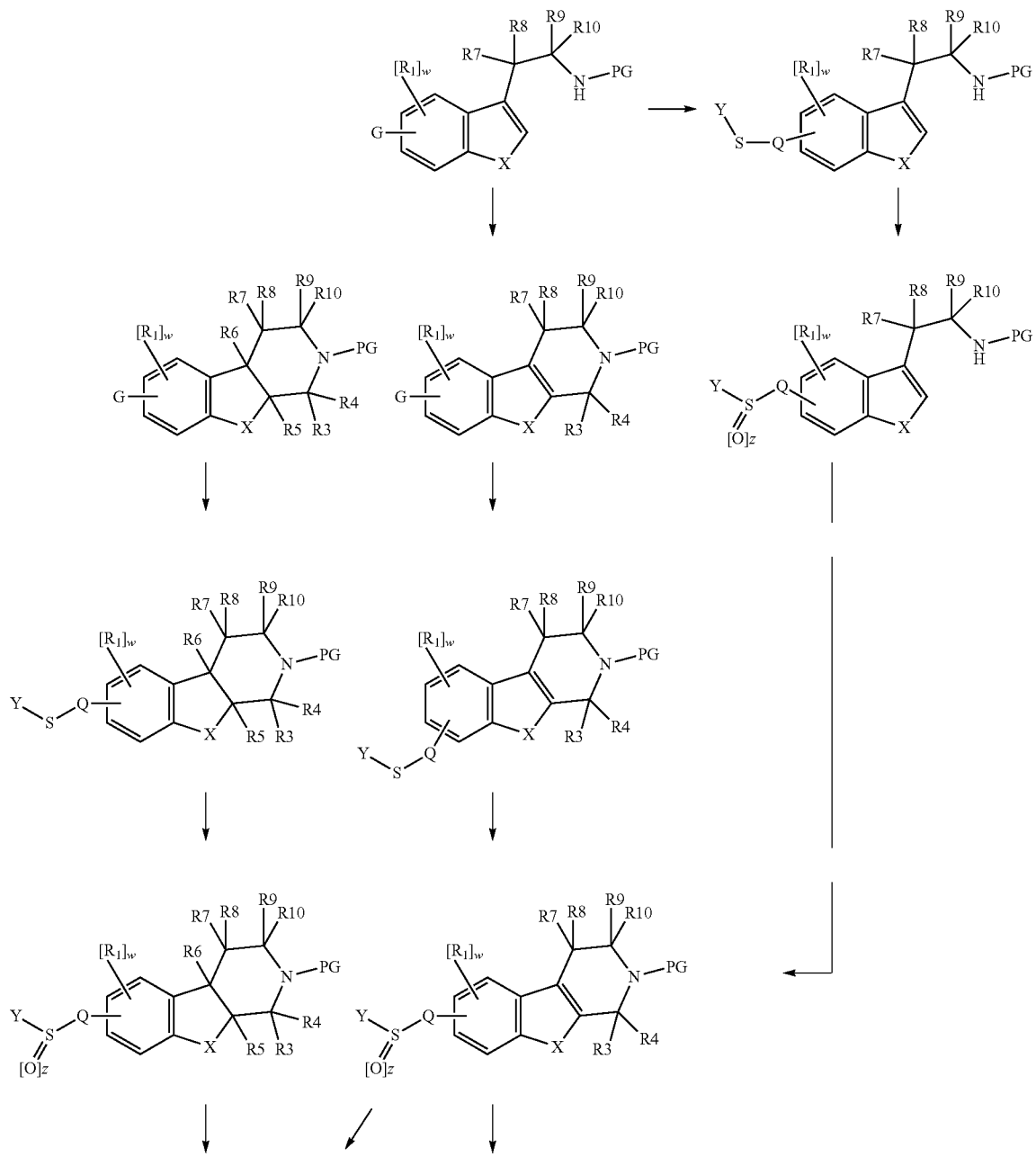

Scheme I

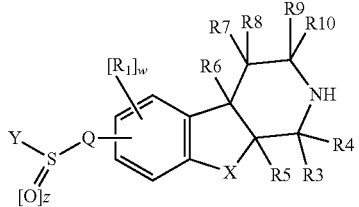
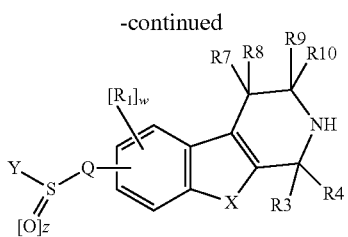
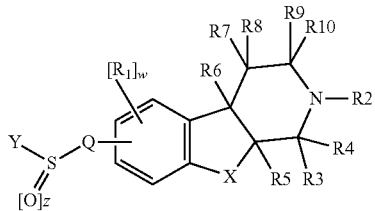
Scheme II
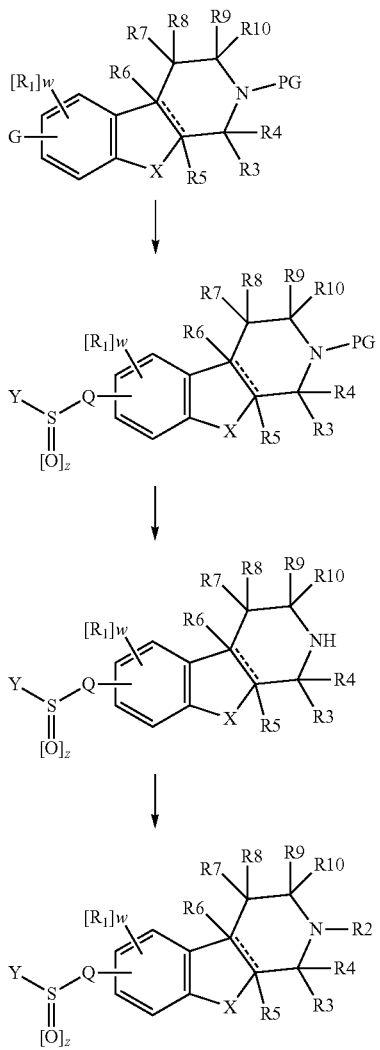
Method A
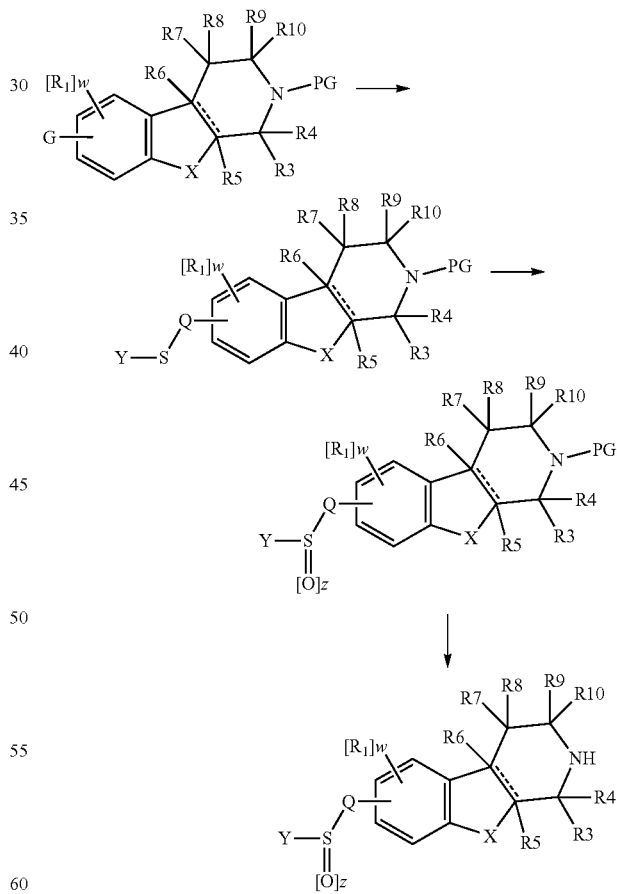
As shown in Method A, various compounds of Formula I may be prepared via an Ullmann type coupling reaction. For compounds where PG denotes a protecting group, and G represents a halogen such as iodine, the coupling reaction between the tricyclic halide and a desired thiol, such as Y—SH, may be carried out using a variety of conditions known in the art. Typically, the reaction is conducted using a catalytic amount of CuI (copper iodide), in the presence of neocuproine (2,9-dimethyl-1,10-phenanthroline) or ethylene glycol, and a base, such as sodium tert-butoxide (NaOtBu), in an appropriate solvent, such as N,N-dimethylformamide (DMF) or toluene, at elevated temperatures, such as between about 70-100° C. Other compounds of Formula I may be accessed by coupling the tricyclic halide with an appropriately functionalized trialkylsilyl thioether, such as for example, Y—S-TIPS where TIPS is a triisopropylsilyl group, using CuI in the presence of neocuproine or ethylene glycol and cesium fluoride (CsF) in an appropriate solvent at elevated temperatures. Alternatively, the tricyclic compound can contain the trialkylsilyl thioether, i.e., G is a trialkylsilyl thioether such as S-TIPS, and may be coupled with the desired Y moiety, where Y is functionalized with a suitable leaving group such as a halogen or triflate.

The resulting tricyclic thioether may be oxidized using a reagent such as meta-chloroperoxybenzoic acid (mCPBA) or Oxone® (potassium peroxymonosulfate) in an appropriate solvent, such as methylene chloride (DCM) or tetrahydrofuran (THF). The protecting group (PG) is subsequently removed using procedures well known in the art. For example, where PG is a t-butyl ester (Boc), PG may be cleaved under acidic conditions such as trifluoroacetic acid (TFA) or hydrochloric acid (HCl) in an appropriate solvent, such as DCM or dioxane, or mixture of solvents.

Method B

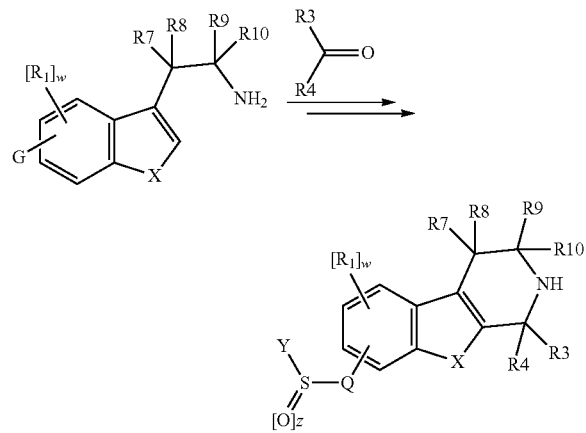

As shown in Method B, various compounds of Formula I may be prepared via a Pictet-Spengler-type reaction with the appropriately substituted protected or unprotected ketone or aldehyde, followed by the introduction and subsequent oxidation of the thioether. For bicyclic amines where G is a halide such as iodine, condensation and cyclization to the corresponding tricyclic compound is affected via treatment with a strong acid, such as for example TFA, at an appropriate temperature, such as between about 60 to 90° C. In practice, the acid may be used as the solvent for the reaction or may be mixed with an appropriate co-solvent such as, for example, dichloroethane (DCE). For compounds where Q is absent, introduction and subsequent oxidation of the thioether may be accomplished using methods analogous to those described above.

Method C

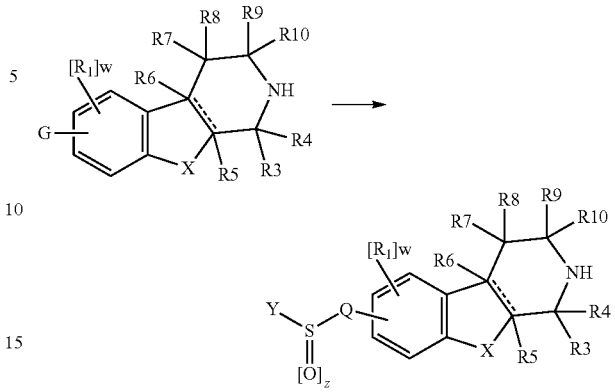

As shown in Method C, various compounds of Formula I may be prepared by directly coupling a desired sulfone moiety, i.e. where z=2, with a tricyclic halide. Typically, for tricyclic compounds where G represents iodine, the reaction proceeds by stirring together CuI and N,N-dimethyl-1,2-ethanediamine in dimethylsulfoxide (DMSO) for a suitable period of time before the addition of an organic base such as N,N-diisopropylethylamine (DIEA) and the desired sulfinate moiety, such as sodium benzenesulfinate. The reaction is usually conducted at elevated temperatures, such as about 100° C.

Alternatively, to arrive at compounds of Formula I where Q is —NR$^{13}$—, the tricyclic halide, where G is iodine, may be converted to the corresponding alkyl amine. Typically, a tricyclic halide, an alkyl amine, such for example, methylamine, may be stirred together in the presence of a base such as sodium tert butoxide (NaOtBu), neocuproine, and CuI in a suitable solvent such as DMF at elevated temperatures. For compounds where G is hydrogen, nitration followed by reduction provides the corresponding tricyclic amino compound.

Although not shown above, in practice, a protecting group (PG) for the piperidine nitrogen is generally necessary. Treatment of the resulting tricyclic amine or alkyl amine with a desired sulfonyl halide, such as for example, 6-chloro-imidazo[2,1-b]thiazole-5-sulfonyl chloride, in the presence of an organic base such as DIEA affords the corresponding sulfonamide. If present, protecting group PG may be removed using standard procedures well known in the art or as described herein.

Method D

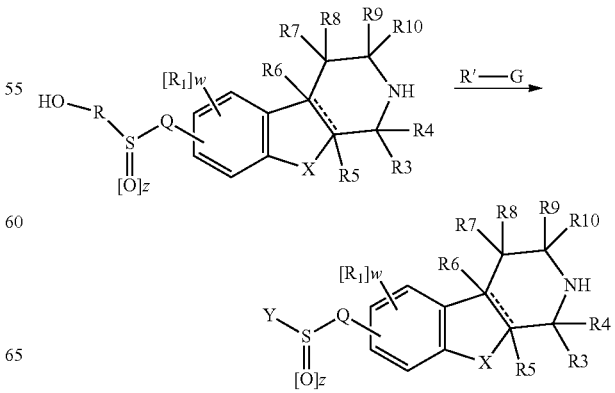

As shown in Method D, the moiety Y may be elaborated in a step-wise fashion after installation of the sulfinyl/sulfonyl group. For example, where a tricyclic compound contains a hydroxyl group, denoted above as R—OH, treatment with the appropriate alkyl halide, denoted above as R'-G, affords the corresponding Y moiety. Typically, the O-alkylation reaction proceeds in the presence of a suitable base, such as cesium carbonate ($Cs_2CO_3$) in an appropriate solvent, such as acetonitrile (ACN). In practice, the reaction may be conducted at elevated temperatures, such as about 60° C.

Alternatively, for tricyclic compounds where G is a halide, introduction of a Y moiety containing a primary or secondary amine, may be affected via a displacement reaction as shown below.

of a suitable base, such as DIEA, in an appropriate solvent such as DMF affords the corresponding N-alkylated product. Typically, the reaction is conducted at elevated temperatures, such as about 60° C., for a suitable period of time.

Alternatively, for $R^2$ moieties in which X is a carbonyl, such as for example, cyclobutanone or benzaldehyde, or a protected carbonyl, various compounds of Formula I may be prepared via reductive amination. Typically, where Q is a bond or —O—, the reaction proceeds in the presence of acid, such as acetic acid, followed by the addition of a hydride reducing agent such as, for example, sodium triacetoxyborohydride ($NaBH(OAc)_3$) or sodium cyanoborohydride (NaC-

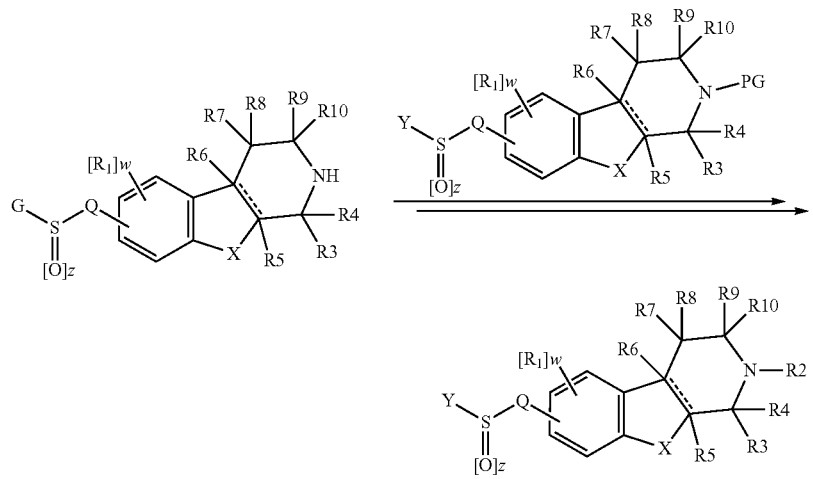

The displacement reaction generally proceeds in the presence of an organic base, such as DIEA, in a suitable solvent, such as DCM or DMF. The protecting group PG may be removed using standard conditions well known in the art or as described herein. Subsequent introduction of the desired $R^2$ moiety to the piperidine ring may be affected using the methods described herein as well as other methods known in the art.

Method E

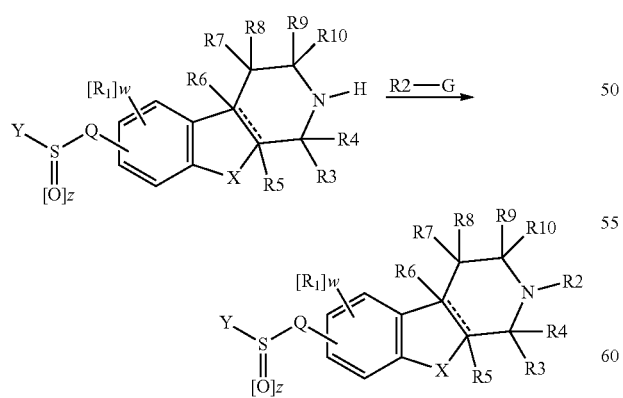

As shown in Method E, various compounds of Formula I may be prepared by N-alkylation of the piperidine ring using conditions well known in the art. For example, treatment with $R^2$—X, where X is a halide, such as bromine, in the presence $NBH_3$), to provide the corresponding N-alkylated compound of Formula I. Suitable solvents include THF, DCM, or dichloroethane (DCE).

Method F

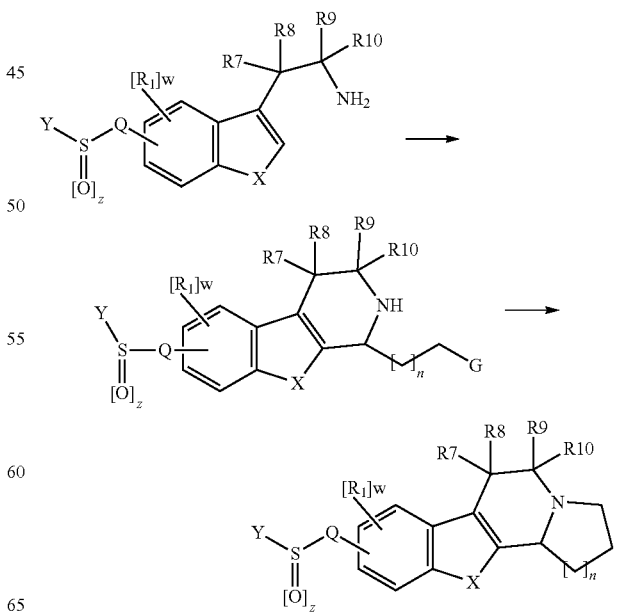

As shown in Method F, various compounds of Formula I may be prepared via a Pictet-Spengler-type reaction with the appropriate halo-acetal, such as, for example, 2-(4-bromobutyl)-[1,3]dioxolane, followed by a second cyclization to form the corresponding tetracyclic compound. Typically, the condensation and subsequent ring closure reaction proceeds in the presence of a strong acid, such as TFA, in a suitable solvent such as dichloroethane (DCE), at elevated temperatures. To affect the second cyclization reaction, the resulting tricyclic halide, where G represents a halide such as, for example, bromine, is treated with a base such as DIEA in an appropriate solvent, such as DMF. In practice this reaction may be conducted at elevated temperatures, such as about 50° C.

Method G

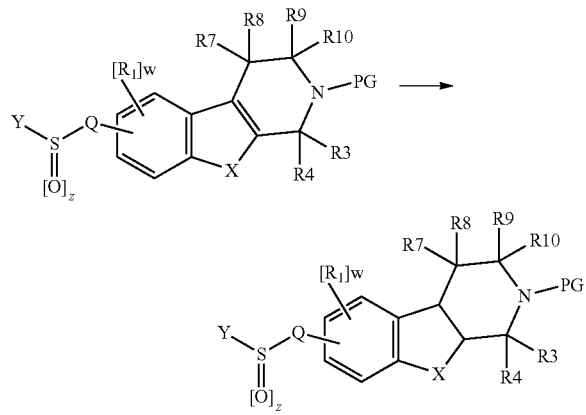

As shown in Method G, various compounds of Formula I can be prepared via hydrogenation using methods well known in the art. For example, for compounds where Q is absent and PG denotes a protecting group such as BOC, treatment with H$_2$ gas in the presence of palladium on carbon (Pd—C) in an appropriate solvent such as methanol (MeOH) or ethanol (EtOH) provides the corresponding saturated compound. The protecting group PG may then be removed using standard methods well-known in the art or as described herein.

Method H

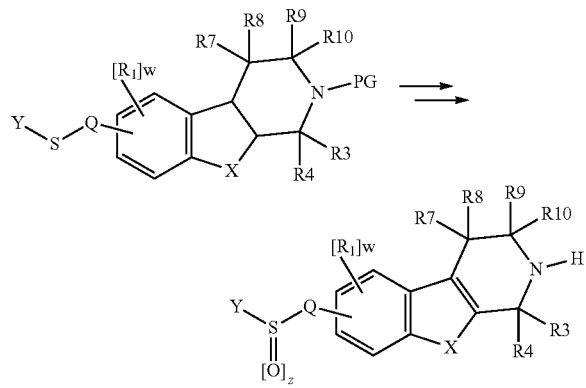

As shown in Method H, various sulfinyl compounds of Formula I, i.e., where z=1, may be prepared via oxidation with benzenesulfonyl-3-phenyl oxaziridine (Davis reagent). Typically, for compounds where Q is absent and PG denotes a protecting group, the oxidation reaction proceeds in an appropriate solvent, such as for example DCM or tetrahydrofuran (THF) at ambient temperature. Removal of the protecting group is affected using standard procedures well known in the art or as described herein.

Method J

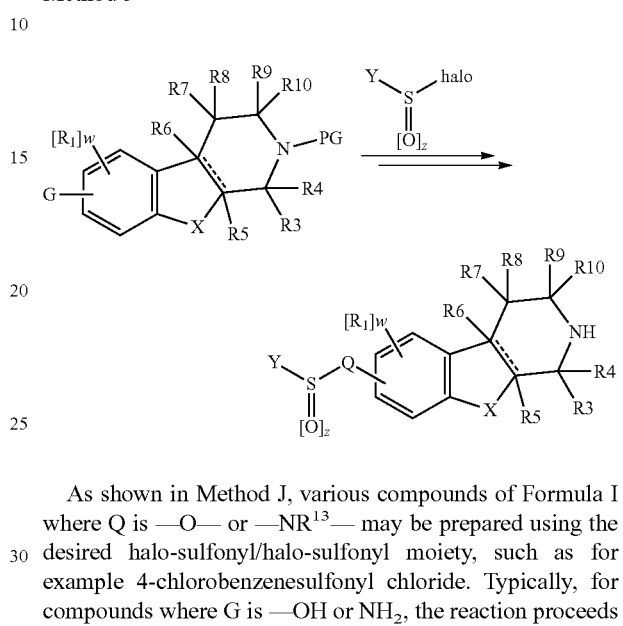

As shown in Method J, various compounds of Formula I where Q is —O— or —NR$^{13}$— may be prepared using the desired halo-sulfonyl/halo-sulfonyl moiety, such as for example 4-chlorobenzenesulfonyl chloride. Typically, for compounds where G is —OH or NH$_2$, the reaction proceeds in the presence of an organic base such as DIEA in a suitable solvent such as for example, DCM or DCE, or mixtures of solvents. Removal of the protecting group, PG, may be affected using standard procedures well known in the art as well as the methods described herein.

Preparations

Various intermediates useful in the preparation of compounds of Formula I may be synthesized using the general methods provided below.

Preparation A

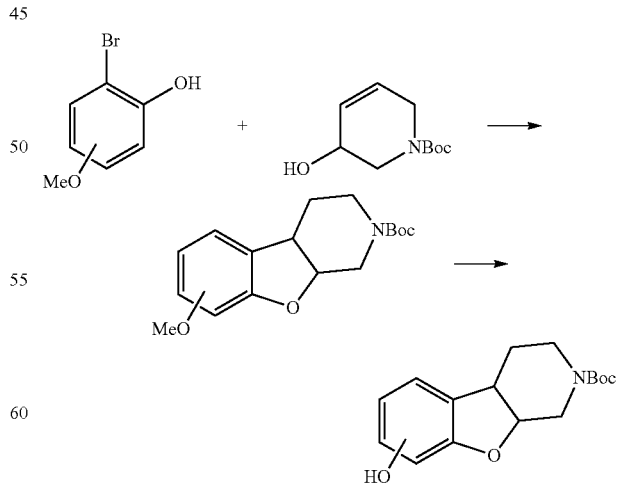

Various intermediates useful in the preparation of compounds of Formula I may be synthesized according to the sequence shown above or by methods known in the art. As shown in Method A, halophenols and N-protected piperidinols may be coupled in the presence of DEAD (diethyl azodicarboxylate) and triphenyl phosphine (P(Ph)$_3$) in a suitable solvent such as for example THF or mixture of solvents. In practice the reaction may be conducted at ambient temperature or below.

The resulting haloethers may then be cyclized using tributyltin hydride (Bu$_3$SnH) and AIBN (2,2'-azobis(isobutyronitrile)) in a suitable solvent, such as toluene. In practice the reaction is conducted at elevated temperatures.

Conversion of the resulting tricyclic adduct to the corresponding alcohol is affected using boron tribromide (BBr$_3$) in a suitable solvent, such as DCM. In practice the reaction may be conducted at or below ambient temperature.

Additional methods for accessing related intermediates are known in the art. See for example, *Tetrahedron Letters*, 2001, 42, 6499-6502.

Conversion of the tricyclic phenol to the corresponding halogen, such as for example where Hal represents iodine, can be affected using or modifying standard procedures known in the art. See for example, *Synthesis*, 2005, 4, 547-550. For example, the tricyclic phenol may be treated with triflic anhydride (Tf$_2$O) to provide the corresponding trifluoromethanesulfonate, which is subsequently converted to the pinacol boronate ester (not shown) using a palladium catalyst, such as, [1,1'-bis(diphenylphosphino)ferrocene]dichloropalladium (II), (PdCl$_2$(dppf)) and pinacol borane, in the presence of a base such as triethyl amine (TEA) and a suitable solvent such as dioxane. Typically, the reaction is conducted at elevated temperatures. Treatment of the resulting tricyclic boronate ester with chloramine-T (N-chloro tosylamide sodium salt) and sodium iodide (NaI) in a mixture of water and THF afforded the corresponding iodotricyclic compound.

Preparation C

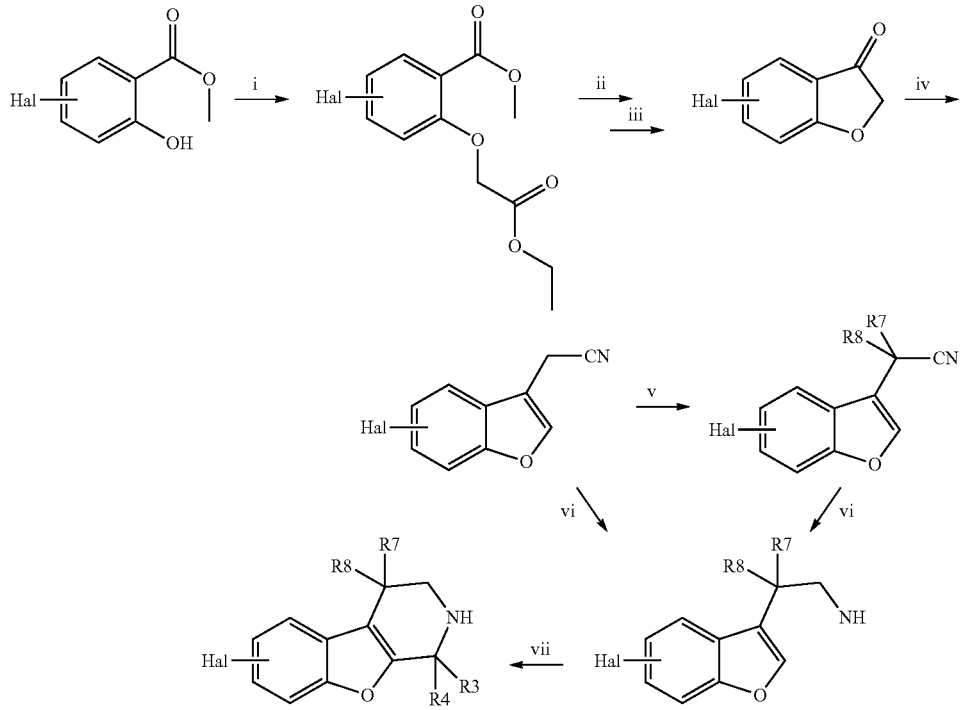

i. Ethyl bromoacetate, K$_2$CO$_3$, KI, acetone. ii. LHMDS, toluene. iii. NaOH, H$_2$O then HCl. iv. NaH, THF, diethylcyanomethylphosphonate. v. LHMDS, R7R8—Hal, THF. vi. BH$_3$, THF. vii. R3R4—C═O, H$^+$.

Preparation B

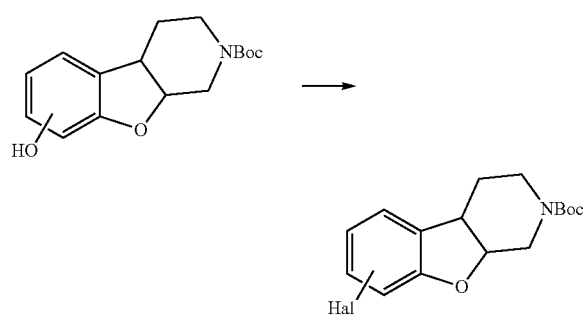

Additional intermediates useful in the preparation of compounds of Formula I may be accessed by the route shown above. Various halo-benzofuran-2-ones may be prepared from an appropriately substituted halophenol, where Hal represents a halogen such as bromine or iodine, which when treated with ethyl bromoacetate in the presence of a base, such as potassium carbonate (K$_2$CO$_3$) and potassium iodide (KI) in a suitable solvent, such as acetone provides the corresponding halobenzoate. In practice, the reaction may be conducted at elevated temperatures, such as about 50° C. Cyclization of the halobenzoate using LHMDS (lithium bis(trimethylsilyl)amide) in THF at low temperature, and treating the resulting halobenzofuran (not shown) with a strong base, such as sodium hydroxide (NaOH) in a mixture of ethanol and water provides the corresponding halo-benzofuran-2-one. In practice, this reaction is conducted at elevated temperatures, such as about 80° C.

Treatment of the halo-benzofuran-2-one with an appropriate base such as sodium hydride and an appropriately substituted cyanophosphonate, such as for example diethylcyanomethylphosphonate, in a suitable solvent such as THF affords the corresponding halobenzofuran nitrile. After treatment with a strong base such as LHMDS in an appropriate solvent such as THF, the halobenzonitrile can be alkylated using the appropriate alkyl bromide or alkyl iodide. Conversion to the amine may then be affected using an appropriate reducing agent, such as for example diborane, in a suitable solvent, such as THF, at low temperature. Completion of the halotricyclic scaffold may be affected via a Pictet-Spengler cyclization reaction with the appropriate aldehyde or ketone, in the presence of an acid such as acetic acid, hydrochloric acid (HCl) or TFA, optionally in the presence of an organic co-solvent such as toluene or DCM. Compounds represented above as $R^3R^4CO$ are commercially available or may be prepared according to standard methods known in the art.

Still other intermediate compounds may be accessed using or adapting the procedures described in U.S. Pat. No. 5,854,245.

While not expressly included in the reaction scheme, substituted indole compounds, analogous to the substituted benzofurans shown directly above, may be used to prepare tricyclic intermediates using similar methods. Appropriately substituted indole derivatives are commercially available or can be prepared according to or adapted from methods known in the art. See for example, *J. Med. Chem.*, 2005, 48, 1781-1795; *Synth. Comm.*, 1993, 23, 65-72.

Preparation D also be prepared from the tricyclic lactam shown above. Specifically, introduction of $R^5$ may be affected by treating the tricyclic lactam with an appropriate base, such as sodium hydride (NaH), and the desired alkyl halide, such as for example, chloromethyl cyclopropane, in an appropriate solvent, such as THF. The resulting alkylated product may be reduced to the corresponding benzofuropiperidine using LAH as described above.

Various tricyclic intermediates, especially where A is $—(CR^9R^{10})_n—$ and n is 2 or 3 may be prepared using methods known in art such as those described in WO 03/099821.

Other useful intermediates and derivatives not specifically described herein generally may be prepared from appropriately substituted materials using transformations and/or reaction sequences known in the art in combination with the knowledge of one of skill in the art. Such procedures and methods are described in reference books such as, for example, *Compendium of Organic Synthetic Methods*, Vols. I-VI (Wiley-Interscience) and elsewhere in the chemical literature.

One of skill in the art will appreciate that in some cases protecting groups may be required during a multi-step or single-step reaction sequence. In practice, a protecting group is used to mask or block a particular site/functional group in preparation for a chemical transformation at a different site/functional group in a molecule. After a particular target or transformation is complete or at some specific step later in a synthetic route, the protecting group can be removed using methods well know to those of ordinary skill in the art. The introduction, use and removal of protecting groups is thor-

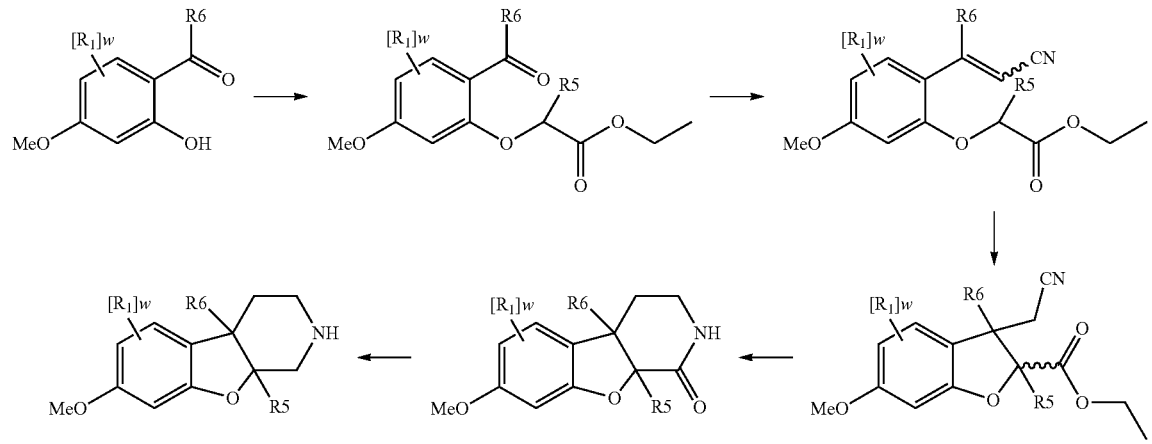

50

Still further useful intermediates may be prepared using the route shown above. Various substituted cyano-benzofuran esters may be prepared from the corresponding phenol using methods and reaction conditions similar to those described in Preparation C. Hydrogenating the cyano-benzofuran ester under about 55 psi of $H_2$ in the presence of platinum oxide ($PtO_2$) in acetic acid (AcOH) provides the tricyclic lactam, which is subsequently reduced using lithium aluminium hydride (LAH). Further elaboration of the resulting benzofuropiperidine, i.e. conversion to the corresponding halogenated tricyclic intermediate, may be affecting using the methods described above or procedures known in the art.

Other useful intermediates may be prepared using or adapting the methods described herein or those known in the art. For example, as described in *J. Med. Chem.* 1989, 32, 2221-2226, various intermediates where $R^5$ is not hydrogen may oughly described in *Protective Groups in Organic Synthesis*, (3$^{rd}$ Ed., John Wiley & Sons, 1999).

Compositions

The compounds of Formula I and the pharmaceutically acceptable salts of such compounds may be administered as crystalline or amorphous materials, and may be administered alone or in combination with one or more of the other compounds described herein. In addition, compounds of Formula I and the pharmaceutically acceptable salts of such compounds may be administered in combination with one or more other therapeutically active agents. Generally, the compound(s) will be administered as a formulation, i.e. pharmaceutical composition, in association with one or more pharmaceutically acceptable excipients. The term "excipient" as used herein refers to any ingredient in the formulation other than the compound(s) of Formula I and any additional therapeutically active agent(s) as described above that may be present. Accordingly, excipient refers to and includes ingredients such as, for example: carriers, vehicles, solvents, adjuvants, lubricants, surfactants, binders, buffers, diluents, flavorings, coloring agents/dyes, disintegrants, emulsifying agents, suspending agents, plasticizers, solubilizers, fillers, bulking agents, and the like. The choice of excipient(s) will largely depend on factors such as: the particular mode of administration, the effect of the excipient(s) on solubility, stability, and release profile, and the nature of the dosage form. One skilled in the art will readily appreciate that this list of factors is not exhaustive. The compound(s) of the general Formula I and any additional therapeutically active agents (if present) may be generally referred to as the active ingredient(s) in a formulation or pharmaceutical composition.

Pharmaceutical compositions suitable for the delivery of compounds of Formula I and methods for their preparation will be readily apparent to those skilled in the art. Such compositions and methods for their preparation may be found, for example, in *Remington's Pharmaceutical Sciences*, 19th Edition (Mack Publishing Company, 1995).

The pharmaceutical composition may, for example, be in a form suitable for oral administration as a tablet, capsule (hard or soft filled), pill, powder, sustained or immediate release formulations, solution, suspension; for parenteral injection as a sterile solution, suspension or emulsion; or for topical administration as an ointment or cream. Additional dosage forms not specifically mentioned herein would be readily appreciated by one of ordinary skill in the art as being within the scope of the present application.

The relative amounts of the active ingredient(s) and the excipient(s) in a formulation or pharmaceutical composition will vary, depending upon the identity, size, and condition of the subject treated and further depending upon the route by which the composition is to be administered. By way of example, the composition may comprise between 0.1% and 100% (w/w) of active ingredient.

A pharmaceutical composition comprising one or more compounds of Formula I may be prepared, packaged, distributed, or sold in bulk, as a single unit dose, or as a plurality of single unit doses. As used herein, a "unit dose" is a discrete amount of a pharmaceutical composition comprising a predetermined amount of the active ingredient(s). The amount of the active ingredient(s) is generally equal to the dosage of the active ingredient(s) which would be administered to a subject or a convenient fraction of such a dosage such as, for example, one-half or one-third of such a dosage.

Dosing

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate pharmaceutical compositions in a unit dosage form for ease of administration and uniformity of treatment/therapeutic effect. As used herein, "unit dosage form" or "unit dose", by themselves or in combination with another term or terms, refer to the physically discreet amount(s) of medication, i.e. the active ingredient(s) in a pharmaceutical formulation, suitable for a one-time administration to the patient or subject to be treated; each unit dose containing a predetermined quantity of active compound(s) calculated to produce the desired therapeutic effect in association with the required pharmaceutical carrier. The more specific composition of the unit dosage forms comprising compounds of Formula I is dictated by and directly dependent on a number of variables, such as, for example: (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount for providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the skilled artisan. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

Utility

This application relates to new compounds with affinity for the 5-$HT_6$ receptor, i.e., 5-$HT_6$ ligands, which may be useful as active ingredients in pharmaceutical preparations for the treatment of certain conditions, disorders or diseases related to the central nervous system (CNS) such as memory disorders, anxiety, epilepsy, migraine, panic attacks, depression, bipolar disorder, obsessive compulsive disorders, cognition/cognitive disorders, mild cognitive impairment (MCI), senile dementia, psychosis, schizophrenia, ADHD/ADD; or for the treatment of neuropathic pain and chronic pain; head trauma or injury; or for the treatment of neurodegenerative conditions, disorders or diseases such as Alzheimer's disease, Parkinson's disease, Huntington's disease, amyotrophic lateral sclerosis (ALS) or multiple sclerosis; or for the treatment of conditions, disorders or diseases related to addiction or withdrawal from substances such as narcotics, ethanol, nicotine, and/or benzodiazepines; sleep/wakefulness disorders; or for the treatment of gastrointestinal (GI) conditions, disorders or diseases such as irritable bowel syndrome (IBS), functional bowel disorder; or for the treatment of conditions, disorders or diseases related to feeding behaviors or food intake such as anorexia, cachexia, and obesity.

These compounds may also be useful for the improvement of cognition (cognitive enhancement) and/or improvement of memory in otherwise healthy subjects.

Due to its unique localization in the central nervous system the 5-$HT_6$ receptor is an attractive target for the development of potential treatments for a variety of CNS-related conditions, disorders or diseases. A thorough overview of the distribution and characteristics of the 5-$HT_6$ receptor can be found in *Current Drug Targets—CNS & Neurological Disorders*, 2004, 3, 59-79.

There is a growing body of evidence that suggests that compounds with $5\text{-}HT_6$ receptor affinity, in particular $5\text{-}HT_6$ receptor antagonists, have potential therapeutic applications in the treatment of cognitive diseases, mild cognitive impairment (MCI), neurodegenerative diseases, schizophrenia, anxiety, and depression. See, for example, *Curr Top Med Chem*, 2008, 8, 1035-48 ($5\text{-}HT_6$ receptor antagonists and Alzheimer's disease); *Curr Opin Drug Discov Devel*, 2008, 11, 642-54 ($5\text{-}HT_6$ receptor antagonists and cognitive disorders); *Neuropsychobiology* 2001, 43, 113-116 (serotonin-6 receptor polymorphism and schizophrenia); *Am. J. Med. Genet.*, 2000, 96, 217-221 ($5\text{-}HT_6$ receptor gene in bipolar affective disorder); *Neuropharmacology*, 2007, 52, 1274-83 ($5\text{-}HT_6$ antagonist SB-399885 and animal models of anxiety and depression). *Pharmacology, Biochemistry, and Behavior*, 2005, 81, 673-82 ($5\text{-}HT_6$ receptor antagonists SB-357134 and SB-399885 and improvement in memory formation); *Pharmacol. Ther.* 2005, 108, 320-333 ($5\text{-}HT_6$ receptors and cognitive enhancement); *Neurotherapeutics*, 2008, 5, 458-469 ($5\text{-}HT_6$ receptor antagonists as cognitive enhancing agents for Alzheimer's disease); *Expert Opin. Invest. Drugs*, 2002, 11, 457-467 (serotonin antagonists and depressive disorders).

Serotonin is also known to influence sleep, wakefulness and circadian rhythms, however the specific 5-HT receptor subtypes involved and their respective roles is still under investigation. $5\text{-}HT_6$ receptors are associated with the hypothalamus, thalamus, and striatum in the brain. These regions are known to be important in the regulation of sleep and wakefulness and recent data in rats appears to confirm that $5\text{-}HT_6$ receptors may be involved in sleep-wake regulation. *Sleep*, 2008, 31, 34-44. In this study, rats treated with RO 4368554, a $5\text{-}HT_6$ receptor antagonist, experienced an increase in non-REM (non-rapid eye movement or NREM) sleep compared to an untreated control group. This observation indicates a possible connection between the $5\text{-}HT_6$ receptor and sleep quality and/or sleep consolidation (i.e., the ability to maintain sleep continuously with minimal interruption), which in turn suggests a potential use of $5\text{-}HT_6$ receptor antagonists in the treatment of sleep maintenance insomnia, i.e., the inability to maintain sleep throughout the night.

Association of the $5\text{-}HT_6$ receptor and/or its mRNA in other areas of the brain, such as the cortex, amygdala, thalamus, periaqueductal grey, spinal cord and dorsal root ganglia implies a potential involvement of the $5\text{-}HT_6$ receptor in pain and the modulation of nociceptive behaviour. The functional role of the $5\text{-}HT_6$ receptor in nociception has been recently demonstrated in rats. See *European J. Pharmacol.*, 2007, 569, 59-63. In this study, SB-271046, a $5\text{-}HT_6$ antagonist, appeared to have a short-lived, antinociceptive effect in a rat model of tonic, persistent pain. The data suggests that $5\text{-}HT_6$ receptors can modulate the neural substrates involved in nociceptive processing.

The $5\text{-}HT_6$ receptor has also generated a great deal of interest in connection with the treatment of food-intake or feeding related conditions or disorders. For example, chronic administration of $5\text{-}HT_6$ receptor antisense oligionucleotides was found to significantly reduce food intake and body mass in rats. *J. Psychopharmacol.* 1997, 11, A64. Other in vivo studies also indicate that $5\text{-}HT_6$ antagonists influence feeding behaviour and body weight. See, e.g., *Br. J. Pharmacol.*, 1999, 126, 1537-1542; *Int. J. Obes.*, 2003, 27, Suppl. 1. Abst T1, 1-094; 34th *Annu. Meet. Soc. Neurosci. Abstract* 75.8. The results of these rat studies suggest that $5\text{-}HT_6$ antagonists may reduce food intake by enhancing satiety. See *Drug Disc Today*, 2006, 11, 283-299; *Pharmacology & Therapeutics* 2008, 117, 207-231.

A small clinical trial in man also appears to suggest that $5\text{-}HT_6$ may have some influence in food intake or appetite. See, "Treatment of cancer-related anorexia with olanzapine and megestrol acetate: a randomized trial" in *Support Care Cancer*, published online, Sep. 11, 2009. In this study, olanzapine (OLN), a potent antagonist of the $5\text{-}HT_6$ receptor, was administered in combination w/megestrol acetate (MA) to patients with cancer-related anorexia (CRA). A second group of patients received only MA. Megestrol acetate is known to be at least partially effective as an appetitie stimulant in cancer patients. However, the group of patients treated with the combination showed significant improvements in appetite, nausea, body weight, and quality of life (improvements in general activity, mood, work, walking, and enjoyment). Whether the $5\text{-}HT_6$ receptor was a factor in the improvements reported in patients receiving the combination of OLN and MA is unclear, however, the authors hypothesize that the improvement in appetite in the combination treatment group could have been due to the improvement in mood. Other studies have shown that OLN as a single agent improves or reduces nausea in patients with advanced pain and cancer. See *J. Pain Symptom Manage.*, 2002, 23, 526-532; *J. Palliative Care*, 2003, 6, 251-255; *J. Pain Symptom Manage.*, 2003, 25, 587-582.

Another therapeutic use for $5\text{-}HT_6$ antagonists may be for the treatment of addiction, such as for example substance and/or alcohol addiction (alcoholism), and in treating withdrawal from drug abuse in particular narcotics, alcohol (alcoholism), nicotine, and benzodiazepines. Novelty-seeking behavior in humans has long been associated with alcoholism and sustance abuse. *Psychiatry Res*, 1979, 1, 255-264. Traditionally, novelty-seeking behavior has been linked to dopamine-mediated neurotransmission. However, there is evidence that behavioral responses to novelty may also be mediated by 5-HT. A reliable animal model of human novelty-seeking behavior that is highly predictive of drug use has been developed. This model and has recently been used to gain insight into the potential contribution of $5\text{-}HT_6$ and 5-HT, receptors to novelty-seeking behavior and associated behaviors such as substance abuse. See *Neuropsychobiology* 1996, 34, 136-145; *Exp. Clin. Psychopharmacol* 2005, 13, 367-375.

The compounds described herein were tested for their ability to bind to the $5\text{-}HT_6$ receptor. The ability of the compounds of the formula I to bind to the $5\text{-}HT_6$ receptor may be measured using the assay and general procedures described below or by methods known in the art. The compounds of Formula I were generally found to be $5\text{-}HT_6$ ligands, more specifically, the compounds of Formula I were generally found to be $5\text{-}HT_6$ receptor antagonists.

In some embodiments, compounds of Formula I have an inhibition constant $K_i$ of the $5\text{-}HT_6$ receptor of less than (<) 500 nM.

In other embodiments, compounds of Formula I have an inhibition constant $K_i$ to the $5\text{-}HT_6$ receptor greater than (>) 500 nM but less than (<) 1000 nM.

In still other embodiments, compounds of Formula I have an inhibition constant $K_i$ to the $5\text{-}HT_6$ receptor greater than (>) 1000 nM.

Human $5\text{-}HT_6$ Receptor Binding Assay
Membrane Preparation

Membranes were prepared from CHO—K1 cells stably transfected with the human $5\text{-}HT_6$ receptor (Euroscreen; ES-316-C). The cells were grown in Gibco Advanced DMEM-F12 (Cat#12634010) containing 2% dialyzed FBS (Hyclone Cat#SH30079.03). The cells were harvested in phosphate buffered saline (PBS) containing 0.1 mM EDTA and pelleted by centrifugation (1000×g), the supernatant was discarded and the pellets were stored at −80° C. prior to membrane preparation. Membranes were prepared as previously described (J Bio Chem. 1992, 267 (14) 9844-51). Briefly, frozen cell pellet was resuspended in a lysis buffer containing 5 mM Tris-HCl (pH 7.5), 5 mM EDTA and 1 complete EDTA-free protease inhibitor tablet (Roche Applied Science, Indianapolis, Ind.) per 50 mL buffer, and homogenized with a tissue homogenizer. The cell lysate was then centrifuged at 40,000×g for 30 min at 4° C. to collect the membranes. The membrane pellets were washed in membrane buffer (50 mM Tris-HCl (pH 7.5), 0.6 mM EDTA, 5 mM $MgCl_2$, 1 complete EDTA-free protease inhibitor tablet per 50 mL buffer) using a tissue homogenizer. The membranes were centrifuged at 40,000×g for 30 min at 4° C. and the pellets were resuspended in membrane buffer containing 250 mM sucrose, and protein concentration was determined using the Coomassie Plus kit (Pierce Biotechnology, Rockford, Ill.).

Receptor Binding Assays

Membranes prepared from cells expressing recombinant human 5-$HT_6$ receptor (h5-$HT_6$) were resuspended in assay buffer containing 50 mM Tris HCl, (pH7.4), 4 mM $CaCl_2$, 10 μg/mL saponin, and 0.1% (w/v) ascorbic acid. Membranes were preincubated using 1.75 μg membrane protein and 0.25 mg FlashBlue scintillation beads (PerkinElmer catalogue #FB001) per well at 4° for 30 min. Vehicle or test compound, and 4 nM [$^3$H]LSD (Perkin Elmer catalogue #NET638) were added and incubated for 3 hours at room temperature in a final volume of 80 μL in a 96-well plate. Test compounds or assay controls for total and non-specific binding were diluted in DMSO as 100× solutions and serially diluted by half log concentrations on a Perkin Elmer JANUS Automated Workstation. Serotonin (10 μM final concentration) was used to determine non-specific binding in the assay. Plates were read using the Microbeta Trilux 1450 LSC and luminescence counter. Data were analyzed by nonlinear repression using the dose-response equation (variable slope) to calculate $IC_{50}$ in XLfit4 (ID Business Solutions Inc.):

$$y = (Bottom + ((Top - Bottom)/(1 + ((IC_{50}/x)^{\wedge} Hill\ slope))))$$

Binding of [$^3$H]LSD to the h5-$HT_6$ membranes was saturable with $B_{max}$=6.2 μmol/mg protein and $K_d$=2.3 nM. $K_i$ value was then calculated according to the Cheng-Prusoff method using the equation below (Cheng and Prusoff, 1973):

$$K_{i,app} = IC_{50}/(1 + [radioligand]/K_d))$$

Compounds of Formula I were tested according to procedures described above. The results are set forth below in Table 1 according to the following key:
A=$K_i$<500 nM
B=$K_i$>500 nM and <1000 nM
C=$K_i$>1000 nM

| Ex No. | h5-HT6 (Ki, nM) |
|---|---|
| 1 | A |
| 2 | A |
| 3 | A |
| 4 | A |
| 5 | B |
| 6 | C |
| 7 | C |
| 8 | C |
| 9 | C |
| 10 | A |
| 11 | A |
| 12 | A |
| 13 | C |
| 14 | C |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | |
| 36 | A |
| 37 | A |
| 38 | A |
| 39 | A |
| 40 | A |
| 41 | A |
| 42 | B |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | C |
| 63 | A |
| 64 | A |
| 65 | A |
| 66 | A |
| 67 | A |
| 68 | A |
| 69 | A |
| 70 | C |
| 71 | C |
| 72 | C |
| 73 | A |
| 74 | A |
| 75 | C |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | C |
| 92 | C |
| 93 | B |
| 94 | A |
| 95 | A |
| 96 | C |
| 97 | C |
| 98 | A |

| Ex No. | h5-HT6 (Ki, nM) |
|---|---|
| 99 | A |
| 100 | A |
| 101 | A |
| 102 | A |
| 103 | A |
| 104 | C |
| 105 | A |
| 106 | A |
| 107 | A |
| 108 | A |
| 109 | A |
| 110 | A |
| 111 | A |
| 112 | A |
| 113 | A |
| 114 | A |
| 115 | C |
| 116 | A |
| 117 | A |
| 118 | A |
| 119 | A |
| 120 | A |
| 121 | A |
| 122 | A |
| 123 | A |
| 124 | C |
| 125 | A |
| 126 | A |
| 127 | A |
| 128 | A |
| 129 | B |
| 130 | A |
| 131 | A |
| 132 | C |
| 133 | A |
| 134 | A |
| 135 | C |
| 136 | A |
| 137 | A |
| 138 | C |
| 139 | C |
| 140 | A |
| 141 | A |
| 142 | C |
| 143 | A |
| 144 | C |
| 145 | C |
| 146 | A |
| 147 | A |
| 148 | A |
| 149 | A |
| 150 | A |
| 151 | B |
| 152 | A |
| 153 | A |
| 154 | C |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | B |
| 169 | B |
| 170 | A |
| 171 | C |
| 172 | A |
| 173 | C |
| 174 | C |
| 175 | A |
| 176 | A |
| 177 | C |
| 178 | A |
| 179 | A |
| 180 | C |
| 181 | C |
| 182 | A |
| 183 | A |
| 184 | A |
| 185 | A |
| 186 | A |
| 187 | B |
| 188 | A |
| 189 | A |
| 190 | C |
| 191 | A |
| 192 | A |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | A |
| 212 | A |
| 213 | A |
| 214 | A |
| 215 | A |
| 216 | A |
| 217 | A |
| 218 | A |
| 219 | A |
| 220 | A |
| 221 | A |
| 222 | A |
| 223 | A |
| 224 | A |
| 225 | A |
| 226 | C |
| 227 | A |
| 228 | B |
| 229 | A |
| 230 | A |
| 231 | A |
| 232 | A |
| 233 | C |
| 234 | C |
| 235 | A |
| 236 | A |
| 237 | A |
| 238 | A |
| 239 | A |
| 240 | A |
| 241 | A |
| 242 | C |
| 243 | A |
| 244 | A |
| 245 | A |
| 246 | A |
| 247 | A |
| 248 | A |
| 249 | A |
| 250 | A |

-continued

| Ex No. | h5-HT6 (Ki, nM) |
|---|---|
| 251 | A |
| 252 | A |
| 253 | C |
| 254 | A |
| 255 | A |
| 256 | A |
| 257 | A |
| 258 | A |
| 259 | A |
| 260 | A |
| 261 | A |
| 262 | A |
| 263 | A |
| 264 | A |
| 265 | A |
| 266 | A |
| 267 | A |
| 268 | A |
| 269 | B |
| 270 | A |
| 271 | C |
| 272 | B |
| 273 | A |
| 274 | A |
| 275 | B |
| 276 | A |
| 277 | A |
| 278 | A |
| 279 | A |
| 280 | C |
| 281 | C |
| 282 | A |
| 283 | A |
| 284 | A |
| 285 | C |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 303 | A |
| 304 | A |
| 305 | A |
| 306 | A |
| 307 | A |
| 308 | |
| 309 | |
| 310 | |
| 311 | A |
| 312 | A |
| 313 | A |
| 314 | A |
| 315 | A |
| 316 | A |
| 317 | A |
| 318 | A |
| 319 | A |
| 320 | A |
| 321 | A |
| 322 | A |
| 323 | C |
| 324 | A |
| 325 | B |
| 326 | A |

-continued

| Ex No. | h5-HT6 (Ki, nM) |
|---|---|
| 327 | C |
| 328 | A |
| 329 | C |
| 330 | C |
| 331 | B |
| 332 | A |
| 333 | A |
| 334 | B |
| 335 | C |
| 336 | C |
| 337 | C |
| 338 | A |
| 339 | A |
| 340 | A |
| 341 | A |
| 342 | A |
| 343 | A |
| 344 | B |
| 345 | A |
| 346 | A |
| 347 | A |
| 348 | A |
| 349 | A |
| 350 | A |
| 351 | C |
| 352 | C |
| 353 | A |
| 354 | A |
| 355 | C |
| 356 | B |
| 357 | A |
| 358 | A |
| 359 | A |
| 360 | A |
| 361 | A |
| 362 | A |
| 363 | A |
| 364 | A |
| 365 | A |
| 366 | A |
| 367 | A |
| 368 | A |
| 369 | C |
| 370 | A |
| 371 | A |
| 372 | A |
| 373 | C |
| 374 | C |
| 375 | A |
| 376 | A |
| 377 | C |
| 378 | A |
| 379 | A |
| 380 | C |
| 381 | A |
| 382 | A |
| 383 | C |
| 384 | A |
| 385 | C |
| 386 | A |
| 387 | C |
| 388 | A |
| 389 | C |
| 390 | A |
| 391 | C |
| 392 | A |
| 393 | C |
| 394 | A |
| 395 | A |
| 396 | C |
| 397 | C |
| 398 | A |
| 399 | A |
| 400 | A |
| 401 | A |
| 402 | A |

-continued

| Ex No. | h5-HT6 (Ki, nM) |
|---|---|
| 403 | A |
| 404 | A |
| 405 | B |
| 406 | A |
| 407 | A |
| 408 | A |
| 409 | A |
| 410 | B |
| 411 | A |
| 412 | A |
| 413 | A |
| 414 | A |
| 415 | A |
| 416 | A |
| 417 | A |
| 418 | A |
| 419 | A |
| 420 | A |
| 421 | A |
| 422 | A |
| 423 | A |
| 424 | A |
| 425 | C |
| 426 | A |
| 427 | A |
| 428 | C |
| 429 | C |
| 430 | A |
| 431 | C |
| 432 | A |
| 433 | A |
| 434 | A |
| 435 | C |
| 436 | A |
| 437 | A |
| 438 | A |
| 439 | A |
| 440 | A |
| 441 | A |
| 442 | C |
| 443 | C |
| 444 | C |
| 445 | C |
| 446 | A |
| 447 | C |
| 448 | A |
| 449 | A |
| 450 | C |
| 451 | A |
| 452 | A |
| 453 | C |
| 454 | A |
| 455 | C |
| 456 | A |
| 457 | A |
| 458 | C |
| 459 | C |
| 460 | A |
| 461 | A |
| 462 | C |
| 463 | A |
| 464 | A |
| 465 | A |
| 466 | A |
| 467 | A |
| 468 | A |
| 469 | A |
| 470 | A |
| 471 | A |
| 472 | A |
| 473 | A |
| 474 | C |
| 475 | |
| 476 | C |
| 477 | C |
| 478 | B |

-continued

| Ex No. | h5-HT6 (Ki, nM) |
|---|---|
| 479 | C |
| 480 | A |
| 481 | A |
| 482 | A |
| 483 | A |
| 484 | A |
| 485 | A |
| 486 | A |
| 487 | A |
| 488 | A |
| 489 | A |
| 490 | A |
| 491 | A |
| 492 | A |
| 493 | A |
| 494 | A |
| 495 | A |
| 496 | A |
| 497 | A |
| 498 | A |
| 499 | A |
| 500 | A |
| 501 | A |
| 502 | A |
| 503 | A |
| 504 | A |
| 505 | A |
| 506 | A |
| 507 | A |
| 508 | A |
| 509 | A |
| 510 | A |
| 511 | C |
| 512 | A |
| 513 | A |
| 514 | A |
| 515 | C |
| 516 | A |
| 517 | A |
| 518 | C |
| 519 | B |
| 520 | A |
| 521 | A |
| 522 | A |
| 523 | A |
| 524 | A |
| 525 | A |
| 526 | |
| 527 | |
| 528 | |
| 529 | |
| 530 | A |
| 531 | A |
| 532 | B |
| 533 | A |
| 534 | A |
| 535 | A |
| 536 | A |
| 537 | A |
| 538 | A |
| 539 | A |
| 540 | A |
| 541 | A |
| 542 | A |
| 543 | A |
| 544 | B |
| 545 | A |
| 546 | A |
| 547 | A |
| 548 | A |
| 549 | A |
| 550 | B |
| 551 | A |
| 552 | |
| 553 | A |
| 554 | A |

-continued

| Ex No. | h5-HT6 (Ki, nM) |
|---|---|
| 555 | A |
| 556 | A |
| 557 | A |
| 558 | B |
| 559 | A |
| 560 | C |
| 561 | A |
| 562 | A |
| 563 | C |
| 564 | C |
| 565 | A |
| 566 | A |
| 567 | A |
| 568 | A |
| 569 | A |
| 570 | A |
| 571 | A |
| 572 | A |
| 573 | A |
| 574 | A |
| 575 | A |
| 576 | A |
| 577 | A |
| 578 | A |
| 579 | A |
| 580 | A |
| 581 | A |
| 582 | A |
| 583 | A |
| 584 | A |
| 585 | A |
| 586 | A |
| 587 | A |
| 588 | A |
| 589 | A |
| 590 | A |
| 591 | A |
| 592 | A |
| 593 | A |
| 594 | A |
| 595 | A |
| 596 | A |
| 597 | B |
| 598 | A |
| 599 | A |
| 600 | A |
| 601 | A |
| 602 | A |
| 603 | A |
| 604 | A |
| 605 | B |
| 606 | A |
| 607 | A |
| 608 | A |
| 609 | A |
| 610 | B |
| 611 | A |
| 612 | A |
| 613 | C |
| 614 | A |
| 615 | A |
| 616 | A |
| 617 | A |
| 618 | C |
| 619 | A |
| 620 | A |
| 621 | A |
| 622 | A |
| 623 | C |
| 624 | A |
| 625 | A |
| 626 | C |
| 627 | A |
| 628 | A |
| 629 | A |
| 630 | A |

-continued

| Ex No. | h5-HT6 (Ki, nM) |
|---|---|
| 631 | A |
| 632 | A |
| 633 | A |
| 634 | A |
| 635 | A |
| 636 | A |
| 637 | C |
| 638 | A |
| 639 | C |
| 640 | C |
| 641 | A |
| 642 | A |
| 643 | A |
| 644 | A |
| 645 | C |
| 646 | B |
| 647 | A |
| 648 | A |
| 649 | A |
| 650 | A |
| 651 | A |
| 652 | B |
| 653 | A |
| 654 | A |
| 655 | A |
| 656 | A |
| 657 | A |
| 658 | A |
| 659 | C |
| 660 | A |
| 661 | A |
| 662 | A |
| 663 | A |
| 664 | A |
| 665 | A |
| 666 | A |
| 667 | C |
| 668 | A |
| 669 | A |
| 670 | A |
| 671 | A |
| 672 | A |
| 673 | A |
| 674 | A |
| 675 | A |
| 676 | A |
| 677 | A |
| 678 | A |
| 679 | A |
| 680 | A |
| 681 | A |
| 682 | A |
| 683 | B |
| 684 | B |
| 685 | C |
| 686 | A |
| 687 | A |
| 688 | B |
| 689 | C |
| 690 | C |
| 691 | C |
| 692 | A |
| 693 | A |
| 694 | A |
| 695 | C |
| 696 | C |
| 697 | C |
| 698 | A |
| 699 | A |
| 700 | A |
| 701 | C |
| 702 | C |
| 703 | C |
| 704 | A |
| 705 | A |
| 706 | A |

| Ex No. | h5-HT6 (Ki, nM) |
|---|---|
| 707 | B |
| 708 | B |
| 709 | B |
| 710 | A |
| 711 | A |
| 712 | C |
| 713 | A |
| 714 | A |
| 715 | A |
| 716 | A |
| 717 | A |
| 718 | A |
| 719 | A |
| 720 | A |
| 721 | A |
| 722 | B |
| 723 | B |
| 724 | A |
| 725 | A |
| 726 | A |
| 727 | B |
| 728 | C |
| 729 | A |
| 730 | C |
| 731 | A |
| 732 | B |
| 733 | B |
| 734 | C |
| 735 | C |
| 736 | C |
| 737 | A |
| 738 | A |
| 739 | A |
| 740 | A |
| 741 | A |
| 742 | A |
| 743 | A |
| 744 | C |
| 745 | C |
| 746 | C |
| 747 | B |
| 748 | A |
| 749 | C |
| 750 | C |
| 751 | C |
| 752 | C |
| 753 | C |
| 754 | C |
| 755 | C |
| 756 | C |
| 757 | C |
| 758 | A |
| 759 | C |
| 760 | C |
| 761 | C |
| 762 | C |
| 763 | C |
| 764 | B |
| 765 | B |
| 766 | B |
| 767 | C |
| 768 | B |
| 769 | A |
| 770 | C |
| 771 | A |
| 772 | A |
| 773 | A |
| 774 | C |
| 775 | A |
| 776 | C |
| 777 | C |
| 778 | C |
| 779 | C |
| 780 | C |
| 781 | C |
| 782 | C |
| 783 | B |
| 784 | A |
| 785 | C |
| 786 | A |
| 787 | C |
| 788 | A |
| 789 | C |
| 790 | C |
| 791 | A |
| 792 | A |
| 793 | A |
| 794 | A |
| 795 | A |
| 796 | A |
| 797 | A |
| 798 | C |
| 799 | B |
| 800 | C |
| 801 | C |
| 802 | B |
| 803 | C |
| 804 | C |
| 805 | C |
| 806 | C |
| 807 | C |
| 808 | C |
| 809 | C |
| 810 | C |
| 811 | C |
| 812 | C |
| 813 | C |
| 814 | C |
| 815 | C |
| 816 | B |
| 817 | C |
| 818 | A |
| 819 | A |
| 820 | A |
| 821 | C |
| 822 | C |
| 823 | A |
| 824 | C |
| 825 | A |
| 826 | A |
| 827 | A |
| 828 | A |
| 829 | A |
| 830 | A |
| 831 | C |
| 832 | C |
| 833 | B |
| 834 | A |
| 835 | A |
| 836 | C |
| 837 | C |
| 838 | B |
| 839 | C |
| 840 | C |
| 841 | C |
| 842 | C |
| 843 | C |
| 844 | C |
| 845 | C |
| 846 | C |
| 847 | C |
| 848 | C |
| 849 | C |
| 850 | C |
| 851 | C |
| 852 | C |
| 853 | B |
| 854 | C |
| 855 | C |
| 856 | A |
| 857 | C |
| 858 | C |

| Ex No. | h5-HT6 (Ki, nM) |
|---|---|
| 859 | C |
| 860 | C |
| 861 | B |
| 862 | C |

Specific data for a select number of compounds is provided below:

| Ex. No. | Chemical name | h5-HT$_6$ (K$_i$, nM) |
|---|---|---|
| 1 | 7-[(3-fluorophenyl)sulfonyl]-1,1-dimethyl-1,2,3,4-tetrahydro[1]benzofuro[2,3-c]pyridine | 1.5 |
| 99 | 6-[(2-fluorophenyl)sulfonyl]-4a-methyl-1,2,3,4,4a,9a-hexahydro[1]benzofuro[2,3-c]pyridine | 243.1 |
| 161 | 7-{[3-(trifluoromethyl)phenyl]sulfonyl}-1,2,3,4,4a,9a-hexahydro[1]benzofuro[2,3-c]pyridine | 44.0 |
| 343 | 7-[(6-methylpyridin-2-yl)sulfonyl]-1,2,3,4-tetrahydro[1]benzofuro[2,3-c]pyridine | 6.6 |
| 527 | 7-[(3-fluorophenyl)sulfonyl]-1-(trifluoromethyl)-2,3,4,9-tetrahydro-1H-beta-carboline | 93.0 |
| 608 | 7-(phenylsulfonyl)-2-(propan-2-yl)-1,2,3,4,4a,9a-hexahydro[1]benzofuro[2,3-c]pyridine | 49.4 |
| 660 | 1,2,3,4,4a,9a-hexahydro[1]benzofuro[2,3-c]pyridin-7-yl naphthalene-2-sulfonate | 11.4 |
| 820 | N-(1,2,3,4,4a,9a-hexahydro[1]benzofuro[2,3-c]pyridin-6-yl)-2,5-dimethylbenzenesulfonamide | 471.5 |

EXAMPLES

The following non-limiting Examples and Preparations illustrate the preparation of compounds of the present application. Proton ($^1$H) Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g., s, singlet; d, doublet; t, triplet; q, quartet; m, multiplet; br, broad. The mass spectra (m/z) were recorded using either electrospray ionisation (ESI) or atmospheric pressure chemical ionisation (APCI). The following abbreviations have been used for common solvents, reagents or reaction conditions: CDCl$_3$, deuterochloroform; D$_6$-DMSO, deuterodimethylsulphoxide; CD$_3$OD, deuteromethanol; THF, tetrahydrofuran; DCM, dichloromethane; TFA, trifluoroacetic acid, MeCN, AcCN, or ACN, acetonitrile; DMF, N,N-dimethylformamide; DMSO, dimethylsulfoxide; MeOH, methanol; mCPBA, meta-chloroperbenzoic acid; HCl, hydrochloric acid; DIEA, N,N-diethylisopropyl amine; DBU, (1,8-diazabicyclo[5.4.0]undec-7-ene); EtOAc, ethyl acetate; rt, RT or r.t., room temperature; h.v., house vacuum; dec., decomposition; SFC, supercritical fluid chromatographie. Where thin layer chromatography (TLC) has been used it refers to silica gel TLC using silica gel 60 F$_{254}$ plates, R$_f$ is the distance travelled by a compound divided by the distance travelled by the solvent front on a TLC plate.

Preparative LC-MS

Various compounds described below were purified using preparative LC-MS. Unless otherwise described, the compounds were purified using a WATERS Fractionlynx system equipped with a YMC Pack Pro C$_{18}$ Column (5 μm, 120 Å, 50×20 mm) and the following solvent system: H$_2$O, AcCN, and 2% TFA in H$_2$O, Specific elution gradients were based on the retention times obtained with an analytical LC-MS, however, in general all elution gradients of H$_2$O and MeCN were run over a 7 minute run time with a flow rate of 35 mL/min. An autoblend method was used to ensure a concentration of 0.1% TFA throughout each run.

Alternatively, the compounds were purified using a WATERS Fractionlynx system equipped with a XBridge Prep O$_{18}$ OBD Column (5 μm, 30×75 mm) using the solvent system and autoblend method described above. Specific elution gradients were based on the retention times obtained with an analytical LC-MS, however, in general all elution gradients of H$_2$O and MeCN were run over a 8 minute run time with a flow rate of 50 mL/min.

Analytical LC-MS

Analytical LC-MS was performed on a WATERS Acquity UPLC-MS instrument equipped with a ACQUITY UPLC BEH C$_{18}$ Column (2.1×50 mm, 1.7 μm), a column temperature of 45° C. and using the following solvent system: Solvent A: 0.1% HCOOH in H$_2$O; and Solvent B: 0.1% HCOOH in AcCN. All compounds were run using the same elution gradient, i.e., 5% to 95% Solvent B over a 1.5 min run time with a flow rate of 0.6 mL/min.

Preparative Chiral SFC Separation

Stereoisomer mixtures were separated using a Berger Minigram SFC instrument on one of the following columns: ChiralPak AS-H (10×250 mm), ChiralPak IA (10×250 mm), ChiralPak AD-H (21×250 mm), Phenomenex Lux-2 (21.2×250 mm), or ChiralPak IC (10×250 mm); eluting with either 0.1% diethylamine in MeOH/CO$_2$, or 0.1% diethylamine in EtOH/CO$_2$ or 0.1% diethylamine in isopropanol/CO$_2$ with a flow rate of 2.5 mL/min and a column temperature of 35° C.

Analytical Chiral SFC Separation

Stereoisomer mixtures or single enantiomers were analyzed using a JASCO analytical SFC instrument on one of the following columns: ChiralPak AS-H (4.6×250 mm), ChiralPak IA (4.6×250 mm), ChiralPak AD-H (4.6×250 mm), Phenomenex Lux-2 (4.6×250 mm), or ChiralPak IC (4.6×250 mm); eluting with either 0.1% diethylamine in MeOH/CO$_2$, or 0.1% diethylamine in EtOH/CO$_2$ or 0.1% diethylamine in isopropanol/CO$_2$, with a flow rate of 6.0 mL/min and a column temperature of 35° C.

It should be understood that for the dihydrofuranopyridine compounds, i.e., compounds where "- - - - - - -" is absent, the configuration at the ring juncture is cis. For examples where a racemic mixture is subjected to chiral separation, the absolute stereochemistry of the isolated compounds was not determined.

Example 1

7-[(3-Fluorophenyl)sulfonyl]-1,1-dimethyl-1,2,3,4-tetrahydro[1]benzofuro[2,3-c]pyridine

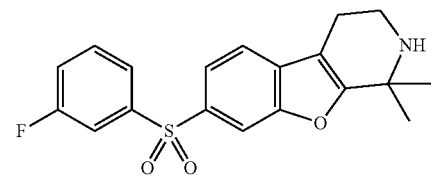 [SMILES: CC1(C)NCCc2c1oc1cc(S(=O)(=O)c3cccc(F)c3)ccc21]

Step 1

7-(3-Fluoro-phenylsulfanyl)-1,1-dimethyl-3,4-dihydro-1H-benzofuro[2,3-c]pyridine-2-carboxylic acid tert-butyl ester

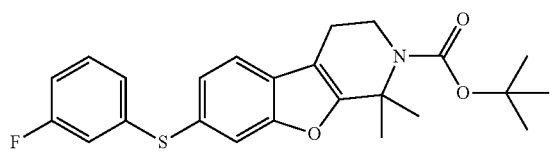 [SMILES: CC(C)(C)OC(=O)N1CCc2c(oc3cc(Sc4cccc(F)c4)ccc23)C1(C)C]

To tert-butyl 7-iodo-1,1-dimethyl-3,4-dihydro[1]benzofuro[2,3-c]pyridine-2(1H)-carboxylate P30 (0.505 g, 1.18 mmol) was added sodium tert-butoxide (341 mg, 3.55 mmol), copper(I) iodide (20 mg, 0.08 mmol), 1,2-ethanediol (132 µL, 2.38 mmol), N,N-dimethylformamide (17 mL, 210 mmol), and finally 3-Fluoro-benzenethiol (101 µL, 1.19 mmol). The reaction mixture was flushed with $N_2$ and heated at 120° C. under $N_2$. After 15 h, the reaction mixture was concentrated under high vacuum, the residue dissolved in 5% methanol-methylene chloride and then filtered through a celite-silica plug. The filtrate was concentrated and purified by silica chromatography (EtOAc/hexane) to afford the product as a pale yellow oil. MS m/z: 428 [M+H]+.

Step 2

7-(3-Fluoro-benzenesulfonyl)-1,1-dimethyl-3,4-dihydro-1H-benzofuro[2,3-c]pyridine-2-carboxylic acid tert-butyl ester

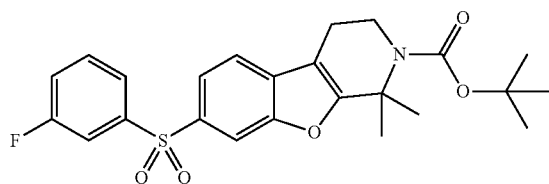 [SMILES: CC(C)(C)OC(=O)N1CCc2c(oc3cc(S(=O)(=O)c4cccc(F)c4)ccc23)C1(C)C]

To a solution of 7-(3-fluoro-phenylsulfanyl)-1,1-dimethyl-3,4-dihydro-1H-benzofuro[2,3-c]pyridine-2-carboxylic acid tert-butyl ester (0.440 g, 1.03 mmol) in methylene chloride (25.00 mL, 390.0 mmol) was added m-CPBA 70-75% (533 mg, 2.16 mmol) portionwise with stirring. After completion, the reaction mixture was diluted with methylene chloride and washed with saturated aqueous sodium bicarbonate, dried ($Na_2SO_4$) and concentrated. Purification by silica chromatography (EtOAc/hexane) afforded a white solid. mp 58-60° C.; MS m/z: 360 [M-Boc+H]+.

Step 3

7-(3-Fluoro-benzenesulfonyl)-1,1-dimethyl-1,2,3,4-tetrahydrobenzo[4,5]furo[2,3-c]pyridine

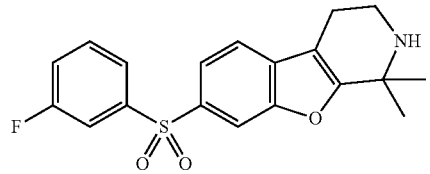 [SMILES: CC1(C)NCCc2c1oc1cc(S(=O)(=O)c3cccc(F)c3)ccc21]

7-(3-Fluoro-benzenesulfonyl)-1,1-dimethyl-3,4-dihydro-1H-benzofuro[2,3-c]pyridine-2-carboxylic acid tert-butyl ester (0.200 g, 0.435 mmol) in 4M HCl in dioxane (5.0 mL, 57.7 mmol) was stirred at rt. After 4 h, the heterogenous mixture was concentrated and triturated with $Et_2O$. The resulting white precipitate was dried under vacuum at 80° C. for 15 h. mp 110-114° C.; MS m/z 360 [M+H]+. $^1$H-NMR (400 MHz, $CDCl_3$): δ 1.7 (s, 6H), 3.0 (m, 2H), 3.5 (m, 2H), 7.5 (m, 1H), 7.7 (m, 1H), 7.9 (m, 4H), 8.3 (s, 1H), 10.0 (brs, 2H).

The following examples were prepared essentially as described in the above synthetic procedures. The enantiomers Example 20 and Example 21 in the Table below were isolated from the corresponding racemic mixture Example 12 using SFC chromatography on a chiral column as described in the general method. All compounds were isolated as HCl salts unless otherwise stated.

| Ex. # | Name | Mp (° C.) | MS m/z [M + H]+ | Stereochemistry | Starting material |
|---|---|---|---|---|---|
| 1 | 7-[(3-fluorophenyl)sulfonyl]-1,1-dimethyl-1,2,3,4-tetrahydro[1]benzofuro[2,3-c]pyridine | 320-325 dec. | 360 | | 3-fluorobenzenethiol |
| 2 | 7-[(3-fluorophenyl)sulfonyl]-4,4-dimethyl-2',3,3',4,5',6'-hexahydro-2H-spiro[1-benzofuro[2,3-c]pyridine-1,4'-pyran] | 286-288 | 430 | | 3-fluorobenzenethiol |
| 3 | 7-[(2-methoxyphenyl)sulfonyl]-4a-methyl-1,2,3,4,4a,9a-hexahydro[1]benzofuro[2,3-c]pyridine | 222-224 | 360 | racemic | 2-methoxybenzenethiol |
| 4 | 7-[(3-methoxyphenyl)sulfonyl]-4a-methyl-1,2,3,4,4a,9a-hexahydro[1]benzofuro[2,3-c]pyridine | 279-280 | 360 | racemic | 3-methoxybenzenethiol |

-continued

| Ex. # | Name | Mp (° C.) | MS m/z [M + H]+ | Stereochemistry | Starting material |
|---|---|---|---|---|---|
| 5 | 7-[(4-methoxyphenyl)sulfonyl]-4a-methyl-1,2,3,4,4a,9a-hexahydro[1]benzofuro[2,3-c]pyridine | 283-284 | 360 | racemic | 4-methoxybenzenethiol |
| 6 | 4a-methyl-7-[(6-methylpyridin-2-yl)sulfonyl]-1,2,3,4,4a,9a-hexahydro[1]benzofuro[2,3-c]pyridine | 255-258 | 345 | racemic | 6-methylpyridine-2-thiol |
| 7 | 4a-methyl-7-[(4-methylpyrimidin-2-yl)sulfonyl]-1,2,3,4,4a,9a-hexahydro[1]benzofuro[2,3-c]pyridine | 199-201 | 346 | racemic | 4-methylpyrimidine-2-thiol |
| 8 | 4a-methyl-7-(pyridin-2-ylsulfonyl)-1,2,3,4,4a,9a-hexahydro[1]benzofuro[2,3-c]pyridine | 282-283 | 331 | racemic | pyridine-2-thiol |
| 9 | 4a-methyl-7-(pyrimidin-2-ylsulfonyl)-1,2,3,4,4a,9a-hexahydro[1]benzofuro[2,3-c]pyridine | 232-234 | 332 | racemic | pyrimidine-2-thiol |
| 10 | 7-[(3-ethoxyphenyl)sulfonyl]-4a-methyl-1,2,3,4,4a,9a-hexahydro[1]benzofuro[2,3-c]pyridine | 271-273 | 374 | racemic | 3-ethoxybenzenethiol |
| 11 | 7-[(3-fluorophenyl)sulfonyl]-4a-methyl-1,2,3,4,4a,9a-hexahydro[1]benzofuro[2,3-c]pyridine | 288-290 | 348 | racemic | 3-fluorobenzenethiol |
| 12 | 4a-methyl-7-{[3-(propan-2-yloxy)phenyl]sulfonyl}-1,2,3,4,4a,9a-hexahydro[1]benzofuro[2,3-c]pyridine | 206-208 | 388 | racemic | 3-(propan-2-yloxy)benzenethiol |
| 13 | 4a-methyl-6-(pyridin-4-ylsulfonyl)-1,2,3,4,4a,9a-hexahydro[1]benzofuro[2,3-c]pyridine | 186-188 | 331 | racemic | pyridine-4-thiol |
| 14 | 4a-methyl-6-[(1-oxidopyridin-4-yl)sulfonyl]-1,2,3,4,4a,9a-hexahydro[1]benzofuro[2,3-c]pyridine | 207-210 | 347 | racemic | pyridine-4-thiol |
| 15 | 1,1-dimethyl-7-{[3-(propan-2-yloxy)phenyl]sulfonyl}-1,2,3,4-tetrahydro[1]benzofuro[2,3-c]pyridine | 243-245 | 400 | | 3-(propan-2-yloxy)benzenethiol |
| 16 | 7-[(3-methoxyphenyl)sulfonyl]-1,1-dimethyl-1,2,3,4-tetrahydro[1]benzofuro[2,3-c]pyridine | 335 dec. | 372 | | 3-methoxybenzenethiol |
| 17 | 7-[(3-chlorophenyl)sulfonyl]-1,1-dimethyl-1,2,3,4-tetrahydro[1]benzofuro[2,3-c]pyridine | >200 dec. | 376 | | 3-chlorobenzenethiol |
| 18 | 7-[(3-chloro-4-fluorophenyl)sulfonyl]-1,1-dimethyl-1,2,3,4-tetrahydro[1]benzofuro[2,3-c]pyridine | >200 dec. | 394 | | 3-chloro-4-fluorobenzenethiol |
| 19 | 1,1-dimethyl-7-[(6-methylpyridin-2-yl)sulfonyl]-1,2,3,4-tetrahydro[1]benzofuro[2,3-c]pyridine | 305-310 | 357 | | 6-methylpyridine-2-thiol |
| 20 | 4a-methyl-7-{[3-(propan-2-yloxy)phenyl]sulfonyl}-1,2,3,4,4a,9a-hexahydro[1]benzofuro[2,3-c]pyridine | 184-185 | 388 | Enantiomer 1 | 3-(propan-2-yloxy)benzenethiol |

| Ex. # | Name | Mp (°C.) | MS m/z [M + H]+ | Stereochemistry | Starting material |
|---|---|---|---|---|---|
| 21 | 4a-methyl-7-{[3-(propan-2-yloxy)phenyl]sulfonyl}-1,2,3,4,4a,9a-hexahydro[1]benzofuro[2,3-c]pyridine | 183-184 | 388 | Enantiomer 2 | 3-(propan-2-yloxy)benzenethiol |

Example 22

7-[(3-Fluorophenyl)sulfonyl]-3,4,5',6'-tetrahydro-2H,4'H-spiro[1-benzofuro[2,3-c]pyridine-1,3'-pyran]

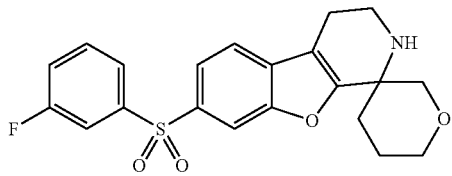 [SMILES: O=S(=O)(c1cccc(F)c1)c1ccc2c3c(oc2c1)C1(CCCOC1)NCC3]

Step 1

7-[(3-Fluorophenyl)sulfanyl]-3,4,5',6'-tetrahydro-2H,4'H-spiro[1-benzofuro[2,3-c]pyridine-1,3'-pyran]

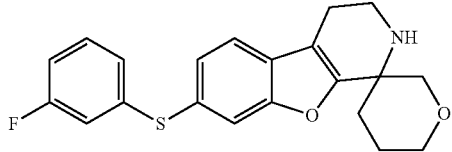 [SMILES: Fc1cccc(Sc2ccc3c4c(oc3c2)C2(CCCOC2)NCC4)c1]

7-Iodo-3,4,5',6'-tetrahydro-2H,4'H-spiro[1-benzofuro[2,3-c]pyridine-1,3'-pyran] (0.20 g, 0.56 mmol), neocuproine (11.6 mg, 0.0558 mmol) and copper(I) iodide (53.1 mg, 0.279 mmol) were dissolved into the anhydrous DMF (4 mL, 50 mmol) in a 20 mL scintillation vial under $N_2$. 3-Fluoro-benzenethiol (104 µL, 1.23 mmol) was added neat followed immediately by the addition of the sodium tert-butoxide (118 mg, 1.23 mmol). The reaction vial was capped with a teflon coated cap and the mixture was stirred at 100° C. overnight. After 15 h, the reaction was cooled to room temperature and concentrated under vacuum. The residual solid was partially dissolved into a 5% MeOH in DCM solution and flushed through a Celite plug. The concentrated filtrate was chromatographed on silica gel using DCM-MeOH—$NH_4OH$ to afford a brownish oil, used directly in the next step.

Step 2

7-[(3-fluorophenyl)sulfonyl]-3,4,5',6'-tetrahydro-2H,4'H-spiro[1-benzofuro[2,3-c]pyridine-1,3'-pyran]

To a solution of 7-[(3-fluorophenyl)sulfanyl]-3,4,5',6'-tetrahydro-2H,4'H-spiro[1-benzofuro[2,3-c]pyridine-1,3'-pyran] (0.160 g, 0.433 mmol) in methanol (5.0 mL, 120 mmol) was added a solution of Oxone® (0.666 g, 1.08 mmol) in water (5.0 mL, 280 mmol) and the mixture was stirred at rt overnight. After 3 h, the reaction mixture was filtered, concentrated, and then extracted with DCM/sat. aq. $NaHCO_3$. The extract was dried, concentrated and then purified by silica gel chromatography (DCM-MeOH—$NH_4OH$) to afford an off-white solid. The product was converted to the HCl salt using excess EtOH—HCl and dried overnight at 80° C. under high vacuum. mp 285-290° C. dec.; MS m/z 401 [M+H]+. $^1$H-NMR (400 MHz, $CDCl_3$): d 1.7 (d, J=12.6 Hz, 1H), 1.83 (d, J=14.2 Hz, 1H), 2.0 (m, 2H), 2.3 (m, 1H), 2.7 (m, 2H), 3.2 (m, 2H), 3.6 (m, 1H), 3.7 (d, J=11.5 Hz, 1H), 3.85 (d, J=12 Hz, 1H), 4.0 (d, J=10.6 Hz, 1H), 7.2 (m, 2H), 7.4 (m, 1H), 7.57 (d, J=8.1 Hz, 1H), 7.66 (d, J=8.1 Hz, 1H), 7.76 (d, J=8.1 Hz, 1H), 7.82 (d, J=8.2 Hz, 1H), 8.08 (s, 1H).

The following examples were prepared essentially as described above. Example 50 and Example 51, in the Table below were isolated from racemic mixture Example 40, and similarly, Example 52 and Example 53 were isolated from the corresponding racemic mixture Example 30 using SFC chromatography on a chiral column as described in the general method. All compounds were isolated as HCl salts unless otherwise stated.

| Ex. # | Name | Mp (°C.) | MS m/z [M + H]+ | Stereochemistry | Salt | Starting material |
|---|---|---|---|---|---|---|
| 23 | 7-{[3-(propan-2-yloxy)phenyl]sulfonyl}-3,4,5',6'-tetrahydro-2H,4'H-spiro[1-benzofuro[2,3-c]pyridine-1,3'-pyran] | 148-155 dec. | 442 | Racemic | HCl | 3-(propan-2-yloxy)benzenethiol |
| 24 | 7-[(3,5-difluorophenyl)sulfonyl]-3,4,5',6'-tetrahydro-2H,4'H-spiro[1-benzofuro[2,3-c]pyridine-1,3'-pyran] | 85-95 | 420 | Racemic | | 3,5-difluorobenzenethiol |
| 25 | 7-[(3-fluorophenyl)sulfonyl]-3,4-dihydro-2H-spiro[1-benzofuro[2,3-c]pyridine-1,1'-cyclobutane] | >200 dec. | 372 | | HCl | 3-fluorobenzenethiol |

-continued

| Ex. # | Name | Mp (° C.) | MS m/z [M + H]+ | Stereochemistry | Salt | Starting material |
|---|---|---|---|---|---|---|
| 26 | 7-{[3-(propan-2-yloxy)phenyl]sulfonyl}-3,4-dihydro-2H-spiro[1-benzofuro[2,3-c]pyridine-1,1'-cyclobutane] | >200 dec. | 412 | | HCl | 3-(propan-2-yloxy)benzenethiol |
| 27 | 1-ethyl-7-[(3-fluorophenyl)sulfonyl]-1-methyl-1,2,3,4-tetrahydro[1]benzofuro[2,3-c]pyridine | >300 | 374 | A mixture of diastereomers | HCl | 3-fluorobenzenethiol |
| 28 | 7-[(3-fluorophenyl)sulfonyl]-3,4-dihydro-2H-spiro[1-benzofuro[2,3-c]pyridine-1,1'-cyclopentane] | >250 | 386 | 0 | HCl | 3-fluorobenzenethiol |
| 29 | 1-cyclopropyl-7-[(3-fluorophenyl)sulfonyl]-1-methyl-1,2,3,4-tetrahydro[1]benzofuro[2,3-c]pyridine | >250 dec. | 386 | Racemic | HCl | 3-fluorobenzenethiol |
| 30 | 7-[(3-fluorophenyl)sulfonyl]-3,4,4',5'-tetrahydro-2H-spiro[1-benzofuro[2,3-c]pyridine-1,3'-furan] | 89-93 | 388 | Racemic | | 3-fluorobenzenethiol |
| 31 | 7-{[3-(propan-2-yloxy)phenyl]sulfonyl}-3,4,4',5'-tetrahydro-2H-spiro[1-benzofuro[2,3-c]pyridine-1,3'-furan] | 261-263 dec. | 428 | enantiomer 1 | HCl | 3-(propan-2-yloxy)benzenethiol |
| 32 | 7-{[3-(propan-2-yloxy)phenyl]sulfonyl}-3,4,4',5'-tetrahydro-2H-spiro[1-benzofuro[2,3-c]pyridine-1,3'-furan] | 259-261 dec. | 428) | enantiomer 2 | HCl | 3-(propan-2-yloxy)benzenethiol |
| 33 | 1-(ethoxymethyl)-7-[(3-fluorophenyl)sulfonyl]-1,2,3,4-tetrahydro[1]benzofuro[2,3-c]pyridine | 230-250 dec. | 390 | Racemic | HCl | 3-fluorobenzenethiol |
| 34 | 1-(difluoromethyl)-1-methyl-7-{[3-(propan-2-yloxy)phenyl]sulfonyl}-1,2,3,4-tetrahydro[1]benzofuro[2,3-c]pyridine | 219-222 | 436 | single enantiomer of unknown configuration | HCl | 3-(propan-2-yloxy)benzenethiol |
| 35 | 1,1-bis(fluoromethyl)-7-[(3-fluorophenyl)sulfonyl]-1,2,3,4-tetrahydro[1]benzofuro[2,3-c]pyridine | 154-157 | 396 | | | 3-fluorobenzenethiol |
| 36 | 7-[(3-fluorophenyl)sulfonyl]-1-methyl-1-(2-methylpropyl)-1,2,3,4-tetrahydro[1]benzofuro[2,3-c]pyridine | 284-286 | 402 | Racemic | HCl | 3-fluorobenzenethiol |
| 37 | 7-[(3-fluorophenyl)sulfonyl]-1-methyl-1-(trifluoromethyl)-1,2,3,4-tetrahydro[1]benzofuro[2,3-c]pyridine | 225-228 | 414 | Racemic | HCl | 3-fluorobenzenethiol |
| 38 | 7-[(3-fluorophenyl)sulfonyl]-2',3,3',4,5',6'-hexahydro-2H-spiro[1-benzofuro[2,3-c]pyridine-1,4'-thiopyran] 1',1'-dioxide | 298-300 dec. | 450 | | HCl | 3-fluorobenzenethiol |
| 39 | 7-[(3-fluorophenyl)sulfonyl]-1,1-bis(methoxymethyl)-1,2,3,4-tetrahydro[1]benzofuro[2,3-c]pyridine | 196-198 | 420 | | HCl | 3-fluorobenzenethiol |

-continued

| Ex. # | Name | Mp (° C.) | MS m/z [M + H]+ | Stereochemistry | Salt | Starting material |
|---|---|---|---|---|---|---|
| 40 | 2-{7-[(3-fluorophenyl)sulfonyl]-1-methyl-1,2,3,4-tetrahydro[1]benzofuro[2,3-c]pyridin-1-yl}-N,N-dimethylacetamide | 220-223 | 431 | Racemic | HCl | 3-fluorobenzenethiol |
| 41 | 1-{7-[(3-fluorophenyl)sulfonyl]-3,4-dihydro-1'H,2H-spiro[1-benzofuro[2,3-c]pyridine-1,4'-piperidin]-1'-yl}ethanone | 256 dec. | 443 | | HCl | 3-fluorobenzenethiol |
| 42 | 6-[(3-fluorophenyl)sulfonyl]-1,1-dimethyl-1,2,3,4-tetrahydro[1]benzofuro[2,3-c]pyridine | >200 | 360 | | HCl | 3-fluorobenzenethiol |
| 43 | 7-[(3-fluorophenyl)sulfonyl]-2',3,3',4,5',6'-hexahydro-2H-spiro[1-benzofuro[2,3-c]pyridine-1,4'-pyran] | >200 | 402 | | HCl | 3-fluorobenzenethiol |
| 44 | 7-{[3-(propan-2-yloxy)phenyl]sulfonyl}-2',3,3',4,5',6'-hexahydro-2H-spiro[1-benzofuro[2,3-c]pyridine-1,4'-pyran] | 250 dec. | 442 | | HCl | 3-(propan-2-yloxy)benzenethiol |
| 45 | 7-[(3-fluorophenyl)sulfonyl]-4,4-dimethyl-1-(tetrahydro-2H-pyran-4-yl)-1,2,3,4-tetrahydro[1]benzofuro[2,3-c]pyridine | 248-252 | 444 | racemic | HCl | 3-fluorobenzenethiol |
| 46 | 7-[(3-fluorophenyl)sulfonyl]-4,4-dimethyl-3,4,4',5'-tetrahydro-2H-spiro[1-benzofuro[2,3-c]pyridine-1,3'-furan] | 263-268 | 416 | racemic | HCl | 3-fluorobenzenethiol |
| 47 | 7-[(3-fluorophenyl)sulfinyl]-4,4-dimethyl-2',3,3',4,5',6'-hexahydro-2H-spiro[1-benzofuro[2,3-c]pyridine-1,4'-pyran] | 248-253 | 414 | racemic | HCl | 3-fluorobenzenethiol |
| 48 | 7-[(3-fluorophenyl)sulfonyl]-3,4-dihydro-2H-spiro[1-benzofuro[2,3-c]pyridine-1,3'-oxetane] | 153-155 | 374 | | | 3-fluorobenzenethiol |
| 49 | 7-[(3-fluorophenyl)sulfonyl]-1-(methoxymethyl)-1-methyl-1,2,3,4-tetrahydro[1]benzofuro[2,3-c]pyridine | >200 | 390 | racemic | HCl | 3-fluorobenzenethiol |
| 50 | 2-{7-[(3-fluorophenyl)sulfonyl]-1-methyl-1,2,3,4-tetrahydro[1]benzofuro[2,3-c]pyridin-1-yl}-N,N-dimethylacetamide | 230-233 | 431 | Enantiomer 1 | HCl | 3-fluorobenzenethiol |
| 51 | 2-{7-[(3-fluorophenyl)sulfonyl]-1-methyl-1,2,3,4-tetrahydro[1]benzofuro[2,3-c]pyridin-1-yl}-N,N-dimethylacetamide | 230-233 | 431 | Enantiomer 2 | HCl | 3-fluorobenzenethiol |
| 52 | 7-[(3-fluorophenyl)sulfonyl]-3,4,4',5'-tetrahydro-2H-spiro[1-benzofuro[2,3-c]pyridine-1,3'-furan] | 318-320 dec. | 388 | enantiomer 1 | HCl | Mixture of 7-[(3-fluorophenyl)sulfonyl]-3,4,4',5'-tetrahydro-2H-spiro[1-benzofuro[2,3-c]pyridine-1,3'-furan] |

-continued

| Ex. # | Name | Mp (° C.) | MS m/z [M + H]+ | Stereochemistry | Salt | Starting material |
|---|---|---|---|---|---|---|
| 53 | 7-[(3-fluorophenyl)sulfonyl]-3,4,4',5'-tetrahydro-2H-spiro[1-benzofuro[2,3-c]pyridine-1,3'-furan] | 315-317 dec. | 388 | enantiomer 2 | HCl | Mixture of 7-[(3-fluorophenyl)sulfonyl]-3,4,4',5'-tetrahydro-2H-spiro[1-benzofuro[2,3-c]pyridine-1,3'-furan] |

Examples 54 and 55

Racemic Diastereoisomers 1 and 2

3'-Fluoro-7-[(3-fluorophenyl)sulfonyl]-2',3,3',4,5',6'-hexahydro-2H-spiro[1-benzofuro[2,3-c]pyridine-1,4'-pyran]

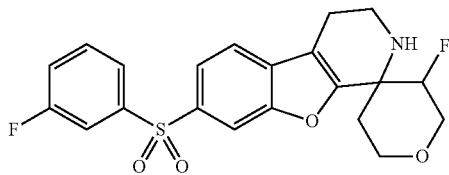 [SMILES: O=S(=O)(c1cccc(F)c1)c1ccc2c3c(oc2c1)C1(CCOCC1F)NCC3]

Step 1

3'-Fluoro-7-iodo-2',3,3',4,5',6'-hexahydro-2H-spiro[1-benzofuro[2,3-c]pyridine-1,4'-pyran]

As described for 7-iodo-3,4,5',6'-tetrahydro-2H,4'H-spiro[1-benzofuro[2,3-c]pyridine-1,3'-pyran] using 3-fluorotetrahydro-4H-pyran-4-one and 2-(6-iodo-benzofuran-3-yl)-ethylamine 2-methyldihydrofuran-3(2H)-one. 3-Fluorotetrahydro-4H-pyran-4-one was prepared as described in WO03/092586. MS m/z 388 [M+H]+.

Step 2

As described for 7-[(3-fluorophenyl)sulfonyl]-3,4,5',6'-tetrahydro-2H,4'H-spiro[1-benzofuro[2,3-c]pyridine-1,3'-pyran] (Example 22) starting from 3'-fluoro-7-iodo-2',3,3',4,5',6'-hexahydro-2H-spiro[1-benzofuro[2,3-c]pyridine-1,4'-pyran] and 3-fluorobenzenethiol The resulting diastereoisomeric mixture was separated using medium pressure liquid chromatography (140 g amine column) eluting with a gradient of EtOAc in hexanes (from 15% to 70% EtOAc).

Example 54 (Racemic diastereoisomer 1): mp 295-303° C. dec.; MS m/z 420 [M+H]+.
Example 55 (Racemic diastereoisomer 2): mp 251-260° C.; MS m/z 420 [M+H]+.

Examples 56 and 57

Racemic Diastereoisomers 1 and 2

7-[(3-Fluorophenyl)sulfonyl]-2'-methyl-3,4,4',5'-tetrahydro-2H-spiro[1-benzofuro[2,3-c]pyridine-1,3'-furan]

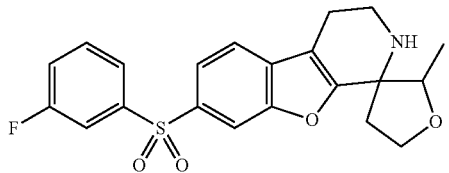 [SMILES: CC1OCCC12NCCc1c2oc2cc(S(=O)(=O)c3cccc(F)c3)ccc12]

Step 1

7-Iodo-2'-methyl-3,4,4',5'-tetrahydro-2H-spiro[1-benzofuro[2,3-c]pyridine-1,3'-furan]

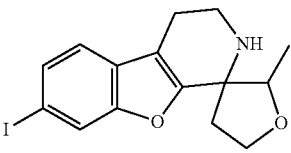 [SMILES: CC1OCCC12NCCc1c2oc2cc(I)ccc12]

Prepared as described for 7-iodo-3,4,5',6'-tetrahydro-2H, 4'H-spiro[1-benzofuro[2,3-c]pyridine-1,3'-pyran] using 2-(6-iodo-benzofuran-3-yl)-ethylamine and 2-methyldihydrofuran-3(2H)-one. The resulting diastereoisomeric mixture was separated using medium pressure liquid chromatography (140 g amine column) eluting with a gradient of EtOAc in hexanes (from 15% to 70% EtOAc).

Step 2

Prepared as described for 7-[(3-fluorophenyl)sulfonyl]-3,4,5',6'-tetrahydro-2H,4'H-spiro[1-benzofuro[2,3-c]pyridine-1,3'-pyran] (Example 22) starting from 3-fluorobenzenethiol and 7-iodo-2'-methyl-3,4,4',5'-tetrahydro-2H-spiro[1-benzofuro[2,3-c]pyridine-1,3'-furan].

Racemic diastereoisomer 1: mp 295-303° C. dec.; MS m/z 370 [M+H]+.
Racemic diastereoisomer 2: mp 251-260° C.; MS m/z 370 [M+H]+.

Example 58 through Example 61

Chiral Diastereoisomers

7-[(3-Fluorophenyl)sulfonyl]-2'-methyl-3,4,4',5'-tetrahydro-2H-spiro[1-benzofuro[2,3-c]pyridine-1,3'-furan]

The racemic diastereomers (Examples 54 and 55) were resolved by using SFC chiral separation (Chiralpak AD-H (3×15 cm with 40% EtOH/CO$_2$ at 100 bar). The four, chiral diastereomers were dissolved in 2 mL of diethyl ether containing 0.25 mL of 2.5 M ethanolic HCl. Trituration with ether afforded each of the 4 enantiomerically pure diastereomers as their HCl salts.

Example 58 (from racemic diastereoisomer 1): mp 262-265° C. dec.; MS m/z 402 [M+H]+.
Example 59 (from racemic diastereoisomer 2): mp 262-265° C.; MS m/z 402 [M+H]+.
Example 60 (from racemic diastereoisomer 1): mp 298-301° C. dec.; MS m/z 402 [M+H]+.
Example 61 (from racemic diastereoisomer 2): mp 298-301° C.; MS m/z 402 [M+H]+.

Example 62

4a-Methyl-6-(phenylsulfonyl)-1,2,3,4,4a,9a-hexahydro[1]benzofuro[2,3-c]pyridine hydrochloride

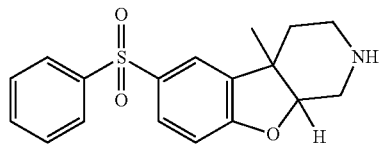 [SMILES: CC12CCNCC1Oc1ccc(S(=O)(=O)c3ccccc3)cc12]

Step 1

4a-Methyl-6-(phenylsulfanyl)-1,2,3,4,4a,9a-hexahydro[1]benzofuro[2,3-c]pyridine-2-carboxylic acid tert-butyl ester

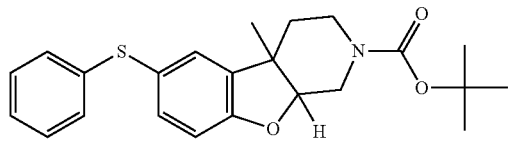 [SMILES: CC(C)(C)OC(=O)N1CCC2(C)c3cc(Sc4ccccc4)ccc3OC2C1]

Into a sealed tube was added tert-butyl 6-iodo-4a-methyl-3,4,4a,9a-tetrahydro[1]benzofuro[2,3-c]pyridine-2(1H)-carboxylate P24 (0.491 g, 1.18 mmol), sodium tert-butoxide (341 mg, 3.55 mmol), copper (I) iodide (20 mg, 0.08 mmol), 1,2-ethanediol (132 μL, 2.38 mmol), N,N-dimethylformamide (17 mL, 210 mmol), and benzenethiol (123 μL, 1.19 mmol). The reaction was heated at 120° C. overnight. The reaction was concentrated and partitioned between DCM and water. The DCM layer was washed with brine, dried, filtered and concentrated under vacuum. The crude product was dissolved in DCM and purified on a 12 g silica gel column eluting with hexanes to 2:1 hexanes:ethyl acetate to give the product which was taken directly into the next step.

Step 2

4a-Methyl-6-(phenylsulfonyl)-1,2,3,4,4a,9a-hexahydro[1]benzofuro[2,3-c]pyridine hydrochloride To a solution of 4a-methyl-6-(phenylsulfanyl)-1,2,3,4,4a,9a-hexahydro[1]benzofuro[2,3-c]pyridine-2-carboxylic acid tert-butyl ester (0.327 g, 0.82 mmol) in methanol (10 mL, 0.2 mol) was added water (0.5 mL, 0.03 mol) and Oxone® (2.0 g, 0.0032 mol). The reaction was stirred overnight at room temperature. The reaction mixture was filtered and the filtrate concentrated. The residue was dissolved in DCM and washed with brine, dried, filtered and concentrated. The crude product was purified on a 12 g silica gel column eluting with hexanes to 2:1 hexanes:ethyl acetate and then stirred in 4 M HCl in dioxane (5 mL, 0.04 mol) for 30 min. The product was precipitated by addition of DCM and ether. The solid was filtered, washed with ether and dried under house vacuum to afford the title compound. mp 236-238° C. dec.; MS m/z 330 [M+H]$^+$. $^1$H-NMR (400 MHz, DMSO): δ 1.45 (s, 3H), 1.75 (m, 1H), 1.90 (m, 1H), 2.82 (m, 1H), 3.03 (m, 1H), 3.35-3.56 (m, 2H), 4.63 (s, 1H), 7.08 (d, J=8.9 Hz, 1H), 7.58-7.70 (m, 3H), 7.81 (d, J=8.85 Hz, 1H), 7.91-7.96 (m, 3H), 8.91 (bs, 1H), 9.91 (bs, 1H).

The following examples were prepared essentially as described above. Example 103 and Example 104 were isolated from racemic mixture Example 100 and Example 105 and Example 106 were isolated from racemic mixture Example 101 using SFC chromatography on a chiral column as described in the general method. All compounds were isolated as the HCl salt unless otherwise specified.

| Ex. # | Name | Mp (° C.) | MS m/z [M + H]$^+$ | Stereochemistry | Starting material |
|---|---|---|---|---|---|
| 62 | 4a-methyl-6-(phenylsulfonyl)-1,2,3,4,4a,9a-hexahydro[1]benzofuro[2,3-c]pyridine | 236-238 | 330 | racemic | benzenethiol |
| 63 | 7-({3-[(6-methylpyrazin-2-yl)oxy]phenyl}sulfonyl)-1,2,3,4,4a,9a-hexahydro[1]benzofuro[2,3-c]pyridine | 128-130 | 424 | racemic | 3-[(6-methylpyrazin-2-yl)oxy]benzenethiol |
| 64 | 7-[(2,6-dichlorophenyl)sulfonyl]-1,2,3,4,4a,9a-hexahydro[1]benzofuro[2,3-c]pyridine | 222-223 | 384 | racemic | 2,6-dichlorobenzenethiol |
| 65 | 7-(1,3-benzothiazol-2-ylsulfonyl)-1,2,3,4,4a,9a-hexahydro[1]benzofuro[2,3-c]pyridine | 195-196 | 373 | racemic | 1,3-benzothiazole-2-thiol |
| 66 | 7-[(3-chloro-2-methylphenyl)sulfonyl]-1,2,3,4,4a,9a-hexahydro[1]benzofuro[2,3-c]pyridine | 188-189 | 364 | racemic | 3-chloro-2-methylbenzenethiol |
| 67 | 7-(2,1,3-benzothiadiazol-4-ylsulfonyl)-1,2,3,4,4a,9a-hexahydro[1]benzofuro[2,3-c]pyridine | 195-196 | 374 | racemic | 2,1,3-benzothiadiazole-4-thiol |

-continued

| Ex. # | Name | Mp (° C.) | MS m/z [M + H]+ | Stereochemistry | Starting material |
|---|---|---|---|---|---|
| 68 | 7-[(1-methyl-1H-indol-4-yl)sulfonyl]-1,2,3,4,4a,9a-hexahydro[1]benzofuro[2,3-c]pyridine | 164-165 | 369 | racemic | 1-methyl-1H-indole-7-thiol |
| 69 | 7-(1H-benzimidazol-2-ylsulfonyl)-1,2,3,4,4a,9a-hexahydro[1]benzofuro[2,3-c]pyridine | 188-189 | 356 | racemic | 1H-benzimidazole-2-thiol |
| 70 | 7-[(5-methyl-2,1,3-benzothiadiazol-4-yl)sulfonyl]-1,2,3,4,4a,9a-hexahydro[1]benzofuro[2,3-c]pyridine | 200-201 | 388 | racemic | 5-methyl-2,1,3-benzothiadiazole-4-thiol |
| 71 | 7-[(5-methoxy-1,3-benzothiazol-2-yl)sulfonyl]-1,2,3,4,4a,9a-hexahydro[1]benzofuro[2,3-c]pyridine | 222-223 | 403 | racemic | 5-methoxy-1,3-benzothiazole-2-thiol |
| 72 | 7-(2,1,3-benzoxadiazol-4-ylsulfonyl)-1,2,3,4,4a,9a-hexahydro[1]benzofuro[2,3-c]pyridine | 189-190 | 358 | racemic | 2,1,3-benzoxadiazole-4-thiol |
| 73 | N-[3-(1,2,3,4,4a,9a-hexahydro[1]benzofuro[2,3-c]pyridin-7-ylsulfonyl)phenyl]acetamide | 228-229 | 373 | racemic | N-(3-sulfanylphenyl)acetamide |
| 74 | 7-{[3-(benzyloxy)phenyl]sulfonyl}-1,2,3,4,4a,9a-hexahydro[1]benzofuro[2,3-c]pyridine | 238-240 | 422 | racemic | 3-(benzyloxy)benzenethiol |
| 75 | 7-{[3-(1H-tetrazol-1-yl)phenyl]sulfonyl}-1,2,3,4,4a,9a-hexahydro[1]benzofuro[2,3-c]pyridine | >300 | 384 | racemic | 3-(1H-tetrazol-1-yl)benzenethiol |
| 76 | 7-{[3-(benzyloxy)-5-methoxyphenyl]sulfonyl}-1,2,3,4,4a,9a-hexahydro[1]benzofuro[2,3-c]pyridine | 202-203 | 452 | racemic | 3-(benzyloxy)-5-methoxybenzenethiol |
| 77 | 7-{[3-methoxy-5-(propan-2-yloxy)phenyl]sulfonyl}-1,2,3,4,4a,9a-hexahydro[1]benzofuro[2,3-c]pyridine | 233-234 | 404 | racemic | 3-methoxy-5-(propan-2-yloxy)benzenethiol |
| 78 | 7-{[3-methoxy-5-(propan-2-yloxy)phenyl]sulfonyl}-1,2,3,4,4a,9a-hexahydro[1]benzofuro[2,3-c]pyridine | 189-193 | 404 | enantiomer 1 | 3-methoxy-5-(propan-2-yloxy)benzenethiol |
| 79 | 7-{[3-methoxy-5-(propan-2-yloxy)phenyl]sulfonyl}-1,2,3,4,4a,9a-hexahydro[1]benzofuro[2,3-c]pyridine | 188-190 | 404 | enantiomer 2 | 3-methoxy-5-(propan-2-yloxy)benzenethiol |
| 80 | 7-[(5-chloro-2-methoxyphenyl)sulfonyl]-1,2,3,4-tetrahydro[1]benzofuro[2,3-c]pyridine | 258-259 | 378 | | 5-chloro-2-methoxybenzenethiol |
| 81 | 7-[(3-chloro-2-fluorophenyl)sulfonyl]-1,2,3,4-tetrahydro[1]benzofuro[2,3-c]pyridine | 245-246 | 366 | | 3-chloro-2-fluorobenzenethiol |
| 82 | 7-[(3-chloro-2-methylphenyl)sulfonyl]-1,2,3,4-tetrahydro[1]benzofuro[2,3-c]pyridine | 258-259 | 362 | | 3-chloro-2-methylbenzenethiol |
| 83 | 7-(2,1,3-benzothiadiazol-4-ylsulfonyl)-1,2,3,4-tetrahydro[1]benzofuro[2,3-c]pyridine | 242-243 | 372 | | 2,1,3-benzothiadiazole-4-thiol |

-continued

| Ex. # | Name | Mp (° C.) | MS m/z [M + H]+ | Stereochemistry | Starting material |
|---|---|---|---|---|---|
| 84 | 7-[(1-methyl-1H-indol-7-yl)sulfonyl]-1,2,3,4-tetrahydro[1]benzofuro[2,3-c]pyridine | 224-225 | 367 | | 1-methyl-1H-indole-7-thiol |
| 85 | 7-{[3-methoxy-5-(propan-2-yloxy)phenyl]sulfonyl}-4,4-dimethyl-1,2,3,4-tetrahydro[1]benzofuro[2,3-c]pyridine | 246-247 | 430 | | 3-methoxy-5-(propan-2-yloxy)benzenethiol |
| 86 | 7-[(3-fluorophenyl)sulfonyl]-4,4-dimethyl-1,2,3,4-tetrahydro[1]benzofuro[2,3-c]pyridine | 291-293 | 360 | | 3-fluorobenzenethiol |
| 87 | 4,4-dimethyl-7-{[3-(propan-2-yloxy)phenyl]sulfonyl}-1,2,3,4-tetrahydro[1]benzofuro[2,3-c]pyridine | 251-252 | 400 | | 3-(propan-2-yloxy)benzenethiol |
| 88 | 6-[(2,3-dichlorophenyl)sulfonyl]-7-methoxy-1,2,3,4,4a,9a-hexahydro[1]benzofuro[2,3-c]pyridine | 216-217 | 414 | racemic | 2,3-dichlorobenzenethiol |
| 89 | 6-[(3-fluorophenyl)sulfonyl]-7-methoxy-1,2,3,4,4a,9a-hexahydro[1]benzofuro[2,3-c]pyridine | 197-204 | 364 | racemic | 3-fluorobenzenethiol |
| 90 | 6-[(3-fluorophenyl)sulfonyl]-4a-methyl-1,2,3,4,4a,9a-hexahydro[1]benzofuro[2,3-c]pyridine | 168-171 | 348 | racemic | 3-fluorobenzenethiol |
| 91 | 4a-methyl-6-(pyridin-2-ylsulfonyl)-1,2,3,4,4a,9a-hexahydro[1]benzofuro[2,3-c]pyridine | 255-257 | 331 | racemic | pyridine-2-thiol |
| 92 | 6-[(4-fluorophenyl)sulfonyl]-4a-methyl-1,2,3,4,4a,9a-hexahydro[1]benzofuro[2,3-c]pyridine | 163-165 | 348 | racemic | 4-fluorobenzenethiol |
| 93 | 6-[(2,4-difluorophenyl)sulfonyl]-4a-methyl-1,2,3,4,4a,9a-hexahydro[1]benzofuro[2,3-c]pyridine | 215-216 | 366 | racemic | 2,4-difluorobenzenethiol |
| 94 | 6-[(3,5-difluorophenyl)sulfonyl]-4a-methyl-1,2,3,4,4a,9a-hexahydro[1]benzofuro[2,3-c]pyridine | 196-198 | 366 | racemic | 3,5-difluorobenzenethiol |
| 95 | 6-[(3-fluoro-4-methoxyphenyl)sulfonyl]-4a-methyl-1,2,3,4,4a,9a-hexahydro[1]benzofuro[2,3-c]pyridine | 185-187 | 378 | racemic | 3-fluoro-4-methoxybenzenethiol |
| 96 | N-(4-{[4a-methyl-1,2,3,4,4a,9a-hexahydro[1]benzofuro[2,3-c]pyridin-6-yl]sulfonyl}phenyl)acetamide | 212-214 | 387 | racemic | N-(4-sulfanylphenyl)acetamide |
| 97 | (2-{[4a-methyl-1,2,3,4,4a,9a-hexahydro[1]benzofuro[2,3-c]pyridin-6-yl]sulfonyl}phenyl)methanol | 204-206 | 360 | racemic | (2-sulfanylphenyl)methanol |
| 98 | 4a-methyl-6-{[3-(propan-2-yloxy)phenyl]sulfonyl}-1,2,3,4,4a,9a-hexahydro[1]benzofuro[2,3-c]pyridine | 162-164 | 388 | racemic | 3-(propan-2-yloxy)benzenethiol |
| 99 | 6-[(2-fluorophenyl)sulfonyl]-4a-methyl-1,2,3,4,4a,9a-hexahydro[1]benzofuro[2,3-c]pyridine | 260-262 | 348 | racemic | 2-fluorobenzenethiol |

-continued

| Ex. # | Name | Mp (°C.) | MS m/z [M + H]+ | Stereochemistry | Starting material |
|---|---|---|---|---|---|
| 100 | 6-[(3-chlorophenyl)sulfonyl]-4a-methyl-1,2,3,4,4a,9a-hexahydro[1]benzofuro[2,3-c]pyridine | 160-162 | 364 | racemic | 2-chlorobenzenethiol |
| 101 | 6-[(2,3-dichlorophenyl)sulfonyl]-4a-methyl-1,2,3,4,4a,9a-hexahydro[1]benzofuro[2,3-c]pyridine | 210-212 | 398 | racemic | 2,3-dichlorobenzenethiol |
| 102 | 7-[(3-fluorophenyl)sulfonyl]-4-methyl-1,2,3,4-tetrahydro[1]benzofuro[2,3-c]pyridine | >300 | 346 | racemic | 3-fluorobenzenethiol |
| 103 | 6-[(3-chlorophenyl)sulfonyl]-4a-methyl-1,2,3,4,4a,9a-hexahydro[1]benzofuro[2,3-c]pyridine | 218-220 | 364 | enantiomer 1 | 2-chlorobenzenethiol |
| 104 | 6-[(3-chlorophenyl)sulfonyl]-4a-methyl-1,2,3,4,4a,9a-hexahydro[1]benzofuro[2,3-c]pyridine | 216-218 | 364 | enantiomer 2 | 2-chlorobenzenethiol |
| 105 | 6-[(2,3-dichlorophenyl)sulfonyl]-4a-methyl-1,2,3,4,4a,9a-hexahydro[1]benzofuro[2,3-c]pyridine | 242-244 | 398 | enantiomer 1 | 2,3-dichlorobenzenethiol |
| 106 | 6-[(2,3-dichlorophenyl)sulfonyl]-4a-methyl-1,2,3,4,4a,9a-hexahydro[1]benzofuro[2,3-c]pyridine | 244-246 | 398 | enantiomer 2 | 2,3-dichlorobenzenethiol |

Example 107

7-(3,5-Difluoro-benzenesulfonyl)-1,2,3,4-tetrahydro-benzo[4,5]furo[2,3-c]pyridine hydrochloride

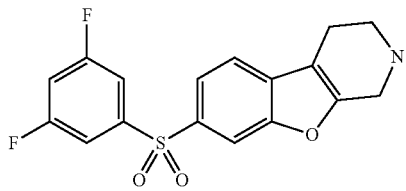 [SMILES: O=S(=O)(c1cc(F)cc(F)c1)c1ccc2c3c(oc2c1)CNCC3]

Step 1

7-(3,5-Difluoro-phenylsulfanyl)-3,4-dihydro-1H-benzo[4,5]furo[2,3-c]pyridine-2-carboxylic acid tert-butyl ester

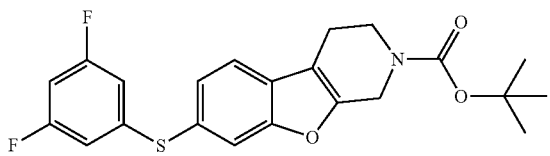 [SMILES: CC(C)(C)OC(=O)N1CCc2c(oc3cc(Sc4cc(F)cc(F)c4)ccc23)C1]

Anhydrous DMF was sparged with argon gas for 1 h before being used. 560 µL of a 0.625 M stock solution of 7-iodo-3,4-dihydro-1H-benzo[4,5]furo[2,3-c]pyridine-2-carboxylic acid tert-butyl ester P08 (120 mg, 0.300 mmol) in DMF, 300 µL of a 0.10 M stock solution of neocuproine (6.2 mg, 0.030 mmol) in DMF and 580 µL of a 0.310 M stock solution of copper (I) iodide (34 mg, 0.180 mmol) in DMF were added sequentially into a reaction vial. 3,5-Difluorobenzenethiol (96.5 µL, 0.660 mmol, 2.2 eq) was added neat followed by 630 µL of a 1.0 M stock solution of sodium tert-butoxide (60.5 mg, 0.630 mmol) in DMF. The reaction mixture was shaken at 100° C. for 16 h and the solvent was evaporated. The residue was suspended into DCE:MeOH 95:5 (2.0 mL), passed through a silica gel column (1 g) and eluted with DCE:MeOH 95:5 (3×2.0 mL). The eluent was concentrated to yield crude 7-(3,5-difluoro-phenylsulfanyl)-3,4-dihydro-1H-benzo[4,5]furo[2,3-c]pyridine-2-carboxylic acid tert-butyl ester which was used in the next step without further purification.

Step 2

7-(3,5-Difluoro-benzenesulfonyl)-1,2,3,4-tetrahydro-benzo[4,5]furo[2,3-c]pyridine hydrochloride 7-(3,5-Difluoro-phenylsulfanyl)-3,4-dihydro-1H-benzo[4,5]furo[2,3-c]pyridine-2-carboxylic acid tert-butyl ester (0.30 mmol, 1.0 eq) was suspended into DCE (1 mL). A 1.0 M solution of m-CPBA (70% from ACROS) in DCE (4.0 eq) was added slowly. The reaction solution was shaken for 10 min and diluted with DCE (2.0 mL) followed by addition of 1N aqueous NaOH (2 mL). The mixture was shaken, centrifugated and the aqueous layer was removed. The organic solution was then washed with 1N aqueous NaOH (2 mL) twice and H₂O (2 mL) once. The organic layer was then transferred into a new glass tube and the solvent was evaporated. The resulting oil was dissolved in a 1:1 mixture of TFA:DCM. (2.0 mL). The solution was shaken for 30 min and then concentrated. The crude product was purified by preparative LC/MS and concentrated to afford the product as a trifluoroacetic acid salt. The product was redissolved into a small amount of DCM and treated with 1.0 N HCl in diethyl ether to afford 7-(3,5-difluoro-benzenesulfonyl)-1,2,3,4-tetrahydro-benzo[4,5]furo[2,3-c]pyridine hydrochloride. MS m/z 350 [M+H]$^+$ The following examples were prepared essentially as described above.

| Ex. # | Name | MS m/z [M + H]$^+$ | Stereo-chemistry | Salt | Starting material |
|---|---|---|---|---|---|
| 107 | 7-[(3,5-difluorophenyl)sulfonyl]-1,2,3,4-tetrahydro[1]benzofuro[2,3-c]pyridine | 350 | | HCl | 3,5-difluorobenzenethiol |
| 108 | (1S)-7-(phenylsulfonyl)-3,4,4',5'-tetrahydro-2H-spiro[1-benzofuro[2,3-c]pyridine-1,3'-furan] | 370 | enantiomer 1 | HCl | benzenethiol |
| 109 | (1S)-7-[(2,5-difluorophenyl)sulfonyl]-3,4,4',5'-tetrahydro-2H-spiro[1-benzofuro[2,3-c]pyridine-1,3'-furan] | 406 | enantiomer 1 | HCl | 2,5-difluorobenzenethiol |
| 110 | (1R)-7-(phenylsulfonyl)-3,4,4',5'-tetrahydro-2H-spiro[1-benzofuro[2,3-c]pyridine-1,3'-furan] | 370 | enantiomer 2 | HCl | benzenethiol |
| 111 | (1R)-7-[(2,5-difluorophenyl)sulfonyl]-3,4,4',5'-tetrahydro-2H-spiro[1-benzofuro[2,3-c]pyridine-1,3'-furan] | 406 | enantiomer 1 | HCl | 2,5-difluorobenzenethiol |
| 112 | 7-[(3-chlorophenyl)sulfonyl]-1,2,3,4,4a,9a-hexahydro[1]benzofuro[2,3-c]pyridine | 350 | racemic | HCl | 3-chlorobenzenethiol |
| 113 | 7-[(2-chlorophenyl)sulfonyl]-1,2,3,4,4a,9a-hexahydro[1]benzofuro[2,3-c]pyridine | 350 | racemic | HCl | 2-chlorobenzenethiol |
| 114 | 7-(naphthalen-1-ylsulfonyl)-1,2,3,4,4a,9a-hexahydro[1]benzofuro[2,3-c]pyridine | 366 | racemic | HCl | naphthalene-1-thiol |
| 115 | 7-[(3,4-dimethoxyphenyl)sulfonyl]-1,2,3,4,4a,9a-hexahydro[1]benzofuro[2,3-c]pyridine | 376 | racemic | HCl | 3,4-dimethoxybenzenethiol |
| 116 | 7-[(4-phenoxyphenyl)sulfonyl]-1,2,3,4,4a,9a-hexahydro[1]benzofuro[2,3-c]pyridine | 408 | racemic | HCl | 4-phenoxybenzenethiol |
| 117 | 7-[(3-fluorophenyl)sulfonyl]-1,2,3,4,4a,9a-hexahydro[1]benzofuro[2,3-c]pyridine | 334 | racemic | TFA | 3-fluorobenzenethiol |
| 118 | 7-[(3-methoxyphenyl)sulfonyl]-1,2,3,4,4a,9a-hexahydro[1]benzofuro[2,3-c]pyridine | 346 | racemic | TFA | 3-methoxybenzenethiol |
| 119 | 7-(2,3-dihydro-1,4-benzodioxin-6-ylsulfonyl)-1,2,3,4,4a,9a-hexahydro[1]benzofuro[2,3-c]pyridine | 374 | racemic | TFA | 2,3-dihydro-1,4-benzodioxine-6-thiol |
| 120 | 7-[(3,4-dichlorophenyl)sulfonyl]-1,2,3,4,4a,9a-hexahydro[1]benzofuro[2,3-c]pyridine | 384 | racemic | TFA | 3,4-dichlorobenzenethiol |
| 121 | 7-[(4-methylphenyl)sulfonyl]-1,2,3,4,4a,9a-hexahydro[1]benzofuro[2,3-c]pyridine | 330 | racemic | TFA | 4-methylbenzenethiol |
| 122 | 7-(naphthalen-2-ylsulfonyl)-1,2,3,4,4a,9a-hexahydro[1]benzofuro[2,3-c]pyridine | 366 | racemic | TFA | naphthalene-2-thiol |

-continued

| Ex. # | Name | MS m/z [M + H]+ | Stereo-chemistry | Salt | Starting material |
|---|---|---|---|---|---|
| 123 | 7-[(2,3-dichlorophenyl)sulfonyl]-1,2,3,4,4a,9a-hexahydro[1]benzofuro[2,3-c]pyridine | 384 | racemic | TFA | 2,3-dichlorobenzenethiol |
| 124 | 7-[(4-nitrophenyl)sulfonyl]-1,2,3,4,4a,9a-hexahydro[1]benzofuro[2,3-c]pyridine | 361 | racemic | TFA | 4-nitrobenzenethiol |
| 125 | 7-{[4-(propan-2-yl)phenyl]sulfonyl}-1,2,3,4,4a,9a-hexahydro[1]benzofuro[2,3-c]pyridine | 358 | racemic | TFA | 4-(propan-2-yl)benzenethiol |
| 126 | 7-{[3-(trifluoromethyl)phenyl]sulfonyl}-1,2,3,4,4a,9a-hexahydro[1]benzofuro[2,3-c]pyridine | 384 | racemic | HCl | 3-(trifluoromethyl)benzenethiol |
| 127 | 7-[(3-chloro-4-fluorophenyl)sulfonyl]-1,2,3,4,4a,9a-hexahydro[1]benzofuro[2,3-c]pyridine | 368 | racemic | HCl | 3-chloro-4-fluorobenzenethiol |
| 128 | 7-[(3,4-difluorophenyl)sulfonyl]-1,2,3,4,4a,9a-hexahydro[1]benzofuro[2,3-c]pyridine | 352 | racemic | HCl | 3,4-difluorobenzenethiol |
| 129 | 7-[(3-fluoro-4-methoxyphenyl)sulfonyl]-1,2,3,4,4a,9a-hexahydro[1]benzofuro[2,3-c]pyridine | 364 | racemic | HCl | 3-fluoro-4-methoxybenzenethiol |
| 130 | 7-[(5-fluoro-2-methylphenyl)sulfonyl]-1,2,3,4,4a,9a-hexahydro[1]benzofuro[2,3-c]pyridine | 348 | racemic | HCl | 5-fluoro-2-methylbenzenethiol |
| 131 | 7-[(3,5-difluorophenyl)sulfonyl]-1,2,3,4,4a,9a-hexahydro[1]benzofuro[2,3-c]pyridine | 352 | racemic | HCl | 3,5-difluorobenzenethiol |
| 132 | 7-[(5-fluoro-2-methoxyphenyl)sulfonyl]-1,2,3,4,4a,9a-hexahydro[1]benzofuro[2,3-c]pyridine | 364 | racemic | HCl | 5-fluoro-2-methoxybenzenethiol |
| 133 | 7-[(3-bromophenyl)sulfonyl]-1,2,3,4,4a,9a-hexahydro[1]benzofuro[2,3-c]pyridine | 394 | racemic | HCl | 3-bromobenzenethiol |
| 134 | 7-[(4-fluorophenyl)sulfonyl]-1,2,3,4,4a,9a-hexahydro[1]benzofuro[2,3-c]pyridine | 334 | racemic | HCl | 4-fluorobenzenethiol |
| 135 | 7-[(2,5-dichlorophenyl)sulfinyl]-1,2,3,4,4a,9a-hexahydro[1]benzofuro[2,3-c]pyridine | 368 | racemic | HCl | 2,5-dichlorobenzenethiol |
| 136 | 7-{[3-(propan-2-yloxy)phenyl]sulfonyl}-1,2,3,4,4a,9a-hexahydro[1]benzofuro[2,3-c]pyridine | 374 | racemic | HCl | 3-(propan-2-yloxy)benzenethiol |
| 137 | 7-[(4-fluoro-3-methylphenyl)sulfonyl]-1,2,3,4,4a,9a-hexahydro[1]benzofuro[2,3-c]pyridine | 348 | racemic | HCl | 4-fluoro-3-methylbenzenethiol |
| 138 | methyl 3-[1,2,3,4,4a,9a-hexahydro[1]benzofuro[2,3-c]pyridin-7-ylsulfonyl]benzoate | 374 | racemic | HCl | methyl 3-sulfanylbenzoate |

-continued

| Ex. # | Name | MS m/z [M + H]+ | Stereo-chemistry | Salt | Starting material |
|---|---|---|---|---|---|
| 139 | 4-[1,2,3,4,4a,9a-hexahydro[1]benzofuro[2,3-c]pyridin-7-ylsulfonyl]benzonitrile | 341 | racemic | HCl | 4-sulfanylbenzonitrile |
| 140 | N-{4-[1,2,3,4,4a,9a-hexahydro[1]benzofuro[2,3-c]pyridin-7-ylsulfonyl]phenyl}acetamide | 373 | racemic | HCl | N-(4-sulfanylphenyl)acetamide |
| 141 | 7-[(3-methylphenyl)sulfonyl]-1,2,3,4,4a,9a-hexahydro[1]benzofuro[2,3-c]pyridine | 330 | racemic | HCl | 3-methylbenzenethiol |
| 142 | 7-[(2,5-difluorophenyl)sulfinyl]-1,2,3,4,4a,9a-hexahydro[1]benzofuro[2,3-c]pyridine | 336 | racemic | HCl | 2,5-difluorobenzenethiol |
| 143 | 7-[(2,5-difluorophenyl)sulfonyl]-1,2,3,4,4a,9a-hexahydro[1]benzofuro[2,3-c]pyridine | 352 | racemic | HCl | 2,5-difluorobenzenethiol |
| 144 | 7-[(2,3,5,6-tetrafluorophenyl)sulfinyl]-1,2,3,4,4a,9a-hexahydro[1]benzofuro[2,3-c]pyridine | 372 | racemic | HCl | 2,3,5,6-tetrafluorobenzenethiol |
| 145 | 7-(biphenyl-4-ylsulfonyl)-1,2,3,4,4a,9a-hexahydro[1]benzofuro[2,3-c]pyridine | 392 | racemic | HCl | biphenyl-4-thiol |
| 146 | 7-[(2-fluorophenyl)sulfonyl]-1,2,3,4,4a,9a-hexahydro[1]benzofuro[2,3-c]pyridine | 334 | racemic | HCl | 2-fluorobenzenethiol |
| 147 | 7-[(3-chloro-5-fluorophenyl)sulfonyl]-1,2,3,4,4a,9a-hexahydro[1]benzofuro[2,3-c]pyridine | 368 | racemic | HCl | 3-chloro-5-fluorobenzenethiol |
| 148 | 7-{[4-chloro-3-(trifluoromethyl)phenyl]sulfonyl}-1,2,3,4,4a,9a-hexahydro[1]benzofuro[2,3-c]pyridine | 418 | racemic | HCl | 4-chloro-3-(trifluoromethyl)benzenethiol |
| 149 | 7-{[3-(trifluoromethoxy)phenyl]sulfonyl}-1,2,3,4,4a,9a-hexahydro[1]benzofuro[2,3-c]pyridine | 400 | racemic | HCl | 3-(trifluoromethoxy)benzenethiol |
| 150 | 7-[(2,3,5,6-tetrafluorophenyl)sulfonyl]-1,2,3,4,4a,9a-hexahydro[1]benzofuro[2,3-c]pyridine | 388 | racemic | HCl | 2,3,5,6-tetrafluorobenzenethiol |
| 151 | 7-{[4-(trifluoromethyl)phenyl]sulfonyl}-1,2,3,4,4a,9a-hexahydro[1]benzofuro[2,3-c]pyridine | 384 | racemic | HCl | 4-(trifluoromethyl)benzenethiol |
| 152 | 7-(biphenyl-2-ylsulfonyl)-1,2,3,4,4a,9a-hexahydro[1]benzofuro[2,3-c]pyridine | 392 | racemic | HCl | biphenyl-2-thiol |
| 153 | 7-(biphenyl-2-ylsulfonyl)-1,2,3,4,4a,9a-hexahydro[1]benzofuro[2,3-c]pyridine | 392 | racemic | HCl | biphenyl-2-thiol |
| 154 | 7-(cyclohexylsulfonyl)-1,2,3,4,4a,9a-hexahydro[1]benzofuro[2,3-c]pyridine | 322 | racemic | HCl | cyclohexanethiol |
| 155 | 7-[(3,5-dichlorophenyl)sulfonyl]-1,2,3,4,4a,9a-hexahydro[1]benzofuro[2,3-c]pyridine | 384 | racemic | HCl | 3,5-dichlorobenzenethiol |

-continued

| Ex. # | Name | MS m/z [M + H]+ | Stereo-chemistry | Salt | Starting material |
|---|---|---|---|---|---|
| 156 | 7-[(2,3-dichlorophenyl)sulfonyl]-1,2,3,4,4a,9a-hexahydro[1]benzofuro[2,3-c]pyridine | 384 | enantiomer 1 | HCl | 2,3-dichlorobenzenethiol |
| 157 | 7-[(3-chloro-5-fluorophenyl)sulfonyl]-1,2,3,4,4a,9a-hexahydro[1]benzofuro[2,3-c]pyridine | 368 | enantiomer 1 | HCl | 3-chloro-5-fluorobenzenethiol |
| 158 | 7-[(3,5-difluorophenyl)sulfonyl]-1,2,3,4,4a,9a-hexahydro[1]benzofuro[2,3-c]pyridine | 352 | enantiomer 1 | HCl | 3,5-difluorobenzenethiol |
| 159 | 7-{[3-(propan-2-yloxy)phenyl]sulfonyl}-1,2,3,4,4a,9a-hexahydro[1]benzofuro[2,3-c]pyridine | 374 | enantiomer 1 | HCl | 3-(propan-2-yloxy)benzenethiol |
| 160 | 7-{[3-(trifluoromethoxy)phenyl]sulfonyl}-1,2,3,4,4a,9a-hexahydro[1]benzofuro[2,3-c]pyridine | 400 | enantiomer 1 | HCl | 3-(trifluoromethoxy)benzenethiol |
| 161 | 7-{[3-(trifluoromethyl)phenyl]sulfonyl}-1,2,3,4,4a,9a-hexahydro[1]benzofuro[2,3-c]pyridine | 384 | enantiomer 1 | HCl | 3-(trifluoromethyl)benzenethiol |
| 162 | 7-[(2,3-dichlorophenyl)sulfonyl]-1,2,3,4,4a,9a-hexahydro[1]benzofuro[2,3-c]pyridine | 384 | enantiomer 2 | HCl | 2,3-dichlorobenzenethiol |
| 163 | 7-[(3-chloro-5-fluorophenyl)sulfonyl]-1,2,3,4,4a,9a-hexahydro[1]benzofuro[2,3-c]pyridine | 368 | enantiomer 2 | HCl | 3-chloro-5-fluorobenzenethiol |
| 164 | 7-[(3,5-difluorophenyl)sulfonyl]-1,2,3,4,4a,9a-hexahydro[1]benzofuro[2,3-c]pyridine | 352 | enantiomer 2 | HCl | 3,5-difluorobenzenethiol |
| 165 | 7-{[3-(propan-2-yloxy)phenyl]sulfonyl}-1,2,3,4,4a,9a-hexahydro[1]benzofuro[2,3-c]pyridine | 374 | enantiomer 2 | HCl | 3-(propan-2-yloxy)benzenethiol |
| 166 | 7-{[3-(trifluoromethoxy)phenyl]sulfonyl}-1,2,3,4,4a,9a-hexahydro[1]benzofuro[2,3-c]pyridine | 400 | enantiomer 2 | HCl | 3-(trifluoromethoxy)benzenethiol |
| 167 | 7-{[3-(trifluoromethyl)phenyl]sulfonyl}-1,2,3,4,4a,9a-hexahydro[1]benzofuro[2,3-c]pyridine | 384 | enantiomer 2 | HCl | 3-(trifluoromethyl)benzenethiol |
| 168 | 6-[(3-fluorophenyl)sulfonyl]-1,2,3,4,4a,9a-hexahydro[1]benzofuro[2,3-c]pyridine | 334 | racemic | HCl | 3-fluorobenzenethiol |
| 169 | 6-[(2-chlorophenyl)sulfonyl]-1,2,3,4,4a,9a-hexahydro[1]benzofuro[2,3-c]pyridine | 350 | racemic | HCl | 2-chlorobenzenethiol |
| 170 | 6-(naphthalen-1-ylsulfonyl)-1,2,3,4,4a,9a-hexahydro[1]benzofuro[2,3-c]pyridine | 366 | racemic | HCl | naphthalene-1-thiol |

-continued

| Ex. # | Name | MS m/z [M + H]+ | Stereo-chemistry | Salt | Starting material |
|---|---|---|---|---|---|
| 171 | 6-[(3,4-dimethoxyphenyl)sulfonyl]-1,2,3,4,4a,9a-hexahydro[1]benzofuro[2,3-c]pyridine | 376 | racemic | HCl | 3,4-dimethoxybenzenethiol |
| 172 | 6-[(3,4-dichlorophenyl)sulfonyl]-1,2,3,4,4a,9a-hexahydro[1]benzofuro[2,3-c]pyridine | 384 | racemic | HCl | 3,4-dichlorobenzenethiol |
| 173 | 6-[(4-phenoxyphenyl)sulfonyl]-1,2,3,4,4a,9a-hexahydro[1]benzofuro[2,3-c]pyridine | 408 | racemic | HCl | 4-phenoxybenzenethiol |
| 174 | 6-[(4-methylphenyl)sulfonyl]-1,2,3,4,4a,9a-hexahydro[1]benzofuro[2,3-c]pyridine | 330 | racemic | HCl | 4-methylbenzenethiol |
| 175 | 6-(naphthalen-2-ylsulfonyl)-1,2,3,4,4a,9a-hexahydro[1]benzofuro[2,3-c]pyridine | 366 | racemic | HCl | naphthalene-2-thiol |
| 176 | 6-[(2,3-dichlorophenyl)sulfonyl]-1,2,3,4,4a,9a-hexahydro[1]benzofuro[2,3-c]pyridine | 384 | racemic | HCl | 2,3-dichlorobenzenethiol |
| 177 | 6-[(4-nitrophenyl)sulfonyl]-1,2,3,4,4a,9a-hexahydro[1]benzofuro[2,3-c]pyridine | 361 | racemic | HCl | 4-nitrobenzenethiol |
| 178 | 6-[(3-methoxyphenyl)sulfonyl]-1,2,3,4,4a,9a-hexahydro[1]benzofuro[2,3-c]pyridine | 346 | racemic | TFA | 3-methoxybenzenethiol |
| 179 | 6-{[4-(propan-2-yl)phenyl]sulfonyl}-1,2,3,4,4a,9a-hexahydro[1]benzofuro[2,3-c]pyridine | 358 | racemic | TFA | 4-(propan-2-yl)benzenethiol |
| 180 | 6-(2,3-dihydro-1,4-benzodioxin-6-ylsulfonyl)-1,2,3,4,4a,9a-hexahydro[1]benzofuro[2,3-c]pyridine | 374 | racemic | TFA | 2,3-dihydro-1,4-benzodioxine-6-thiol |
| 181 | 6-(phenylsulfonyl)-1,2,3,4,4a,9a-hexahydro[1]benzofuro[2,3-c]pyridine | 316 | racemic | TFA | benzenethiol |
| 182 | 8-[(3-methoxyphenyl)sulfonyl]-1,2,3,4,4a,9a-hexahydro[1]benzofuro[2,3-c]pyridine | 346 | racemic | TFA | 3-methoxybenzenethiol |
| 183 | 8-[(2-chlorophenyl)sulfonyl]-1,2,3,4,4a,9a-hexahydro[1]benzofuro[2,3-c]pyridine | 350 | racemic | TFA | 2-chlorobenzenethiol |
| 184 | 8-(naphthalen-1-ylsulfonyl)-1,2,3,4,4a,9a-hexahydro[1]benzofuro[2,3-c]pyridine | 366 | racemic | TFA | naphthalene-1-thiol |
| 185 | 8-(2,3-dihydro-1,4-benzodioxin-6-ylsulfonyl)-1,2,3,4,4a,9a-hexahydro[1]benzofuro[2,3-c]pyridine | 374 | racemic | TFA | 2,3-dihydro-1,4-benzodioxine-6-thiol |
| 186 | 8-[(3,4-dichlorophenyl)sulfonyl]-1,2,3,4,4a,9a-hexahydro[1]benzofuro[2,3-c]pyridine | 384 | racemic | TFA | 3,4-dichlorobenzenethiol |
| 187 | 8-[(4-methoxyphenyl)sulfonyl]-1,2,3,4,4a,9a-hexahydro[1]benzofuro[2,3-c]pyridine | 346 | racemic | TFA | 4-methoxybenzenethiol |

-continued

| Ex. # | Name | MS m/z [M + H]+ | Stereo-chemistry | Salt | Starting material |
|---|---|---|---|---|---|
| 188 | 8-[(4-chlorophenyl)sulfonyl]-1,2,3,4,4a,9a-hexahydro[1]benzofuro[2,3-c]pyridine | 350 | racemic | TFA | 4-chlorobenzenethiol |
| 189 | 8-(naphthalen-2-ylsulfonyl)-1,2,3,4,4a,9a-hexahydro[1]benzofuro[2,3-c]pyridine | 366 | racemic | TFA | naphthalene-2-thiol |
| 190 | 8-[(4-nitrophenyl)sulfonyl]-1,2,3,4,4a,9a-hexahydro[1]benzofuro[2,3-c]pyridine | 361 | racemic | TFA | 4-nitrobenzenethiol |
| 191 | 8-(biphenyl-2-ylsulfonyl)-1,2,3,4,4a,9a-hexahydro[1]benzofuro[2,3-c]pyridine | 392 | racemic | TFA | biphenyl-2-thiol |
| 192 | 7-{[3-(trifluoromethyl)phenyl]sulfonyl}-1,2,3,4-tetrahydro[1]benzofuro[2,3-c]pyridine | 382 | | HCl | 3-(trifluoromethyl)benzenethiol |
| 193 | 7-[(3-chloro-4-fluorophenyl)sulfonyl]-1,2,3,4-tetrahydro[1]benzofuro[2,3-c]pyridine | 366 | | HCl | 3-chloro-4-fluorobenzenethiol |
| 194 | 7-[(3-fluoro-4-methoxyphenyl)sulfonyl]-1,2,3,4-tetrahydro[1]benzofuro[2,3-c]pyridine | 362 | | HCl | 3-fluoro-4-methoxybenzenethiol |
| 195 | 7-{[4-(propan-2-yl)phenyl]sulfonyl}-1,2,3,4-tetrahydro[1]benzofuro[2,3-c]pyridine | 356 | | HCl | 4-(propan-2-yl)benzenethiol |
| 196 | 7-[(2,3-dichlorophenyl)sulfonyl]-1,2,3,4-tetrahydro[1]benzofuro[2,3-c]pyridine | 381 | | HCl | 2,3-dichlorobenzenethiol |
| 197 | 7-[(3,4-dichlorophenyl)sulfonyl]-1,2,3,4-tetrahydro[1]benzofuro[2,3-c]pyridine | 381 | | HCl | 3,4-dichlorobenzenethiol |
| 198 | 7-[(4-methoxyphenyl)sulfonyl]-1,2,3,4-tetrahydro[1]benzofuro[2,3-c]pyridine | 344 | | HCl | 4-methoxybenzenethiol |
| 199 | 7-[(3-methoxyphenyl)sulfonyl]-1,2,3,4-tetrahydro[1]benzofuro[2,3-c]pyridine | 344 | | HCl | 3-methoxybenzenethiol |
| 200 | 7-(2,3-dihydro-1,4-benzodioxin-6-ylsulfonyl)-1,2,3,4-tetrahydro[1]benzofuro[2,3-c]pyridine | 372 | | HCl | 2,3-dihydro-1,4-benzodioxine-6-thiol |
| 201 | 7-[(4-phenoxyphenyl)sulfonyl]-1,2,3,4-tetrahydro[1]benzofuro[2,3-c]pyridine | 406 | | HCl | 4-phenoxybenzenethiol |
| 202 | 7-(naphthalen-1-ylsulfonyl)-1,2,3,4-tetrahydro[1]benzofuro[2,3-c]pyridine | 364 | | HCl | naphthalene-1-thiol |
| 203 | 7-[(4-chlorophenyl)sulfonyl]-1,2,3,4-tetrahydro[1]benzofuro[2,3-c]pyridine | 348 | | HCl | 4-chlorobenzenethiol |
| 204 | 7-[(4-methylphenyl)sulfonyl]-1,2,3,4-tetrahydro[1]benzofuro[2,3-c]pyridine | 328 | | HCl | 4-methylbenzenethiol |

-continued

| Ex. # | Name | MS m/z [M + H]+ | Stereo-chemistry | Salt | Starting material |
|---|---|---|---|---|---|
| 205 | 7-[(4-nitrophenyl)sulfonyl]-1,2,3,4-tetrahydro[1]benzofuro[2,3-c]pyridine | 359 | | HCl | 4-nitrobenzenethiol |
| 206 | 7-[(5-fluoro-2-methylphenyl)sulfonyl]-1,2,3,4-tetrahydro[1]benzofuro[2,3-c]pyridine | 346 | | HCl | 5-fluoro-2-methylbenzenethiol |
| 207 | 7-[(3-chloro-5-fluorophenyl)sulfonyl]-1,2,3,4-tetrahydro[1]benzofuro[2,3-c]pyridine | 366 | | HCl | 3-chloro-5-fluorobenzenethiol |
| 208 | 7-[(3,5-difluorophenyl)sulfonyl]-1,2,3,4-tetrahydro[1]benzofuro[2,3-c]pyridine | 350 | | HCl | 3,5-difluorobenzenethiol |
| 209 | 7-{[4-chloro-3-(trifluoromethyl)phenyl]sulfinyl}-1,2,3,4-tetrahydro[1]benzofuro[2,3-c]pyridine | 400 | racemic | HCl | 4-chloro-3-(trifluoromethyl)benzenethiol |
| 210 | 7-{[4-chloro-3-(trifluoromethyl)phenyl]sulfonyl}-1,2,3,4-tetrahydro[1]benzofuro[2,3-c]pyridine | 416 | | HCl | 4-chloro-3-(trifluoromethyl)benzenethiol |
| 211 | 7-[(3,5-dichlorophenyl)sulfonyl]-1,2,3,4-tetrahydro[1]benzofuro[2,3-c]pyridine | 381 | | HCl | 3,5-dichlorobenzenethiol |
| 212 | 7-[(3-bromophenyl)sulfonyl]-1,2,3,4-tetrahydro[1]benzofuro[2,3-c]pyridine | 391 | | HCl | 3-bromobenzenethiol |
| 213 | 7-[(4-fluorophenyl)sulfonyl]-1,2,3,4-tetrahydro[1]benzofuro[2,3-c]pyridine | 332 | | HCl | 4-fluorobenzenethiol |
| 214 | 7-[(2,5-dichlorophenyl)sulfinyl]-1,2,3,4-tetrahydro[1]benzofuro[2,3-c]pyridine | 366 | racemic | HCl | 2,5-dichlorobenzenethiol |
| 215 | 7-[(2,5-dichlorophenyl)sulfonyl]-1,2,3,4-tetrahydro[1]benzofuro[2,3-c]pyridine | 381 | | HCl | 2,5-dichlorobenzenethiol |
| 216 | 7-{[3-(propan-2-yloxy)phenyl]sulfinyl}-1,2,3,4-tetrahydro[1]benzofuro[2,3-c]pyridine | 356 | racemic | HCl | 3-(propan-2-yloxy)benzenethiol |
| 217 | 7-{[3-(propan-2-yloxy)phenyl]sulfonyl}-1,2,3,4-tetrahydro[1]benzofuro[2,3-c]pyridine | 372 | | HCl | 3-(propan-2-yloxy)benzenethiol |
| 218 | 7-[(4-fluoro-3-methylphenyl)sulfonyl]-1,2,3,4-tetrahydro[1]benzofuro[2,3-c]pyridine | 346 | | HCl | 4-fluoro-3-methylbenzenethiol |
| 219 | methyl 3-(1,2,3,4-tetrahydro[1]benzofuro[2,3-c]pyridin-7-ylsulfonyl)benzoate | 372 | | HCl | methyl 3-sulfanylbenzoate |
| 220 | 4-(1,2,3,4-tetrahydro[1]benzofuro[2,3-c]pyridin-7-ylsulfonyl)benzonitrile | 339 | | HCl | 4-sulfanylbenzonitrile |
| 221 | 7-[(3-methylphenyl)sulfonyl]-1,2,3,4-tetrahydro[1]benzofuro[2,3-c]pyridine | 328 | | HCl | 3-methylbenzenethiol |

-continued

| Ex. # | Name | MS m/z [M + H]+ | Stereo- chemistry | Salt | Starting material |
|---|---|---|---|---|---|
| 222 | 7-[(2,5-difluorophenyl)sulfinyl]-1,2,3,4-tetrahydro[1]benzofuro[2,3-c]pyridine | 334 | racemic | HCl | 2,5-difluorobenzenethiol |
| 223 | 7-[(2,5-difluorophenyl)sulfonyl]-1,2,3,4-tetrahydro[1]benzofuro[2,3-c]pyridine | 350 | | HCl | 2,5-difluorobenzenethiol |
| 224 | 7-[(2,3,5,6-tetrafluorophenyl)sulfinyl]-1,2,3,4-tetrahydro[1]benzofuro[2,3-c]pyridine | 370 | racemic | HCl | 2,3,5,6-tetrafluorobenzenethiol |
| 225 | 7-[(2,3,5,6-tetrafluorophenyl)sulfonyl]-1,2,3,4-tetrahydro[1]benzofuro[2,3-c]pyridine | 386 | | HCl | 2,3,5,6-tetrafluorobenzenethiol |
| 226 | 7-{[4-(trifluoromethoxy)phenyl]sulfinyl}-1,2,3,4-tetrahydro[1]benzofuro[2,3-c]pyridine | 382 | racemic | HCl | 4-(trifluoromethoxy)benzenethiol |
| 227 | 7-{[4-(trifluoromethoxy)phenyl]sulfonyl}-1,2,3,4-tetrahydro[1]benzofuro[2,3-c]pyridine | 398 | | HCl | 4-(trifluoromethoxy)benzenethiol |
| 228 | 7-(biphenyl-4-ylsulfonyl)-1,2,3,4-tetrahydro[1]benzofuro[2,3-c]pyridine | 390 | | HCl | biphenyl-4-thiol |
| 229 | 7-[(2-chlorophenyl)sulfinyl]-1,2,3,4-tetrahydro[1]benzofuro[2,3-c]pyridine | 332 | racemic | HCl | 2-chlorobenzenethiol |
| 230 | 7-[(2-chlorophenyl)sulfonyl]-1,2,3,4-tetrahydro[1]benzofuro[2,3-c]pyridine | 348 | | HCl | 2-chlorobenzenethiol |
| 231 | 7-[(2-fluorophenyl)sulfonyl]-1,2,3,4-tetrahydro[1]benzofuro[2,3-c]pyridine | 332 | | HCl | 2-fluorobenzenethiol |
| 232 | 7-(biphenyl-2-ylsulfonyl)-1,2,3,4-tetrahydro[1]benzofuro[2,3-c]pyridine | 390 | | HCl | biphenyl-2-thiol |
| 233 | 7-(cyclohexylsulfonyl)-1,2,3,4-tetrahydro[1]benzofuro[2,3-c]pyridine | 320 | | HCl | cyclohexanethiol |
| 234 | 7-(propan-2-ylsulfonyl)-1,2,3,4-tetrahydro[1]benzofuro[2,3-c]pyridine | 280 | | HCl | propane-2-thiol |
| 235 | 1-methyl-7-(phenylsulfonyl)-1,2,3,4-tetrahydro[1]benzofuro[2,3-c]pyridine | 328 | | HCl | benzenethiol |
| 236 | 7-[(3-fluoro-4-methoxyphenyl)sulfonyl]-1-methyl-1,2,3,4-tetrahydro[1]benzofuro[2,3-c]pyridine | 376 | racemic | HCl | 3-fluoro-4-methoxybenzenethiol |
| 237 | 1-methyl-7-{[3-(trifluoromethyl)phenyl]sulfonyl}-1,2,3,4-tetrahydro[1]benzofuro[2,3-c]pyridine | 396 | racemic | HCl | 3-(trifluoromethyl)benzenethiol |
| 238 | 7-[(3,4-difluorophenyl)sulfonyl]-1-methyl-1,2,3,4-tetrahydro[1]benzofuro[2,3-c]pyridine | 364 | racemic | HCl | 3,4-difluorobenzenethiol |

| Ex. # | Name | MS m/z [M + H]+ | Stereo-chemistry | Salt | Starting material |
|---|---|---|---|---|---|
| 239 | 6-{[3-(trifluoromethyl)phenyl]sulfonyl}-1,2,3,4-tetrahydro[1]benzofuro[2,3-c]pyridine | 382 | | HCl | 3-(trifluoromethyl)benzenethiol |
| 240 | 6-[(3,4-difluorophenyl)sulfonyl]-1,2,3,4-tetrahydro[1]benzofuro[2,3-c]pyridine | 350 | | HCl | 3,4-difluorobenzenethiol |
| 241 | 6-[(3-fluoro-4-methoxyphenyl)sulfonyl]-1,2,3,4-tetrahydro[1]benzofuro[2,3-c]pyridine | 362 | | HCl | 3-fluoro-4-methoxybenzenethiol |
| 242 | 6-[(3,4-dimethoxyphenyl)sulfonyl]-1,2,3,4-tetrahydro[1]benzofuro[2,3-c]pyridine | 374 | | HCl | 3,4-dimethoxybenzenethiol |
| 243 | 6-[(3-chlorophenyl)sulfonyl]-1,2,3,4-tetrahydro[1]benzofuro[2,3-c]pyridine | 348 | | HCl | 3-chlorobenzenethiol |
| 244 | 6-[(3-fluorophenyl)sulfonyl]-1,2,3,4-tetrahydro[1]benzofuro[2,3-c]pyridine | 332 | | HCl | 3-fluorobenzenethiol |
| 245 | 6-[(4-methoxyphenyl)sulfonyl]-1,2,3,4-tetrahydro[1]benzofuro[2,3-c]pyridine | 344 | | HCl | 4-methoxybenzenethiol |
| 246 | 6-[(3-methoxyphenyl)sulfonyl]-1,2,3,4-tetrahydro[1]benzofuro[2,3-c]pyridine | 344 | | HCl | 3-methoxybenzenethiol |
| 247 | 6-(2,3-dihydro-1,4-benzodioxin-6-ylsulfonyl)-1,2,3,4-tetrahydro[1]benzofuro[2,3-c]pyridine | 372 | | HCl | 2,3-dihydro-1,4-benzodioxine-6-thiol |
| 248 | 6-[(4-phenoxyphenyl)sulfonyl]-1,2,3,4-tetrahydro[1]benzofuro[2,3-c]pyridine | 406 | | HCl | 4-phenoxybenzenethiol |
| 249 | 6-(naphthalen-1-ylsulfonyl)-1,2,3,4-tetrahydro[1]benzofuro[2,3-c]pyridine | 364 | | HCl | naphthalene-1-thiol |
| 250 | 6-[(4-chlorophenyl)sulfonyl]-1,2,3,4-tetrahydro[1]benzofuro[2,3-c]pyridine | 348 | | HCl | 4-chlorobenzenethiol |
| 251 | 6-(naphthalen-2-ylsulfonyl)-1,2,3,4-tetrahydro[1]benzofuro[2,3-c]pyridine | 364 | | HCl | naphthalene-2-thiol |
| 252 | 6-[(4-methylphenyl)sulfonyl]-1,2,3,4-tetrahydro[1]benzofuro[2,3-c]pyridine | 328 | | HCl | 4-methylbenzenethiol |
| 253 | 6-[(4-nitrophenyl)sulfonyl]-1,2,3,4-tetrahydro[1]benzofuro[2,3-c]pyridine | 359 | | HCl | 4-nitrobenzenethiol |
| 254 | 6-[(5-fluoro-2-methylphenyl)sulfonyl]-1,2,3,4-tetrahydro[1]benzofuro[2,3-c]pyridine | 346 | | HCl | 5-fluoro-2-methylbenzenethiol |
| 255 | 6-[(3-chloro-5-fluorophenyl)sulfonyl]-1,2,3,4-tetrahydro[1]benzofuro[2,3-c]pyridine | 366 | | HCl | 3-chloro-5-fluorobenzenethiol |

-continued

| Ex. # | Name | MS m/z [M + H]+ | Stereo-chemistry | Salt | Starting material |
|---|---|---|---|---|---|
| 256 | 6-[(3,5-difluorophenyl)sulfonyl]-1,2,3,4-tetrahydro[1]benzofuro[2,3-c]pyridine | 350 | | HCl | 3,5-difluorobenzenethiol |
| 257 | 6-{[4-chloro-3-(trifluoromethyl)phenyl]sulfonyl}-1,2,3,4-tetrahydro[1]benzofuro[2,3-c]pyridine | 416 | | HCl | 4-chloro-3-(trifluoromethyl)benzenethiol |
| 258 | 6-[(3-chloro-4-fluorophenyl)sulfonyl]-1,2,3,4-tetrahydro[1]benzofuro[2,3-c]pyridine | 366 | | HCl | 3-chloro-4-fluorobenzenethiol |
| 259 | 6-{[4-(propan-2-yl)phenyl]sulfonyl}-1,2,3,4-tetrahydro[1]benzofuro[2,3-c]pyridine | 356 | | HCl | 4-(propan-2-yl)benzenethiol |
| 260 | 6-[(2,3-dichlorophenyl)sulfonyl]-1,2,3,4-tetrahydro[1]benzofuro[2,3-c]pyridine | 381 | | HCl | 2,3-dichlorobenzenethiol |
| 261 | 6-[(3,4-dichlorophenyl)sulfonyl]-1,2,3,4-tetrahydro[1]benzofuro[2,3-c]pyridine | 381 | | HCl | 3,4-dichlorobenzenethiol |
| 262 | 6-[(3,5-dichlorophenyl)sulfonyl]-1,2,3,4-tetrahydro[1]benzofuro[2,3-c]pyridine | 381 | | HCl | 3,5-dichlorobenzenethiol |
| 263 | 6-[(3-bromophenyl)sulfonyl]-1,2,3,4-tetrahydro[1]benzofuro[2,3-c]pyridine | 391 | | HCl | 3-bromobenzenethiol |
| 264 | 6-[(4-fluorophenyl)sulfonyl]-1,2,3,4-tetrahydro[1]benzofuro[2,3-c]pyridine | 332 | | HCl | 4-fluorobenzenethiol |
| 265 | 6-[(4-fluorophenyl)sulfonyl]-1,2,3,4-tetrahydro[1]benzofuro[2,3-c]pyridine | 332 | | HCl | 4-fluorobenzenethiol |
| 266 | 6-[(2,5-dichlorophenyl)sulfonyl]-1,2,3,4-tetrahydro[1]benzofuro[2,3-c]pyridine | 381 | | HCl | 2,5-dichlorobenzenethiol |
| 267 | 6-{[3-(propan-2-yloxy)phenyl]sulfonyl}-1,2,3,4-tetrahydro[1]benzofuro[2,3-c]pyridine | 372 | | HCl | 3-(propan-2-yloxy)benzenethiol |
| 268 | 6-[(4-fluoro-3-methylphenyl)sulfonyl]-1,2,3,4-tetrahydro[1]benzofuro[2,3-c]pyridine | 346 | | HCl | 4-fluoro-3-methylbenzenethiol |
| 269 | methyl 3-(1,2,3,4-tetrahydro[1]benzofuro[2,3-c]pyridin-6-ylsulfonyl)benzoate | 372 | | HCl | methyl 3-sulfanylbenzoate |
| 270 | 6-{[3-(trifluoromethoxy)phenyl]sulfonyl}-1,2,3,4-tetrahydro[1]benzofuro[2,3-c]pyridine | 398 | | HCl | 3-(trifluoromethoxy)benzenethiol |
| 271 | 4-(1,2,3,4-tetrahydro[1]benzofuro[2,3-c]pyridin-6-ylsulfonyl)benzonitrile | 339 | | HCl | 4-sulfanylbenzonitrile |
| 272 | N-[4-(1,2,3,4-tetrahydro[1]benzofuro[2,3-c]pyridin-6-ylsulfonyl)phenyl]acetamide | 371 | | HCl | N-(4-sulfanylphenyl)acetamide |

| Ex. # | Name | MS m/z [M + H]+ | Stereo-chemistry | Salt | Starting material |
|---|---|---|---|---|---|
| 273 | 6-[(2,5-difluorophenyl)sulfonyl]-1,2,3,4-tetrahydro[1]benzofuro[2,3-c]pyridine | 350 | | HCl | 2,5-difluorobenzenethiol |
| 274 | 6-[(2,3,5,6-tetrafluorophenyl)sulfonyl]-1,2,3,4-tetrahydro[1]benzofuro[2,3-c]pyridine | 386 | | HCl | 2,3,5,6-tetrafluorobenzenethiol |
| 275 | 6-{[4-(trifluoromethoxy)phenyl]sulfonyl}-1,2,3,4-tetrahydro[1]benzofuro[2,3-c]pyridine | 398 | | HCl | 4-(trifluoromethoxy)benzenethiol |
| 276 | 6-[(2-chlorophenyl)sulfonyl]-1,2,3,4-tetrahydro[1]benzofuro[2,3-c]pyridine | 348 | | HCl | 2-chlorobenzenethiol |
| 277 | 6-[(2-fluorophenyl)sulfonyl]-1,2,3,4-tetrahydro[1]benzofuro[2,3-c]pyridine | 332 | | HCl | 2-fluorobenzenethiol |
| 278 | 6-{[4-(trifluoromethyl)phenyl]sulfonyl}-1,2,3,4-tetrahydro[1]benzofuro[2,3-c]pyridine | 382 | | HCl | 4-(trifluoromethyl)benzenethiol |
| 279 | 6-(biphenyl-2-ylsulfinyl)-1,2,3,4-tetrahydro[1]benzofuro[2,3-c]pyridine | 374 | racemic | HCl | biphenyl-2-thiol |
| 280 | 6-(cyclohexylsulfonyl)-1,2,3,4-tetrahydro[1]benzofuro[2,3-c]pyridine | 320 | | HCl | cyclohexanethiol |
| 281 | 6-(propan-2-ylsulfonyl)-1,2,3,4-tetrahydro[1]benzofuro[2,3-c]pyridine | 280 | | HCl | propane-2-thiol |
| 282 | 1-methyl-6-{[3-(trifluoromethyl)phenyl]sulfonyl}-1,2,3,4-tetrahydro[1]benzofuro[2,3-c]pyridine | 396 | racemic | HCl | 3-(trifluoromethyl)benzenethiol |
| 283 | 6-[(3-fluorophenyl)sulfonyl]-1-methyl-1,2,3,4-tetrahydro[1]benzofuro[2,3-c]pyridine | 346 | racemic | HCl | 3-fluorobenzenethiol |
| 284 | 6-[(3,4-difluorophenyl)sulfonyl]-1-methyl-1,2,3,4-tetrahydro[1]benzofuro[2,3-c]pyridine | 364 | racemic | HCl | 3,4-difluorobenzenethiol |
| 285 | 6-[(3-fluoro-4-methoxyphenyl)sulfonyl]-1-methyl-1,2,3,4-tetrahydro[1]benzofuro[2,3-c]pyridine | 376 | racemic | HCl | 3-fluoro-4-methoxybenzenethiol |
| 286 | 4,4-dimethyl-7-(phenylsulfonyl)-1,2,3,4-tetrahydro[1]benzofuro[2,3-c]pyridine | 342 | | HCl | benzenethiol |
| 287 | 7-[(3,5-difluorophenyl)sulfonyl]-4,4-dimethyl-1,2,3,4-tetrahydro[1]benzofuro[2,3-c]pyridine | 378 | | HCl | 3,5-difluorobenzenethiol |
| 288 | 7-[(3-fluoro-4-methoxyphenyl)sulfonyl]-1,1-dimethyl-1,2,3,4-tetrahydro[1]benzofuro[2,3-c]pyridine | 390 | | HCl | 3-fluoro-4-methoxybenzenethiol |

-continued

| Ex. # | Name | MS m/z [M + H]+ | Stereo-chemistry | Salt | Starting material |
|---|---|---|---|---|---|
| 289 | 1,1-dimethyl-7-{[3-(trifluoromethyl)phenyl]sulfonyl}-1,2,3,4-tetrahydro[1]benzofuro[2,3-c]pyridine | 410 | | HCl | 3-(trifluoromethyl)benzenethiol |
| 290 | 7-[(3,4-difluorophenyl)sulfonyl]-1,1-dimethyl-1,2,3,4-tetrahydro[1]benzofuro[2,3-c]pyridine | 378 | | HCl | 3,4-difluorobenzenethiol |
| 291 | 1,1-dimethyl-7-{[3-(trifluoromethoxy)phenyl]sulfonyl}-1,2,3,4-tetrahydro[1]benzofuro[2,3-c]pyridine | 426 | | HCl | 3-(trifluoromethoxy)benzenethiol |
| 292 | 1,1-dimethyl-7-(phenylsulfonyl)-1,2,3,4-tetrahydro[1]benzofuro[2,3-c]pyridine | 342 | | TFA | benzenethiol |
| 293 | 7-[(3,5-difluorophenyl)sulfonyl]-1,1-dimethyl-1,2,3,4-tetrahydro[1]benzofuro[2,3-c]pyridine | 378 | | TFA | 3,5-difluorobenzenethiol |
| 294 | 6-[(3-chlorophenyl)sulfonyl]-1,2,3,4,4a,9a-hexahydro[1]benzofuro[2,3-c]pyridine | 350 | racemic | TFA | 3-chlorobenzenethiol |

Example 294

6-[(3-Chlorophenyl)sulfonyl]-1,2,3,4,4a,9a-hexahydro[1]benzofuro[2,3-c]pyridine trifluoroacetic acid salt

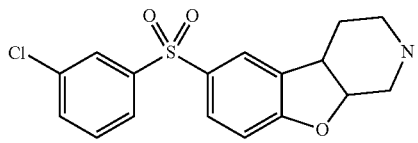 [SMILES: O=S(=O)(c1cccc(Cl)c1)c1ccc2c(c1)C1CCNCC1O2]

Step 1

6-(3-Chlorophenylsulfanyl)-3,4,4a,9a-tetrahydro-1H-benzo[4,5]furo[2,3-c]pyridine-2-carboxylic acid tert-butyl ester

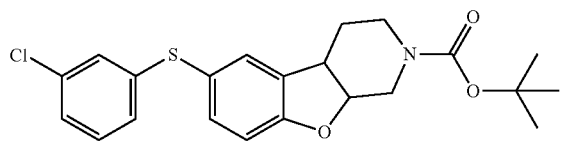 [SMILES: CC(C)(C)OC(=O)N1CCC2c3cc(Sc4cccc(Cl)c4)ccc3OC2C1]

Anhydrous DMF was sparged with argon gas for 1 h before being used. 6-Iodo-3,4,4a,9a-tetrahydro-1H-benzofuro[2,3-c]pyridine-2-carboxylic acid tert-butyl ester (80.25 mg, 0.200 mmol) was dissolved into anhydrous DMF (2.50 mL) in a one dram vial. The sodium tert-butoxide (58 mg, 0.60 mmol), neocuproine (4.2 mg, 0.020 mmol) and copper (I) iodide (11 mg, 0.060 mmol) were added sequentially at room temperature. 3-Chlorobenzenethiol (63.6 mg, 0.440 mmol) was added neat last. The reaction was shaken at 110° C. overnight. It was cooled to room temperature and concentrated. The residue was partially dissolved into a 2% MeOH in DCM solvent mixture (2.0 mL) with sonication. Silica gel (~55 mg) was added into a filter plate. The suspension of product was flushed through the dry silica gel using 2% MeOH in DCM. The eluent was then concentrated to yield crude 6-(3-chlorophenylsulfanyl)-3,4,4a,9a-tetrahydro-1H-benzo[4,5]furo[2,3-c]pyridine-2-carboxylic acid tert-butyl ester which was used in the next step without further purification. MS m/z 418 [M+H]+

Step 2

6-(3-Chloro-benzenesulfonyl)-3,4,4a,9a-tetrahydro-1H-benzo[4,5]furo[2,3-c]pyridine-2-carboxylic acid tert-butyl ester

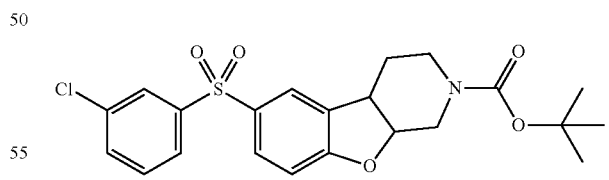

6-(3-Chlorophenylsulfanyl)-3,4,4a,9a-tetrahydro-1H-benzo[4,5]furo[2,3-c]pyridine-2-carboxylic acid tert-butyl ester (83.6 mg, 0.20 mmol, 1.0 eq) was dissolved into DCM (1 mL). To this was added 70% m-Chloroperbenzoic acid (120 mg, 0.50 mmol) in one portion at room temperature. The reaction was shaken at room temperature for 2 h and then concentrated. The crude product, 6-(3-chloro-benzenesulfonyl)-3,4,4a,9a-tetrahydro-1H-benzo[4,5]furo[2,3-c]pyridine-2-carboxylic acid tert-butyl ester was taken on to the next step without further purification. MS m/z 472 [M+Na]+

Step 3

6-[(3-Chlorophenyl)sulfonyl]-1,2,3,4,4a,9a-hexahydro[1]benzofuro[2,3-c]pyridine trifluoroacetic acid salt 6-(3-Chloro-benzenesulfonyl)-3,4,4a,9a-tetrahydro-1H-benzo[4,5]furo[2,3-c]pyridine-2-carboxylic acid tert-butyl ester (0.20 mmol, 1.0 eq) was dissolved into 20% TFA in DCM and shaken at room temperature for 3 h. The reaction solution was then concentrated and the crude product purified by preparative LC/MS to afford 6-[(3-chlorophenyl)sulfonyl]-1,2,3,4,4a,9a-hexahydro[1]benzofuro[2,3-c]pyridine as a trifluoroacetic acid salt. MS m/z 350 [M+H]+

The following examples were prepared essentially as described above. Example 360 and Example 361 were isolated from racemic mixture Example 100, and Example 362 and Example 363 were isolated from racemic mixture Example 101 using SFC chromatography on a chiral column as described in the general method.

| Ex. # | Name | MS m/z [M + H]+ | Stereo-chemistry | Salt | Starting material |
|---|---|---|---|---|---|
| 294 | 6-[(3-chlorophenyl)sulfonyl]-1,2,3,4,4a,9a-hexahydro[1]benzofuro[2,3-c]pyridine | 350 | racemic | TFA | 3-chlorobenzenethiol |
| 295 | 4,4-dimethyl-7-(phenylsulfonyl)-3,4,4',5'-tetrahydro-2H-spiro[1-benzofuro[2,3-c]pyridine-1,3'-furan] | 398 | racemic | HCl | benzenethiol |
| 296 | 7-(phenylsulfonyl)-2',3,3',4,5',6'-hexahydro-2H-spiro[1-benzofuro[2,3-c]pyridine-1,4'-pyran] | 384 | | HCl | benzenethiol |
| 297 | 7-{[3-(trifluoromethyl)phenyl]sulfinyl}-2',3,3',4,5',6'-hexahydro-2H-spiro[1-benzofuro[2,3-c]pyridine-1,4'-pyran] | 436 | racemic | HCl | 3-(trifluoromethyl)benzenethiol |
| 298 | 7-{[3-(trifluoromethyl)phenyl]sulfonyl}-2',3,3',4,5',6'-hexahydro-2H-spiro[1-benzofuro[2,3-c]pyridine-1,4'-pyran] | 452 | | HCl | 3-(trifluoromethyl)benzenethiol |
| 299 | 7-{[3-(trifluoromethoxy)phenyl]sulfinyl}-2',3,3',4,5',6'-hexahydro-2H-spiro[1-benzofuro[2,3-c]pyridine-1,4'-pyran] | 452 | racemic | HCl | 3-(trifluoromethoxy)benzenethiol |
| 300 | 7-{[3-(trifluoromethoxy)phenyl]sulfonyl}-2',3,3',4,5',6'-hexahydro-2H-spiro[1-benzofuro[2,3-c]pyridine-1,4'-pyran] | 468 | | HCl | 3-(trifluoromethoxy)benzenethiol |
| 301 | 7-[(3,5-difluorophenyl)sulfonyl]-2',3,3',4,5',6'-hexahydro-2H-spiro[1-benzofuro[2,3-c]pyridine-1,4'-pyran] | 420 | | HCl | 3,5-difluorobenzenethiol |
| 302 | 7-[(3,5-difluorophenyl)sulfonyl]-3,4,4',5'-tetrahydro-2H-spiro[1-benzofuro[2,3-c]pyridine-1,3'-furan] | 406 | enantiomer 1 | HCl | 3,5-difluorobenzenethiol |
| 303 | (7-[(3-chlorophenyl)sulfonyl]-3,4,4',5'-tetrahydro-2H-spiro[1-benzofuro[2,3-c]pyridine-1,3'-furan] | 404 | enantiomer 1 | HCl | 3-chlorobenzenethiol |
| 304 | 7-{[3-(trifluoromethyl)phenyl]sulfonyl}-3,4,4',5'-tetrahydro-2H-spiro[1-benzofuro[2,3-c]pyridine-1,3'-furan] | 438 | enantiomer 1 | HCl | 3-(trifluoromethyl)benzenethiol |
| 305 | 7-[(3,5-difluorophenyl)sulfonyl]-3,4,4',5'-tetrahydro-2H-spiro[1-benzofuro[2,3-c]pyridine-1,3'-furan] | 406 | enantiomer 2 | HCl | 3,5-difluorobenzenethiol |
| 306 | 7-[(3-chlorophenyl)sulfonyl]-3,4,4',5'-tetrahydro-2H-spiro[1-benzofuro[2,3-c]pyridine-1,3'-furan] | 404 | enantiomer 2 | HCl | 3-chlorobenzenethiol |

-continued

| Ex. # | Name | MS m/z [M + H]+ | Stereo-chemistry | Salt | Starting material |
|---|---|---|---|---|---|
| 307 | 7-{[3-(trifluoromethyl)phenyl]sulfonyl}-3,4,4',5'-tetrahydro-2H-spiro[1-benzofuro[2,3-c]pyridine-1,3'-furan] | 438 | enantiomer 2 | HCl | 3-(trifluoromethyl)benzenethiol |
| 308 | 6-{[3-fluorophenyl]sulfonyl}-3,4,4',5'-tetrahydro-2H-spiro[1-benzofuro[2,3-c]pyridine-1,3'-furan] | 388 | racemate | | 3-fluorobenzenethiol |
| 309 | 6-{[3-(trifluoromethyl)phenyl]sulfonyl}-3,4,4',5'-tetrahydro-2H-spiro[1-benzofuro[2,3-c]pyridine-1,3'-furan] | 438 | racemate | | 3-(trifluoromethyl)benzenethiol |
| 310 | 6-{[3,5-difluorophenyl]sulfonyl}-3,4,4',5'-tetrahydro-2H-spiro[1-benzofuro[2,3-c]pyridine-1,3'-furan] | 406 | racemate | | 3,5-difluorobenzenethiol |
| 311 | 7-(phenylsulfonyl)-2,3,4,5',6',9-hexahydro-4'H-spiro[beta-carboline-1,3'-pyran] | 384 | enantiomer 1 | HCl | benzenethiol |
| 312 | 7-[(3,5-difluorophenyl)sulfonyl]-2,3,4,5',6',9-hexahydro-4'H-spiro[beta-carboline-1,3'-pyran] | 419 | enantiomer 1 | HCl | 3,5-difluorobenzenethiol |
| 313 | 7-{[3-(trifluoromethoxy)phenyl]sulfonyl}-2,3,4,5',6',9-hexahydro-4'H-spiro[beta-carboline-1,3'-pyran] | 468 | enantiomer 1 | HCl | 3-(trifluoromethoxy)benzenethiol |
| 314 | 7-{[3-(trifluoromethyl)phenyl]sulfonyl}-2,3,4,5',6',9-hexahydro-4'H-spiro[beta-carboline-1,3'-pyran] | 452 | enantiomer 1 | HCl | 3-(trifluoromethyl)benzenethiol |
| 315 | 7-(phenylsulfonyl)-2,3,4,5',6',9-hexahydro-4'H-spiro[beta-carboline-1,3'-pyran] | 384 | enantiomer 2 | HCl | benzenethiol |
| 316 | 7-[(3-chlorophenyl)sulfonyl]-2,3,4,5',6',9-hexahydro-4'H-spiro[beta-carboline-1,3'-pyran] | 418 | enantiomer 2 | HCl | 3-chlorobenzenethiol |
| 317 | (7-[(3-fluorophenyl)sulfonyl]-2,3,4,5',6',9-hexahydro-4'H-spiro[beta-carboline-1,3'-pyran] | 402 | enantiomer 2 | HCl | 3-difluorobenzenethiol |
| 318 | 7-[(3,5-difluorophenyl)sulfonyl]-2,3,4,5',6',9-hexahydro-4'H-spiro[beta-carboline-1,3'-pyran] | 420 | enantiomer 2 | HCl | 3,5-difluorobenzenethiol |
| 319 | 7-{[3-(trifluoromethoxy)phenyl]sulfonyl}-2,3,4,5',6',9-hexahydro-4'H-spiro[beta-carboline-1,3'-pyran] | 468 | enantiomer 2 | HCl | 3-(trifluoromethoxy)benzenethiol |
| 320 | 7-{[3-(trifluoromethyl)phenyl]sulfonyl}-2,3,4,5',6',9-hexahydro-4'H-spiro[beta-carboline-1,3'-pyran] | 452 | enantiomer 2 | HCl | 3-(trifluoromethyl)benzenethiol |
| 321 | 7-(phenylsulfonyl)-1,2,3,4,4a,9a-hexahydro[1]benzofuro[2,3-c]pyridine | 316 | racemic | TFA | benzenethiol |
| 322 | 7-[(4-chlorophenyl)sulfonyl]-1,2,3,4,4a,9a-hexahydro[1]benzofuro[2,3-c]pyridine | 350 | racemic | TFA | 4-chlorobenzenethiol |

-continued

| Ex. # | Name | MS m/z [M + H]+ | Stereo-chemistry | Salt | Starting material |
|---|---|---|---|---|---|
| 323 | 7-[(4-methoxyphenyl)sulfonyl]-1,2,3,4,4a,9a-hexahydro[1]benzofuro[2,3-c]pyridine | 346 | racemic | TFA | 4-methoxybenzenethiol |
| 324 | 7-(phenylsulfonyl)-1,2,3,4,4a,9a-hexahydro[1]benzofuro[2,3-c]pyridine | 316 | racemic | HCl | benzenethiol |
| 325 | 7-[(4-methoxyphenyl)sulfonyl]-1,2,3,4,4a,9a-hexahydro[1]benzofuro[2,3-c]pyridine | 346 | racemic | HCl | 4-methoxybenzenethiol |
| 326 | 7-(phenylsulfonyl)-1,2,3,4,4a,9a-hexahydro[1]benzofuro[2,3-c]pyridine | 316 | racemic | HCl | benzenethiol |
| 327 | 7-[(6-methylpyridin-2-yl)sulfinyl]-1,2,3,4,4a,9a-hexahydro[1]benzofuro[2,3-c]pyridine | 315 | racemic | HCl | 6-methylpyridine-2-thiol |
| 328 | 7-[(6-methylpyridin-2-yl)sulfonyl]-1,2,3,4,4a,9a-hexahydro[1]benzofuro[2,3-c]pyridine | 331 | racemic | HCl | 6-methylpyridine-2-thiol |
| 329 | 7-[(1-oxidopyridin-4-yl)sulfonyl]-1,2,3,4,4a,9a-hexahydro[1]benzofuro[2,3-c]pyridine | 333 | racemic | HCl | pyridine-4-thiol |
| 330 | 7-(pyridin-4-ylsulfonyl)-1,2,3,4,4a,9a-hexahydro[1]benzofuro[2,3-c]pyridine | 317 | racemic | HCl | pyridine-4-thiol |
| 331 | 7-(pyridin-2-ylsulfonyl)-1,2,3,4,4a,9a-hexahydro[1]benzofuro[2,3-c]pyridine | 317 | racemic | HCl | pyridine-2-thiol |
| 332 | 7-(quinolin-8-ylsulfonyl)-1,2,3,4,4a,9a-hexahydro[1]benzofuro[2,3-c]pyridine | 367 | racemic | HCl | quinoline-8-thiol |
| 333 | 7-(quinolin-8-ylsulfonyl)-1,2,3,4,4a,9a-hexahydro[1]benzofuro[2,3-c]pyridine | 367 | racemic | HCl | quinoline-8-thiol |
| 334 | 6-(phenylsulfonyl)-1,2,3,4,4a,9a-hexahydro[1]benzofuro[2,3-c]pyridine | 316 | Racemic | HCl | benzenethiol |
| 335 | 6-[(4-chlorophenyl)sulfonyl]-1,2,3,4,4a,9a-hexahydro[1]benzofuro[2,3-c]pyridine | 350 | racemic | TFA | 4-chlorobenzenethiol |
| 336 | 6-[(4-methoxyphenyl)sulfonyl]-1,2,3,4,4a,9a-hexahydro[1]benzofuro[2,3-c]pyridine | 346 | racemic | TFA | 4-methoxybenzenethiol |
| 337 | 6-(phenylsulfonyl)-1,2,3,4,4a,9a-hexahydro[1]benzofuro[2,3-c]pyridine | 316 | Racemic | HCl | benzenethiol |
| 338 | 8-[(2,3-dichlorophenyl)sulfonyl]-1,2,3,4,4a,9a-hexahydro[1]benzofuro[2,3-c]pyridine | 384 | racemic | TFA | 2,3-dichlorobenzenethiol |
| 339 | 7-(phenylsulfonyl)-1,2,3,4-tetrahydro[1]benzofuro[2,3-c]pyridine | 314 | | TFA | benzenethiol |
| 340 | 7-[(3-chlorophenyl)sulfonyl]-1,2,3,4-tetrahydro[1]benzofuro[2,3-c]pyridine | 348 | | HCl | 3-chlorobenzenethiol |
| 341 | 7-[(3-fluorophenyl)sulfonyl]-1,2,3,4-tetrahydro[1]benzofuro[2,3-c]pyridine | 332 | | HCl | 3-fluorobenzenethiol |

-continued

| Ex. # | Name | MS m/z [M + H]+ | Stereo-chemistry | Salt | Starting material |
|---|---|---|---|---|---|
| 342 | 3-(1,2,3,4-tetrahydro[1]benzofuro[2,3-c]pyridin-7-ylsulfonyl)aniline | 329 | | HCl | 3-aminobenzenethiol |
| 343 | 7-[(6-methylpyridin-2-yl)sulfonyl]-1,2,3,4-tetrahydro[1]benzofuro[2,3-c]pyridine | 329 | | HCl | 6-methylpyridine-2-thiol |
| 344 | 7-(pyridin-4-ylsulfonyl)-1,2,3,4-tetrahydro[1]benzofuro[2,3-c]pyridine | 315 | | HCl | pyridine-4-thiol |
| 345 | 7-(pyridin-2-ylsulfonyl)-1,2,3,4-tetrahydro[1]benzofuro[2,3-c]pyridine | 315 | | HCl | pyridine-2-thiol |
| 346 | 7-(quinolin-8-ylsulfonyl)-1,2,3,4-tetrahydro[1]benzofuro[2,3-c]pyridine | 365 | | HCl | quinoline-8-thiol |
| 347 | N,N-dimethyl-3-(1,2,3,4-tetrahydro[1]benzofuro[2,3-c]pyridin-7-ylsulfonyl)aniline | 357 | | HCl | 3-(dimethylamino)benzenethiol |
| 348 | 6-(phenylsulfonyl)-1,2,3,4-tetrahydro[1]benzofuro[2,3-c]pyridine | 314 | | HCl | benzenethiol |
| 349 | 3-(1,2,3,4-tetrahydro[1]benzofuro[2,3-c]pyridin-6-ylsulfonyl)aniline | 329 | | HCl | 3-aminobenzenethiol |
| 350 | 6-[(6-methylpyridin-2-yl)sulfonyl]-1,2,3,4-tetrahydro[1]benzofuro[2,3-c]pyridine | 329 | | HCl | 6-methylpyridine-2-thiol |
| 351 | 6-[(1-oxidopyridin-4-yl)sulfonyl]-1,2,3,4-tetrahydro[1]benzofuro[2,3-c]pyridine | 331 | | HCl | pyridine-4-thiol |
| 352 | 6-(pyridin-4-ylsulfonyl)-1,2,3,4-tetrahydro[1]benzofuro[2,3-c]pyridine | 315 | | HCl | pyridine-4-thiol |
| 353 | 6-(pyridin-2-ylsulfonyl)-1,2,3,4-tetrahydro[1]benzofuro[2,3-c]pyridine | 315 | | HCl | pyridine-2-thiol |
| 354 | 6-(quinolin-8-ylsulfonyl)-1,2,3,4-tetrahydro[1]benzofuro[2,3-c]pyridine | 365 | | HCl | quinoline-8-thiol |
| 355 | N,N-dimethyl-3-(1,2,3,4-tetrahydro[1]benzofuro[2,3-c]pyridin-6-ylsulfonyl)aniline | 357 | | HCl | 3-(dimethylamino)benzenethiol |
| 356 | 7-[(4-fluorophenyl)sulfonyl]-4a-methyl-1,2,3,4,4a,9a-hexahydro[1]benzofuro[2,3-c]pyridine | 348 | racemic | HCl | 4-fluorobenzenethiol |
| 357 | 4a-methyl-7-{[3-(trifluoromethyl)phenyl]sulfonyl}-1,2,3,4,4a,9a-hexahydro[1]benzofuro[2,3-c]pyridine | 398 | racemic | HCl | 3-(trifluoromethyl)benzenethiol |
| 358 | 4a-methyl-7-{[3-(trifluoromethoxy)phenyl]sulfonyl}-1,2,3,4,4a,9a-hexahydro[1]benzofuro[2,3-c]pyridine | 414 | racemic | HCl | 3-(trifluoromethoxy)benzenethiol |
| 359 | 7-[(3,5-difluorophenyl)sulfonyl]-4a-methyl-1,2,3,4,4a,9a-hexahydro[1]benzofuro[2,3-c]pyridine | 366 | racemic | HCl | 3,5-difluorobenzenethiol |
| 360 | 7-[(3-fluorophenyl)sulfonyl]-1,2,3,4,4a,9a-hexahydro[1]benzofuro[2,3-c]pyridine | 334 | Eantiomer 1 | HCl | 3-fluorobenzenethiol |

-continued

| Ex. # | Name | MS m/z [M + H]+ | Stereo-chemistry | Salt | Starting material |
|---|---|---|---|---|---|
| 361 | 7-[(3-fluorophenyl)sulfonyl]-1,2,3,4,4a,9a-hexahydro[1]benzofuro[2,3-c]pyridine | 334 | Eantiomer 2 | HCl | 3-fluorobenzenethiol |
| 362 | 7-(phenylsulfonyl)-1,2,3,4,4a,9a-hexahydro[1]benzofuro[2,3-c]pyridine | 316 | Eantiomer 1 | HCl | benzenethiol |
| 363 | 7-(phenylsulfonyl)-1,2,3,4,4a,9a-hexahydro[1]benzofuro[2,3-c]pyridine | 316 | Eantiomer 2 | HCl | benzenethiol |

Example 364

7-(3-Fluoro-5-isopropoxy-benzenesulfonyl)-1,2,3,4,4a,9a-hexahydro-benzo[4,5]furo[2,3-c]pyridine hydrochloride (Enantiomer 1)

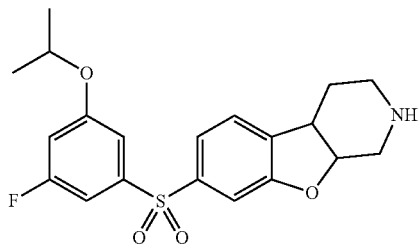 [SMILES: CC(C)Oc1cc(F)cc(S(=O)(=O)c2ccc3c(c2)OC2CNCCC32)c1]

Step 1

7-(3-Fluoro-5-isopropoxy-phenylsulfanyl)-3,4,4a,9a-tetrahydro-1H-benzo[4,5]furo[2,3-c]pyridine-2-carboxylic acid tert-butyl ester

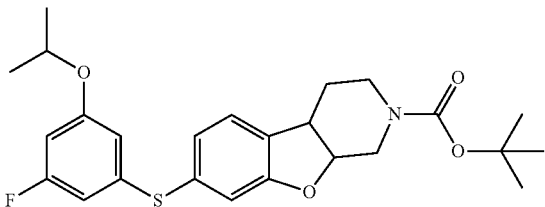 [SMILES: CC(C)Oc1cc(F)cc(Sc2ccc3c(c2)OC2CN(C(=O)OC(C)(C)C)CCC32)c1]

Anhydrous DMF was sparged with argon gas for 1 h before being used. 600 µL (0.30 mmol) of a 0.5 M stock solution of 7-triisopropylsilanylsulfanyl-3,4,4a,9a-tetrahydro-1H-benzo[4,5]furo[2,3-c]pyridine-2-carboxylic acid tert-butyl ester (enantiomer 1) in DMF was introduced into a one dram vial containing neocuproine (6.25 mg, 0.03 mmol) and copper (I) iodide (20.0 mg, 0.10 mmol). DMF (900 µL), 3-fluoro-5-isopropoxy-iodobenzene (0.45 mmol, 1.5 eq) and cesium fluoride (50.1 mg, 0.33 mmol) were added sequentially. The reaction mixture was shaken at 90° C. for 3 h and then concentrated. The residual solid was suspended into DCE:MeOH 95:5 (2.0 mL), passed through a silica gel column (1 g), eluted with DCE:MeOH 95:5 (3×2.0 mL). The combined eluent was concentrated to provide crude 7-(3-fluoro-5-isopropoxy-phenylsulfanyl)-3,4,4a,9a-tetrahydro-1H-benzo[4,5]furo[2,3-c]pyridine-2-carboxylic acid tert-butyl ester which was used in the next step without further purification. MS m/z 460 [M+H]+

Step 2

7-(3-Fluoro-5-isopropoxy-benzenesulfonyl)-1,2,3,4,4a,9a-hexahydro-benzo[4,5]furo[2,3-c]pyridine hydrochloride 7-(3-Fluoro-5-isopropoxy-phenylsulfanyl)-3,4,4a,9a-tetrahydro-1H-benzo[4,5]furo[2,3-c]pyridine-2-carboxylic acid tert-butyl ester was suspended into DCE (1.0 mL). A 0.5 M solution of m-CPBA (70% from ACROS) in DCE (4.0 eq) was added slowly. The reaction solution was shaken for 10 minutes and diluted with DCE (2.0 mL). 1N aqueous NaOH (2 mL) was added, the mixture was shaken, centrifugated and the aqueous layer removed. The organic solution was then washed with 1N aqueous NaOH (2 mL) twice and H₂O (2 mL) once. The organic layer was transferred into a new glass tube and the solvent was evaporated. The resulting oil was dissolved in a 1:1 mixture of TFA:DCM. (2.0 mL). This solution was shaken for 30 min and then concentrated. The crude product was purified by preparative LC/MS and concentrated to afford the product as a trifluoroacetic acid salt. The product was redissolved into a small amount of DCM and treated with 1.0 N HCl in diethyl ether to afford 7-(3-fluoro-5-isopropoxy-benzenesulfonyl)-1,2,3,4,4a,9a-hexahydro-benzo[4,5]furo[2,3-c]pyridine hydrochloride. MS m/z 392 [M+H]+.

The following examples were prepared essentially as described above.

| Ex. # | Name | MS m/z [M + H]+ | Stereochemistry | Salt | Starting material |
|---|---|---|---|---|---|
| 364 | 7-{[3-fluoro-5-(propan-2-yloxy)phenyl]sulfonyl}-1,2,3,4,4a,9a-hexahydro[1]benzofuro[2,3-c]pyridine | 392 | enantiomer 1 | HCl | 1-fluoro-3-iodo-5-(propan-2-yloxy)benzene |

-continued

| Ex. # | Name | MS m/z [M + H]+ | Stereochemistry | Salt | Starting material |
|---|---|---|---|---|---|
| 365 | 7-[(2,3-difluorophenyl)sulfonyl]-1,1-dimethyl-1,2,3,4-tetrahydro[1]benzofuro[2,3-c]pyridine | 378 | | TFA | 1,2-difluoro-3-iodobenzene |
| 366 | 4-[(1,1-dimethyl-1,2,3,4-tetrahydro[1]benzofuro[2,3-c]pyridin-7-yl)sulfonyl]pyridin-2(1H)-one | 359 | | TFA | 4-iodopyridin-2(1H)-one |
| 367 | 7-[(5-bromopyridin-3-yl)sulfonyl]-1,1-dimethyl-1,2,3,4-tetrahydro[1]benzofuro[2,3-c]pyridine | 421 | | TFA | 3-bromo-5-iodopyridine |
| 368 | 1,1-dimethyl-7-{[2-(morpholin-4-yl)pyridin-3-yl]sulfonyl}-1,2,3,4-tetrahydro[1]benzofuro[2,3-c]pyridine | 428 | | TFA | 4-(3-iodopyridin-2-yl)morpholine |
| 369 | 7-[(5-methoxy-1-oxidopyridin-3-yl)sulfonyl]-1,1-dimethyl-1,2,3,4-tetrahydro[1]benzofuro[2,3-c]pyridine | 389 | | TFA | 3-iodo-5-methoxypyridine |
| 370 | 7-[(5-methoxypyridin-3-yl)sulfonyl]-1,1-dimethyl-1,2,3,4-tetrahydro[1]benzofuro[2,3-c]pyridine | 373 | | TFA | 3-iodo-5-methoxypyridine |
| 371 | 5-chloro-3-[(1,1-dimethyl-1,2,3,4-tetrahydro[1]benzofuro[2,3-c]pyridin-7-yl)sulfonyl]pyridin-2-amine 1-oxide | 408 | | TFA | 5-chloro-3-iodopyridin-2-amine |
| 372 | 5-chloro-3-[(1,1-dimethyl-1,2,3,4-tetrahydro[1]benzofuro[2,3-c]pyridin-7-yl)sulfonyl]pyridin-2-amine | 392 | | TFA | 5-chloro-3-iodopyridin-2-amine |
| 373 | 5-chloro-3-[(1,1-dimethyl-1,2,3,4-tetrahydro[1]benzofuro[2,3-c]pyridin-7-yl)sulfonyl]pyridin-2-ol | 393 | | TFA | 5-chloro-3-iodopyridin-2-ol |
| 374 | 1,1-dimethyl-7-[(2-methyl-1-oxidopyridin-3-yl)sulfonyl]-1,2,3,4-tetrahydro[1]benzofuro[2,3-c]pyridine | 373 | | TFA | 3-iodo-2-methylpyridine |
| 375 | 1,1-dimethyl-7-[(2-methylpyridin-3-yl)sulfonyl]-1,2,3,4-tetrahydro[1]benzofuro[2,3-c]pyridine | 357 | | TFA | 3-iodo-2-methylpyridine |
| 376 | 7-[(5-chloropyridin-3-yl)sulfonyl]-1,1-dimethyl-1,2,3,4-tetrahydro[1]benzofuro[2,3-c]pyridine | 377 | | TFA | 3-chloro-5-iodopyridine |
| 377 | 5-[(1,1-dimethyl-1,2,3,4-tetrahydro[1]benzofuro[2,3-c]pyridin-7-yl)sulfonyl]-3-(trifluoromethyl)pyridin-2(1H)-one | 427 | | TFA | 5-iodo-3-(trifluoromethyl)pyridin-2(1H)-one |
| 378 | 1,1-dimethyl-7-{[2-(trifluoromethyl)pyridin-3-yl]sulfonyl}-1,2,3,4-tetrahydro[1]benzofuro[2,3-c]pyridine | 411 | | HCl | 3-iodo-2-(trifluoromethyl)pyridine |
| 379 | 1,1-dimethyl-7-[(4-methylpyridin-3-yl)sulfonyl]-1,2,3,4-tetrahydro[1]benzofuro[2,3-c]pyridine | 357 | | TFA | 3-iodo-4-methylpyridine |
| 380 | 1,1-dimethyl-7-{[6-(pyrrolidin-1-yl)pyridin-3-yl]sulfonyl}-1,2,3,4-tetrahydro[1]benzofuro[2,3-c]pyridine | 412 | | TFA | 5-iodo-2-(pyrrolidin-1-yl)pyridine |
| 381 | 7-[(5-fluoropyridin-3-yl)sulfonyl]-1,1-dimethyl-1,2,3,4-tetrahydro[1]benzofuro[2,3-c]pyridine | 361 | | HCl | 3-fluoro-5-iodopyridine |

-continued

| Ex. # | Name | MS m/z [M + H]+ | Stereochemistry | Salt | Starting material |
|---|---|---|---|---|---|
| 382 | 7-[(2-fluoropyridin-3-yl)sulfonyl]-1,2,3,4,4a,9a-hexahydro[1]benzofuro[2,3-c]pyridine | 335 | racemic | HCl | 2-fluoro-3-iodopyridine |
| 383 | 7-[(2-fluoropyridin-3-yl)sulfinyl]-1,2,3,4,4a,9a-hexahydro[1]benzofuro[2,3-c]pyridine | 319 | racemic | HCl | 2-fluoro-3-iodopyridine |
| 384 | 7-[(2,3-difluorophenyl)sulfinyl]-1,2,3,4,4a,9a-hexahydro[1]benzofuro[2,3-c]pyridine | 336 | racemic | HCl | 1,2-difluoro-3-iodobenzene |
| 385 | 7-[(2,3,5-trifluorophenyl)sulfinyl]-1,2,3,4,4a,9a-hexahydro[1]benzofuro[2,3-c]pyridine | 354 | racemic | HCl | 1,2,5-trifluoro-3-iodobenzene |
| 386 | 7-[(2,3,5-trifluorophenyl)sulfonyl]-1,2,3,4,4a,9a-hexahydro[1]benzofuro[2,3-c]pyridine | 370 | racemic | HCl | 1,2,5-trifluoro-3-iodobenzene |
| 387 | methyl 3-chloro-5-[1,2,3,4,4a,9a-hexahydro[1]benzofuro[2,3-c]pyridin-7-ylsulfonyl]benzoate | 408 | racemic | HCl | methyl 3-chloro-5-iodobenzoate |
| 388 | 7-[(2,3-difluorophenyl)sulfonyl]-1,2,3,4,4a,9a-hexahydro[1]benzofuro[2,3-c]pyridine | 352 | racemic | HCl | 2,3-difluorobenzenethiol |
| 389 | 7-[(2-chloropyridin-3-yl)sulfinyl]-1,2,3,4,4a,9a-hexahydro[1]benzofuro[2,3-c]pyridine | 335 | diastereoisomers | HCl | 2-chloro-3-iodopyridine |
| 390 | 7-[(2-chloropyridin-3-yl)sulfonyl]-1,2,3,4,4a,9a-hexahydro[1]benzofuro[2,3-c]pyridine | 351 | racemic | HCl | 2-chloro-3-iodopyridine |
| 391 | 7-[(5-chloropyridin-3-yl)sulfinyl]-1,2,3,4,4a,9a-hexahydro[1]benzofuro[2,3-c]pyridine | 335 | diastereoisomers | HCl | 3-chloro-5-iodopyridine |
| 392 | 7-[(5-chloropyridin-3-yl)sulfonyl]-1,2,3,4,4a,9a-hexahydro[1]benzofuro[2,3-c]pyridine | 351 | racemic | HCl | 3-chloro-5-iodopyridine |
| 393 | 7-(pyridin-3-ylsulfonyl)-1,2,3,4,4a,9a-hexahydro[1]benzofuro[2,3-c]pyridine | 317 | racemic | HCl | 3-iodopyridine |
| 394 | 7-{[2-(2,2,2-trifluoroethoxy)pyridin-3-yl]sulfonyl}-1,2,3,4,4a,9a-hexahydro[1]benzofuro[2,3-c]pyridine | 415 | diastereoisomers | HCl | 3-iodo-2-(2,2,2-trifluoroethoxy)pyridine |
| 395 | 7-{[2-(2,2,2-trifluoroethoxy)pyridin-3-yl]sulfonyl}-1,2,3,4,4a,9a-hexahydro[1]benzofuro[2,3-c]pyridine | 415 | racemic | HCl | 3-iodo-2-(2,2,2-trifluoroethoxy)pyridine |
| 396 | 7-[(5-fluoropyridin-3-yl)sulfinyl]-1,2,3,4,4a,9a-hexahydro[1]benzofuro[2,3-c]pyridine | 319 | racemic | HCl | 3-fluoro-5-iodopyridine |
| 397 | 7-[(5-fluoropyridin-3-yl)sulfonyl]-1,2,3,4,4a,9a-hexahydro[1]benzofuro[2,3-c]pyridine | 335 | racemic | HCl | 3-fluoro-5-iodopyridine |
| 398 | 7-[(2-fluoropyridin-3-yl)sulfonyl]-1,2,3,4,4a,9a-hexahydro[1]benzofuro[2,3-c]pyridine | 335 | racemic | HCl | 2-fluoro-3-iodopyridine |
| 399 | 7-[(2,3-difluorophenyl)sulfonyl]-1,2,3,4,4a,9a-hexahydro[1]benzofuro[2,3-c]pyridine | 352 | Enantiomer 1 | HCl | 1,2-difluoro-3-iodobenzene |

-continued

| Ex. # | Name | MS m/z [M + H]+ | Stereochemistry | Salt | Starting material |
|---|---|---|---|---|---|
| 400 | 7-[(2,3,5-trifluorophenyl)sulfonyl]-1,2,3,4,4a,9a-hexahydro[1]benzofuro[2,3-c]pyridine | 370 | Enantiomer 1 | HCl | 1,2,5-trifluoro-3-iodobenzene |
| 401 | 7-[(3-ethoxy-5-fluorophenyl)sulfonyl]-1,2,3,4,4a,9a-hexahydro[1]benzofuro[2,3-c]pyridine | 378 | Enantiomer 1 | HCl | 1-ethoxy-3-fluoro-5-iodobenzene |
| 402 | 7-{[3-fluoro-5-(2-methylpropoxy)phenyl]sulfonyl}-1,2,3,4,4a,9a-hexahydro[1]benzofuro[2,3-c]pyridine | 406 | Enantiomer 1 | HCl | 1-fluoro-3-iodo-5-(2-methylpropoxy)benzene |
| 403 | 7-{[3-fluoro-5-(2,2,2-trifluoroethoxy)phenyl]sulfonyl}-1,2,3,4,4a,9a-hexahydro[1]benzofuro[2,3-c]pyridine | 432 | Enantiomer 1 | HCl | 1-fluoro-3-iodo-5-(2,2,2-trifluoroethoxy)benzene |
| 404 | 7-[(2-fluoro-3-methoxyphenyl)sulfonyl]-1,2,3,4,4a,9a-hexahydro[1]benzofuro[2,3-c]pyridine | 364 | Enantiomer 1 | HCl | 2-fluoro-1-iodo-3-methoxybenzene |
| 405 | 7-(2,3-dihydro-1-benzofuran-4-ylsulfonyl)-1,2,3,4,4a,9a-hexahydro[1]benzofuro[2,3-c]pyridine | 358 | Enantiomer 1 | HCl | 4-iodo-2,3-dihydro-1-benzofuran |
| 406 | 7-{[2-(propan-2-yloxy)phenyl]sulfonyl}-1,2,3,4,4a,9a-hexahydro[1]benzofuro[2,3-c]pyridine | 374 | Enantiomer 1 | HCl | 1-iodo-2-(propan-2-yloxy)benzene |
| 407 | 7-[(3-fluoro-5-methoxyphenyl)sulfonyl]-1,2,3,4,4a,9a-hexahydro[1]benzofuro[2,3-c]pyridine | 364 | Enantiomer 1 | HCl | 1-fluoro-3-iodo-5-methoxybenzene |
| 408 | 7-{[2-(2,2,2-trifluoroethoxy)phenyl]sulfonyl}-1,2,3,4,4a,9a-hexahydro[1]benzofuro[2,3-c]pyridine | 414 | Enantiomer 1 | HCl | 1-iodo-2-(2,2,2-trifluoroethoxy)benzene |
| 409 | 7-[(3-chloro-2-fluorophenyl)sulfonyl]-1,2,3,4,4a,9a-hexahydro[1]benzofuro[2,3-c]pyridine | 368 | Enantiomer 1 | HCl | 1-chloro-2-fluoro-3-iodobenzene |
| 410 | 7-{[2-(trifluoromethyl)pyridin-3-yl]sulfonyl}-1,2,3,4,4a,9a-hexahydro[1]benzofuro[2,3-c]pyridine | 385 | Enantiomer 1 | HCl | 3-iodo-2-(trifluoromethyl)pyridine |
| 411 | 7-[(2,3-difluorophenyl)sulfonyl]-1,2,3,4,4a,9a-hexahydro[1]benzofuro[2,3-c]pyridine | 352 | Enantiomer 2 | HCl | 1,2-difluoro-3-iodobenzene |
| 412 | 7-[(2,3,5-trifluorophenyl)sulfonyl]-1,2,3,4,4a,9a-hexahydro[1]benzofuro[2,3-c]pyridine | 370 | Enantiomer 2 | HCl | 1,2,5-trifluoro-3-iodobenzene |
| 413 | 7-[(3-ethoxy-5-fluorophenyl)sulfonyl]-1,2,3,4,4a,9a-hexahydro[1]benzofuro[2,3-c]pyridine | 378 | Enantiomer 2 | HCl | 1-ethoxy-3-fluoro-5-iodobenzene |
| 414 | 7-{[3-fluoro-5-(2-methylpropoxy)phenyl]sulfonyl}-1,2,3,4,4a,9a-hexahydro[1]benzofuro[2,3-c]pyridine | 406 | Enantiomer 2 | HCl | 1-fluoro-3-iodo-5-(2-methylpropoxy)benzene |

| Ex. # | Name | MS m/z [M + H]+ | Stereochemistry | Salt | Starting material |
|---|---|---|---|---|---|
| 415 | 7-{[3-fluoro-5-(2,2,2-trifluoroethoxy)phenyl]sulfonyl}-1,2,3,4,4a,9a-hexahydro[1]benzofuro[2,3-c]pyridine | 432 | Enantiomer 2 | HCl | 1-fluoro-3-iodo-5-(2,2,2-trifluoroethoxy)benzene |
| 416 | 7-[(2-fluoro-3-methoxyphenyl)sulfonyl]-1,2,3,4,4a,9a-hexahydro[1]benzofuro[2,3-c]pyridine | 364 | Enantiomer 2 | HCl | 2-fluoro-1-iodo-3-methoxybenzene |
| 417 | 7-{[3-fluoro-5-(propan-2-yloxy)phenyl]sulfonyl}-1,2,3,4,4a,9a-hexahydro[1]benzofuro[2,3-c]pyridine | 392 | Enantiomer 2 | HCl | 1-fluoro-3-iodo-5-(propan-2-yloxy)benzene |
| 418 | 7-(2,3-dihydro-1-benzofuran-4-ylsulfonyl)-1,2,3,4,4a,9a-hexahydro[1]benzofuro[2,3-c]pyridine | 358 | Enantiomer 2 | HCl | 4-iodo-2,3-dihydro-1-benzofuran |
| 419 | 7-{[2-(propan-2-yloxy)phenyl]sulfonyl}-1,2,3,4,4a,9a-hexahydro[1]benzofuro[2,3-c]pyridine | 374 | Enantiomer 2 | HCl | 1-iodo-2-(propan-2-yloxy)benzene |
| 420 | 7-[(3-fluoro-5-methoxyphenyl)sulfonyl]-1,2,3,4,4a,9a-hexahydro[1]benzofuro[2,3-c]pyridine | 364 | Enantiomer 2 | HCl | 1-fluoro-3-iodo-5-methoxybenzene |
| 421 | 7-{[2-(2,2,2-trifluoroethoxy)phenyl]sulfonyl}-1,2,3,4,4a,9a-hexahydro[1]benzofuro[2,3-c]pyridine | 414 | Enantiomer 2 | HCl | 1-iodo-2-(2,2,2-trifluoroethoxy)benzene |
| 422 | 7-[(3-chloro-2-fluorophenyl)sulfonyl]-1,2,3,4,4a,9a-hexahydro[1]benzofuro[2,3-c]pyridine | 368 | Enantiomer 2 | HCl | 1-chloro-2-fluoro-3-iodobenzene |
| 423 | 7-{[2-(trifluoromethyl)pyridin-3-yl]sulfonyl}-1,2,3,4,4a,9a-hexahydro[1]benzofuro[2,3-c]pyridine | 385 | Enantiomer 2 | HCl | 3-iodo-2-(trifluoromethyl)pyridine |
| 424 | 7-{[3-fluoro-5-(2-methylpropoxy)phenyl]sulfonyl}-4a-methyl-1,2,3,4,4a,9a-hexahydro[1]benzofuro[2,3-c]pyridine | 420 | racemic | HCl | 1-fluoro-3-iodo-5-(2-methylpropoxy)benzene |
| 425 | N,N-dimethyl-3-{[4a-methyl-1,2,3,4,4a,9a-hexahydro[1]benzofuro[2,3-c]pyridin-7-yl]sulfonyl}benzamide | 401 | racemic | HCl | 3-iodo-N,N-dimethylbenzamide |
| 426 | 7-[(3-ethoxy-5-fluorophenyl)sulfonyl]-4a-methyl-1,2,3,4,4a,9a-hexahydro[1]benzofuro[2,3-c]pyridine | 392 | racemic | HCl | 1-ethoxy-3-fluoro-5-iodobenzene |
| 427 | 7-{[3-fluoro-5-(propan-2-yloxy)phenyl]sulfonyl}-4a-methyl-1,2,3,4,4a,9a-hexahydro[1]benzofuro[2,3-c]pyridine | 406 | racemic | HCl | 1-fluoro-3-iodo-5-(propan-2-yloxy)benzene |
| 428 | 4-{[4a-methyl-1,2,3,4,4a,9a-hexahydro[1]benzofuro[2,3-c]pyridin-7-yl]sulfonyl}pyridin-2(1H)-one | 347 | racemic | HCl | 4-iodopyridin-2(1H)-one |
| 429 | 7-[(5-fluoropyridin-3-yl)sulfonyl]-4a-methyl-1,2,3,4,4a,9a-hexahydro[1]benzofuro[2,3-c]pyridine | 349 | racemic | HCl | 3-fluoro-5-iodopyridine |
| 430 | 7-[(5-chloropyridin-3-yl)sulfonyl]-4a-methyl-1,2,3,4,4a,9a-hexahydro[1]benzofuro[2,3-c]pyridine | 365 | racemic | HCl | 3-chloro-5-iodopyridine |

-continued

| Ex. # | Name | MS m/z [M + H]+ | Stereochemistry | Salt | Starting material |
|---|---|---|---|---|---|
| 431 | 4a-methyl-7-{[5-(trifluoromethyl)pyridin-3-yl]sulfonyl}-1,2,3,4,4a,9a-hexahydro[1]benzofuro[2,3-c]pyridine | 399 | racemic | HCl | 3-(trifluoromethyl)-5-[(tripropan-2-ylsilyl)sulfanyl]pyridine |
| 432 | 7-[(2,3-difluorophenyl)sulfonyl]-1,2,3,4-tetrahydro[1]benzofuro[2,3-c]pyridine | 350 | | HCl | 1,2-difluoro-3-iodobenzene |
| 433 | 7-[(2-fluoropyridin-3-yl)sulfinyl]-4-1,2,3,4-tetrahydro[1]benzofuro[2,3-c]pyridine | 317 | Racemic | HCl | 2-fluoro-3-iodopyridine |
| 434 | 7-[(2-fluoropyridin-3-yl)sulfonyl]-1,2,3,4-tetrahydro[1]benzofuro[2,3-c]pyridine | 333 | | HCl | 2-fluoro-3-iodopyridine |
| 435 | 7-[(2-chloropyridin-3-yl)sulfinyl]-1,2,3,4-tetrahydro[1]benzofuro[2,3-c]pyridine | 333 | Racemic | HCl | 2-chloro-3-iodopyridine |
| 436 | 7-[(2-chloropyridin-3-yl)sulfonyl]-1,2,3,4-tetrahydro[1]benzofuro[2,3-c]pyridine | 349 | | HCl | 2-chloro-3-iodopyridine |
| 437 | 7-[(5-chloropyridin-3-yl)sulfonyl]-1,2,3,4-tetrahydro[1]benzofuro[2,3-c]pyridine | 349 | | HCl | 3-chloro-5-iodopyridine |
| 438 | 7-(pyridin-3-ylsulfonyl)-1,2,3,4-tetrahydro[1]benzofuro[2,3-c]pyridine | 315 | | HCl | 3-iodopyridine |
| 439 | 7-{[2-(propan-2-yloxy)pyridin-3-yl]sulfonyl}-1,2,3,4-tetrahydro[1]benzofuro[2,3-c]pyridine | 373 | | HCl | 3-iodo-2-(propan-2-yloxy)pyridine |
| 440 | 7-{[2-(2,2,2-trifluoroethoxy)pyridin-3-yl]sulfonyl}-1,2,3,4-tetrahydro[1]benzofuro[2,3-c]pyridine | 413 | | HCl | 3-iodo-2-(2,2,2-trifluoroethoxy)pyridine |
| 441 | 7-[(5-fluoropyridin-3-yl)sulfonyl]-1,2,3,4-tetrahydro[1]benzofuro[2,3-c]pyridine | 333 | | HCl | 3-fluoro-5-iodopyridine |
| 442 | 6-[(2,3-difluorophenyl)sulfinyl]-1,2,3,4-tetrahydro[1]benzofuro[2,3-c]pyridine | 334 | Racemic | TFA | 1,2-difluoro-3-iodobenzene |
| 443 | 6-[(2,3,5-trifluorophenyl)sulfinyl]-1,2,3,4-tetrahydro[1]benzofuro[2,3-c]pyridine | 352 | Racemic | TFA | 1,2,5-trifluoro-3-iodobenzene |
| 444 | 6-[(2-fluoropyridin-3-yl)sulfinyl]-1,2,3,4-tetrahydro[1]benzofuro[2,3-c]pyridine | 317 | Racemic | TFA | 2-fluoro-3-iodopyridine |
| 445 | 6-[(2-chloropyridin-3-yl)sulfinyl]-1,2,3,4-tetrahydro[1]benzofuro[2,3-c]pyridine | 333 | Racemic | TFA | 2-chloro-3-iodopyridine |
| 446 | 6-{[2-(propan-2-yloxy)pyridin-3-yl]sulfinyl}-1,2,3,4-tetrahydro[1]benzofuro[2,3-c]pyridine | 357 | Racemic | TFA | 3-iodo-2-(propan-2-yloxy)pyridine |
| 447 | 6-{[2-(2,2,2-trifluoroethoxy)pyridin-3-yl]sulfinyl}-1,2,3,4-tetrahydro[1]benzofuro[2,3-c]pyridine | 397 | Racemic | TFA | 3-iodo-2-(2,2,2-trifluoroethoxy)pyridine |
| 448 | 6-{[2-(2,2,2-trifluoroethoxy)pyridin-3-yl]sulfonyl}-1,2,3,4-tetrahydro[1]benzofuro[2,3-c]pyridine | 413 | | TFA | 3-iodo-2-(2,2,2-trifluoroethoxy)pyridine |

-continued

| Ex. # | Name | MS m/z [M + H]+ | Stereochemistry | Salt | Starting material |
|---|---|---|---|---|---|
| 449 | 6-{[2-(propan-2-yloxy)pyridin-3-yl]sulfonyl}-1,2,3,4-tetrahydro[1]benzofuro[2,3-c]pyridine | 373 | | TFA | 3-iodo-2-(propan-2-yloxy)pyridine |
| 450 | 7-[(5-methoxy-1-oxidopyridin-3-yl)sulfonyl]-4,4-dimethyl-1,2,3,4-tetrahydro[1]benzofuro[2,3-c]pyridine | 389 | | HCl | 3-iodo-5-methoxypyridine |
| 451 | 7-[(5-methoxypyridin-3-yl)sulfonyl]-4,4-dimethyl-1,2,3,4-tetrahydro[1]benzofuro[2,3-c]pyridine | 373 | | HCl | 3-iodo-5-methoxypyridine |
| 452 | 7-[(5-chloropyridin-3-yl)sulfonyl]-4,4-dimethyl-1,2,3,4-tetrahydro[1]benzofuro[2,3-c]pyridine | 377 | | HCl | 3-chloro-5-iodopyridine |
| 453 | 7-[(5-methoxy-1-oxidopyridin-3-yl)sulfonyl]-4,4-dimethyl-3,4,4',5'-tetrahydro-2H-spiro[1-benzofuro[2,3-c]pyridine-1,3'-furan] | 445 | racemic | HCl | 3-iodo-5-methoxypyridine |
| 454 | 7-[(5-methoxypyridin-3-yl)sulfonyl]-4,4-dimethyl-3,4,4',5'-tetrahydro-2H-spiro[1-benzofuro[2,3-c]pyridine-1,3'-furan] | 429 | racemic | HCl | 3-iodo-5-methoxypyridine |
| 455 | 7-[(5-chloropyridin-3-yl)sulfinyl]-4,4-dimethyl-3,4,4',5'-tetrahydro-2H-spiro[1-benzofuro[2,3-c]pyridine-1,3'-furan] | 417 | racemic | HCl | 3-chloro-5-iodopyridine |
| 456 | 7-[(5-chloropyridin-3-yl)sulfonyl]-4,4-dimethyl-3,4,4',5'-tetrahydro-2H-spiro[1-benzofuro[2,3-c]pyridine-1,3'-furan] | 433 | racemic | HCl | 3-chloro-5-iodopyridine |
| 457 | 7-(2,3-dihydro-1,4-benzodioxin-5-ylsulfonyl)-1,2,3,4,4a,9a-hexahydro[1]benzofuro[2,3-c]pyridine | 374 | enantiomer 1 | HCl | (2,3-dihydro-1,4-benzodioxin-5-ylsulfanyl)(tripropan-2-yl)silane |
| 458 | 7-[(3,5-difluoro-2-methoxyphenyl)sulfonyl]-1,2,3,4,4a,9a-hexahydro[1]benzofuro[2,3-c]pyridine | 382 | enantiomer 1 | HCl | [(3,5-difluoro-2-methoxyphenyl)sulfanyl](tripropan-2-yl)silane |
| 459 | 7-{[5-(trifluoromethyl)pyridin-3-yl]sulfonyl}-1,2,3,4,4a,9a-hexahydro[1]benzofuro[2,3-c]pyridine | 385 | enantiomer 1 | HCl | 3-(trifluoromethyl)-5-[(tripropan-2-ylsilyl)sulfanyl]pyridine |
| 460 | 7-[(2,2-difluoro-1,3-benzodioxol-4-yl)sulfonyl]-4a-methyl-1,2,3,4,4a,9a-hexahydro[1]benzofuro[2,3-c]pyridine | 410 | racemic | HCl | [(2,2-difluoro-1,3-benzodioxol-4-yl)sulfanyl](tripropan-2-yl)silane |
| 461 | 7-[(2,2-difluoro-1,3-benzodioxol-4-yl)sulfonyl]-1,2,3,4,4a,9a-hexahydro[1]benzofuro[2,3-c]pyridine | 396 | enantiomer 2 | HCl | [(2,2-difluoro-1,3-benzodioxol-4-yl)sulfanyl](tripropan-2-yl)silane |
| 462 | 7-(2,3-dihydro-1,4-benzodioxin-5-ylsulfonyl)-1,2,3,4,4a,9a-hexahydro[1]benzofuro[2,3-c]pyridine | 374 | enantiomer 2 | HCl | (2,3-dihydro-1,4-benzodioxin-5-ylsulfanyl)(tripropan-2-yl)silane |
| 463 | 7-[(3,5-difluoro-2-methoxyphenyl)sulfonyl]-1,2,3,4,4a,9a-hexahydro[1]benzofuro[2,3-c]pyridine | 382 | enantiomer 2 | HCl | [(3,5-difluoro-2-methoxyphenyl)sulfanyl](tripropan-2-yl)silane |
| 464 | 7-{[5-(trifluoromethyl)pyridin-3-yl]sulfonyl}-1,2,3,4,4a,9a-hexahydro[1]benzofuro[2,3-c]pyridine | 385 | enantiomer 2 | HCl | 3-(trifluoromethyl)-5-[(tripropan-2-ylsilyl)sulfanyl]pyridine |
| 465 | 7-[(2,2-difluoro-1,3-benzodioxol-4-yl)sulfonyl]-1,1-dimethyl-1,2,3,4-tetrahydro[1]benzofuro[2,3-c]pyridine | 422 | | TFA | [(2,2-difluoro-1,3-benzodioxol-4-yl)sulfanyl](tripropan-2-yl)silane |

| Ex. # | Name | MS m/z [M + H]+ | Stereochemistry | Salt | Starting material |
|---|---|---|---|---|---|
| 466 | 7-(2,3-dihydro-1,4-benzodioxin-5-ylsulfonyl)-1,1-dimethyl-1,2,3,4-tetrahydro[1]benzofuro[2,3-c]pyridine | 400 | | HCl | (2,3-dihydro-1,4-benzodioxin-5-ylsulfanyl)(tripropan-2-yl)silane |
| 467 | 7-(2,3-dihydro-1,4-benzodioxin-5-ylsulfonyl)-1,2,3,4-tetrahydro[1]benzofuro[2,3-c]pyridine | 372 | | HCl | (2,3-dihydro-1,4-benzodioxin-5-ylsulfanyl)(tripropan-2-yl)silane |
| 468 | 7-(2,3-dihydro-1,4-benzodioxin-5-ylsulfonyl)-4a-methyl-1,2,3,4,4a,9a-hexahydro[1]benzofuro[2,3-c]pyridine | 388 | racemic | HCl | (2,3-dihydro-1,4-benzodioxin-5-ylsulfanyl)(tripropan-2-yl)silane |
| 469 | 7-[(2,2-difluoro-1,3-benzodioxol-4-yl)sulfonyl]-1,2,3,4,4a,9a-hexahydro[1]benzofuro[2,3-c]pyridine | 396 | single enantiomer, absolute stereochemistry unknown | HCl | [(2,2-difluoro-1,3-benzodioxol-4-yl)sulfanyl](tripropan-2-yl)silane |
| 470 | 7-[(3,5-difluoro-2-methoxyphenyl)sulfonyl]-1,1-dimethyl-1,2,3,4-tetrahydro[1]benzofuro[2,3-c]pyridine | 408 | | HCl | [(3,5-difluoro-2-methoxyphenyl)sulfanyl](tripropan-2-yl)silane |

Example 471

Enantiomer 1

1-(Difluoromethyl)-7-[(2,3-difluorophenyl)sulfonyl]-1-methyl-1,2,3,4-tetrahydro[1]benzofuro[2,3-c]pyridine, enantiomer 1

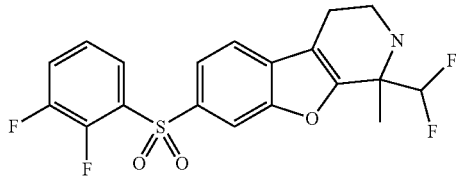 [SMILES: CC1(C(F)F)NCCc2c1oc1cc(S(=O)(=O)c3cccc(F)c3F)ccc21]

Step 1

1-(Difluoromethyl)-7-[(2,3-difluorophenyl)sulfanyl]-1-methyl-1,2,3,4-tetrahydro[1]benzofuro[2,3-c]pyridine

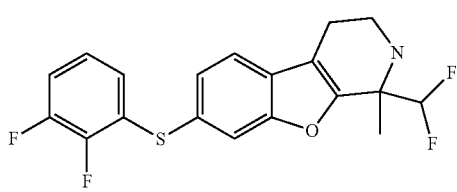 [SMILES: CC1(C(F)F)NCCc2c1oc1cc(Sc3cccc(F)c3F)ccc21]

Into a Schlenk flask equipped with a magnetic stir bar was added 1-difluoromethyl-7-iodo-1-methyl-1,2,3,4-tetrahydro-benzofuro[2,3-C]pyridine (enantiomer 1, 100 mg, 0.30 mmol), (2,3-difluorophenylsulfanyl)-triisopropylsilane (125 mg, 0.43 mmol), CsF (189 mg, 1.24 mmol), CuI (25 mg, 0.13 mmol), ethylene glycol (85 µL, 1.5 mmol) and anhydrous DMF (3 mL, 0.30 mmol). The Schlenck flask was evacuated and flushed with argon three times. The reaction mixture was heated at 105° C. under argon for 17 h. Upon cooling, the reaction was diluted with DCM, filtered through celite and solvent was evaporated. Purification using preparative TLC (2000 micron silica gfel plate; elution with 15% EtOAc in dichloromethane) afforded 155 mg of product as a viscous, pale oil. MS m/z: 382 [M+H]+.

Step 2

1-(Difluoromethyl)-7-[(2,3-difluorophenyl)sulfonyl]-1-methyl-1,2,3,4-tetrahydro[1]benzofuro[2,3-c]pyridine, enantiomer 1

To a suspension of 1-difluoromethyl-7-(2,3-difluorophenylsulfanyl)-1-methyl-1,2,3,4-tetrahydrobenzofuro[2,3-c]pyridine (155 mg, 0.53 mmol) in methanol (3 mL) and water (2 mL) stirring at rt was added Oxone® (0.390 g, 0.63 mmol). The reaction was stirred at rt for 36 h, then filtered through celite. The filtrate was extracted with dichloromethane, the organic phase was washed with water, sat. sodium bicarbonate and dried over sodium sulfate. Concentration and preparative TLC (2000 micron silica gel plate eluting with 12% EtOAc in dichloromethane) afforded 45 mg of the free base as a clear, viscous oil. The oil was dissolved in 4 M HCl in 1,4-dioxanes (1 mL) and triturated with anhydrous diethyl ether. The precipitate was collected by filtration, dried under high vacuum at 90° C. for 16 h to afford 36 mg of product as an off-white solid, mp 247-250° C. MS m/z: 414 [M+H]+.
$^1$HNMR (DMSO) δ 8.28 (s, 1H), 7.98 (d, J=8.2 Hz, 1H), 7.95 (m, 2H), 7.88 (m, 1H), 6.62 (t, J=55 Hz, 1H), 3.75 (br.s, 2H), 3.57 (m, 2H), 2.98 (m, 2H), 1.72 (s, 3H).

Example 472

Enantiomer 2

1-(Difluoromethyl)-7-[(2,3-difluorophenyl)sulfonyl]-1-methyl-1,2,3,4-tetrahydro[1]benzofuro[2,3-c]pyridine, enantiomer 2

Prepared as described for example 471 starting from enantiomer 2 of 1-difluoromethyl-7-iodo-1-methyl-1,2,3,4-tetrahydro-benzofuro[2,3-c]pyridine and (2,3-difluorophenylsulfanyl)-triisopropylsilane. mp 249-252° C.; MS m/z: 414 [M+H]+.

Example 473

Enantiomer 2

7-[(2,3-Difluorophenyl)sulfonyl]-3,4,4',5-tetrahydro-2H-spiro[1-benzofuro[2,3-c]pyridine-1,3'-furan], enantiomer 1

Prepared as described for example 471 starting from enantiomer 1 of 7-iodo-3,4,4',5'-tetrahydro-2H-spiro[1-benzofuro[2,3-c]pyridine-1,3'-furan] and (2,3-difluorophenylsulfanyl)-triisopropylsilane. mp 269-272° C.; MS m/z: 406 [M+H]$^+$.

Example 474

N,N-Dimethyl-3-(1,2,3,4-tetrahydro[1]benzofuro[2,3-c]pyridin-7-ylsulfonyl)benzamide hydrochloride

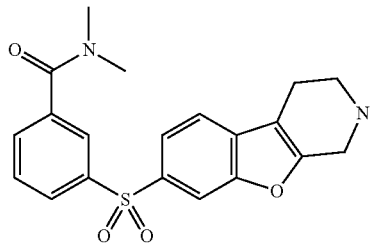 [SMILES: CN(C)C(=O)c1cccc(S(=O)(=O)c2ccc3c4c(oc3c2)CNCC4)c1]

Into a Schlenk apparatus was added 7-triisopropylsilanyl-sulfanyl-3,4-dihydro-1H-benzo[4,5]furo[2,3-c]pyridine-2-carboxylic acid tert-butyl ester (140 mg, 0.303 mmol), 3-iodo-N,N-dimethylbenzamide (170 mg, 0.61 mmol), copper (I) iodide (30 mg, 0.20 mmol), cesium fluoride (92 mg, 0.61 mmole), 1,2-ethanediol (0.07 mL, 1.0 mmol), and anhydrous DMF (1 mL, 10 mmol). The suspension was evacuated three times under high vacuum flushing with argon each time. After heating at 105° C. for 18 h, the reaction mixture was cooled, diluted with DCM, filtered through celite and the filtrate concentrated. Purification using preparative thin layer chromatography (2000 micron silica gel plate; 5% MeOH in dichloromethane) afforded N,N-dimethyl-3-(1,2,3,4-tetrahydro[1]benzofuro[2,3-c]pyridin-7-ylsulfonyl)benzamide, which was dissolved in DCM (2 mL). mCPBA (50%) was added, the reaction mixture was stirred for 18 h, diluted with DCM, and washed with sat. sodium bicarbonate. The organic phase was dried over sodium sulfate, concentrated and the resulting oil was purified by preparative TLC (2000 micron silica gel plate; 5% MeOH containing 2% isopropanol in dichloromethane) to afforded 34 mg of N,N-dimethyl-3-(1,2,3,4-tetrahydro[1]benzofuro[2,3-c]pyridin-7-ylsulfonyl)benzamide. The solid was converted to the HCl salt by adding 4M HCl in 1,4-dioxane (2 mL, 8.0 mmol) which was collected by filtration and dried under vacuum at 90° C. overnight to afford 18.8 mg of N,N-dimethyl-3-(1,2,3,4-tetrahydro[1]benzofuro[2,3-c]pyridin-7-ylsulfonyl)benzamide hydrochloride as a light tan solid, mp 262-265° C. MS m/z: 385 [M+H]$^+$. $^1$HNMR (DMSO) δ 9.78 (br.s, 2H), 8.36 (d, J=1.2 Hz, 1H), 8.06 (m, 1H), 7.99 (s, 1H), 7.92 (m, 1H), 7.86 (d, J=8.2 Hz, 1H), 7.69 (m, 2H), 4.47 (s, 2H), 3.44 (m, 2H), 2.99 (s, 3H), 2.95 (m, 2H), 2.84 (s, 3H).

The following examples were prepared essentially as described above. Example 489 and Example 490 in the Table below were isolated from racemic mixture Example 487 using SFC chromatography on a chiral column as described in the general method.

| Ex. # | Name | Mp (° C.) | MS m/z [M + H]$^+$ | Stereochemistry | Salt | Starting material |
|---|---|---|---|---|---|---|
| 474 | N,N-dimethyl-3-(1,2,3,4-tetrahydro[1]benzofuro[2,3-c]pyridin-7-ylsulfonyl)benzamide | 262-265 | 385 | | HCl | 3-iodo-N,N-dimethylbenzamide |
| 475 | 7-[(2,3-difluorophenyl)sulfonyl]-2',3,3',4,5',6'-hexahydro-2H-spiro[1-benzofuro[2,3-c]pyridine-1,4'-pyran] | 250-265 | 420 | | HCl | [(2,3-difluorophenyl)sulfanyl](tripropan-2-yl)silane |
| 476 | 2-fluoro-6-(1,2,3,4,4a,9a-hexahydro[1]benzofuro[2,3-c]pyridin-7-ylsulfonyl)-N,N-dimethylbenzamide | 283-286 | 405 | Racemic | HCl | 2-fluoro-6-iodo-N,N-dimethylbenzamide |
| 477 | 2-fluoro-6-(1,2,3,4,4a,9a-hexahydro[1]benzofuro[2,3-c]pyridin-7-ylsulfonyl)-N-methylbenzamide | >200 | 391 | Racemic | HCl | 2-fluoro-6-iodo-N,N-dimethylbenzamide |
| 478 | N-methyl-3-(1,2,3,4-tetrahydro[1]benzofuro[2,3-c]pyridin-7-ylsulfonyl)benzamide | >290 | 371 | | HCl | 3-iodo-N-methylbenzamide |
| 479 | 2-fluoro-N,N-dimethyl-6-(1,2,3,4-tetrahydro[1]benzofuro[2,3-c]pyridin-7-ylsulfonyl)benzamide | 245-248 | 403 | | HCl | 2-fluoro-6-iodo-N,N-dimethylbenzamide |
| 480 | 7-[(3,5-dimethoxyphenyl)sulfonyl]-1,2,3,4,4a,9a-hexahydro[1]benzofuro[2,3-c]pyridine | 248-251 | 376 | racemic | HCl | [(3,5-dimethoxyphenyl)sulfanyl](tripropan-2-yl)silane |

-continued

| Ex. # | Name | Mp (° C.) | MS m/z [M + H]+ | Stereochemistry | Salt | Starting material |
|---|---|---|---|---|---|---|
| 481 | 7-{[2-fluoro-3-(propan-2-yloxy)phenyl]sulfonyl}-1,2,3,4,4a,9a-hexahydro[1]benzofuro[2,3-c]pyridine | 221-223 | 392 | Enantiomer 1 | HCl | {[2-fluoro-3-(propan-2-yloxy)phenyl]sulfanyl}(tripropan-2-yl)silane |
| 482 | 7-{[2-fluoro-3-(tetrahydro-2H-pyran-4-ylmethoxy)phenyl]sulfonyl}-1,2,3,4,4a,9a-hexahydro[1]benzofuro[2,3-c]pyridine | 175-177 | 448 | Enantiomer 2 | HCl | {[(2E,4Z)-4-fluoro-5-(tetrahydro-2H-pyran-4-ylmethoxy)hepta-2,4,6-trien-3-yl]sulfanyl}(tripropan-2-yl)silane |
| 483 | 7-{[2-fluoro-3-(propan-2-yloxy)phenyl]sulfonyl}-1,2,3,4,4a,9a-hexahydro[1]benzofuro[2,3-c]pyridine | 221-224 | 392 | Enantiomer 2 | HCl | {[2-fluoro-3-(propan-2-yloxy)phenyl]sulfanyl}(tripropan-2-yl)silane |
| 484 | 7-{[3-(benzyloxy)-5-fluorophenyl]sulfonyl}-1,2,3,4,4a,9a-hexahydro[1]benzofuro[2,3-c]pyridine | 171-172 | 440 | Enantiomer 2 | HCl | {[3-(benzyloxy)-5-fluorophenyl]sulfanyl}(tripropan-2-yl)silane |
| 485 | 7-{[2-chloro-3-(tetrahydro-2H-pyran-4-ylmethoxy)phenyl]sulfonyl}-1,2,3,4,4a,9a-hexahydro[1]benzofuro[2,3-c]pyridine | 185-187 | 464 | Enantiomer 2 | HCl | {[(2E,4Z)-4-chloro-5-(tetrahydro-2H-pyran-4-ylmethoxy)hepta-2,4,6-trien-3-yl]sulfanyl}(tripropan-2-yl)silane |
| 486 | 7-[(3,5-difluoro-2-methoxyphenyl)sulfonyl]-4a-methyl-1,2,3,4,4a,9a-hexahydro[1]benzofuro[2,3-c]pyridine | 259-261 | 396 | racemic | HCl | [(3,5-difluoro-2-methoxyphenyl)sulfanyl](tripropan-2-yl)silane |
| 487 | 7-[(3,5-dimethoxyphenyl)sulfonyl]-4a-methyl-1,2,3,4,4a,9a-hexahydro[1]benzofuro[2,3-c]pyridine | 283-285 | 390 | racemic | HCl | [(3,5-dimethoxyphenyl)sulfanyl](tripropan-2-yl)silane |
| 488 | 7-[(2,3-difluorophenyl)sulfonyl]-4a-methyl-1,2,3,4,4a,9a-hexahydro[1]benzofuro[2,3-c]pyridine | 202-204 | 366 | racemic | HCl | [(2,3-difluorophenyl)sulfanyl](tripropan-2-yl)silane |
| 489 | 7-[(3,5-dimethoxyphenyl)sulfonyl]-4a-methyl-1,2,3,4,4a,9a-hexahydro[1]benzofuro[2,3-c]pyridine | 254-255 | 390 | Enantiomer1 | HCl | [(3,5-dimethoxyphenyl)sulfanyl](tripropan-2-yl)silane |
| 490 | 7-[(3,5-dimethoxyphenyl)sulfonyl]-4a-methyl-1,2,3,4,4a,9a-hexahydro[1]benzofuro[2,3-c]pyridine | 250-252 | 390 | Enantiomer2 | HCl | [(3,5-dimethoxyphenyl)sulfanyl](tripropan-2-yl)silane |

Example 491

N-[7-(3-Fluoro-benzenesulfonyl)-1-methyl-1,2,3,4-tetrahydro-benzofuro[2,3-c]pyridin-1-ylmethyl]-isobutyramide

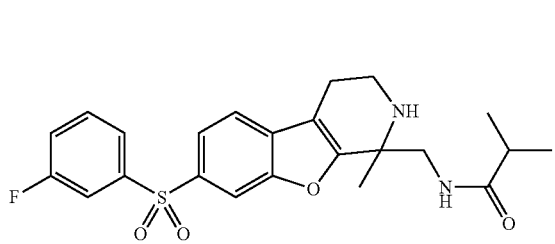 [SMILES: CC(C)C(=O)NCC1(C)NCCc2c1oc1cc(S(=O)(=O)c3cccc(F)c3)ccc21]

Step 1

2-(7-Iodo-1-methyl-1,2,3,4-tetrahydro-benzofuro[2,3-c]pyridin-1-ylmethyl)-isoindole-1,3-dione

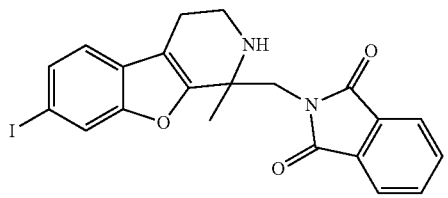 [SMILES: CC1(CN2C(=O)c3ccccc3C2=O)NCCc2c1oc1cc(I)ccc21]

To a mixture of 2-(6-iodo-benzofuran-3-yl)-ethylamine (2.00 g, 6.97 mmol) and 2-(2-oxo-propyl)-isoindole-1,3-dione (4.25 g, 20.9 mmol) was added trifluoroacetic acid (8.00 mL, 104 mmol) and then heated at 80° C. After 16 h, additional ketone (3 eq) was added and heating continued. After a total of 3 days, the reaction mixture was basified (DCM-aq. NaHCO₃) and the resulting precipitate was filtered, rinsed with DCM and dried to give an off-white solid. mp 302-304° C. dec.; MS m/z 473 [M+H]⁺.

Step 2

N-[7-(3-Fluoro-phenylsulfanyl)-1-methyl-1,2,3,4-tetrahydro-benzofuro[2,3-c]pyridin-1-ylmethyl]-isobutyramide

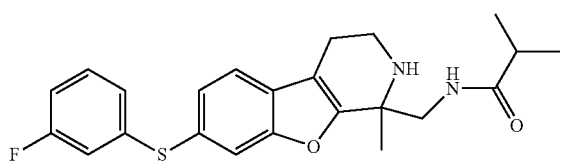 [SMILES: CC(C)C(=O)NCC1(C)NCCc2c1oc1cc(Sc3cccc(F)c3)ccc21]

A suspension of 2-(7-iodo-1-methyl-1,2,3,4-tetrahydro-benzofuro[2,3-c]pyridin-1-ylmethyl)-isoindole-1,3-dione (0.472 g, 1.00 mmol) in ethanol (10.00 mL, 171.3 mmol) was refluxed with hydrazine monohydrate (200 mg, 4 mmol). After 4 h, cooled, filtered, rinsed with MeOH, the filtrate concentrated and dried under vacuum. The resulting deprotected amine was dissolved in pyridine (5.00 mL, 61.8 mmol) and propanoic acid-2-methyl-anhydride (0.332 mL, 2.00 mmol) was added. After 1 h at room temperature, water was added (30 mL) and the mixture was stirred overnight. DCM was added and the organic layer was washed with NaHCO₃ and evaporated. The crude product was purified using silica gel chromatography using DCM/MeOH/NH₄OH to afford (7-iodo-1-methyl-1,2,3,4-tetrahydro-benzofuro[2,3-c]pyridin-1-ylmethyl)-isobutyramide. MS m/z 413 [M+H]⁺, which was taken directly into the next step.

To N-(7-iodo-1-methyl-1,2,3,4-tetrahydro-benzofuro[2,3-c]pyridin-1-ylmethyl)-isobutyramide (230 mg, 0.56 mmol), neocuproine (11.6 mg, 0.0558 mmol) and copper (I) iodide (53.1 mg, 0.279 mmol) was added dry N,N-dimethylformamide (4 mL, 50 mmol). 3-Fluorobenzenethiol (104 µL, 1.23 mmol) was added neat followed immediately by the addition of the sodium tert-butoxide (118 mg, 1.23 mmol). The reaction mixture was stirred at 100° C. After 48 h, the reaction mixture was cooled to room temperature and concentrated. The residual solid was partially dissolved into a 5% MeOH in DCE solution and flushed through a plug of Celite. The concentrated filtrate was chromatographed with DCM-MeOH—NH₄OH to afford a brownish yellow gum. MS m/z 413 [M+H]⁺.

Step 3

N-[7-(3-Fluoro-benzenesulfonyl)-1-methyl-1,2,3,4-tetrahydro-benzofuro[2,3-c]pyridin-1-ylmethyl]-isobutyramide

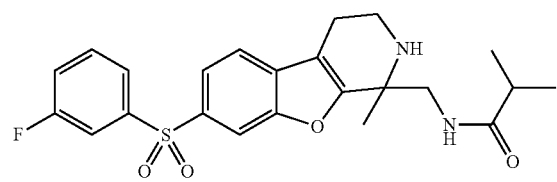 [SMILES: CC(C)C(=O)NCC1(C)NCCc2c1oc1cc(S(=O)(=O)c3cccc(F)c3)ccc21]

To a solution of N-[7-(3-fluoro-phenylsulfanyl)-1-methyl-1,2,3,4-tetrahydro-benzofuro[2,3-c]pyridin-1-ylmethyl] isobutyramide (0.200 g, 0.485 mmol) in methanol (10.0 mL, 247 mmol) was added a solution of Oxone® (0.745 g, 1.21 mmol) in water (5.0 mL, 280 mmol) and the reaction was stirred at room temperature overnight. After 6 h, the mixture was filtered, concentrated, and then extracted with DCM/sat. aq. NaHCO₃. The organic phase was dried, concentrated and then purified by silica gel chromatography with DCM-MeOH—NH₄OH to obtain the free base. The HCl salt was made (EtOH—HCl) to provide an off-white solid. mp 220-225° C. dec.; MS m/z 445 [M+H]⁺. ¹H-NMR (400 MHz, CDCl₃): δ 1.1 (dd, J=7 Hz, 6H), 1.45 (s, 3H), 2.3 (m, 1H), 2.66 (m, 2H), 3.15 (m, 2H), 3.5 (m, 1H), 3.67 (m, 1H), 5.9 (brs, 1H), 7.25 (m, 1H), 7.5 (m, 1H), 7.56 (m, 1H), 7.66 (m, 1H), 7.77 (m, 1H), 7.83 (m, 1H), 8.07 (s, 1H).

Example 492

N-({7-[(3-fluorophenyl)sulfonyl]-1-methyl-1,2,3,4-tetrahydro[1]benzofuro[2,3-c]pyridin-1-yl}methyl) acetamide Prepared as described for N-[7-(3-Fluoro-benzenesulfonyl)-1-methyl-1,2,3,4-tetrahydro-benzofuro[2,3-c]pyridin-1-ylmethyl]isobutyramide using acetic anhhydride instead of 2-methylpropanoic anhydride. mp 140-155° C. dec.; MS m/z 417 [M+H]⁺.

Example 493

1-{7-[(3-Fluorophenyl)sulfonyl]-1-methyl-1,2,3,4-tetrahydro[1]benzofuro[2,3-c]pyridin-1-yl}methanamine

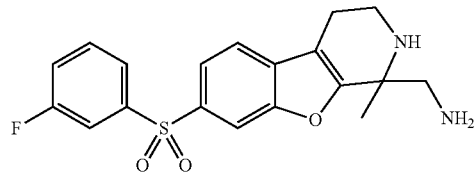 [SMILES: CC1(CN)NCCc2c1oc1cc(S(=O)(=O)c3cccc(F)c3)ccc21]

Step 1

2-({7-[(3-Fluorophenyl)sulfanyl]-1-methyl-1,2,3,4-tetrahydro[1]benzofuro[2,3-c]pyridin-1-yl}methyl)-1H-isoindole-1,3(2H)-dione

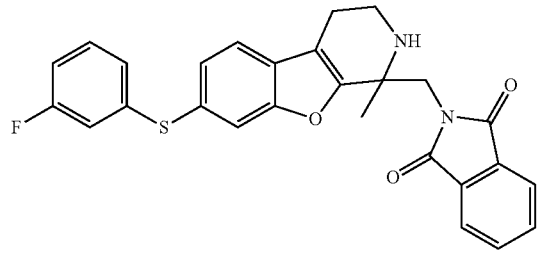 [SMILES: CC1(CN2C(=O)c3ccccc3C2=O)NCCc2c1oc1cc(Sc3cccc(F)c3)ccc21]

To 2-(7-iodo-1-methyl-1,2,3,4-tetrahydro-benzofuro[2,3-c]pyridin-1-ylmethyl)-isoindole-1,3-dione (0.192 g, 0.406 mmol) was added sodium tert-butoxide (117 mg, 1.22 mmol), copper (I) iodide (7.74 mg, 0.0406 mmol), 1,2-ethanediol (45.3 µL, 0.812 mmol), N,N-dimethylformamide (4.00 mL, 51.6 mmol), and finally 3-fluorobenzenethiol (36.0 µL, 0.427 mmol). The reaction mixture was flushed with N₂ and heated at 120° C. under a N₂ atmosphere. After 72 h, the reaction was cooled to room temperature and concentrated. The residual solid was partially dissolved into a 5% MeOH in DCM solution and flushed through a plug of Celite. The concentrated filtrate was chromatographed on silica gel using DCM-MeOH—NH₄OH to afford a brownish yellow gum. MS m/z 473 [M+H]⁺.

Step 2

1-{7-[(3-Fluorophenyl)sulfonyl]-1-methyl-1,2,3,4-tetrahydro[1]benzofuro[2,3-c]pyridin-1-yl}methanamine To a solution of 2-[7-(3-fluoro-phenylsulfanyl)-1-methyl-1,2,3,4-tetrahydro-benzofuro[2,3-c]pyridin-1-ylmethyl]isoindole-1,3-dione (0.150 g, 0.317 mmol) in methanol (10.0 mL, 247 mmol) was added a solution of Oxone® (0.488 g, 0.794 mmol) in water (5.0 mL, 280 mmol) and the reaction mixture was stirred at room temperature overnight. After 3 h, the reaction was filtered, concentrated, and extracted with DCM/sat. aq. NaHCO₃. The organic layer was dried, concentrated and purified by chromatography to afford 2-[7-(3-fluoro-benzenesulfonyl)-1-methyl-1,2,3,4-tetrahydro-benzofuro[2,3-c]pyridin-1-ylmethyl]isoindole-1,3-dione as an off-white solid. A suspension of 2-[7-(3-fluoro-benzenesulfonyl)-1-methyl-1,2,3,4-tetrahydro-benzofuro[2,3-c]pyridin-1-ylmethyl]isoindole-1,3-dione (0.015 g, 0.030 mmol) in ethanol (5.00 mL, 85.6 mmol) was refluxed with hydrazine monohydrate (0.040 mL, 0.80 mmol). After 4 h, the reaction was cooled, filtered, rinsed with MeOH, and the filtrate concentrated and dried under vacuum to afford a yellowish white solid. mp>250° C. dec.; MS m/z 375 [M+H]⁺. ¹H-NMR (400 MHz, CDCl₃): δ 1.5 (s, 3H), 2.7 (m, 2H), 3.15 (m, 1H), 3.36 (m, 1H), 4.0 (d, J=14 Hz, 1H), 4.15 (d, J=14 Hz, 1H), 7.2-8.0 (m, 7H)

Example 494

1-Butyl-6-[(3-fluorophenyl)sulfonyl]-1,2,3,4-tetrahydro[1]benzofuro[2,3-c]pyridine

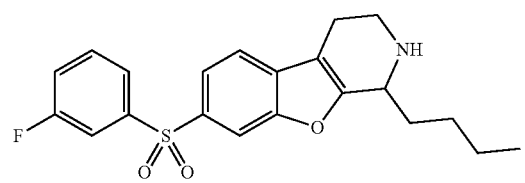 [SMILES: CCCCC1NCCc2c1oc1cc(S(=O)(=O)c3cccc(F)c3)ccc21]

Pentanal (12 μL, 1.5 eq) was added to a solution of {2-[6-(3-fluoro-benzenesulfonyl)-benzofuran-3-yl]-ethyl}-carbamic acid tert-butyl ester (800 μL, 0.125 M) in DCE:TFA 1:1. The reaction mixture was shaken at 100° C. for 16 h and the solvent was evaporated. The crude product was purified by preparative LC/MS and concentrated to afford the product as a trifluoroacetic acid salt. MS m/z 388 [M+H]⁺.

The following examples were prepared essentially as described above. Example 530 was isolated from the corresponding racemic mixture (Example 508) using SFC chromatography on a chiral column as described in the general method.

| Ex. # | Name | MS m/z [M + H]⁺ | Stereochemistry | Salt | Starting material |
|---|---|---|---|---|---|
| 494 | 1-butyl-6-[(3-fluorophenyl)sulfonyl]-1,2,3,4-tetrahydro[1]benzofuro[2,3-c]pyridine | 388 | Racemic | TFA | pentanal |
| 495 | 7-[(3-fluorophenyl)sulfonyl]-1-(propan-2-yl)-1,2,3,4-tetrahydro[1]benzofuro[2,3-c]pyridine | 374 | Racemic | HCl | 2-methylpropanal |
| 496 | 7-[(3-fluorophenyl)sulfonyl]-1-(tetrahydro-2H-pyran-4-yl)-1,2,3,4-tetrahydro[1]benzofuro[2,3-c]pyridine | 416 | Racemic | TFA | tetrahydro-2H-pyran-4-carbaldehyde |
| 497 | 1-(2-bromoethyl)-7-[(3-fluorophenyl)sulfonyl]-1,2,3,4-tetrahydro[1]benzofuro[2,3-c]pyridine | 438 | Racemic | TFA | 3-bromo-1,1-dimethoxypropane |
| 498 | 7-[(3-fluorophenyl)sulfonyl]-1-(methoxymethyl)-1,2,3,4-tetrahydro[1]benzofuro[2,3-c]pyridine | 376 | Racemic | TFA | 1,1,2-trimethoxyethane |
| 499 | 1-butyl-7-[(3-chlorophenyl)sulfonyl]-1,2,3,4-tetrahydro[1]benzofuro[2,3-c]pyridine | 404 | Racemic | TFA | pentanal |
| 500 | 7-[(3-chlorophenyl)sulfonyl]-1-(tetrahydro-2H-pyran-4-yl)-1,2,3,4-tetrahydro[1]benzofuro[2,3-c]pyridine | 432 | Racemic | TFA | tetrahydro-2H-pyran-4-carbaldehyde |

-continued

| Ex. # | Name | MS m/z [M + H]+ | Stereochemistry | Salt | Starting material |
|---|---|---|---|---|---|
| 501 | 1-(2-bromoethyl)-7-[(3-chlorophenyl)sulfonyl]-1,2,3,4-tetrahydro[1]benzofuro[2,3-c]pyridine | 453 | Racemic | TFA | 3-bromo-1,1-dimethoxypropane |
| 502 | 7-[(3-chlorophenyl)sulfonyl]-1-(methoxymethyl)-1,2,3,4-tetrahydro[1]benzofuro[2,3-c]pyridine | 392 | Racemic | TFA | 1,1,2-trimethoxyethane |
| 503 | 7-[(3-chlorophenyl)sulfonyl]-1-cyclopropyl-1,2,3,4-tetrahydro[1]benzofuro[2,3-c]pyridine | 388 | Racemic | TFA | cyclopropanecarbaldehyde |
| 504 | 7-[(3-chlorophenyl)sulfonyl]-1-(2,2,2-trifluoroethyl)-1,2,3,4-tetrahydro[1]benzofuro[2,3-c]pyridine | 430 | Racemic | TFA | 3,3,3-trifluoropropanal |
| 505 | 7-[(3-chlorophenyl)sulfonyl]-1-(propan-2-yl)-1,2,3,4-tetrahydro[1]benzofuro[2,3-c]pyridine | 390 | Racemic | TFA | 2-methylpropanal |
| 506 | 1-butyl-7-[(3-fluorophenyl)sulfonyl]-1,2,3,4-tetrahydro[1]benzofuro[2,3-c]pyridine | 388 | Racemic | TFA | pentanal |
| 507 | 7-[(3-fluorophenyl)sulfonyl]-1-(2,2,2-trifluoroethyl)-1,2,3,4-tetrahydro[1]benzofuro[2,3-c]pyridine | 414 | Racemic | TFA | 3,3,3-trifluoropropanal |
| 508 | 1-(difluoromethyl)-7-[(3-fluorophenyl)sulfonyl]-1-methyl-1,2,3,4-tetrahydro[1]benzofuro[2,3-c]pyridine | 396 | racemic | 0 | 1,1-difluoropropan-2-one |
| 509 | 1-(difluoromethyl)-7-[(3-fluorophenyl)sulfonyl]-1,2,3,4-tetrahydro[1]benzofuro[2,3-c]pyridine | 382 | racemic | HCl | 1-ethoxy-2,2-difluoroethanol |
| 510 | 7-[(3-fluorophenyl)sulfonyl]-1-(trifluoromethyl)-1,2,3,4-tetrahydro[1]benzofuro[2,3-c]pyridine | 400 | Racemic | HCl | trifluoroacetaldehyde hydrate |
| 511 | 6-[(3-fluorophenyl)sulfonyl]-1-(trifluoromethyl)-1,2,3,4-tetrahydro[1]benzofuro[2,3-c]pyridine | 400 | racemic | HCl | trifluoroacetaldehyde hydrate |
| 512 | 6-[(3-fluorophenyl)sulfonyl]-1-(propan-2-yl)-1,2,3,4-tetrahydro[1]benzofuro[2,3-c]pyridine | 374 | Racemic | HCl | 2-methylpropanal |
| 513 | 1-cyclopentyl-6-[(3-fluorophenyl)sulfonyl]-1,2,3,4-tetrahydro[1]benzofuro[2,3-c]pyridine | 400 | diastereoisomers | TFA | cyclopentanecarbaldehyde |
| 514 | 1-(2-bromoethyl)-6-[(3-fluorophenyl)sulfonyl]-1,2,3,4-tetrahydro[1]benzofuro[2,3-c]pyridine | 438 | Racemic | TFA | 3-bromo-1,1-dimethoxypropane |
| 515 | 6-[(3-fluorophenyl)sulfonyl]-1-(methoxymethyl)-1,2,3,4-tetrahydro[1]benzofuro[2,3-c]pyridine | 376 | Racemic | TFA | 1,1,2-trimethoxyethane |

-continued

| Ex. # | Name | MS m/z [M + H]+ | Stereochemistry | Salt | Starting material |
|---|---|---|---|---|---|
| 516 | 6-[(3-fluorophenyl)sulfonyl]-1-(tetrahydrofuran-3-yl)-1,2,3,4-tetrahydro[1]benzofuro[2,3-c]pyridine | 402 | diastereoisomers | TFA | tetrahydrofuran-3-carbaldehyde |
| 517 | 1-cyclopropyl-6-[(3-fluorophenyl)sulfonyl]-1,2,3,4-tetrahydro[1]benzofuro[2,3-c]pyridine | 372 | Racemic | TFA | cyclopropanecarbaldehyde |
| 518 | 6-[(3-fluorophenyl)sulfonyl]-1-(2,2,2-trifluoroethyl)-1,2,3,4-tetrahydro[1]benzofuro[2,3-c]pyridine | 414 | Racemic | TFA | 3,3,3-trifluoropropanal |
| 519 | 6-[(3-fluorophenyl)sulfonyl]-1-(3,3,3-trifluoropropyl)-1,2,3,4-tetrahydro[1]benzofuro[2,3-c]pyridine | 428 | Racemic | TFA | 4,4,4-trifluorobutanal |
| 520 | 6-[(3-fluorophenyl)sulfonyl]-1-(tetrahydro-2H-pyran-4-yl)-1,2,3,4-tetrahydro[1]benzofuro[2,3-c]pyridine | 416 | Racemic | TFA | tetrahydro-2H-pyran-4-carbaldehyde |
| 521 | 7-[(3-chlorophenyl)sulfonyl]-1-(tetrahydrofuran-3-yl)-1,2,3,4-tetrahydro[1]benzofuro[2,3-c]pyridine | 418 | diastereoisomers | TFA | tetrahydrofuran-3-carbaldehyde |
| 522 | 7-[(3-chlorophenyl)sulfonyl]-1-(3,3,3-trifluoropropyl)-1,2,3,4-tetrahydro[1]benzofuro[2,3-c]pyridine | 444 | Racemic | TFA | 4,4,4-trifluorobutanal |
| 523 | 1-(difluoromethyl)-7-(phenylsulfonyl)-1,2,3,4-tetrahydro[1]benzofuro[2,3-c]pyridine | 364 | racemic | | 1-ethoxy-2,2-difluoroethanol |
| 524 | 1-(difluoromethyl)-1-methyl-7-(phenylsulfonyl)-1,2,3,4-tetrahydro[1]benzofuro[2,3-c]pyridine | 378 | racemic | HCl | 1,1-difluoropropan-2-one |
| 525 | [1-methyl-7-(phenylsulfonyl)-1,2,3,4-tetrahydro[1]benzofuro[2,3-c]pyridin-1-yl]methanol | 358 | racemic | HCl | 1-hydroxypropan-2-one |
| 526 | 1-(difluoromethyl)-7-[(3-fluorophenyl)sulfonyl]-1-methyl-2,3,4,9-tetrahydro-1H-beta-carboline | 394.1 | racemic | HCl | 1,1-difluoropropan-2-one |
| 527 | 7-[(3-fluorophenyl)sulfonyl]-1-(trifluoromethyl)-2,3,4,9-tetrahydro-1H-beta-carboline | 398.1 | racemic | HCl | trifluoroacetaldehyde hydrate |
| 528 | 7-[(3-fluorophenyl)sulfonyl]-1-methyl-1-(trifluoromethyl)-2,3,4,9-tetrahydro-1H-beta-carboline | 412.1 | racemic | HCl | 1,1,1-trifluoropropan-2-one |
| 529 | 1-(difluoromethyl)-7-[(3-fluorophenyl)sulfonyl]-2,3,4,9-tetrahydro-1H-beta-carboline | 380.1 | racemic | HCl | 1-ethoxy-2,2-difluoroethanol |
| 530 | 1-(difluoromethyl)-7-[(3-fluorophenyl)sulfonyl]-1-methyl-1,2,3,4-tetrahydro[1]benzofuro[2,3-c]pyridine | 396 | enantiomer 1 | HCl | 1,1-difluoropropan-2-one |

Example 531

N-({6-[(3-fluorophenyl)sulfonyl]-1,2,3,4-tetrahydro[1]benzofuro[2,3-c]pyridin-1-yl}methyl)acetamide

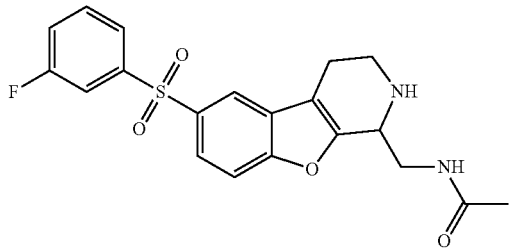 [SMILES: CC(=O)NCC1NCCc2c1oc1ccc(S(=O)(=O)c3cccc(F)c3)cc21]

2,2-Dimethoxyethylamine (16 µL, 1.5 eq) was dissolved in DCE (400 µL), acetic anhydride (15 µL, 1.5 eq) was added and the solution was shaken for 10 min. The resulting solution of N-(2,2-dimethoxyethyl)acetamide in DCE was added to a solution of tert-butyl (2-{5-[(3-fluorophenyl)sulfonyl]-1-benzofuran-3-yl}ethyl)carbamate (800 µL, 0.125 M) in DCE:TFA 1:1. The reaction mixture was shaken at 100° C. for 16 h and the solvent was evaporated. The crude product was purified by preparative LC/MS and concentrated to afford the product as a trifluoroacetic acid salt. MS m/z 403 [M+H]$^+$.

Example 532

N-(2-{6-[(3-fluorophenyl)sulfonyl]-1,2,3,4-tetrahydro[1]benzofuro[2,3-c]pyridin-1-yl}ethyl)acetamide

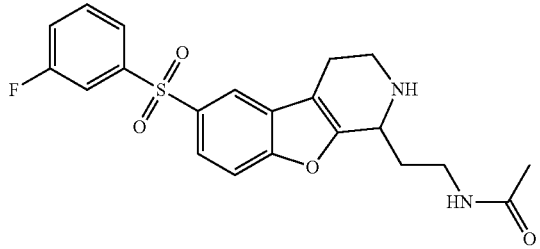 [SMILES: CC(=O)NCCC1NCCc2c1oc1ccc(S(=O)(=O)c3cccc(F)c3)cc21]

Prepared as described for N-({6-[(3-fluorophenyl)sulfonyl]-1,2,3,4-tetrahydro[1]benzofuro[2,3-c]pyridin-1-yl}methyl)acetamide using tert-butyl (2-{5-[(3-fluorophenyl)sulfonyl]-1-benzofuran-3-yl}ethyl)carbamate and N-[1,3]dioxolan-2-yl-ethylamine)-acetamide, which was prepared from 2-[1,3]dioxolan-2-yl-ethylamine and acetic anhydride. MS m/z 417 [M+H]$^+$.

Example 533

N-({6-[(3-Fluorophenyl)sulfonyl]-1,2,3,4-tetrahydro[1]benzofuro[2,3-c]pyridin-1-yl}methyl)-N-methylacetamide

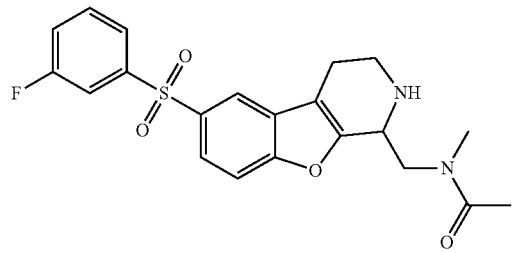 [SMILES: CC(=O)N(C)CC1NCCc2c1oc1ccc(S(=O)(=O)c3cccc(F)c3)cc21]

Prepared as described for N-({6-[(3-fluorophenyl)sulfonyl]-1,2,3,4-tetrahydro[1]benzofuro[2,3-c]pyridin-1-yl}methyl)acetamide using tert-butyl (2-{5-[(3-fluorophenyl)sulfonyl]-1-benzofuran-3-yl}ethyl)carbamate and N-[1,3]dioxolan-2-ylmethyl-methyl)-acetamide, which was prepared from [1,3]dioxolan-2-ylmethyl-methyl-amine and acetic anhydride. MS m/z 417 [M+H]$^+$.

Example 534

N-(2-{6-[(3-Fluorophenyl)sulfonyl]-1,2,3,4-tetrahydro[1]benzofuro[2,3-c]pyridin-1-yl}ethyl)-N-methylacetamide

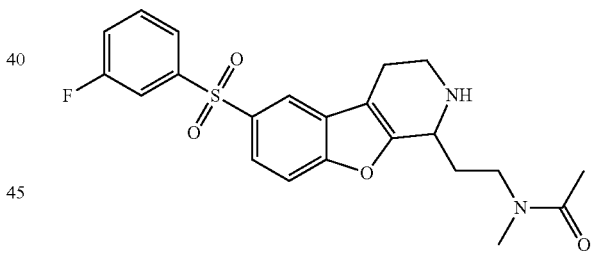

Prepared as described for N-({6-[(3-fluorophenyl)sulfonyl]-1,2,3,4-tetrahydro[1]benzofuro[2,3-c]pyridin-1-yl}methyl)acetamide using tert-butyl (2-{5-[(3-fluorophenyl)sulfonyl]-1-benzofuran-3-yl}ethyl)carbamate and N-(2-[1,3]dioxolan-2-yl-ethyl)-methyl-acetamide, which was prepared from (2-[1,3]dioxolan-2-yl-ethyl)-methyl-amine and acetic anhydride. MS m/z 431 [M+H]$^+$.

The following examples were prepared essentially as described in the above synthetic procedures.

| Ex. # | Name | MS m/z [M + H]$^+$ | Stereochemistry | Salt | Starting material |
|---|---|---|---|---|---|
| 535 | N-({7-[(3-fluorophenyl)sulfonyl]-1,2,3,4-tetrahydro[1]benzofuro[2,3-c]pyridin-1-yl}methyl)acetamide | 403 | Racemic | TFA | N-(2,2-dimethoxyethyl)-acetamide |

| Ex. # | Name | MS m/z [M + H]+ | Stereochemistry | Salt | Starting material |
|---|---|---|---|---|---|
| 536 | N-(2-{7-[(3-fluorophenyl)sulfonyl]-1,2,3,4-tetrahydro[1]benzofuro[2,3-c]pyridin-1-yl}ethyl)acetamide | 417 | Racemic | TFA | N-(2-[1,3]Dioxolan-2-yl-ethylamine)-acetamide |
| 537 | N-({7-[(3-fluorophenyl)sulfonyl]-1,2,3,4-tetrahydro[1]benzofuro[2,3-c]pyridin-1-yl}methyl)-N-methylacetamide | 417 | Racemic | TFA | N-[1,3]dioxolan-2-ylmethyl-methyl)-acetamide |
| 538 | N-(2-{7-[(3-fluorophenyl)sulfonyl]-1,2,3,4-tetrahydro[1]benzofuro[2,3-c]pyridin-1-yl}ethyl)-N-methylacetamide | 431 | racemic | HCl | N-(2-[1,3]dioxolan-2-yl-ethyl)-methyl-acetamide |
| 539 | N-({7-[(3-chlorophenyl)sulfonyl]-1,2,3,4-tetrahydro[1]benzofuro[2,3-c]pyridin-1-yl}methyl)acetamide | 419 | Racemic | TFA | N-(2,2-dimethoxy-ethyl)-acetamide |
| 540 | N-(2-{7-[(3-chlorophenyl)sulfonyl]-1,2,3,4-tetrahydro[1]benzofuro[2,3-c]pyridin-1-yl}ethyl)acetamide | 433 | Racemic | TFA | N-(2-[1,3]Dioxolan-2-yl-ethylamine)-acetamide |
| 541 | N-({7-[(3-chlorophenyl)sulfonyl]-1,2,3,4-tetrahydro[1]benzofuro[2,3-c]pyridin-1-yl}methyl)-N-methylacetamide | 433 | Racemic | TFA | N-[1,3]dioxolan-2-ylmethyl-methyl)-acetamide |
| 542 | N-(2-{7-[(3-chlorophenyl)sulfonyl]-1,2,3,4-tetrahydro[1]benzofuro[2,3-c]pyridin-1-yl}ethyl)-N-methylacetamide | 447 | Racemic | TFA | N-(2-[1,3]dioxolan-2-yl-ethyl)-methyl-acetamide |

Example 543

7-(Phenylsulfonyl)-3,4,5',6'-tetrahydro-2H,4'H-spiro[1-benzofuro[2,3-c]pyridine-1,3'-pyran]hydrochloride Enantiomer 1

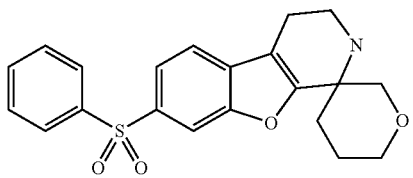 [SMILES: O=S(=O)(c1ccccc1)c1ccc2c3c(oc2c1)C1(CCCOC1)NCC3]

Copper (I) iodide (0.144 g, 0.758 mmol) was added to a stirring solution of N,N-dimethyl-1,2-ethanediamine (0.166 mL, 1.52 mmol) in DMSO (8 mL, 70 mmol). The reaction was stirred at RT for 10 minutes to yield a dark green solution. N,N-diisopropylethylamine (0.991 mL, 5.69 mmol), sodium benzenesulfinate (1.87 g, 11.4 mmol) and 7-iodo-2',3,3',4,5',6'-hexahydro-2H-spiro[1-benzofuro[2,3-c]pyridine-1,4'-pyran] (enantiomer 1, 1.4 g, 3.8 mmol) were added sequentially. The reaction was flushed with argon and stirred at 100° C. for 18 h. After cooling to r.t., the reaction mixture was poured into water (24 mL), the solids were filtered and washed with water. The combined solids were dissolved in DCM, washed with water (2×), saturated aqueous ammonium chloride (3×) and brine, dried over anhydrous sodium sulfate, filtered and concentrated. This crude product was purified by preparative LC/MS. The resulting product was suspended in DCM and washed with 1N aqueous sodium hydroxide (3×) and water (3×). The free base was dissolved into a small amount of DCM and 1.0 N HCl in diethyl ether was added. Solvent evaporation afforded 1.06 g of 7-(phenylsulfonyl)-3,4,5',6'-tetrahydro-2H,4'H-spiro[1-benzofuro[2,3-c]pyridine-1,3'-pyran]hydrochloride. MS m/z 384 [M+H]+.

Example 544

7-(Phenylsulfonyl)-3,4,5',6'-tetrahydro-2H,4'H-spiro[1-benzofuro[2,3-c]pyridine-1,3'-pyran]hydrochloride (Enantiomer 2)

Prepared as described for 7-(phenylsulfonyl)-3,4,5',6'-tetrahydro-2H,4'H-spiro[1-benzofuro[2,3-c]pyridine-1,3'-pyran]hydrochloride Enantiomer 1 using enantiomer 2 of 7-iodo-2',3,3',4,5',6'-hexahydro-2H-spiro[1-benzofuro[2,3-c]pyridine-1,4'-pyran] and sodium benzenesulfinate. MS m/z 384 [M+H]+.

Example 545

7-(Phenylsulfonyl)-2,2',3,3',4,5',6',9-octahydrospiro[beta-carboline-1,4'-pyran]trifluoroacetate

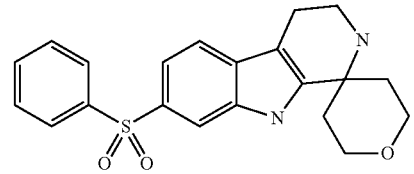 [SMILES: O=S(=O)(c1ccccc1)c1ccc2c3c([nH]c2c1)C1(CCOCC1)NCC3]

Prepared as described for 7-(phenylsulfonyl)-3,4,5',6'-tetrahydro-2H,4'H-spiro[1-benzofuro[2,3-c]pyridine-1,3'-pyran]hydrochloride using 7-iodo-2,2',3,3',4,5',6',9-octahydrospiro[beta-carboline-1,4'-pyran] and sodium benzenesulfinate. After 18 h heating at 100° C., the reaction mixture was cooled to r.t., diluted with DMSO, filtered and purified by preparative LC/MS to afford 7-(phenylsulfonyl)-2,2',3,3',4,5',6',9-octahydrospiro[beta-carboline-1,4'-pyran] trifluoroacetic acid salt. MS m/z 383 [M+H]+.

Example 546

7-(Phenylsulfonyl)-2,3,4,4',5',9-hexahydrospiro[beta-carboline-1,3'-furan]trifluoroacetate Prepared as described for 7-(phenylsulfonyl)-2,2',3,3',4,5',6',9-octahydrospiro[beta-carboline-1,4'-pyran] using 7-iodo-2,3,4,4',5',9-hexahydrospiro[beta-carboline-1,3'-furan] and sodium benzenesulfinate. MS m/z 369 [M+H]+.

Example 547

7-Iodo-2,3,4,5',6',9-hexahydro-4'H-spiro[beta-carboline-1,3'-pyran]trifluoroacetate Prepared as described for 7-(phenylsulfonyl)-2,2',3,3',4,5',6',9-octahydrospiro[beta-carboline-1,4'-pyran] using 7-iodo- 2,3,4,5',6',9-hexahydro-4'H-spiro[beta-carboline-1,3'-pyran] and sodium benzenesulfinate. MS m/z 369 [M+H]$^+$.

Example 548

7-{[3-(Tetrahydro-2H-pyran-4-ylmethoxy)phenyl]sulfonyl}-1,2,3,4,4a,9a-hexahydro[1]benzofuro[2,3-c]pyridine

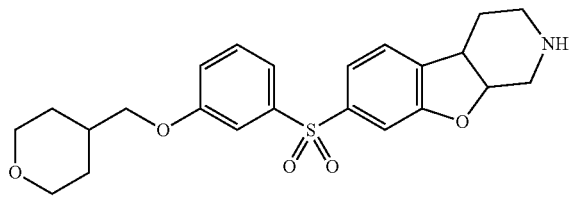 [SMILES: O=S(=O)(c1cccc(OCC2CCOCC2)c1)c1ccc2c(c1)OC1CNCCC21]

7-(3-Hydroxy-benzenesulfonyl)-3,4,4a,9a-tetrahydro-1H-benzo[4,5]furo[2,3-c]pyridine-2-carboxylic acid tert-butyl ester (enantiomer 2, 42 mg, 0.097 mmol) and 4-bromomethyl-tetrahydropyran (26 mg, 0.15 mmol) were dissolved in acetonitrile (1 ml). Cesium carbonate (95 mg, 0.29 mmol) was added, and the mixture was heated to 60° C. overnight. The solvent was evaporated and the residue purified by preparative TLC (30% EtOAc/hexane). The residue was dissolved in 1 mL of 4N HCl in dioxane (1 mL) and stirred for 2 h. The solvent was evaporated and the mixture was triturated with ether. The resulting solid was filtered, washed with ether (twice) and dried at 90° C. for 2 h. MS m/z 430 [M+H]$^+$. $^1$H-NMR (400 MHz, CDCl$_3$): δ 1.28-1.40 (m, 2H), 1.46-1.58 (m, 1H), 1.63-1.71 (m, 2H), 1.95-2.07 (m, 1H), 2.09-2.18 (m, 1H), 2.92-3.00 (m, 2H), 3.28-3.46 (m, 4H), 3.52-3.61 (m, 2H), 3.82-3.94 (m, 4H), 4.90-4.96 (m, 1H), 7.22-7.28 (m, 1H), 7.45 (s, 1H), 7.49-7.61 (m, 4H), 8.98 (s, 1H).

The following examples were prepared essentially as described above.

| Ex. # | Name | Mp (° C.) | MS m/z [M + H]$^+$ | Stereochemistry | Salt | Starting material |
|---|---|---|---|---|---|---|
| 548 | 7-{[3-(tetrahydro-2H-pyran-4-ylmethoxy)phenyl]sulfonyl}-1,2,3,4,4a,9a-hexahydro[1]benzofuro[2,3-c]pyridine | 187-189 | 430 | enantiomer 2 | HCl | 4-(bromomethyl)tetrahydro-2H-pyran |
| 549 | 7-{[3-(prop-2-yn-1-yloxy)phenyl]sulfonyl}-1,2,3,4,4a,9a-hexahydro[1]benzofuro[2,3-c]pyridine | 174-175 | 370 | racemic | HCl | 3-bromoprop-1-yne |
| 550 | 2-{[3-(1,2,3,4,4a,9a-hexahydro[1]benzofuro[2,3-c]pyridin-7-ylsulfonyl)phenoxy]methyl}benzonitrile | 194-195 | 447 | racemic | HCl | 2-(bromomethyl)benzonitrile |
| 551 | 4-{[3-(1,2,3,4,4a,9a-hexahydro[1]benzofuro[2,3-c]pyridin-7-ylsulfonyl)phenoxy]methyl}benzonitrile | 203-204 | 447 | racemic | HCl | 4-(bromomethyl)benzonitrile |
| 552 | 3-{[3-(1,2,3,4,4a,9a-hexahydro[1]benzofuro[2,3-c]pyridin-7-ylsulfonyl)phenoxy]methyl}benzonitrile | 200-201 | 447 | racemic | HCl | 3-(bromomethyl)benzonitrile |
| 553 | 7-{[3-(tetrahydro-2H-pyran-2-ylmethoxy)phenyl]sulfonyl}-1,2,3,4,4a,9a-hexahydro[1]benzofuro[2,3-c]pyridine | 192-194 | 430 | mixture of diastereomers | HCl | 2-(bromomethyl)tetrahydro-2H-pyran |
| 554 | 7-[(3-butoxyphenyl)sulfonyl]-1,2,3,4,4a,9a-hexahydro[1]benzofuro[2,3-c]pyridine | 206-208 | 388 | racemic | HCl | 1-bromobutane |
| 555 | 7-{[3-(cyclopropylmethoxy)phenyl]sulfonyl}-1,2,3,4,4a,9a-hexahydro[1]benzofuro[2,3-c]pyridine | 208-210 | 386 | racemic | HCl | (bromomethyl)cyclopropane |
| 556 | methyl 5-[3-(1,2,3,4,4a,9a-hexahydro[1]benzofuro[2,3-c]pyridin-7-ylsulfonyl)phenoxy]pentanoate | 179-181 | 446 | racemic | HCl | methyl 5-bromopentanoate |
| 557 | 7-{[3-(pentyloxy)phenyl]sulfonyl}-1,2,3,4,4a,9a-hexahydro[1]benzofuro[2,3-c]pyridine | 199-201 | 402 | racemic | HCl | 1-bromopentane |
| 558 | 7-{[3-(2-methoxyethoxy)phenyl]sulfonyl}-1,2,3,4,4a,9a-hexahydro[1]benzofuro[2,3-c]pyridine | 210-213 | 390 | Racemic | HCl | 1-bromo-2-methoxyethane |

-continued

| Ex. # | Name | Mp (° C.) | MS m/z [M + H]+ | Stereochemistry | Salt | Starting material |
|---|---|---|---|---|---|---|
| 559 | 7-{[3-(pyridin-3-ylmethoxy)phenyl]sulfonyl}-1,2,3,4,4a,9a-hexahydro[1]benzofuro[2,3-c]pyridine | 167-171 | 423 | racemic | HCl | 3-(bromomethyl)pyridine |
| 560 | 7-({3-[(1-methyl-1H-1,2,4-triazol-3-yl)methoxy]phenyl}sulfonyl)-1,2,3,4,4a,9a-hexahydro[1]benzofuro[2,3-c]pyridine | 187-190 | 427 | racemic | HCl | 3-(bromomethyl)-1-methyl-1H-1,2,4-triazole |
| 561 | 7-{[3-(pyridin-4-ylmethoxy)phenyl]sulfonyl}-1,2,3,4,4a,9a-hexahydro[1]benzofuro[2,3-c]pyridine | 182-185 | 423 | Racemic | HCl | 4-(bromomethyl)pyridine |
| 562 | 7-{[3-(pyridin-2-ylmethoxy)phenyl]sulfonyl}-1,2,3,4,4a,9a-hexahydro[1]benzofuro[2,3-c]pyridine | 179-182 | 423 | racemic | HCl | 2-(bromomethyl)pyridine |
| 563 | 2-{3-[1,2,3,4,4a,9a-hexahydro[1]benzofuro[2,3-c]pyridin-7-ylsulfonyl]phenoxy}acetamide | 237-239 | 389 | Racemic | HCl | 2-bromoacetamide |
| 564 | 2-{3-[1,2,3,4,4a,9a-hexahydro[1]benzofuro[2,3-c]pyridin-7-ylsulfonyl]phenoxy}-1-(pyrrolidin-1-yl)ethanone | 195-196 | 443 | | HCl | 2-bromo-1-(pyrrolidin-1-yl)ethanone |
| 565 | 7-({3-[(5-methyl-1,2-oxazol-3-yl)methoxy]phenyl}sulfonyl)-1,2,3,4,4a,9a-hexahydro[1]benzofuro[2,3-c]pyridine | 215-217 | 427 | racemic | HCl | 3-(bromomethyl)-5-methyl-1,2-oxazole |
| 566 | 7-{[2-methyl-3-(pyridin-3-ylmethoxy)phenyl]sulfonyl}-1,2,3,4,4a,9a-hexahydro[1]benzofuro[2,3-c]pyridine | 179-182 | 437 | Racemic | HCl | 3-(bromomethyl)pyridine |
| 567 | 7-{[3-(pyrazin-2-ylmethoxy)phenyl]sulfonyl}-1,2,3,4,4a,9a-hexahydro[1]benzofuro[2,3-c]pyridine | 244-245 | 424 | Racemic | HCl | 2-(bromomethyl)pyrazine |
| 568 | 3-{3-[1,2,3,4,4a,9a-hexahydro[1]benzofuro[2,3-c]pyridin-7-ylsulfonyl]phenoxy}propan-1-ol | 206-209 | 390 | Racemic | HCl | 3-bromopropan-1-ol |
| 569 | 7-({3-[(2-methyl-1,3-thiazol-4-yl)methoxy]phenyl}sulfonyl)-1,2,3,4,4a,9a-hexahydro[1]benzofuro[2,3-c]pyridine | 205-208 | 443 | Racemic | HCl | 4-(bromomethyl)-2-methyl-1,3-thiazole |
| 570 | 7-{[3-(tetrahydro-2H-pyran-4-ylmethoxy)phenyl]sulfonyl}-1,2,3,4,4a,9a-hexahydro[1]benzofuro[2,3-c]pyridine | 188-190 | 430 | Racemic | HCl | 4-(bromomethyl)tetrahydro-2H-pyran |
| 571 | 7-{[3-(tetrahydro-2H-pyran-4-yloxy)phenyl]sulfonyl}-1,2,3,4,4a,9a-hexahydro[1]benzofuro[2,3-c]pyridine | 184-186 | 416 | Racemic | HCl | 4-bromotetrahydro-2H-pyran |
| 572 | 7-[(3-propoxyphenyl)sulfonyl]-1,2,3,4,4a,9a-hexahydro[1]benzofuro[2,3-c]pyridine | 210-213 | 374 | Racemic | HCl | 1-bromopropane |
| 573 | 7-({3-[2-(1H-pyrrol-1-yl)ethoxy]phenyl}sulfonyl)-1,2,3,4,4a,9a-hexahydro[1]benzofuro[2,3-c]pyridine | 233-234 | 425 | Racemic | HCl | 1-(2-bromoethyl)-1H-pyrrole |
| 574 | 5-{3-[1,2,3,4,4a,9a-hexahydro[1]benzofuro[2,3-c]pyridin-7-ylsulfonyl]phenoxy}pentanenitrile | 189-190 | 413 | Racemic | HCl | 5-bromopentanenitrile |

-continued

| Ex. # | Name | Mp (° C.) | MS m/z [M + H]+ | Stereochemistry | Salt | Starting material |
|---|---|---|---|---|---|---|
| 575 | 7-({3-[(3-methoxybenzyl)oxy]phenyl}sulfonyl)-1,2,3,4,4a,9a-hexahydro[1]benzofuro[2,3-c]pyridine | 247-248 | 452 | Racemic | HCl | 1-(bromomethyl)-3-methoxybenzene |
| 576 | 7-{[3-(3-methoxypropoxy)phenyl]sulfonyl}-1,2,3,4,4a,9a-hexahydro[1]benzofuro[2,3-c]pyridine | 179-181 | 404 | Racemic | HCl | 1-bromo-3-methoxypropane |
| 577 | 7-{[3-(tetrahydrofuran-2-ylmethoxy)phenyl]sulfonyl}-1,2,3,4,4a,9a-hexahydro[1]benzofuro[2,3-c]pyridine | 205-206 | 416 | Racemic, mixture of diastereomers | HCl | 2-(bromomethyl)tetrahydrofuran |
| 578 | 7-{[3-(2,2-difluoroethoxy)phenyl]sulfonyl}-1,2,3,4,4a,9a-hexahydro[1]benzofuro[2,3-c]pyridine | 263-266 | 396 | racemic | HCl | 2-bromo-1,1-difluoroethane |
| 579 | 7-{[3-(pyridin-2-yloxy)phenyl]sulfonyl}-1,2,3,4,4a,9a-hexahydro[1]benzofuro[2,3-c]pyridine | 198-203 | 409 | Racemic | HCl | 2-bromopyridine |
| 580 | 7-{[3-(pyrazin-2-yloxy)phenyl]sulfonyl}-1,2,3,4,4a,9a-hexahydro[1]benzofuro[2,3-c]pyridine | 234-236 | 410 | Racemic | HCl | 2-bromopyrazine |
| 581 | 7-{[3-(tetrahydro-2H-pyran-4-ylmethoxy)phenyl]sulfonyl}-1,2,3,4,4a,9a-hexahydro[1]benzofuro[2,3-c]pyridine | 186-188C | 430 | enantiomer 1 | HCl | 4-(bromomethyl)tetrahydro-2H-pyran |
| 582 | 7-{[2-methyl-3-(tetrahydro-2H-pyran-4-ylmethoxy)phenyl]sulfonyl}-1,2,3,4,4a,9a-hexahydro[1]benzofuro[2,3-c]pyridine | 201-202 | 444 | enantiomer 2 | HCl | 4-(bromomethyl)tetrahydro-2H-pyran |
| 583 | 7-{[3-(cyclobutyloxy)-5-methoxyphenyl]sulfonyl}-1,2,3,4,4a,9a-hexahydro[1]benzofuro[2,3-c]pyridine | 218-220 | 416 | racemic | HCl | bromocyclobutane |
| 584 | 7-{[3-methoxy-5-(tetrahydro-2H-pyran-4-ylmethoxy)phenyl]sulfonyl}-1,2,3,4,4a,9a-hexahydro[1]benzofuro[2,3-c]pyridine | 207-208 | 460 | Racemic | HCl | 4-(bromomethyl)tetrahydro-2H-pyran |
| 585 | 7-{[3-(cyclopropylmethoxy)-5-methoxyphenyl]sulfonyl}-1,2,3,4,4a,9a-hexahydro[1]benzofuro[2,3-c]pyridine | 224-225 | 416 | Racemic | HCl | (bromomethyl)cyclopropane |
| 586 | 7-{[3-(cyclopentyloxy)-5-methoxyphenyl]sulfonyl}-1,2,3,4,4a,9a-hexahydro[1]benzofuro[2,3-c]pyridine | 239-241 | 430 | racemic | HCl | bromocyclopentane |
| 587 | 7-[(3-butoxy-5-methoxyphenyl)sulfonyl]-1,2,3,4,4a,9a-hexahydro[1]benzofuro[2,3-c]pyridine | | 418 | racemic | HCl | 1-bromobutane |
| 588 | 7-{[3-(3-methoxypropoxy)-5-(propan-2-yloxy)phenyl]sulfonyl}-1,2,3,4,4a,9a-hexahydro[1]benzofuro[2,3-c]pyridine | 164-166 | 462 | enantiomer 1 | HCl | 1-bromo-3-methoxypropane |
| 589 | 3-chloro-2-{3-[1,2,3,4,4a,9a-hexahydro[1]benzofuro[2,3-c]pyridin-7-ylsulfonyl]-5-(propan-2-yloxy)phenoxy}propan-1-ol | 211-213 dec. | 482 | Mixture of diastereomers | HCl | 3-bromooxetane |

| Ex. # | Name | Mp (° C.) | MS m/z [M + H]+ | Stereochemistry | Salt | Starting material |
|---|---|---|---|---|---|---|
| 590 | 2-{3-[1,2,3,4,4a,9a-hexahydro[1]benzofuro[2,3-c]pyridin-7-ylsulfonyl]-5-(propan-2-yloxy)phenoxy}ethanol | 205-208 | 434 | enantiomer 1 | HCl | (2-bromoethoxy)(tert-butyl)dimethylsilane |
| 591 | 7-{[3-fluoro-5-(tetrahydro-2H-pyran-4-ylmethoxy)phenyl]sulfonyl}-1,2,3,4,4a,9a-hexahydro[1]benzofuro[2,3-c]pyridine | 203-204 | 448 | enantiomer 2 | HCl | 4-(bromomethyl)tetrahydro-2H-pyran |

Example 592

2-[7-(Phenylsulfonyl)-3,4-dihydro[1]benzofuro[2,3-c]pyridin-2(1H)-yl]ethanol

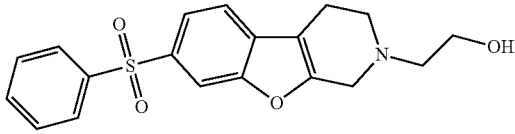 [SMILES: O=S(=O)(c1ccccc1)c1ccc2c3c(oc2c1)CN(CCO)CC3]

A 0.50 N stock solution of 7-(phenylsulfonyl)-1,2,3,4-tetrahydro[1]benzofuro[2,3-c]pyridine trifluoroacetate (1.12 g) and DIEA (1.8 mL, 4 eq) in DMF was prepared. To 500 μL (0.250 mmol) of this stock solution 1-bromoethanol (31 μL, 0.9 eq) was added. The reaction was stirred at 60° C. for 2 h. The crude product was purified by preparative LC/MS and concentrated to afford the product as a trifluoroacetic acid salt. Conversion to the HCl salt was accomplished by dissolving the product in DCM, adding 2M HCl in Et$_2$O and evaporation of the solvent. MS m/z 358 [M+H]+.

The following examples were prepared essentially as described above.

| Ex. # | Name | MS m/z [M + H]+ | Stereochemistry | Salt | Starting material |
|---|---|---|---|---|---|
| 592 | 2-[7-(phenylsulfonyl)-3,4-dihydro[1]benzofuro[2,3-c]pyridin-2(1H)-yl]ethanol | 358 | | HCl | 2-bromoethanol |
| 593 | 2-(2-methylpropyl)-7-(phenylsulfonyl)-1,2,3,4-tetrahydro[1]benzofuro[2,3-c]pyridine | 370 | | HCl | 1-bromo-2-methylpropane |
| 594 | 2-(2-methoxyethyl)-7-(phenylsulfonyl)-1,2,3,4-tetrahydro[1]benzofuro[2,3-c]pyridine | 372 | | HCl | 1-bromo-2-methoxyethane |
| 595 | 3-[7-(phenylsulfonyl)-3,4-dihydro[1]benzofuro[2,3-c]pyridin-2(1H)-yl]propan-1-ol | 372 | | HCl | 3-bromopropan-1-ol |
| 596 | 2-(2-phenylethyl)-7-(phenylsulfonyl)-1,2,3,4-tetrahydro[1]benzofuro[2,3-c]pyridine | 418 | | HCl | (2-bromoethyl)benzene |
| 597 | 2-benzyl-7-(phenylsulfonyl)-1,2,3,4-tetrahydro[1]benzofuro[2,3-c]pyridine | 404 | | HCl | (bromomethyl)benzene |
| 598 | 7-(phenylsulfonyl)-2-(2,2,2-trifluoroethyl)-1,2,3,4-tetrahydro[1]benzofuro[2,3-c]pyridine | 396 | | HCl | 1,1,1-trifluoro-2-iodoethane |
| 599 | 2-{7-[(3-chlorophenyl)sulfonyl]-3,4-dihydro[1]benzofuro[2,3-c]pyridin-2(1H)-yl}ethanol | 392 | | HCl | 2-bromoethanol |
| 600 | 7-[(3-chlorophenyl)sulfonyl]-2-(2-methylpropyl)-1,2,3,4-tetrahydro[1]benzofuro[2,3-c]pyridine | 404 | | HCl | 1-bromo-2-methylpropane |
| 601 | 3-{7-[(3-chlorophenyl)sulfonyl]-3,4-dihydro[1]benzofuro[2,3-c]pyridin-2(1H)-yl}propan-1-ol | 406 | | HCl | 3-bromopropan-1-ol |

| Ex. # | Name | MS m/z [M + H]+ | Stereochemistry | Salt | Starting material |
|---|---|---|---|---|---|
| 602 | 7-[(3-chlorophenyl)sulfonyl]-2-(2-phenylethyl)-1,2,3,4-tetrahydro[1]benzofuro[2,3-c]pyridine | 452 | | HCl | (2-bromoethyl)benzene |
| 603 | 2-benzyl-7-[(3-chlorophenyl)sulfonyl]-1,2,3,4-tetrahydro[1]benzofuro[2,3-c]pyridine | 438 | | HCl | (bromomethyl)benzene |
| 604 | 7-[(3-chlorophenyl)sulfonyl]-2-(2,2,2-trifluoroethyl)-1,2,3,4-tetrahydro[1]benzofuro[2,3-c]pyridine | 430 | | HCl | 1,1,1-trifluoro-2-iodoethane |
| 605 | 2-ethyl-7-(phenylsulfonyl)-1,2,3,4,4a,9a-hexahydro[1]benzofuro[2,3-c]pyridine | 344 | Racemic | TFA | bromoethane |

Example 606

2-Cyclobutyl-7-(phenylsulfonyl)-1,2,3,4,4a,9a-hexahydro[1]benzofuro[2,3-c]pyridine trifluoroacetic acid salt

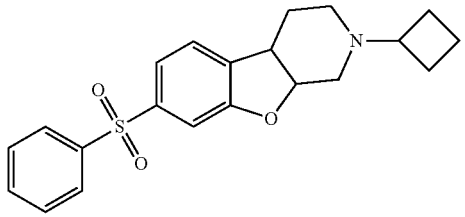 [SMILES: O=S(=O)(c1ccccc1)c1ccc2c(c1)OC1CN(C3CCC3)CCC21]

A 0.20 N stock solution of 7-benzenesulfonyl-1,2,3,4,4a,9a-hexahydro-benzo[4,5]furo[2,3-c]pyridine trifluoroacetic acid salt and DIEA (2.5 eq) in anhydrous THF was prepared. 750 µL (0.150 mmol) of this amine stock solution and neat cyclobutanone (0.225 mmol) were combined. 450 µL (0.450 mmol) of a 1.0 N stock solution of acetic acid in anhydrous THF was added and the reaction was stirred at RT for 30 min. Sodium triacetoxyborohydride (95.4 mg, 0.450 mmol) was added last and the reaction was shaken at RT overnight. It was then quenched with aqueous saturated sodium bicarbonate solution (500 µL) to pH 6.0 and concentrated. Any remaining water was removed by azeotropic distillation with toluene. The crude product was purified by preparative LC/MS and concentrated to afford 7-benzenesulfonyl-2-cyclobutyl-1,2,3,4,4a,9a-hexahydro-benzo[4,5]furo[2,3-c]pyridine as a trifluoroacetic acid salt. MS m/z 370 [M+H]+.

The following examples were prepared essentially as described above.

| Ex. # | Name | MS m/z [M + H]+ | Stereochemistry | Salt | Starting material |
|---|---|---|---|---|---|
| 606 | 2-cyclobutyl-7-(phenylsulfonyl)-1,2,3,4,4a,9a-hexahydro[1]benzofuro[2,3-c]pyridine | 370 | Racemic | TFA | cyclobutanone |
| 607 | 2-methyl-7-(phenylsulfonyl)-1,2,3,4,4a,9a-hexahydro[1]benzofuro[2,3-c]pyridine | 330 | Racemic | TFA | paraformaldehyde |
| 608 | 7-(phenylsulfonyl)-2-(propan-2-yl)-1,2,3,4,4a,9a-hexahydro[1]benzofuro[2,3-c]pyridine | 358 | Racemic | HCl | propan-2-one |
| 609 | 2-cyclopentyl-7-(phenylsulfonyl)-1,2,3,4,4a,9a-hexahydro[1]benzofuro[2,3-c]pyridine | 384 | Racemic | TFA | cyclopentanone |
| 610 | 2-cyclohexyl-7-(phenylsulfonyl)-1,2,3,4,4a,9a-hexahydro[1]benzofuro[2,3-c]pyridine | 398 | Racemic | TFA | cyclohexanone |

-continued

| Ex. # | Name | MS m/z [M + H]+ | Stereochemistry | Salt | Starting material |
|---|---|---|---|---|---|
| 611 | 2-benzyl-7-(phenylsulfonyl)-1,2,3,4,4a,9a-hexahydro[1]benzofuro[2,3-c]pyridine | 406 | Racemic | TFA | benzaldehyde |
| 612 | 2-cyclobutyl-7-{[3-methoxy-5-(propan-2-yloxy)phenyl]sulfonyl}-1,2,3,4,4a,9a-hexahydro[1]benzofuro[2,3-c]pyridine | 458 | enantiomer 1 | HCl | cyclobutanone |

Example 613

1-[7-(Phenylsulfonyl)-3,4,4a,9a-tetrahydro[1]benzofuro[2,3-c]pyridin-2(1H)-yl]ethanone

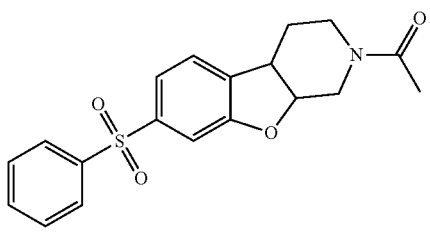 [SMILES: CC(=O)N1CCC2c3ccc(S(=O)(=O)c4ccccc4)cc3OC2C1]

A 0.20 N stock solution of 7-benzenesulfonyl-1,2,3,4,4a,9a-hexahydro-benzo[4,5]furo[2,3-c]pyridine trifluoroacetic acid salt and DIEA (2.5 eq) in anhydrous THF was prepared. To 750 μL (0.150 mmol) of this stock solution, DIEA (39.2 μL, 0.225 mmol) and acetic anhydride (21.2 μL, 0.225 mmol) were added sequentially at RT. The reaction was shaken at room temperature overnight and concentrated. The crude product was purified by preparative LC/MS and concentrated to afford 1-[7-(phenylsulfonyl)-3,4,4a,9a-tetrahydro[1]benzofuro[2,3-c]pyridin-2(1H)-yl]ethanone as a trifluoroacetic acid salt. MS m/z 358 [M+H]+.

Example 614

1-[7-(Phenylsulfonyl)-3,4-dihydro[1]benzofuro[2,3-c]pyridin-2(1H)-yl]ethanone trifluoroacetate Prepared as described for Example 612 using 7-(phenylsulfonyl)-1,2,3,4-tetrahydro[1]benzofuro[2,3-c]pyridine (Example 343) and acetic anhydride. MS m/z 356 [M+H]+.

Example 615

1-{7-[(3-Chlorophenyl)sulfonyl]-3,4-dihydro[1]benzofuro[2,3-c]pyridin-2(1H)-yl}ethanone Prepared as described for Example 612 using 7-[(3-chlorophenyl)sulfonyl]-1,2,3,4-tetrahydro[1]benzofuro[2,3-c]pyridine (Example 344) and acetic anhydride. MS m/z 390 [M+H]+.

Example 616

8-[(3-Fluorophenyl)sulfonyl]-1,4,5,10b-tetrahydro-2H-azeto[1,2-a][1]benzofuro[2,3-c]pyridine

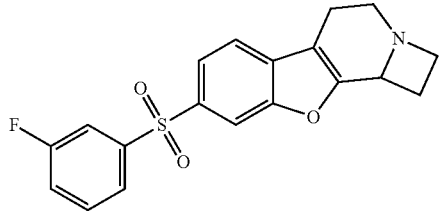 [SMILES: O=S(=O)(c1cccc(F)c1)c1ccc2c3c(oc2c1)C1CCN1CC3]

3-Bromo-1,1-dimethoxypropane (27 uL, 1.5 eq) was added to a solution of {2-[6-(3-Fluoro-benzenesulfonyl)-benzofuran-3-yl]-ethyl}-carbamic acid tert-butyl ester (800 μL, 0.125 M) in DCE:TFA 1:1. The reaction mixture was shaken at 100° C. for 16 h and the solvent was evaporated. The crude product was purified by preparative LC/MS, concentrated, dissolved in DMF and DIEA (50 μL) was added. The reaction mixture was shaken at 50° C. for 2 h, purified by preparative LC/MS and concentrated to afford the product as a trifluoroacetic acid salt. Conversion of the trifluoroacetic acid salt to the hydrochloric acid salt was performed by adding DCM followed by 2M HCl in ether and evaporation of the solvent. MS m/z 358 [M+H]+

The following examples were prepared essentially as described above and isolated as HCl salts

| Ex. # | Name | MS m/z [M + H]+ | Stereochemistry | Starting material |
|---|---|---|---|---|
| 616 | 8-[(3-fluorophenyl)sulfonyl]-1,4,5,10b-tetrahydro-2H-azeto[1,2-a][1]benzofuro[2,3-c]pyridine | 358 | racemic | 3-bromo-1,1-dimethoxypropane |
| 617 | 10-[(3-fluorophenyl)sulfonyl]-1,3,4,6,7,12b-hexahydro-2H-[1]benzofuro[2,3-a]quinolizine | 386 | racemic | 2-(4-Bromo-butyl)-[1,3]dioxolane |
| 618 | 9-[(3-fluorophenyl)sulfonyl]-1,3,4,6,7,12b-hexahydro-2H-[1]benzofuro[2,3-a]quinolizine | 386 | racemic | 2-(4-Bromo-butyl)-[1,3]dioxolane |
| 619 | 7-[(3-fluorophenyl)sulfonyl]-1,4,5,10b-tetrahydro-2H-azeto[1,2-a][1]benzofuro[2,3-c]pyridine | 358 | racemic | 3-bromo-1,1-dimethoxypropane |

-continued

| Ex. # | Name | MS m/z [M + H]+ | Stereochemistry | Starting material |
|---|---|---|---|---|
| 620 | 10-[(3-chlorophenyl)sulfonyl]-1,3,4,6,7,12b-hexahydro-2H-[1]benzofuro[2,3-a]quinolizine | 402 | racemic | 2-(4-Bromo-butyl)-[1,3]dioxolane |
| 621 | 8-[(3-chlorophenyl)sulfonyl]-1,4,5,10b-tetrahydro-2H-azeto[1,2-a][1]benzofuro[2,3-c]pyridine | 374 | racemic | 3-bromo-1,1-dimethoxypropane |

Example 622

7-{[3-(Propan-2-yloxy)phenyl]sulfonyl}-3,4,4a,9a-tetrahydro-2H-spiro[1-benzofuro[2,3-c]pyridine-1,1'-cyclobutane]hydrochloride

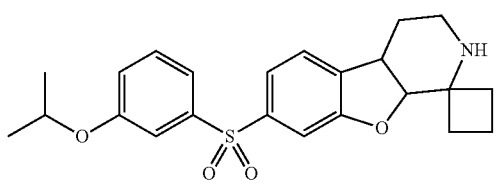 [SMILES: CC(C)Oc1cccc(S(=O)(=O)c2ccc3c(c2)OC2C3CCNC23CCC3)c1]

A solution 7-{[3-(propan-2-yloxy)phenyl]sulfonyl}-3,4-dihydro-2H-spiro[1-benzofuro[2,3-c]pyridine-1,1'-cyclobutane]-2-carboxylic acid tert-butyl ester (0.050 g, 0.098 mmol) in MeOH was reduced at 30° C., 450 psi using a H-Cube® hydrogenator and a 10% Pd—C catalyst cartridge. After 50 min, the reaction mixture was concentrated and purified by silica gel column eluting with ethyl acetate/hexane. The residue was stirred in 4M HCl in dioxane for 1 h. Diethylether was added and the precipitate was filtered and dried under vacuum at 80° C. for 15 h to provide the title compound. MS m/z 414 [M+H]+. 1H-NMR (400 MHz, CDCl3): δ 1.3 (d, J=6.2 Hz, 6H), 1.4 (m, 2H), 2.2 (m, 2H), 2.3-2.4 (m, 2H), 2.7 (m, 1H), 3.2 (m, 2H), 3.6-3.8 (m, 2H), 4.7 (m, 1H), 5.1 (d, J=6.7 Hz, 1H), 7.17 (m, 1H), 7.4-7.7 (m, 6H).

Example 623

7-[(3,5-Difluorophenyl)sulfonyl]-2',3,3',4,4a,5',6',9a-octahydro-2H-spiro[1-benzofuro[2,3-c]pyridine-1,4'-pyran]hydrochloride Prepared as described for Example 621 starting from 7-[(3,5-difluorophenyl)sulfonyl]-2',3,3',4,5',6'-hexahydro-2H-spiro[1-benzofuro[2,3-c]pyridine-1,4'-pyran]-2-carboxylic acid tert-butyl ester. MS m/z 420 [M+H]+

Example 624

7-[(3-Fluorophenyl)sulfonyl]-1,1-dimethyl-1,2,3,4,4a,9a-hexahydro[1]benzofuro[2,3-c]pyridine Prepared as described for Example 621 starting from 7-(3-fluoro-benzenesulfonyl)-1,1-dimethyl-3,4-dihydro-1H-benzofuro[2,3-c]pyridine-2-carboxylic acid tert-butyl ester. MS m/z 362 [M+]+

Example 625

7-[(3-Fluorophenyl)sulfinyl]-1,2,3,4,4a,9a-hexahydro[1]benzofuro[2,3-c]pyridine trifluoroacetic acid salt

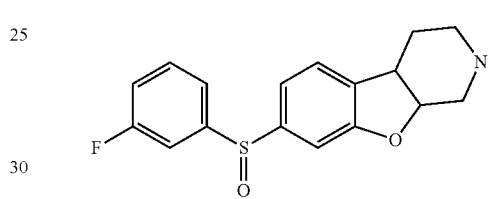

7-(3-Fluoro-phenylsulfanyl)-3,4,4a,9a-tetrahydro-1H-benzofuro[2,3-c]pyridine-2-carboxylic acid tert-butyl ester (500 mg, 1 mmol) was dissolved into anhydrous methylene chloride (2.0 mL). (2R,3R)-2-Benzenesulfonyl-3-phenyl-oxaziridine (488 mg, 1.87 mmol) was added and the reaction was stirred at RT for 1.5 hours. The reaction solution was concentrated and the crude product was partially purified by preparative LC/MS. The resulting product was dissolved into methylene chloride (1.0 mL) and trifluoroacetic acid (1.0 mL). The reaction was shaken at RT for 15 minutes and concentrated. The crude product was purified by preparative LC/MS and concentrated to afford 7-[(3-fluorophenyl)sulfinyl]-1,2,3,4,4a,9a-hexahydro[1]benzofuro[2,3-c]pyridine as a trifluoroacetic acid salt. MS m/z 318.0 [M+H]+.

Example 626

7-[(3-Fluoro-5-{3-[(2R)-2-methylpyrrolidin-1-yl]propoxy}phenyl)sulfonyl]-1,2,3,4,4a,9a-hexahydro[1]benzofuro[2,3-c]pyridine (Enantiomer 2)

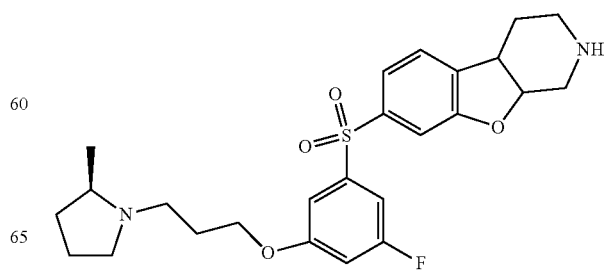

Step 1

{6-[3-(3-Chloro-propoxy)-5-fluoro-benzenesulfonyl]-3-methyl-2,3-dihydro-benzofuran-2-ylmethyl}-methyl-carbamic acid tert-butyl ester (Enantiomer 2)

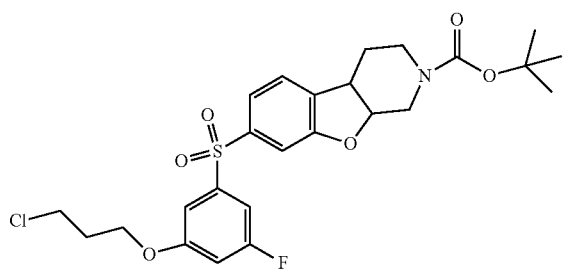 [SMILES: CC(C)(C)OC(=O)N1CCC2c3ccc(S(=O)(=O)c4cc(F)cc(OCCCCl)c4)cc3OC2C1]

A mixture of 7-(3-fluoro-5-hydroxy-benzenesulfonyl)-3,4,4a,9a-tetrahydro-1H-benzofuro[2,3-c]pyridine-2-carboxylic acid tert-butyl ester (100 mg, 0.2 mmol) and cesium carbonate (220 mg, 0.67 mmol) in acetonitrile (2 mL, 40 mmol) was stirred at 70° C. overnight. After 18 h the mixture was filtered through a pad of celite and was washed with dichloromethane. After solvent evaporation, the crude product was purified by preparative TLC (hexane:EtOAc 4:1) to provide desired product (120 mg).

Step 2

7-[(3-Fluoro-5-{3-[(2R)-2-methylpyrrolidin-1-yl]propoxy}phenyl)sulfonyl]-1,2,3,4,4a,9a-hexahydro[1]benzofuro[2,3-c]pyridine (Enantiomer 2)

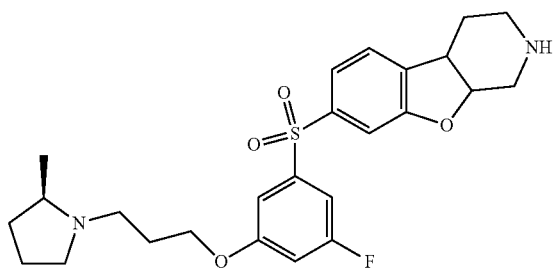 [SMILES: C[C@@H]1CCCN1CCCOc1cc(F)cc(S(=O)(=O)c2ccc3c(c2)OC2CNCCC32)c1]

A mixture of 7-[3-(3-chloro-propoxy)-5-fluoro-benzenesulfonyl]-3,4,4a,9a-tetrahydro-1H-benzofuro[2,3-c]pyridine-2-carboxylic acid tert-butyl ester (100 mg, 0.2 mmol), (R)-2-methyl-pyrrolidine, benzenesulfonic acid salt (92.5 mg, 0.380 mmol), sodium iodide (28.5 mg, 0.190 mmol), potassium carbonate (78.8 mg, 0.570 mmol), N,N-diisopropylethylamine (99.3 uL, 0.570 mmol) in acetonitrile (8.04 mL, 154 mmol) was heated at 70° C. After 3 days the reaction was cooled to room temperature, diluted with 10 mL solvent (MeOH:CH$_2$Cl$_2$ 1:1) and filtered through a pad of silica-gel. The filtrate was concentrated. Purification by preparative TLC (MeOH:CH$_2$Cl$_2$ 1:9) followed by removal of N-Boc protecting group with 4N HCl using the general procedure described afforded the desired product. mp 208-212° C., MS m/z 475 [M+H]$^+$. $^1$H-NMR (400 MHz, DMSOd$_6$): δ 10.58 (br s, 1H), 9.52 (br s, 1H), 8.84 (br s, 1H), 7.58 (m, 2H), 7.49 (s, 1H), 7.43 (d, J=6.82 Hz, 1H), 7.34 (s, 1H), 7.22 (d, J=9.92 Hz, 1H), 4.95 (s, 1H), 4.19 (s, 2H), 4.03 (m, 1H), 3.58-3.31 (overlapping m & s, 4H), 3.04 (s, 2H), 2.94 (s, 2H), 2.16 (br s, 4H), 1.99 (s, 1H), 1.94 (br s, 2H), 1.40 (d, J=5.33 Hz, 3H), 1.17 (m, 2H).

Example 627

3-(1,2,3,4-Tetrahydro-benzo[4,5]furo[2,3-c]pyridine-7-sulfonyl)-phenol

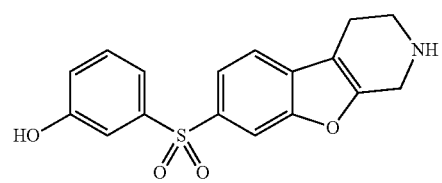 [SMILES: O=S(=O)(c1cccc(O)c1)c1ccc2c3c(oc2c1)CNCC3]

Step 1

7-(3-Benzyloxy-benzenesulfonyl)-3,4-dihydro-1H-benzo[4,5]furo[2,3-c]pyridine-2-carboxylic acid tert-butyl ester

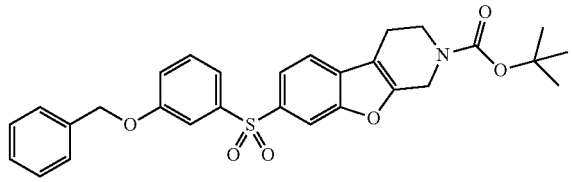 [SMILES: CC(C)(C)OC(=O)N1CCc2c(oc3cc(S(=O)(=O)c4cccc(OCc5ccccc5)c4)ccc23)C1]

Prepared as described for 7-(3-benzyloxy-benzenesulfonyl)-3,4,4a,9a-tetrahydro-1H-benzo[4,5]furo[2,3-c]pyridine-2-carboxylic acid tert-butyl ester using 7-iodo-1,2,3,4-tetrahydro-benzo[4,5]furo[2,3-c]pyridine and 3-benzyloxy-thiophenol

Step 2

3-(1,2,3,4-Tetrahydro-benzo[4,5]furo[2,3-c]pyridine-7-sulfonyl)-phenol

To a solution of 7-(3-benzyloxy-benzenesulfonyl)-3,4-dihydro-1H-benzofuro[2,3-c]pyridine-2-carboxylic acid tert-butyl ester (50 mg, 0.1 mmol) in 5 mL methanol and 1 mL EtOAc was added Pd black (10% on carbon, 45 mg, 3.4 mmol). The mixture was kept under hydrogenation at 40 psi overnight and the solvent was evaporated. After filtration, the debenzylated product was taken to the next step without further purification. Removal of N-Boc protecting group with 4N HCl using a general procedure afforded the title product. mp 279-281° C., MS m/z 330 [M+H]$^+$. $^1$H-NMR (400 MHz, DMSOd$_6$): δ 10.26 (s, 1H), 9.76 (br s, 2H), 8.24 (s, 1H), 7.84 (m, 2H), 7.39 (m, 2H), 7.30 (s, 1H), 7.02 (m, 1H), 4.47 (s, 2H), 3.44 (m, 2H), 2.94 (m, 2H).

Example 628

3-[1,2,3,4,4a,9a-Hexahydro[1]benzofuro[2,3-c]pyridin-7-ylsulfonyl]phenyl ethylcarbamate

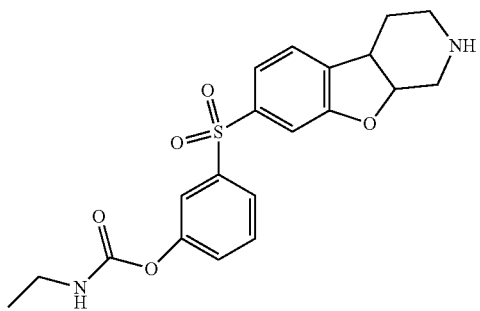 [SMILES: CCNC(=O)Oc1cccc(S(=O)(=O)c2ccc3c(c2)OC2CNCCC32)c1]

A mixture of 7-(3-hydroxy-benzenesulfonyl)-3,4,4a,9a-tetrahydro-1H-benzofuro[2,3-c]pyridine-2-carboxylic acid tert-butyl ester (30 mg, 0.07 mmol), ethyl isocyanate (0.5 ml, excess) and triethylamine (0.5 mL, excess) was stirred at r.t. After 18 h, the mixture was filtered, and the filtrate evaporated. Purification by preparative TLC (hexane:EtOAc 40:60) followed by removal of N-Boc protecting group with 4N HCl using a general procedure afforded the title product. mp 217-219° C., MS m/z 403 [M+H]$^+$. $^1$H-NMR (400 MHz, DMSOd$_6$): δ 8.97 (br s, 1H), 7.80 (d, J=7.96 Hz, 1H), 7.62 (s, 1H), 7.60-7.55 (m, 3H), 7.43 (overlapping s and d, 2H), 4.95 (m, 1H), 3.57 (m, 2H), 3.44 (m, 1H), 3.14 (m, 2H), 2.94 (m; 2H), 2.55 (s, 2H), 2.12 (m, 1H), 1.52 (m, 1H), 1.09 (t, 3H).

Chiral Separations

The stereoisomers in the Table below were isolated from the corresponding stereoisomer mixture using SFC chromatography on a chiral column as described in the general method.

| Ex. # | Name | Mp (° C.) | MS m/z [M + H]$^+$ | Stereochemistry | Salt | Starting material |
|---|---|---|---|---|---|---|
| 629 | 7-[(3-fluorophenyl)sulfonyl]-3,4,5',6'-tetrahydro-2H,4'H-spiro[1-benzofuro[2,3-c]pyridine-1,3'-pyran] | >200 | 402 | Enantiomer 1 | HCl | Mixture of 7-[(3-fluorophenyl)sulfonyl]-3,4,5',6'-tetrahydro-2H,4'H-spiro[1-benzofuro[2,3-c]pyridine-1,3'-pyran] |
| 630 | 7-[(3-fluorophenyl)sulfonyl]-3,4,5',6'-tetrahydro-2H,4'H-spiro[1-benzofuro[2,3-c]pyridine-1,3'-pyran] | >200 | 402 | Enantiomer 2 | HCl | Mixture of 7-[(3-fluorophenyl)sulfonyl]-3,4,5',6'-tetrahydro-2H,4'H-spiro[1-benzofuro[2,3-c]pyridine-1,3'-pyran] |
| 631 | N-({7-[(3-fluorophenyl)sulfonyl]-1-methyl-1,2,3,4-tetrahydro[1]benzofuro[2,3-c]pyridin-1-yl}methyl)acetamide | 217-227 | 417 | Enantiomer 1 | HCl | Mixture of N-({7-[(3-fluorophenyl)sulfonyl]-1-methyl-1,2,3,4-tetrahydro[1]benzofuro[2,3-c]pyridin-1-yl}methyl)acetamide |
| 632 | N-({7-[(3-fluorophenyl)sulfonyl]-1-methyl-1,2,3,4-tetrahydro[1]benzofuro[2,3-c]pyridin-1-yl}methyl)acetamide | 210-260 | 417 | Enantiomer 2 | HCl | Mixture of N-({7-[(3-fluorophenyl)sulfonyl]-1-methyl-1,2,3,4-tetrahydro[1]benzofuro[2,3-c]pyridin-1-yl}methyl)acetamide |
| 633 | 7-[(3-fluorophenyl)sulfonyl]-1-(methoxymethyl)-1-methyl-1,2,3,4-tetrahydro[1]benzofuro[2,3-c]pyridine | >200 | 390 | Enantiomer 1 | HCl | Mixture of 7-[(3-fluorophenyl)sulfonyl]-1-(methoxymethyl)-1-methyl-1,2,3,4-tetrahydro[1]benzofuro[2,3-c]pyridine |
| 634 | 7-[(3-fluorophenyl)sulfonyl]-1-(methoxymethyl)-1-methyl-1,2,3,4-tetrahydro[1]benzofuro[2,3-c]pyridine | >200 | 390 | Enantiomer 2 | HCl | Mixture of 7-[(3-fluorophenyl)sulfonyl]-1-(methoxymethyl)-1-methyl-1,2,3,4-tetrahydro[1]benzofuro[2,3-c]pyridine |

Example 635

1,2,3,4,4a,9a-Hexahydro[1]benzofuro[2,3-c]pyridin-7-yl 4-chlorobenzenesulfonate

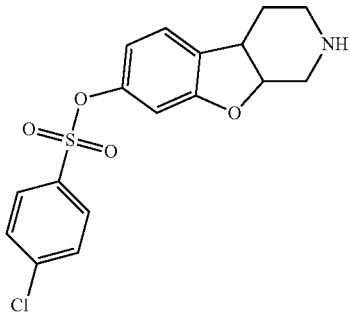 [SMILES: O=S(=O)(Oc1ccc2c(c1)OC1CNCCC21)c1ccc(Cl)cc1]

A 0.2 M solution of tert-butyl 7-hydroxy-3,4,4a,9a-tetrahydro[1]benzofuro[2,3-c]pyridine-2(1H)-carboxylate (1.17 g) in DCM (20.1 mL) was prepared. To 300 μL of the 0.2 M solution of the phenol in DCM prepared above, DIEA (21 uL) was added followed by a 0.4 M solution of 4-chlorobenzenesulfonyl chloride (138 μL) in DCM. The reaction mixture was shaken for 16 h and TFA (500 μL) was added. After an additional 3 h of shaking the solvent was evaporated. Purification using preparative LC-MS afforded the title product as the trifluoroacetic acid salt. Conversion to the HCl salt was accomplished by dissolving the product in DCM, adding 2M HCl in Et$_2$O and evaporating the solvent. MS m/z 366 [M+H]$^+$ The following examples were prepared essentially as described above.

| Ex. # | Name | MS m/z [M + H]$^+$ | Stereochemistry | Salt | Starting material |
|---|---|---|---|---|---|
| 635 | 1,2,3,4,4a,9a-hexahydro[1]benzofuro[2,3-c]pyridin-7-yl 4-chlorobenzenesulfonate | 366 | racemic | TFA | 4-chlorobenzenesulfonyl chloride |
| 636 | 1,2,3,4,4a,9a-hexahydro[1]benzofuro[2,3-c]pyridin-7-yl benzenesulfonate | 332 | racemic | TFA | benzenesulfonyl chloride |
| 637 | 1,2,3,4,4a,9a-hexahydro[1]benzofuro[2,3-c]pyridin-7-yl phenylmethanesulfonate | 346 | racemic | HCl | phenylmethanesulfonyl chloride |
| 638 | 1,2,3,4,4a,9a-hexahydro[1]benzofuro[2,3-c]pyridin-7-yl 6-chloroimidazo[2,1-b][1,3]thiazole-5-sulfonate | 412 | racemic | TFA | 6-chloroimidazo[2,1-b][1,3]thiazole-5-sulfonyl chloride |
| 639 | 1,2,3,4,4a,9a-hexahydro[1]benzofuro[2,3-c]pyridin-7-yl 1-methyl-1H-imidazole-4-sulfonate | 336 | racemic | TFA | 1-methyl-1H-imidazole-4-sulfonyl chloride |
| 640 | 1,2,3,4,4a,9a-hexahydro[1]benzofuro[2,3-c]pyridin-7-yl 5-methyl-1,2-oxazole-4-sulfonate | 337 | racemic | TFA | 5-methyl-1,2-oxazole-4-sulfonyl chloride |
| 641 | 1,2,3,4,4a,9a-hexahydro[1]benzofuro[2,3-c]pyridin-7-yl 3-methylbenzenesulfonate | 346 | racemic | TFA | 3-methylbenzenesulfonyl chloride |
| 642 | 1,2,3,4,4a,9a-hexahydro[1]benzofuro[2,3-c]pyridin-7-yl 4-methylbenzenesulfonate | 346 | racemic | TFA | 4-methylbenzenesulfonyl chloride |
| 643 | 1,2,3,4,4a,9a-hexahydro[1]benzofuro[2,3-c]pyridin-7-yl 3-fluorobenzenesulfonate | 350 | racemic | TFA | 3-fluorobenzenesulfonyl chloride |
| 644 | 1,2,3,4,4a,9a-hexahydro[1]benzofuro[2,3-c]pyridin-7-yl 4-fluorobenzenesulfonate | 350 | racemic | TFA | 4-fluorobenzenesulfonyl chloride |
| 645 | 1,2,3,4,4a,9a-hexahydro[1]benzofuro[2,3-c]pyridin-7-yl 1,2-dimethyl-1H-imidazole-4-sulfonate | 350 | racemic | TFA | 1,2-dimethyl-1H-imidazole-4-sulfonyl chloride |
| 646 | 1,2,3,4,4a,9a-hexahydro[1]benzofuro[2,3-c]pyridin-7-yl 3,5-dimethyl-1,2-oxazole-4-sulfonate | 351 | racemic | TFA | 3,5-dimethyl-1,2-oxazole-4-sulfonyl chloride |
| 647 | 1,2,3,4,4a,9a-hexahydro[1]benzofuro[2,3-c]pyridin-7-yl 2,5-dimethylbenzenesulfonate | 360 | racemic | TFA | 2,5-dimethylbenzenesulfonyl chloride |

| Ex. # | Name | MS m/z [M + H]+ | Stereochemistry | Salt | Starting material |
|---|---|---|---|---|---|
| 648 | 1,2,3,4,4a,9a-hexahydro[1]benzofuro[2,3-c]pyridin-7-yl 3,5-dimethylbenzenesulfonate | 360 | racemic | TFA | 3,5-dimethylbenzenesulfonyl chloride |
| 649 | 1,2,3,4,4a,9a-hexahydro[1]benzofuro[2,3-c]pyridin-7-yl 3,4-dimethylbenzenesulfonate | 360 | racemic | TFA | 3,4-dimethylbenzenesulfonyl chloride |
| 650 | 1,2,3,4,4a,9a-hexahydro[1]benzofuro[2,3-c]pyridin-7-yl 4-methoxybenzenesulfonate | 362 | racemic | TFA | 4-methoxybenzenesulfonyl chloride |
| 651 | 1,2,3,4,4a,9a-hexahydro[1]benzofuro[2,3-c]pyridin-7-yl 3-methoxybenzenesulfonate | 362 | racemic | TFA | 3-methoxybenzenesulfonyl chloride |
| 652 | 1,2,3,4,4a,9a-hexahydro[1]benzofuro[2,3-c]pyridin-7-yl 3-fluoro-4-methylbenzenesulfonate | 364 | racemic | TFA | 3-fluoro-4-methylbenzenesulfonyl chloride |
| 653 | 1,2,3,4,4a,9a-hexahydro[1]benzofuro[2,3-c]pyridin-7-yl 3-chlorobenzenesulfonate | 366 | racemic | TFA | 3-chlorobenzenesulfonyl chloride |
| 654 | 1,2,3,4,4a,9a-hexahydro[1]benzofuro[2,3-c]pyridin-7-yl 2-chlorobenzenesulfonate | 366 | racemic | TFA | 2-chlorobenzenesulfonyl chloride |
| 655 | 1,2,3,4,4a,9a-hexahydro[1]benzofuro[2,3-c]pyridin-7-yl 1-benzofuran-2-sulfonate | 372 | racemic | TFA | 1-benzofuran-2-sulfonyl chloride |
| 656 | 1,2,3,4,4a,9a-hexahydro[1]benzofuro[2,3-c]pyridin-7-yl 2,4,6-trimethylbenzenesulfonate | 374 | racemic | TFA | 2,4,6-trimethylbenzenesulfonyl chloride |
| 657 | 1,2,3,4,4a,9a-hexahydro[1]benzofuro[2,3-c]pyridin-7-yl 4-(propan-2-yl)benzenesulfonate | 374 | racemic | TFA | 4-(propan-2-yl)benzenesulfonyl chloride |
| 658 | 1,2,3,4,4a,9a-hexahydro[1]benzofuro[2,3-c]pyridin-7-yl 3-chloro-2-methylbenzenesulfonate | 380 | racemic | TFA | 3-chloro-2-methylbenzenesulfonyl chloride |
| 659 | 1,2,3,4,4a,9a-hexahydro[1]benzofuro[2,3-c]pyridin-7-yl 3-chloro-4-methylbenzenesulfonate | 380 | racemic | TFA | 3-chloro-4-methylbenzenesulfonyl chloride |
| 660 | 1,2,3,4,4a,9a-hexahydro[1]benzofuro[2,3-c]pyridin-7-yl naphthalene-1-sulfonate | 382 | racemic | TFA | naphthalene-1-sulfonyl chloride |
| 661 | 1,2,3,4,4a,9a-hexahydro[1]benzofuro[2,3-c]pyridin-7-yl naphthalene-2-sulfonate | 382 | racemic | TFA | naphthalene-2-sulfonyl chloride |
| 662 | 1,2,3,4,4a,9a-hexahydro[1]benzofuro[2,3-c]pyridin-7-yl quinoline-8-sulfonate | 383 | racemic | TFA | quinoline-8-sulfonyl chloride |
| 663 | 1,2,3,4,4a,9a-hexahydro[1]benzofuro[2,3-c]pyridin-7-yl 3-chloro-4-fluorobenzenesulfonate | 384 | racemic | TFA | 3-chloro-4-fluorobenzenesulfonyl chloride |
| 664 | 1,2,3,4,4a,9a-hexahydro[1]benzofuro[2,3-c]pyridin-7-yl 1-benzothiophene-2-sulfonate | 388 | racemic | TFA | 1-benzothiophene-2-sulfonyl chloride |
| 665 | 1,2,3,4,4a,9a-hexahydro[1]benzofuro[2,3-c]pyridin-7-yl 1-benzothiophene-3-sulfonate | 388 | racemic | TFA | 1-benzothiophene-3-sulfonyl chloride |
| 666 | 1,2,3,4,4a,9a-hexahydro[1]benzofuro[2,3-c]pyridin-7-yl 4-tert-butylbenzenesulfonate | 388 | racemic | TFA | 4-tert-butylbenzenesulfonyl chloride |

| Ex. # | Name | MS m/z [M + H]+ | Stereochemistry | Salt | Starting material |
|---|---|---|---|---|---|
| 667 | 1,2,3,4,4a,9a-hexahydro[1]benzofuro[2,3-c]pyridin-7-yl 4-(acetylamino)benzenesulfonate | 389 | racemic | TFA | 4-(acetylamino)benzenesulfonyl chloride |
| 668 | 1,2,3,4,4a,9a-hexahydro[1]benzofuro[2,3-c]pyridin-7-yl 2,3-dihydro-1,4-benzodioxine-6-sulfonate | 390 | racemic | TFA | 2,3-dihydro-1,4-benzodioxine-6-sulfonyl chloride |
| 669 | 1,2,3,4,4a,9a-hexahydro[1]benzofuro[2,3-c]pyridin-7-yl 2,1,3-benzothiadiazole-4-sulfonate | 390 | racemic | TFA | 2,1,3-benzothiadiazole-4-sulfonyl chloride |
| 670 | 1,2,3,4,4a,9a-hexahydro[1]benzofuro[2,3-c]pyridin-7-yl 2,5-dimethoxybenzenesulfonate | 392 | racemic | TFA | 2,5-dimethoxybenzenesulfonyl chloride |
| 671 | 1,2,3,4,4a,9a-hexahydro[1]benzofuro[2,3-c]pyridin-7-yl 4-(1H-pyrazol-1-yl)benzenesulfonate | 398 | racemic | TFA | 4-(1H-pyrazol-1-yl)benzenesulfonyl chloride |
| 672 | 1,2,3,4,4a,9a-hexahydro[1]benzofuro[2,3-c]pyridin-7-yl 4-(1,3-oxazol-5-yl)benzenesulfonate | 399 | racemic | TFA | 4-(1,3-oxazol-5-yl)benzenesulfonyl chloride |
| 673 | 1,2,3,4,4a,9a-hexahydro[1]benzofuro[2,3-c]pyridin-7-yl 4-(trifluoromethyl)benzenesulfonate | 400 | racemic | TFA | 4-(trifluoromethyl)benzenesulfonyl chloride |
| 674 | 1,2,3,4,4a,9a-hexahydro[1]benzofuro[2,3-c]pyridin-7-yl 2-(trifluoromethyl)benzenesulfonate | 400 | racemic | TFA | 2-(trifluoromethyl)benzenesulfonyl chloride |
| 675 | 1,2,3,4,4a,9a-hexahydro[1]benzofuro[2,3-c]pyridin-7-yl 3-(trifluoromethyl)benzenesulfonate | 400 | racemic | TFA | 3-(trifluoromethyl)benzenesulfonyl chloride |
| 676 | 1,2,3,4,4a,9a-hexahydro[1]benzofuro[2,3-c]pyridin-7-yl 3,4-dichlorobenzenesulfonate | 400 | racemic | TFA | 3,4-dichlorobenzenesulfonyl chloride |
| 677 | 1,2,3,4,4a,9a-hexahydro[1]benzofuro[2,3-c]pyridin-7-yl 3,5-dichlorobenzenesulfonate | 400 | racemic | TFA | 3,5-dichlorobenzenesulfonyl chloride |
| 678 | 1,2,3,4,4a,9a-hexahydro[1]benzofuro[2,3-c]pyridin-7-yl 2,3-dichlorobenzenesulfonate | 400 | racemic | TFA | 2,3-dichlorobenzenesulfonyl chloride |
| 679 | 1,2,3,4,4a,9a-hexahydro[1]benzofuro[2,3-c]pyridin-7-yl 2,6-dichlorobenzenesulfonate | 400 | racemic | TFA | 2,6-dichlorobenzenesulfonyl chloride |
| 680 | 1,2,3,4,4a,9a-hexahydro[1]benzofuro[2,3-c]pyridin-7-yl 5-(1,2-oxazol-3-yl)thiophene-2-sulfonate | 405 | racemic | TFA | 5-(1,2-oxazol-3-yl)thiophene-2-sulfonyl chloride |
| 681 | 1,2,3,4,4a,9a-hexahydro[1]benzofuro[2,3-c]pyridin-7-yl biphenyl-4-sulfonate | 408 | racemic | TFA | biphenyl-4-sulfonyl chloride |
| 682 | 1,2,3,4,4a,9a-hexahydro[1]benzofuro[2,3-c]pyridin-7-yl 4-(trifluoromethoxy)benzenesulfonate | 416 | racemic | TFA | 4-(trifluoromethoxy)benzenesulfonyl chloride |
| 683 | 1,2,3,4,4a,9a-hexahydro[1]benzofuro[2,3-c]pyridin-7-yl 6-(morpholin-4-yl)pyridine-3-sulfonate | 418 | racemic | TFA | 6-(morpholin-4-yl)pyridine-3-sulfonyl chloride |
| 684 | 1,2,3,4,4a,9a-hexahydro[1]benzofuro[2,3-c]pyridin-7-yl isoquinoline-5-sulfonate | 383 | racemic | TFA | isoquinoline-5-sulfonyl chloride |
| 685 | 1,2,3,4,4a,9a-hexahydro[1]benzofuro[2,3-c]pyridin-7-yl 6-phenoxypyridine-3-sulfonate | 425 | racemic | TFA | 6-phenoxypyridine-3-sulfonyl chloride |

| Ex. # | Name | MS m/z [M + H]+ | Stereochemistry | Salt | Starting material |
|---|---|---|---|---|---|
| 686 | 1,2,3,4,4a,9a-hexahydro[1]benzofuro[2,3-c]pyridin-7-yl 4-phenyl-5-(trifluoromethyl)thiophene-3-sulfonate | 482 | racemic | TFA | 4-phenyl-5-(trifluoromethyl)thiophene-3-sulfonyl chloride |
| 687 | 1,2,3,4,4a,9a-hexahydro[1]benzofuro[2,3-c]pyridin-7-yl 5-chloro-3-methyl-1-benzothiophene-2-sulfonate | 436 | racemic | TFA | 5-chloro-3-methyl-1-benzothiophene-2-sulfonyl chloride |
| 688 | 1,2,3,4,4a,9a-hexahydro[1]benzofuro[2,3-c]pyridin-7-yl 4-nitrobenzenesulfonate | 377 | racemic | TFA | 4-nitrobenzenesulfonyl chloride |
| 689 | 1,2,3,4,4a,9a-hexahydro[1]benzofuro[2,3-c]pyridin-7-yl pyridine-2-sulfonate | 333 | racemic | TFA | pyridine-2-sulfonyl chloride |
| 690 | 1,2,3,4,4a,9a-hexahydro[1]benzofuro[2,3-c]pyridin-7-yl cyclohexylmethanesulfonate | 352 | racemic | TFA | cyclohexylmethanesulfonyl chloride |
| 691 | 1,2,3,4,4a,9a-hexahydro[1]benzofuro[2,3-c]pyridin-7-yl 2-phenylethanesulfonate | 360 | racemic | TFA | 2-phenylethanesulfonyl chloride |
| 692 | 1,2,3,4,4a,9a-hexahydro[1]benzofuro[2,3-c]pyridin-7-yl 6-chloroimidazo[2,1-b][1,3]thiazole-5-sulfonate | 412 | racemic | HCl | 6-chloroimidazo[2,1-b][1,3]thiazole-5-sulfonyl chloride |
| 693 | 1,2,3,4,4a,9a-hexahydro[1]benzofuro[2,3-c]pyridin-7-yl 4-(propan-2-yl)benzenesulfonate | 374 | racemic | HCl | 4-(propan-2-yl)benzenesulfonyl chloride |
| 694 | 1,2,3,4,4a,9a-hexahydro[1]benzofuro[2,3-c]pyridin-7-yl 5-chloro-3-methyl-1-benzothiophene-2-sulfonate | 436 | racemic | HCl | 5-chloro-3-methyl-1-benzothiophene-2-sulfonyl chloride |
| 695 | 1,2,3,4,4a,9a-hexahydro[1]benzofuro[2,3-c]pyridin-6-yl 4-chlorobenzenesulfonate | 366 | racemic | HCl | 4-chlorobenzenesulfonyl chloride |
| 696 | 1,2,3,4,4a,9a-hexahydro[1]benzofuro[2,3-c]pyridin-6-yl benzenesulfonate | 332 | racemic | TFA | benzenesulfonyl chloride |
| 697 | 1,2,3,4,4a,9a-hexahydro[1]benzofuro[2,3-c]pyridin-6-yl phenylmethanesulfonate | 346 | racemic | TFA | phenylmethanesulfonyl chloride |
| 698 | 1,2,3,4,4a,9a-hexahydro[1]benzofuro[2,3-c]pyridin-6-yl 6-chloroimidazo[2,1-b][1,3]thiazole-5-sulfonate | 412 | racemic | TFA | 6-chloroimidazo[2,1-b][1,3]thiazole-5-sulfonyl chloride |
| 699 | 1,2,3,4,4a,9a-hexahydro[1]benzofuro[2,3-c]pyridin-6-yl 3-methylbenzenesulfonate | 346 | racemic | TFA | 3-methylbenzenesulfonyl chloride |
| 700 | 1,2,3,4,4a,9a-hexahydro[1]benzofuro[2,3-c]pyridin-6-yl 4-methylbenzenesulfonate | 346 | racemic | TFA | 4-methylbenzenesulfonyl chloride |
| 701 | 1,2,3,4,4a,9a-hexahydro[1]benzofuro[2,3-c]pyridin-6-yl 3-fluorobenzenesulfonate | 350 | racemic | TFA | 3-fluorobenzenesulfonyl chloride |
| 702 | 1,2,3,4,4a,9a-hexahydro[1]benzofuro[2,3-c]pyridin-6-yl 4-fluorobenzenesulfonate | 350 | racemic | TFA | 4-fluorobenzenesulfonyl chloride |

-continued

| Ex. # | Name | MS m/z [M + H]+ | Stereochemistry | Salt | Starting material |
|---|---|---|---|---|---|
| 703 | 1,2,3,4,4a,9a-hexahydro[1]benzofuro[2,3-c]pyridin-6-yl 3,5-dimethyl-1,2-oxazole-4-sulfonate | 351 | racemic | TFA | 3,5-dimethyl-1,2-oxazole-4-sulfonyl chloride |
| 704 | 1,2,3,4,4a,9a-hexahydro[1]benzofuro[2,3-c]pyridin-6-yl 2,5-dimethylbenzenesulfonate | 360 | racemic | TFA | 2,5-dimethylbenzenesulfonyl chloride |
| 705 | 1,2,3,4,4a,9a-hexahydro[1]benzofuro[2,3-c]pyridin-6-yl 3,5-dimethylbenzenesulfonate | 360 | racemic | TFA | 3,5-dimethylbenzenesulfonyl chloride |
| 706 | 1,2,3,4,4a,9a-hexahydro[1]benzofuro[2,3-c]pyridin-6-yl 3,4-dimethylbenzenesulfonate | 360 | racemic | TFA | 3,4-dimethylbenzenesulfonyl chloride |
| 707 | 1,2,3,4,4a,9a-hexahydro[1]benzofuro[2,3-c]pyridin-6-yl 4-methoxybenzenesulfonate | 362 | racemic | TFA | 4-methoxybenzenesulfonyl chloride |
| 708 | 1,2,3,4,4a,9a-hexahydro[1]benzofuro[2,3-c]pyridin-6-yl 3-methoxybenzenesulfonate | 362 | racemic | TFA | 3-methoxybenzenesulfonyl chloride |
| 709 | 1,2,3,4,4a,9a-hexahydro[1]benzofuro[2,3-c]pyridin-6-yl 3-fluoro-4-methylbenzenesulfonate | 364 | racemic | TFA | 3-fluoro-4-methylbenzenesulfonyl chloride |
| 710 | 1,2,3,4,4a,9a-hexahydro[1]benzofuro[2,3-c]pyridin-6-yl 3-chlorobenzenesulfonate | 366 | racemic | TFA | 3-chlorobenzenesulfonyl chloride |
| 711 | 1,2,3,4,4a,9a-hexahydro[1]benzofuro[2,3-c]pyridin-6-yl 2-chlorobenzenesulfonate | 366 | racemic | TFA | 2-chlorobenzenesulfonyl chloride |
| 712 | 1,2,3,4,4a,9a-hexahydro[1]benzofuro[2,3-c]pyridin-6-yl 2,4-difluorobenzenesulfonate | 368 | racemic | TFA | 2,4-difluorobenzenesulfonyl chloride |
| 713 | 1,2,3,4,4a,9a-hexahydro[1]benzofuro[2,3-c]pyridin-6-yl 1-benzofuran-2-sulfonate | 372 | racemic | TFA | 1-benzofuran-2-sulfonyl chloride |
| 714 | 1,2,3,4,4a,9a-hexahydro[1]benzofuro[2,3-c]pyridin-6-yl 1-benzofuran-2-sulfonate | 372 | racemic | TFA | 1-benzofuran-2-sulfonyl chloride |
| 715 | 1,2,3,4,4a,9a-hexahydro[1]benzofuro[2,3-c]pyridin-6-yl 2,4,6-trimethylbenzenesulfonate | 374 | racemic | TFA | 2,4,6-trimethylbenzenesulfonyl chloride |
| 716 | 1,2,3,4,4a,9a-hexahydro[1]benzofuro[2,3-c]pyridin-6-yl 4-(propan-2-yl)benzenesulfonate | 374 | racemic | TFA | 4-(propan-2-yl)benzenesulfonyl chloride |
| 717 | 1,2,3,4,4a,9a-hexahydro[1]benzofuro[2,3-c]pyridin-6-yl 3-chloro-2-methylbenzenesulfonate | 380 | racemic | TFA | 3-chloro-2-methylbenzenesulfonyl chloride |
| 718 | 1,2,3,4,4a,9a-hexahydro[1]benzofuro[2,3-c]pyridin-6-yl 3-chloro-2-methylbenzenesulfonate | 380 | racemic | TFA | 3-chloro-2-methylbenzenesulfonyl chloride |
| 719 | 1,2,3,4,4a,9a-hexahydro[1]benzofuro[2,3-c]pyridin-6-yl 3-chloro-4-methylbenzenesulfonate | 380 | racemic | TFA | 3-chloro-4-methylbenzenesulfonyl chloride |
| 720 | 1,2,3,4,4a,9a-hexahydro[1]benzofuro[2,3-c]pyridin-6-yl naphthalene-1-sulfonate | 382 | racemic | TFA | naphthalene-1-sulfonyl chloride |
| 721 | 1,2,3,4,4a,9a-hexahydro[1]benzofuro[2,3-c]pyridin-6-yl naphthalene-2-sulfonate | 382 | racemic | TFA | naphthalene-2-sulfonyl chloride |

-continued

| Ex. # | Name | MS m/z [M + H]+ | Stereochemistry | Salt | Starting material |
|---|---|---|---|---|---|
| 722 | 1,2,3,4,4a,9a-hexahydro[1]benzofuro[2,3-c]pyridin-6-yl quinoline-8-sulfonate | 383 | racemic | TFA | quinoline-8-sulfonyl chloride |
| 723 | 1,2,3,4,4a,9a-hexahydro[1]benzofuro[2,3-c]pyridin-6-yl 3-chloro-4-fluorobenzenesulfonate | 384 | racemic | TFA | 3-chloro-4-fluorobenzenesulfonyl chloride |
| 724 | 1,2,3,4,4a,9a-hexahydro[1]benzofuro[2,3-c]pyridin-6-yl 1-benzothiophene-2-sulfonate | 388 | racemic | TFA | 1-benzothiophene-2-sulfonyl chloride |
| 725 | 1,2,3,4,4a,9a-hexahydro[1]benzofuro[2,3-c]pyridin-6-yl 1-benzothiophene-3-sulfonate | 388 | racemic | TFA | 1-benzothiophene-3-sulfonyl chloride |
| 726 | 1,2,3,4,4a,9a-hexahydro[1]benzofuro[2,3-c]pyridin-6-yl 1-benzothiophene-3-sulfonate | 388 | racemic | TFA | 1-benzothiophene-3-sulfonyl chloride |
| 727 | 1,2,3,4,4a,9a-hexahydro[1]benzofuro[2,3-c]pyridin-6-yl 4-tert-butylbenzenesulfonate | 388 | racemic | TFA | 4-tert-butylbenzenesulfonyl chloride |
| 728 | 1,2,3,4,4a,9a-hexahydro[1]benzofuro[2,3-c]pyridin-6-yl 4-(acetylamino)benzenesulfonate | 389 | racemic | TFA | 4-(acetylamino)benzenesulfonyl chloride |
| 729 | 1,2,3,4,4a,9a-hexahydro[1]benzofuro[2,3-c]pyridin-6-yl 2,3-dihydro-1,4-benzodioxine-6-sulfonate | 390 | racemic | TFA | 2,3-dihydro-1,4-benzodioxine-6-sulfonyl chloride |
| 730 | 1,2,3,4,4a,9a-hexahydro[1]benzofuro[2,3-c]pyridin-6-yl 2,1,3-benzothiadiazole-4-sulfonate | 390 | racemic | TFA | 2,1,3-benzothiadiazole-4-sulfonyl chloride |
| 731 | 1,2,3,4,4a,9a-hexahydro[1]benzofuro[2,3-c]pyridin-6-yl 2,5-dimethoxybenzenesulfonate | 392 | racemic | TFA | 2,5-dimethoxybenzenesulfonyl chloride |
| 732 | 1,2,3,4,4a,9a-hexahydro[1]benzofuro[2,3-c]pyridin-6-yl 3,4-dimethoxybenzenesulfonate | 392 | racemic | TFA | 3,4-dimethoxybenzenesulfonyl chloride |
| 733 | 1,2,3,4,4a,9a-hexahydro[1]benzofuro[2,3-c]pyridin-6-yl 4-(1H-pyrazol-1-yl)benzenesulfonate | 398 | racemic | TFA | 4-(1H-pyrazol-1-yl)benzenesulfonyl chloride |
| 734 | 1,2,3,4,4a,9a-hexahydro[1]benzofuro[2,3-c]pyridin-6-yl 4-(1,3-oxazol-5-yl)benzenesulfonate | 399 | racemic | TFA | 4-(1,3-oxazol-5-yl)benzenesulfonyl chloride |
| 735 | 1,2,3,4,4a,9a-hexahydro[1]benzofuro[2,3-c]pyridin-6-yl 4-(trifluoromethyl)benzenesulfonate | 400 | racemic | TFA | 4-(trifluoromethyl)benzenesulfonyl chloride |
| 736 | 1,2,3,4,4a,9a-hexahydro[1]benzofuro[2,3-c]pyridin-6-yl 2-(trifluoromethyl)benzenesulfonate | 400 | racemic | TFA | 2-(trifluoromethyl)benzenesulfonyl chloride |
| 737 | 1,2,3,4,4a,9a-hexahydro[1]benzofuro[2,3-c]pyridin-6-yl 3-(trifluoromethyl)benzenesulfonate | 400 | racemic | TFA | 3-(trifluoromethyl)benzenesulfonyl chloride |
| 738 | 1,2,3,4,4a,9a-hexahydro[1]benzofuro[2,3-c]pyridin-6-yl 3,4-dichlorobenzenesulfonate | 400 | racemic | TFA | 3,4-dichlorobenzenesulfonyl chloride |
| 739 | 1,2,3,4,4a,9a-hexahydro[1]benzofuro[2,3-c]pyridin-6-yl 3,5-dichlorobenzenesulfonate | 400 | racemic | TFA | 3,5-dichlorobenzenesulfonyl chloride |
| 740 | 1,2,3,4,4a,9a-hexahydro[1]benzofuro[2,3-c]pyridin-6-yl 2,3-dichlorobenzenesulfonate | 400 | racemic | TFA | 2,3-dichlorobenzenesulfonyl chloride |

-continued

| Ex. # | Name | MS m/z [M + H]+ | Stereochemistry | Salt | Starting material |
|---|---|---|---|---|---|
| 741 | 1,2,3,4,4a,9a-hexahydro[1]benzofuro[2,3-c]pyridin-6-yl 2,6-dichlorobenzenesulfonate | 400 | racemic | TFA | 2,6-dichlorobenzenesulfonyl chloride |
| 742 | 1,2,3,4,4a,9a-hexahydro[1]benzofuro[2,3-c]pyridin-6-yl 5-(1,2-oxazol-3-yl)thiophene-2-sulfonate | 405 | racemic | TFA | 5-(1,2-oxazol-3-yl)thiophene-2-sulfonyl chloride |
| 743 | 1,2,3,4,4a,9a-hexahydro[1]benzofuro[2,3-c]pyridin-6-yl biphenyl-4-sulfonate | 408 | racemic | TFA | biphenyl-4-sulfonyl chloride |
| 744 | 1,2,3,4,4a,9a-hexahydro[1]benzofuro[2,3-c]pyridin-6-yl 4-(trifluoromethoxy)benzenesulfonate | 416 | racemic | TFA | 4-(trifluoromethoxy)benzenesulfonyl chloride |
| 745 | 1,2,3,4,4a,9a-hexahydro[1]benzofuro[2,3-c]pyridin-6-yl isoquinoline-5-sulfonate | 383 | racemic | TFA | isoquinoline-5-sulfonyl chloride |
| 746 | 1,2,3,4,4a,9a-hexahydro[1]benzofuro[2,3-c]pyridin-6-yl 6-phenoxypyridine-3-sulfonate | 425 | racemic | TFA | 6-phenoxypyridine-3-sulfonyl chloride |
| 747 | 1,2,3,4,4a,9a-hexahydro[1]benzofuro[2,3-c]pyridin-6-yl 4-phenyl-5-(trifluoromethyl)thiophene-3-sulfonate | 482 | racemic | TFA | 4-phenyl-5-(trifluoromethyl)thiophene-3-sulfonyl chloride |
| 748 | 1,2,3,4,4a,9a-hexahydro[1]benzofuro[2,3-c]pyridin-6-yl 5-chloro-3-methyl-1-benzothiophene-2-sulfonate | 436 | racemic | TFA | 5-chloro-3-methyl-1-benzothiophene-2-sulfonyl chloride |
| 749 | 1,2,3,4,4a,9a-hexahydro[1]benzofuro[2,3-c]pyridin-6-yl 4-nitrobenzenesulfonate | 377 | racemic | TFA | 4-nitrobenzenesulfonyl chloride |
| 750 | 1,2,3,4,4a,9a-hexahydro[1]benzofuro[2,3-c]pyridin-6-yl [3-(trifluoromethyl)phenyl]methanesulfonate | 414 | racemic | TFA | [3-(trifluoromethyl)phenyl]methanesulfonyl chloride |
| 751 | 1,2,3,4,4a,9a-hexahydro[1]benzofuro[2,3-c]pyridin-6-yl [4-(trifluoromethyl)phenyl]methanesulfonate | 414 | racemic | TFA | [4-(trifluoromethyl)phenyl]methanesulfonyl chloride |
| 752 | 1,2,3,4,4a,9a-hexahydro[1]benzofuro[2,3-c]pyridin-6-yl (3-chlorophenyl)methanesulfonate | 380 | racemic | TFA | (3-chlorophenyl)methanesulfonyl chloride |
| 753 | 1,2,3,4,4a,9a-hexahydro[1]benzofuro[2,3-c]pyridin-6-yl pyridine-2-sulfonate | 333 | racemic | TFA | pyridine-2-sulfonyl chloride |
| 754 | 1,2,3,4,4a,9a-hexahydro[1]benzofuro[2,3-c]pyridin-6-yl (2-chlorophenyl)methanesulfonate | 380 | racemic | TFA | (2-chlorophenyl)methanesulfonyl chloride |
| 755 | 1,2,3,4,4a,9a-hexahydro[1]benzofuro[2,3-c]pyridin-6-yl 2-phenylethanesulfonate | 360 | racemic | TFA | 2-phenylethanesulfonyl chloride |
| 756 | 1,2,3,4,4a,9a-hexahydro[1]benzofuro[2,3-c]pyridin-6-yl (2,4-difluorophenyl)methanesulfonate | 382 | racemic | TFA | (2,4-difluorophenyl)methanesulfonyl chloride |
| 757 | 4a-methyl-1,2,3,4,4a,9a-hexahydro[1]benzofuro[2,3-c]pyridin-6-yl 4-chlorobenzenesulfonate | 380 | racemic | TFA | 4-chlorobenzenesulfonyl chloride |
| 758 | 4a-methyl-1,2,3,4,4a,9a-hexahydro[1]benzofuro[2,3-c]pyridin-6-yl phenylmethanesulfonate | 360 | racemic | HCl | phenylmethanesulfonyl chloride |

| Ex. # | Name | MS m/z [M + H]+ | Stereochemistry | Salt | Starting material |
|---|---|---|---|---|---|
| 759 | 4a-methyl-1,2,3,4,4a,9a-hexahydro[1]benzofuro[2,3-c]pyridin-6-yl benzenesulfonate | 346 | racemic | HCl | benzenesulfonyl chloride |
| 760 | 4a-methyl-1,2,3,4,4a,9a-hexahydro[1]benzofuro[2,3-c]pyridin-6-yl 4-methoxybenzenesulfonate | 376 | racemic | TFA | 4-methoxybenzenesulfonyl chloride |
| 761 | 4a-methyl-1,2,3,4,4a,9a-hexahydro[1]benzofuro[2,3-c]pyridin-6-yl 3-methoxybenzenesulfonate | 376 | racemic | TFA | 3-methoxybenzenesulfonyl chloride |
| 762 | 4a-methyl-1,2,3,4,4a,9a-hexahydro[1]benzofuro[2,3-c]pyridin-6-yl 3-chlorobenzenesulfonate | 380 | racemic | TFA | 3-chlorobenzenesulfonyl chloride |
| 763 | 4a-methyl-1,2,3,4,4a,9a-hexahydro[1]benzofuro[2,3-c]pyridin-6-yl 2-chlorobenzenesulfonate | 380 | racemic | TFA | 2-chlorobenzenesulfonyl chloride |
| 764 | 4a-methyl-1,2,3,4,4a,9a-hexahydro[1]benzofuro[2,3-c]pyridin-6-yl 1-benzofuran-2-sulfonate | 386 | racemic | TFA | 1-benzofuran-2-sulfonyl chloride |
| 765 | 4a-methyl-1,2,3,4,4a,9a-hexahydro[1]benzofuro[2,3-c]pyridin-6-yl 1-benzofuran-2-sulfonate | 386 | racemic | TFA | 1-benzofuran-2-sulfonyl chloride |
| 766 | 4a-methyl-1,2,3,4,4a,9a-hexahydro[1]benzofuro[2,3-c]pyridin-6-yl 4-(propan-2-yl)benzenesulfonate | 388 | racemic | TFA | 4-(propan-2-yl)benzenesulfonyl chloride |
| 767 | 4a-methyl-1,2,3,4,4a,9a-hexahydro[1]benzofuro[2,3-c]pyridin-6-yl 3-chloro-2-methylbenzenesulfonate | 394 | racemic | TFA | 3-chloro-2-methylbenzenesulfonyl chloride |
| 768 | 4a-methyl-1,2,3,4,4a,9a-hexahydro[1]benzofuro[2,3-c]pyridin-6-yl naphthalene-1-sulfonate | 396 | racemic | TFA | naphthalene-1-sulfonyl chloride |
| 769 | 4a-methyl-1,2,3,4,4a,9a-hexahydro[1]benzofuro[2,3-c]pyridin-6-yl naphthalene-2-sulfonate | 396 | racemic | TFA | naphthalene-2-sulfonyl chloride |
| 770 | 4a-methyl-1,2,3,4,4a,9a-hexahydro[1]benzofuro[2,3-c]pyridin-6-yl quinoline-8-sulfonate | 397 | racemic | TFA | quinoline-8-sulfonyl chloride |
| 771 | 4a-methyl-1,2,3,4,4a,9a-hexahydro[1]benzofuro[2,3-c]pyridin-6-yl 1-benzothiophene-3-sulfonate | 402 | racemic | TFA | 1-benzothiophene-3-sulfonyl chloride |
| 772 | 4a-methyl-1,2,3,4,4a,9a-hexahydro[1]benzofuro[2,3-c]pyridin-6-yl 1-benzothiophene-3-sulfonate | 402 | racemic | TFA | 1-benzothiophene-3-sulfonyl chloride |
| 773 | 4a-methyl-1,2,3,4,4a,9a-hexahydro[1]benzofuro[2,3-c]pyridin-6-yl 1-benzothiophene-2-sulfonate | 402 | racemic | TFA | 1-benzothiophene-2-sulfonyl chloride |
| 774 | 4a-methyl-1,2,3,4,4a,9a-hexahydro[1]benzofuro[2,3-c]pyridin-6-yl 4-tert-butylbenzenesulfonate | 402 | racemic | TFA | 4-tert-butylbenzenesulfonyl chloride |
| 775 | 4a-methyl-1,2,3,4,4a,9a-hexahydro[1]benzofuro[2,3-c]pyridin-6-yl 2,3-dihydro-1,4-benzodioxine-6-sulfonate | 404 | racemic | TFA | 2,3-dihydro-1,4-benzodioxine-6-sulfonyl chloride |
| 776 | 4a-methyl-1,2,3,4,4a,9a-hexahydro[1]benzofuro[2,3-c]pyridin-6-yl 4-(1H-pyrazol-1-yl)benzenesulfonate | 412 | racemic | TFA | 4-(1H-pyrazol-1-yl)benzenesulfonyl chloride |
| 777 | 4a-methyl-1,2,3,4,4a,9a-hexahydro[1]benzofuro[2,3-c]pyridin-6-yl 4-(1,3-oxazol-5-yl)benzenesulfonate | 413 | racemic | TFA | 4-(1,3-oxazol-5-yl)benzenesulfonyl chloride |

-continued

| Ex. # | Name | MS m/z [M + H]+ | Stereochemistry | Salt | Starting material |
|---|---|---|---|---|---|
| 778 | 4a-methyl-1,2,3,4,4a,9a-hexahydro[1]benzofuro[2,3-c]pyridin-6-yl 4-(trifluoromethyl)benzenesulfonate | 414 | racemic | TFA | 4-(trifluoromethyl)benzenesulfonyl chloride |
| 779 | 4a-methyl-1,2,3,4,4a,9a-hexahydro[1]benzofuro[2,3-c]pyridin-6-yl 2-(trifluoromethyl)benzenesulfonate | 414 | racemic | TFA | 2-(trifluoromethyl)benzenesulfonyl chloride |
| 780 | 4a-methyl-1,2,3,4,4a,9a-hexahydro[1]benzofuro[2,3-c]pyridin-6-yl 3-(trifluoromethyl)benzenesulfonate | 414 | racemic | TFA | 3-(trifluoromethyl)benzenesulfonyl chloride |
| 781 | 4a-methyl-1,2,3,4,4a,9a-hexahydro[1]benzofuro[2,3-c]pyridin-6-yl 5-(1,2-oxazol-3-yl)thiophene-2-sulfonate | 419 | racemic | TFA | 5-(1,2-oxazol-3-yl)thiophene-2-sulfonyl chloride |
| 782 | 4a-methyl-1,2,3,4,4a,9a-hexahydro[1]benzofuro[2,3-c]pyridin-6-yl 6-phenoxypyridine-3-sulfonate | 439 | racemic | TFA | 6-phenoxypyridine-3-sulfonyl chloride |
| 783 | 4a-methyl-1,2,3,4,4a,9a-hexahydro[1]benzofuro[2,3-c]pyridin-6-yl 5-chloro-3-methyl-1-benzothiophene-2-sulfonate | 450 | racemic | TFA | 5-chloro-3-methyl-1-benzothiophene-2-sulfonyl chloride |
| 784 | 4a-methyl-1,2,3,4,4a,9a-hexahydro[1]benzofuro[2,3-c]pyridin-6-yl (2-chlorophenyl)methanesulfonate | 394 | racemic | TFA | (2-chlorophenyl)methanesulfonyl chloride |
| 785 | 4a-methyl-1,2,3,4,4a,9a-hexahydro[1]benzofuro[2,3-c]pyridin-6-yl 2-phenylethanesulfonate | 374 | racemic | TFA | 2-phenylethanesulfonyl chloride |
| 786 | 4a-methyl-1,2,3,4,4a,9a-hexahydro[1]benzofuro[2,3-c]pyridin-6-yl (2-fluorophenyl)methanesulfonate | 378 | racemic | TFA | (2-fluorophenyl)methanesulfonyl chloride |
| 787 | 4a-methyl-1,2,3,4,4a,9a-hexahydro[1]benzofuro[2,3-c]pyridin-6-yl (2,4-difluorophenyl)methanesulfonate | 396 | racemic | TFA | (2,4-difluorophenyl)methanesulfonyl chloride |
| 788 | 4a-methyl-1,2,3,4,4a,9a-hexahydro[1]benzofuro[2,3-c]pyridin-6-yl [3-(trifluoromethyl)phenyl]methanesulfonate | 428 | racemic | TFA | [3-(trifluoromethyl)phenyl]methanesulfonyl chloride |
| 789 | 4a-methyl-1,2,3,4,4a,9a-hexahydro[1]benzofuro[2,3-c]pyridin-6-yl (4-chlorophenyl)methanesulfonate | 394 | racemic | TFA | (4-chlorophenyl)methanesulfonyl chloride |
| 790 | 4a-methyl-1,2,3,4,4a,9a-hexahydro[1]benzofuro[2,3-c]pyridin-6-yl (4-fluorophenyl)methanesulfonate | 378 | racemic | TFA | (4-fluorophenyl)methanesulfonyl chloride |
| 791 | 4a-methyl-1,2,3,4,4a,9a-hexahydro[1]benzofuro[2,3-c]pyridin-6-yl (3-chlorophenyl)methanesulfonate | 394 | racemic | TFA | (3-chlorophenyl)methanesulfonyl chloride |

Chiral Separations

The stereoisomers in the Table below were isolated from the corresponding stereoisomer mixture using SFC chromatography on a chiral column as described in the general method.

| Ex. # | Name | MS m/z [M + H]+ | Stereochemistry | Salt | Starting material |
|---|---|---|---|---|---|
| 792 | 1,2,3,4,4a,9a-hexahydro[1]benzofuro[2,3-c]pyridin-7-yl 6-chloroimidazo[2,1-b][1,3]thiazole-5-sulfonate | 412 | enantiomer 1 | HCl | Example 692 |

| Ex. # | Name | MS m/z [M + H]+ | Stereochemistry | Salt | Starting material |
|---|---|---|---|---|---|
| 793 | 1,2,3,4,4a,9a-hexahydro[1]benzofuro[2,3-c]pyridin-7-yl 6-chloroimidazo[2,1-b][1,3]thiazole-5-sulfonate | 412 | enantiomer 2 | HCl | Example 692 |
| 794 | 1,2,3,4,4a,9a-hexahydro[1]benzofuro[2,3-c]pyridin-7-yl 4-(propan-2-yl)benzenesulfonate | 374 | enantiomer 1 | HCl | Example 693 |
| 795 | 1,2,3,4,4a,9a-hexahydro[1]benzofuro[2,3-c]pyridin-7-yl 4-(propan-2-yl)benzenesulfonate | 374 | enantiomer 2 | HCl | Example 693 |
| 796 | 1,2,3,4,4a,9a-hexahydro[1]benzofuro[2,3-c]pyridin-7-yl 5-chloro-3-methyl-1-benzothiophene-2-sulfonate | 436 | enantiomer 1 | HCl | Example 694 |
| 797 | 1,2,3,4,4a,9a-hexahydro[1]benzofuro[2,3-c]pyridin-7-yl 5-chloro-3-methyl-1-benzothiophene-2-sulfonate | 436 | enantiomer 2 | HCl | Example 694 |

Example 798

2-(Propan-2-yl)-1,2,3,4,4a,9a-hexahydro[1]benzofuro[2,3-c]pyridin-7-yl-4-chlorobenzenesulfonate

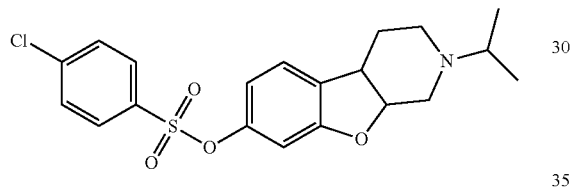

Prepared as described for 2-cyclobutyl-7-(phenylsulfonyl)-1,2,3,4,4a,9a-hexahydro[1]benzofuro[2,3-c]pyridine (Example 606) starting from 1,2,3,4,4a,9a-hexahydro[1]benzofuro[2,3-c]pyridin-7-yl 4-chlorobenzenesulfonate (example 634) and propan-2-one. MS m/z 408 [M+H]+

The following examples were prepared essentially as described above. All compounds were isolated as TFA salts.

| Ex. # | Name | MS m/z [M + H]+ | Stereochemistry | Starting material |
|---|---|---|---|---|
| 798 | 2-(propan-2-yl)-1,2,3,4,4a,9a-hexahydro[1]benzofuro[2,3-c]pyridin-7-yl 4-chlorobenzenesulfonate | 408 | racemic | propan-2-one |
| 799 | 2-methyl-1,2,3,4,4a,9a-hexahydro[1]benzofuro[2,3-c]pyridin-7-yl 4-chlorobenzenesulfonate | 380 | racemic | paraformaldehyde |
| 800 | 2-cyclobutyl-1,2,3,4,4a,9a-hexahydro[1]benzofuro[2,3-c]pyridin-7-yl 4-chlorobenzenesulfonate | 420 | racemic | cyclobutanone |
| 801 | 2-cyclopentyl-1,2,3,4,4a,9a-hexahydro[1]benzofuro[2,3-c]pyridin-7-yl 4-chlorobenzenesulfonate | 434 | racemic | cyclopentanone |
| 802 | 2-cyclohexyl-1,2,3,4,4a,9a-hexahydro[1]benzofuro[2,3-c]pyridin-7-yl 4-chlorobenzenesulfonate | 448 | racemic | cyclohexanone |
| 803 | 2-benzyl-1,2,3,4,4a,9a-hexahydro[1]benzofuro[2,3-c]pyridin-7-yl 4-chlorobenzenesulfonate | 456 | racemic | benzaldehyde |
| 804 | 4a-methyl-2-(propan-2-yl)-1,2,3,4,4a,9a-hexahydro[1]benzofuro[2,3-c]pyridin-6-yl phenylmethanesulfonate | 402 | racemic | propan-2-one |

-continued

| Ex. # | Name | MS m/z [M + H]+ | Stereochemistry | Starting material |
|---|---|---|---|---|
| 805 | 2-cyclobutyl-4a-methyl-1,2,3,4,4a,9a-hexahydro[1]benzofuro[2,3-c]pyridin-6-yl phenylmethanesulfonate | 414 | racemic | cyclobutanone |
| 806 | 2-cyclopentyl-4a-methyl-1,2,3,4,4a,9a-hexahydro[1]benzofuro[2,3-c]pyridin-6-yl phenylmethanesulfonate | 428 | racemic | cyclopentanone |
| 807 | 2-cyclohexyl-4a-methyl-1,2,3,4,4a,9a-hexahydro[1]benzofuro[2,3-c]pyridin-6-yl phenylmethanesulfonate | 442 | racemic | cyclohexanone |
| 808 | 2-benzyl-4a-methyl-1,2,3,4,4a,9a-hexahydro[1]benzofuro[2,3-c]pyridin-6-yl phenylmethanesulfonate | 450 | racemic | benzaldehyde |
| 809 | 2,4a-dimethyl-1,2,3,4,4a,9a-hexahydro[1]benzofuro[2,3-c]pyridin-6-yl phenylmethanesulfonate | 374 | racemic | paraformaldehyde |

Example 810

2-Ethyl-4a-methyl-1,2,3,4,4a,9a-hexahydro[1]benzofuro[2,3-c]pyridin-6-yl phenylmethanesulfonate

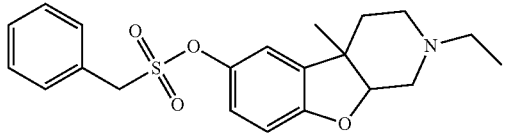 [SMILES: CCN1CCC2(C)c3cc(OS(=O)(=O)Cc4ccccc4)ccc3OC2C1]

Prepared as described for 2-[7-(phenylsulfonyl)-3,4-dihydro[1]benzofuro[2,3-c]pyridin-2(1H)-yl]ethanol (Example 592) starting from 4a-methyl-1,2,3,4,4a,9a-hexahydro[1]benzofuro[2,3-c]pyridin-6-yl phenylmethanesulfonate (Example 757) and bromoethane. MS m/z 388 [M+H]+

The following examples were prepared essentially as described described above. All compounds were isolated as TFA salts.

Example 814

N-(2-Acetyl-1,2,3,4,4a,9a-hexahydro[1]benzofuro[2,3-c]pyridin-6-yl)naphthalene-2-sulfonamide

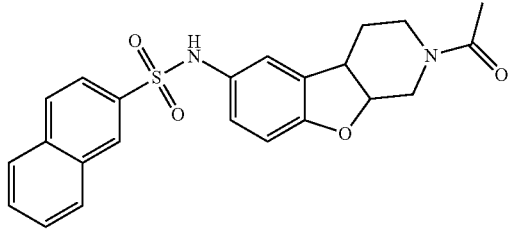 [SMILES: CC(=O)N1CCC2c3cc(NS(=O)(=O)c4ccc5ccccc5c4)ccc3OC2C1]

Step 1

1-(3,4,4a,9a-Tetrahydro-1H-benzo[4,5]furo[2,3-c]pyridin-2-yl)-ethanone

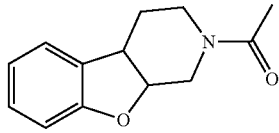 [SMILES: CC(=O)N1CCC2c3ccccc3OC2C1]

| Ex. # | Name | MS m/z [M + H]+ | Stereochemistry | Starting material |
|---|---|---|---|---|
| 810 | 2-ethyl-4a-methyl-1,2,3,4,4a,9a-hexahydro[1]benzofuro[2,3-c]pyridin-6-yl phenylmethanesulfonate | 388 | racemic | bromoethane |
| 811 | 4a-methyl-2-(2-phenylethyl)-1,2,3,4,4a,9a-hexahydro[1]benzofuro[2,3-c]pyridin-6-yl phenylmethanesulfonate | 464 | racemic | (2-bromoethyl)benzene |
| 812 | 2-ethyl-1,2,3,4,4a,9a-hexahydro[1]benzofuro[2,3-c]pyridin-7-yl 4-chlorobenzenesulfonate | 394 | racemic | bromoethane |
| 813 | 2-(2-phenylethyl)-1,2,3,4,4a,9a-hexahydro[1]benzofuro[2,3-c]pyridin-7-yl 4-chlorobenzenesulfonate | 470 | racemic | (2-bromoethyl)benzene |

3,4,4a,9a-Tetrahydro-1H-benzo[4,5]furo[2,3-c]pyridine-2-carboxylic acid tert-butyl ester was prepared as described for tert-butyl 7-methoxy-3,4,4a,9a-tetrahydro[1]benzofuro[2,3-c]pyridine-2(1H)-carboxylate starting from N-Boc-3-hydroxy-1,2,3,6-tetrahydropyridine and 2-bromophenol. Then 3,4,4a,9a-tetrahydro-1H-benzo[4,5]furo[2,3-c]pyridine-2-carboxylic acid tert-butyl ester (4.5 g, 16.6 mmol) was stirred in 4M HCl in dioxane (70 mL). The solvent was evaporated, diethylether was added, and the resulting solid was filtered, washed with diethylether and dried to provide the amine as an hydrochloric acid salt.

To a mixture of 3,4,4a,9a-tetrahydro-1H-benzo[4,5]furo[2,3-c]pyridine hydrochloride (3.2 g, 15.1 mmol) and sodium hydrogenocarbonate (14 g) in chloroform (40 mL), was slowly added a solution of acetyl chloride (1.5 mL, 21 mmol) in chloroform (5 mL). After stirring for 2 h another portion of acetyl chloride was added. After 5 h the solvent was evaporated. Purification using silica gel chromatography (78 g SiO₂) eluting with ethyl acetate yielded 1-(3,4,4a,9a-tetrahydro-1H-benzo[4,5]furo[2,3-c]pyridin-2-yl)-ethanone.

Step 2

1-(6-Amino-3,4,4a,9a-tetrahydro-1H-benzo[4,5]furo[2,3-c]pyridin-2-yl)-ethanone

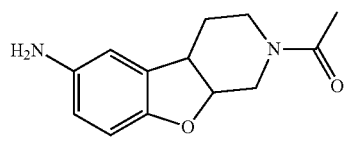 [SMILES: CC(=O)N1CCC2c3cc(N)ccc3OC2C1]

Fuming (90%) nitric acid (2.9 g) was added to 1-(3,4,4a,9a-tetrahydro-1H-benzo[4,5]furo[2,3-c]pyridin-2-yl)-ethanone (2.7 g, 12.5 mmol). The reaction mixture was stirred at 85° C. for 2 h, poured into H₂O (350 mL) and the product was extracted with DCM (3×). The combined organic layers were washed with sodium hydrogenocarbonate and brine, and solvent was evaporated. Purification using silica gel chromatography (150 g SiO₂) eluting with ethyl acetate yielded 1-(6-nitro-3,4,4a,9a-tetrahydro-1H-benzo[4,5]furo[2,3-c]pyridin-2-yl)-ethanone.

A mixture of 1-(6-nitro-3,4,4a,9a-tetrahydro-1H-benzo[4,5]furo[2,3-c]pyridin-2-yl)-ethanone (600 mg) in MeOH (60 mL) was hydrogenated for 16 h at 10 bar using a H-Cube® instrument with a 70 mm cartridge of 10% Pd—C. The solvent was evaporated to yield 1-(6-amino-3,4,4a,9a-tetrahydro-1H-benzo[4,5]furo[2,3-c]pyridin-2-yl)-ethanone. MS m/z 233 [M+H]⁺

Step 3

N-(2-Acetyl-1,2,3,4,4a,9a-hexahydro[1]benzofuro[2,3-c]pyridin-6-yl)naphthalene-2-sulfonamide A 0.5 M solution of 1-(6-amino-3,4,4a,9a-tetrahydro-1H-benzo[4,5]furo[2,3-c]pyridin-2-yl)-ethanone (557 mg) in DCE (4.8 mL) was prepared. To 1.2 mL of the 0.5 M solution of aniline in DCM prepared above, was added DIEA (215 µL) followed by naphthalene-2-sulfonyl chloride (125 mg). The reaction mixture was shaken for 16 h and the solvent was evaporated. A portion of the residue was purified by preparative LC-MS. MS m/z 423 [M+H]⁺

The following examples were prepared essentially as described above.

| Ex. # | Name | MS m/z [M + H]⁺ | Stereochemistry | Starting material |
|---|---|---|---|---|
| 814 | N-(2-acetyl-1,2,3,4,4a,9a-hexahydro[1]benzofuro[2,3-c]pyridin-6-yl)naphthalene-2-sulfonamide | 423 | racemic | naphthalene-2-sulfonyl chloride |
| 815 | N-(2-acetyl-1,2,3,4,4a,9a-hexahydro[1]benzofuro[2,3-c]pyridin-6-yl)-2,5-dimethylbenzenesulfonamide | 401 | Racemic | 2,5-dimethylbenzenesulfonyl chloride |
| 816 | N-(2-acetyl-1,2,3,4,4a,9a-hexahydro[1]benzofuro[2,3-c]pyridin-6-yl)-6-chloroimidazo[2,1-b][1,3]thiazole-5-sulfonamide | 453 | racemic | 6-chloroimidazo[2,1-b][1,3]thiazole-5-sulfonyl chloride |

Example 817

N-(1,2,3,4,4a,9a-Hexahydro[1]benzofuro[2,3-c]pyridin-6-yl)benzenesulfonamide

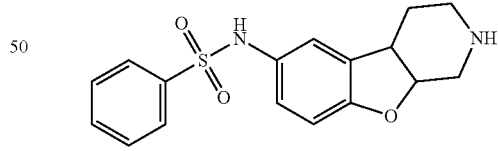

Prepared as described in step 2 of Example 813 except that benzensulfonylchloride was used instead of naphthalene-2-sulfonyl chloride. The crude product was dissolved in dioxane (500 µL) and 6 M HCl in H₂O (1 mL) was added. The reaction mixture was shaken at 100° C. for 4 h and the solvent was evaporated to give a dark residue which was suspended in DCE:MeOH 85:15 and then passed through a silica gel plug. The solvent was evaporated and the resulting material was purified by preparative LC-MS. MS m/z 331 [M+H]⁺

The following examples in the table were prepared essentially as described above.

| Ex. # | Name | MS m/z [M + H]+ | Stereochemistry | Salt | Starting material |
|---|---|---|---|---|---|
| 817 | N-(1,2,3,4,4a,9a-hexahydro[1]benzofuro[2,3-c]pyridin-6-yl)benzenesulfonamide | 331 | racemic | TFA | benzenesulfonyl chloride |
| 818 | 6-chloro-N-(1,2,3,4,4a,9a-hexahydro[1]benzofuro[2,3-c]pyridin-6-yl)imidazo[2,1-b][1,3]thiazole-5-sulfonamide | 411 | Racemic | HCl | 6-chloroimidazo[2,1-b][1,3]thiazole-5-sulfonyl chloride |
| 819 | N-(1,2,3,4,4a,9a-hexahydro[1]benzofuro[2,3-c]pyridin-6-yl)naphthalene-2-sulfonamide | 381 | Racemic | TFA | naphthalene-2-sulfonyl chloride |
| 820 | N-(1,2,3,4,4a,9a-hexahydro[1]benzofuro[2,3-c]pyridin-6-yl)-2,5-dimethylbenzenesulfonamide | 359 | Racemic | TFA | 2,5-dimethylbenzenesulfonyl chloride |
| 821 | N-(1,2,3,4,4a,9a-hexahydro[1]benzofuro[2,3-c]pyridin-6-yl)-4-methoxybenzenesulfonamide | 361 | racemic | TFA | 4-methoxybenzenesulfonyl chloride |
| 822 | N-(1,2,3,4,4a,9a-hexahydro[1]benzofuro[2,3-c]pyridin-6-yl)-3-methoxybenzenesulfonamide | 361 | racemic | TFA | 3-methoxybenzenesulfonyl chloride |
| 823 | 4-chloro-N-(1,2,3,4,4a,9a-hexahydro[1]benzofuro[2,3-c]pyridin-6-yl)benzenesulfonamide | 365 | racemic | TFA | 4-chlorobenzenesulfonyl chloride |
| 824 | N-(1,2,3,4,4a,9a-hexahydro[1]benzofuro[2,3-c]pyridin-6-yl)-4-(propan-2-yl)benzenesulfonamide | 373 | racemic | TFA | 4-(propan-2-yl)benzenesulfonyl chloride |
| 825 | N-(1,2,3,4,4a,9a-hexahydro[1]benzofuro[2,3-c]pyridin-6-yl)naphthalene-1-sulfonamide | 381 | racemic | TFA | naphthalene-1-sulfonyl chloride |
| 826 | 3-chloro-N-(1,2,3,4,4a,9a-hexahydro[1]benzofuro[2,3-c]pyridin-6-yl)benzenesulfonamide | 365 | racemic | TFA | 3-chlorobenzenesulfonyl chloride |
| 827 | 3,4-dichloro-N-(1,2,3,4,4a,9a-hexahydro[1]benzofuro[2,3-c]pyridin-6-yl)benzenesulfonamide | 399 | racemic | TFA | 3,4-dichlorobenzenesulfonyl chloride |
| 828 | 3,5-dichloro-N-(1,2,3,4,4a,9a-hexahydro[1]benzofuro[2,3-c]pyridin-6-yl)benzenesulfonamide | 399 | racemic | TFA | 3,5-dichlorobenzenesulfonyl chloride |
| 829 | 2,3-dichloro-N-(1,2,3,4,4a,9a-hexahydro[1]benzofuro[2,3-c]pyridin-6-yl)benzenesulfonamide | 399 | racemic | TFA | 2,3-dichlorobenzenesulfonyl chloride |
| 830 | 5-chloro-N-(1,2,3,4,4a,9a-hexahydro[1]benzofuro[2,3-c]pyridin-6-yl)-3-methyl-1-benzothiophene-2-sulfonamide | 435 | racemic | TFA | 5-chloro-3-methyl-1-benzothiophene-2-sulfonyl chloride |
| 831 | N-(1,2,3,4,4a,9a-hexahydro[1]benzofuro[2,3-c]pyridin-6-yl)-1-phenylmethanesulfonamide | 345 | racemic | TFA | phenylmethanesulfonyl chloride |
| 832 | N-(1,2,3,4,4a,9a-hexahydro[1]benzofuro[2,3-c]pyridin-6-yl)propane-2-sulfonamide | 297 | racemic | TFA | propane-2-sulfonyl chloride |
| 833 | N-(1,2,3,4,4a,9a-hexahydro[1]benzofuro[2,3-c]pyridin-6-yl)-1-benzofuran-2-sulfonamide | 371 | racemic | TFA | 1-benzofuran-2-sulfonyl chloride |
| 834 | N-(1,2,3,4,4a,9a-hexahydro[1]benzofuro[2,3-c]pyridin-6-yl)-1-benzothiophene-2-sulfonamide | 387 | racemic | TFA | 1-benzothiophene-2-sulfonyl chloride |

Example 835

6-Chloro-N-[1,2,3,4,4a,9a-hexahydro[1]benzofuro[2,3-c]pyridin-7-yl]-N-methylimidazo[2,1-b][1,3]thiazole-5-sulfonamide

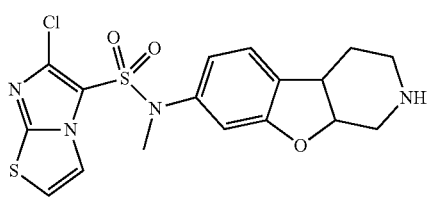 [SMILES: CN(c1ccc2c(c1)OC1CNCCC21)S(=O)(=O)c1c(Cl)nc2sccn12]

Step 1

7-Methylamino-3,4,4a,9a-tetrahydro-1H-benzo[4,5]furo[2,3-c]pyridine-2-carboxylic acid tert-butyl ester

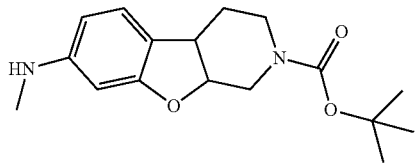 [SMILES: CNc1ccc2c(c1)OC1CN(C(=O)OC(C)(C)C)CCC21]

Anhydrous DMF was sparged with argon gas for 1 h before being used. Tert-butyl 7-iodo-3,4,4a,9a-tetrahydro[1]benzofuro[2,3-c]pyridine-2(1H)-carboxylate (1 g, 2.5 mmol) sodium tert-butoxide (723 mg, 7.5 mmol), neocuproine (52 mg, 0.25 mmol) and copper (I) iodide (290 mg, 1.5 mmol) were dissolved in anhydrous DMF (20 mL). To this mixture was added a 2M solution of methylamine in THF (6 mL) and the reaction shaken at 80° C. for 16 h. The solvent was evaporated and the residue dissolved in DCM and washed with $H_2O$ (3×). The solvent was evaporated and the crude residue used as such in the next reaction step.

Step 2

Crude N-methyl aniline (200 mg, 0.8 mmol) was dissolved in DCE (7 mL) and DIEA (210 µL, 1.2 mmol) was added followed by 6-chloro-N-[1,2,3,4,4a,9a-hexahydro[1]benzofuro[2,3-c]pyridin-7-yl]-N-methylimidazo[2,1-b][1,3]thiazole-5-sulfonamide (217 mg, 0.84 mmol). The reaction mixture was shaken for 1 h and TFA (7 mL) was added. After shaking for 30 min the solvent was evaporated and the residue purified by preparative LC-MS. The product was converted to the HCl salt by dissolving the product in DCM, adding 2M HCl in $Et_2O$ and evaporating the solvent. MS m/z 425 $[M+H]^+$

Example 836

N-(4-Chlorophenyl)-1,2,3,4,4a,9a-hexahydro[1]benzofuro[2,3-c]pyridine-6-sulfonamide

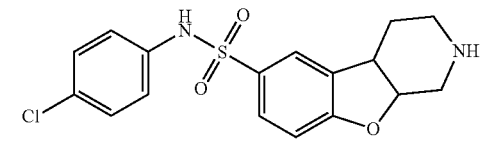 [SMILES: O=S(=O)(Nc1ccc(Cl)cc1)c1ccc2c(c1)C1CCNCC1O2]

Step 1

2-Acetyl-1,2,3,4,4a,9a-hexahydro-benzo[4,5]furo[2,3-c]pyridine-6-sulfonyl chloride

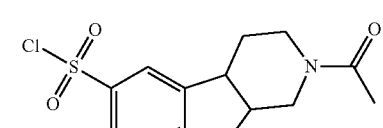

To a solution of 1-(3,4,4a,9a-tetrahydro-1H-benzo[4,5]furo[2,3-c]pyridin-2-yl)-ethanone (825 mg, 3.8 mmol) and thionyl chloride at 0° C., was added dropwise chlorosulfonic acid (1.25 g). The reaction mixture was stirred for 5 min at 0° C., for 2 h at r.t. and poured tehn into ice/$H_2O$ (75 g). The solution was brought to pH 7 by adding sodium carbonate and extracted with 75 mL ethyl acetate (2×). The combined organic layers were washed with $H_2O$ (2×), separated, and the solvent was evaporated. The resulting sulfonyl chloride was used in the next reaction step without further purification.

Step 2

N-(4-Chlorophenyl)-1,2,3,4,4a,9a-hexahydro[1]benzofuro[2,3-c]pyridine-6-sulfonamide A 0.4 M solution of 2-acetyl-1,2,3,4,4a,9a-hexahydro-benzo[4,5]furo[2,3-c]pyridine-6-sulfonyl chloride (6.8 g) in DMF (54 mL) was prepared. To 1.5 mL of the 0.4 M solution of sulfonylchloride prepared above, was added DIEA (112 µL) followed by 4-chloro-penylamine (84 mg). The reaction mixture was shaken for 16 h and the solvent was evaporated. The crude product was dissolved in dioxane (500 µL) and 6 M HCl in $H_2O$ (1 mL) was added. The reaction mixture was shaken at 100° C. for 4 h, the solvent was then evaporated. The resulting dark residue was suspended in DCE:MeOH 85:15 and passed through a silica gel plug. The eluate was evaporated and the resulting product purified by preparative LC-MS. MS m/z 365 $[M+H]^+$ The following examples were prepared essentially as described above. All compounds were isolated as HCl salts.

| Ex. # | Name | MS m/z [M + H]+ | Stereochemistry | Starting material |
|---|---|---|---|---|
| 836 | N-(4-chlorophenyl)-1,2,3,4,4a,9a-hexahydro[1]benzofuro[2,3-c]pyridine-6-sulfonamide | 365 | racemic | 4-chloroaniline |
| 837 | N-(naphthalen-1-yl)-1,2,3,4,4a,9a-hexahydro[1]benzofuro[2,3-c]pyridine-6-sulfonamide | 381 | racemic | naphthalen-1-amine |
| 838 | 6-(2,3-dihydro-1H-indol-1-ylsulfonyl)-1,2,3,4,4a,9a-hexahydro[1]benzofuro[2,3-c]pyridine | 357 | racemic | 2,3-dihydro-1H-indole |
| 839 | N-(2-fluorophenyl)-1,2,3,4,4a,9a-hexahydro[1]benzofuro[2,3-c]pyridine-6-sulfonamide | 349 | racemic | 2-fluoroaniline |
| 840 | N-(2-chlorophenyl)-1,2,3,4,4a,9a-hexahydro[1]benzofuro[2,3-c]pyridine-6-sulfonamide | 365 | racemic | 2-chloroaniline |
| 841 | N-(2-methoxyphenyl)-1,2,3,4,4a,9a-hexahydro[1]benzofuro[2,3-c]pyridine-6-sulfonamide | 361 | racemic | 2-methoxyaniline |
| 842 | N-(2,3-difluorophenyl)-1,2,3,4,4a,9a-hexahydro[1]benzofuro[2,3-c]pyridine-6-sulfonamide | 367 | racemic | 2,3-difluoroaniline |
| 843 | N-(3,5-dichlorophenyl)-1,2,3,4,4a,9a-hexahydro[1]benzofuro[2,3-c]pyridine-6-sulfonamide | 399 | racemic | 3,5-dichloroaniline |
| 844 | N-(2,4-dichlorophenyl)-1,2,3,4,4a,9a-hexahydro[1]benzofuro[2,3-c]pyridine-6-sulfonamide | 399 | racemic | 2,4-dichloroaniline |
| 845 | 6-[(4-phenylpiperazin-1-yl)sulfonyl]-1,2,3,4,4a,9a-hexahydro[1]benzofuro[2,3-c]pyridine | 400 | racemic | 1-phenylpiperazine |
| 846 | N-(3-fluorophenyl)-1,2,3,4,4a,9a-hexahydro[1]benzofuro[2,3-c]pyridine-6-sulfonamide | 349 | racemic | 3-fluoroaniline |
| 847 | N-(4-fluorophenyl)-1,2,3,4,4a,9a-hexahydro[1]benzofuro[2,3-c]pyridine-6-sulfonamide | 349 | racemic | 4-fluoroaniline |
| 848 | N-phenyl-1,2,3,4,4a,9a-hexahydro[1]benzofuro[2,3-c]pyridine-6-sulfonamide | 331 | racemic | aniline |
| 849 | N-cyclohexy1-1,2,3,4,4a,9a-hexahydro[1]benzofuro[2,3-c]pyridine-6-sulfonamide | 337 | racemic | cyclohexanamine |
| 850 | N-(3-methoxyphenyl)-1,2,3,4,4a,9a-hexahydro[1]benzofuro[2,3-c]pyridine-6-sulfonamide | 361 | racemic | 3-methoxyaniline |
| 851 | N-(3-fluoro-4-methylphenyl)-1,2,3,4,4a,9a-hexahydro[1]benzofuro[2,3-c]pyridine-6-sulfonamide | 363 | racemic | 3-fluoro-4-methylaniline |
| 852 | N-(3,4-dichlorophenyl)-1,2,3,4,4a,9a-hexahydro[1]benzofuro[2,3-c]pyridine-6-sulfonamide | 399 | racemic | 3,4-dichloroaniline |
| 853 | N-(3-chlorophenyl)-1,2,3,4,4a,9a-hexahydro[1]benzofuro[2,3-c]pyridine-6-sulfonamide | 365 | racemic | 3-chloroaniline |
| 854 | N-(4-chlorobenzyl)-1,2,3,4,4a,9a-hexahydro[1]benzofuro[2,3-c]pyridine-6-sulfonamide | 379 | racemic | 1-(4-chlorophenyl)methanamine |
| 855 | N-(2-phenylethyl)-1,2,3,4,4a,9a-hexahydro[1]benzofuro[2,3-c]pyridine-6-sulfonamide | 359 | racemic | 2-phenylethanamine |
| 856 | 6-(3,4-dihydroisoquinolin-2(1H)-ylsulfonyl)-1,2,3,4,4a,9a-hexahydro[1]benzofuro[2,3-c]pyridine | 371 | racemic | 1,2,3,4-tetrahydroisoquinoline |
| 857 | N-(2,3-dihydro-1H-inden-2-yl)-1,2,3,4,4a,9a-hexahydro[1]benzofuro[2,3-c]pyridine-6-sulfonamide | 371 | racemic | 2,3-dihydro-1H-inden-2-amine |
| 858 | N-benzyl-N-methyl-1,2,3,4,4a,9a-hexahydro[1]benzofuro[2,3-c]pyridine-6-sulfonamide | 359 | racemic | N-methyl-1-phenylmethanamine |

-continued

| Ex. # | Name | MS m/z [M + H]+ | Stereochemistry | Starting material |
|---|---|---|---|---|
| 859 | 6-[(6,7-dimethoxy-3,4-dihydroisoquinolin-2(1H)-yl)sulfonyl]-1,2,3,4,4a,9a-hexahydro[1]benzofuro[2,3-c]pyridine | 431 | racemic | 6,7-dimethoxy-1,2,3,4-tetrahydroisoquinoline |
| 860 | 6-(octahydroisoquinolin-2(1H)-ylsulfonyl)-1,2,3,4,4a,9a-hexahydro[1]benzofuro[2,3-c]pyridine | 377 | racemic | decahydroisoquinoline |
| 861 | 6-[(4-phenylpiperidin-1-yl)sulfonyl]-1,2,3,4,4a,9a-hexahydro[1]benzofuro[2,3-c]pyridine | 399 | racemic | 4-phenylpiperidine |
| 862 | 1'-(1,2,3,4,4a,9a-hexahydro[1]benzofuro[2,3-c]pyridin-6-ylsulfonyl)-3H-spiro[2-benzofuran-1,4'-piperidine] | 427 | racemic | 3H-spiro[2-benzofuran-1,4'-piperidine] |

NMR data for a select number of Examples is provided below:

| Ex. No. | Name | $^1$H-NMR Data (400 MHz) |
|---|---|---|
| 30 | 7-[(3-fluorophenyl)sulfonyl]-3,4,4',5'-tetrahydro-2H-spiro[1-benzofuro[2,3-c]pyridine-1,3'-furan] | (CDCl$_3$): δ 8.08 (s, 1H), 7.83 (d, J = 8.2 Hz, 1H), 7.77 (d, J = 7.8 Hz, 1H), 7.66 (d, J = 8.5 Hz, 1H), 7.56 (d, J = 8.2 Hz, 1H), 7.49 (m, 1H), 7.25 (m, 1H), 4.19 (m, 1H), 4.13 (m, 1H), 3.97 (m, 2H), 3.24 (m, 1H), 3.17 (m, 1H), 2.74 (m, 1H), 2.58 (m, 1H), 2.10 (m, 1H) |
| 34 | 1-(difluoromethyl)-1-methyl-7-{[3-(propan-2-yloxy)phenyl]sulfonyl}-1,2,3,4-tetrahydro[1]benzofuro[2,3-c]pyridine | (DMSO-d$_6$): δ 8.34 (s, 1H), 7.92 (m, 2H), 7.50 (m, 2H), 7.44 (d, J = 1.8 Hz, 1H), 7.20 (m, 1H), 6.58 (t, J = 52.6 Hz, 1H), 4.73 (m, 1H), 3.43 (m, 2H), 2.93 (m, 2H), 1.70 (br.s, 3H), 1.26 (d, J = 6.0 Hz, 6H) |
| 35 | 1,1-bis(fluoromethyl)-7-[(3-fluorophenyl)sulfonyl]-1,2,3,4-tetrahydro[1]benzofuro[2,3-c]pyridine | (CDCl$_3$): δ 8.12 (s, 1H), 7.85 (dd, J = 1.4, 8.3 Hz, 1H), 7.77 (d, J = 7.9 Hz, 1H), 7.66 (d, J = 8.0 Hz, 1H), 7.62 (d, J = 8.2 Hz, 1H), 7.50 (m, 1H), 7.25 (m, 1H), 4.70 (m, 4H), 3.26 (t, J = 5.5 Hz, 2H), 2.75 (t, J = 5.5 Hz) |
| 37 | 7-[(3-fluorophenyl)sulfonyl]-1-methyl-1-(trifluoromethyl)-1,2,3,4-tetrahydro[1]benzofuro[2,3-c]pyridine | (DMSO-d$_6$): δ 8.36 (s, 1H), 7.91 (m, 2H), 7.86 (m, 2H), 7.67 (m, 1H), 7.55 (m, 1H), 3.13 (m, 1H), 3.08 (m, 1H), 2.72 (m, 2H), 1.59 (s, 3H) |
| 40 | 2-{7-[(3-fluorophenyl)sulfonyl]-1-methyl 1,2,3,4-tetrahydro[1]benzofuro[2,3-c]pyridin-1-yl}-N,N-dimethylacetamide | (DMSO-d$_6$): δ 9.90 (br.s, 1H), 9.58 (br.s, 1H), 8.30 (d, J = 1.3 Hz, 1H), 7.90 (m, 4H), 7.67 (m, 1H), 7.56 (m, 1H), 3.57 (s, 2H), 3.56 (m, 1H), 3.26 (m, 1H), 3.01 (s, 3H), 2.96 (m, 2H), 2.84 (s, 3H), 1.78 (s, 3H) |
| 50 | 2-{7-[(3-fluorophenyl)sulfonyl]-1-methyl-1,2,3,4-tetrahydro[1]benzofuro[2,3-c]pyridin-1-yl}-N,N-dimethylacetamide | (DMSO-d$_6$): δ 9.80 (br, m, 2 H), 8.26 (s, 1H), 7.90 (m, 4H), 7.67 (q, J = 6.1 Hz, 1H), 7.55 (t, J = 8.1 Hz, 1H), 3.55 (m, 2H), 3.32 (s, 2H), 3.24 (m, 1H), 3.01 (s, 3H), 2.95 (m, 1H), 2.84 (s, 3H), 1.76 (s, 3H) |
| 56 | 7-[(3-fluorophenyl)sulfonyl]-2'-methyl-3,4,4',5'-tetrahydro-2H-spiro[1-benzofuro[2,3-c]pyridine-1,3'-furan] | (CDCl$_3$): δ 8.08 (s, 1H), 7.83 (d J = 8.1 Hz, 1H), 7.78 (d, J = 7.7 Hz, 1H), 7.67 (d, J = 7.7 Hz, 1H), 7.58 (d, J = 8.2 Hz, 1H), 7.49 (m, 1H), 7.25 (m, 1H), 4.23 (m, 1H), 4.03 (m, 2H), 3.17 (m, 2H), 2.72 (m, 2H), 2.64 (m, 1H), 2.04 (m, 1H), 1.77 (br.s, 1H), 1.13 (d, J = 6.3 Hz) |
| 57 | 7-[(3-fluorophenyl)sulfonyl]-2'-methyl-3,4,4',5'-tetrahydro-2H-spiro[1-benzofuro[2,3-c]pyridine-1,3'-furan] | (CDCl$_3$): δ 8.07 (s, 1H), 7.83 (d, J = 8.3 Hz, 1H), 7.77 (d, J = 7.8 Hz, 1H), 7.66 (d, J = 8.1 Hz, 1H), 7.56 (d, J = 8.1 Hz, 1H), 7.49 (m, 1H), 7.25 (m, 1H), 4.35 (m, 1H), 4.14 (m, 1H), 4.05 (m, 1H), 3.28 (m, 1H), 3.10 (m, 1H), 2.70 (m, 2H), 2.49 (m, 1H), 2.19 (m, 1H), 1.21 (d, J = 6.2 Hz, 3H) |
| 58 | 7-[(3-fluorophenyl)sulfonyl]-2'-methyl-3,4,4',5'-tetrahydro-2H-spiro[1-benzofuro[2,3-c]pyridine-1,3'-furan] | (DMSO-d$_6$): δ 10.39 (br.s, 2H), 8.36 (s, 1H), 7.90 (m, 3H), 7.87 (d, J = 7.7 Hz, 1H), 7.67 (m, 1H), 7.56 (m, 1H), 4.32 (m, 1H), 4.15 (m, 1H), 3.50 (m, 2H), 3.00 (m, 2H), 2.64 (m, 1H), 2.56 (m, 1H), 1.10 (d, J = 6.0 Hz, 3H) |
| 59 | 7-[(3-fluorophenyl)sulfonyl]-2'-methyl-3,4,4',5'-tetrahydro-2H-spiro[1-benzofuro[2,3-c]pyridine-1,3'-furan] | (DMSO-d$_6$): δ 10.39 (br.s, 2H), 8.36 (s, 1H), 7.90 (m, 3H), 7.87 (d, J = 7.7 Hz, 1H), 7.67 (m, 1H), 7.56 (m, 1H), 4.32 (m, 1H), 4.15 (m, 1H), 3.50 (m, 2H), 3.00 (m, 2H), 2.64 (m, 1H), 2.56 (m, 1H), 1.10 (d, J = 6.0 Hz, 3H) |

-continued

| Ex. No. | Name | $^1$H-NMR Data (400 MHz) |
| --- | --- | --- |
| 60 | 7-[(3-fluorophenyl)sulfonyl]-2'-methyl-3,4,4',5'-tetrahydro-2H-spiro[1-benzofuro[2,3-c]pyridine-1,3'-furan] | (DMSO-$d_6$): δ 10.50 (br.s, 1H), 9.55 br.s, 1H), 8.33 (s, 1H), 7.89 (m, 4H), 7.66 (m, 1H), 7.55 (m, 1H), 4.35 (m, 1H), 4.11 (m, 1H), 3.95 (m, 1H), 3.48 (m, 2H), 3.02 (m, 2H), 2.59 (m, 2H), 1.29 (d, J = 6.0 Hz, 3H) |
| 61 | 7-[(3-fluorophenyl)sulfonyl]-2'-methyl-3,4,4',5'-tetrahydro-2H-spiro[1-benzofuro[2,3-c]pyridine-1,3'-furan] | (DMSO-$d_6$): δ 10.50 (br.s, 1H), 9.55 (br.s, 1H), 8.33 (s, 1H), 7.89 (m, 4H), 7.66 (m, 1H), 7.55 (m, 1H), 4.35 (m, 1H), 4.11 (m, 1H), 3.95 (m, 1H), 3.48 (m, 2H), 3.02 (m, 2H), 2.59 (m, 2H), 1.29 (d, J = 6.0 Hz, 3H) |
| 63 | 7-({3-[(6-methylpyrazin-2-yl)oxy]phenyl}sulfonyl)-1,2,3,4,4a,9a-hexahydro[1]benzofuro[2,3-c]pyridine | (DMSO-$d_6$): δ 1.49-1.65 (m, 2H), 2.08-2.16 (m, 2H), 2.95 (s, 3H), 3.53-3.60 (m, 2H), 4.91-4.98 (m, 2H), 7.04 (d, J = 4.1 Hz, 1H), 7.24-7.58 (m, 7H), 8.78 (s, 1H), 9.59 (s, 1H), 10.36 (br s, 1H) |
| 64 | 7-[(2,6-dichlorophenyl)sulfonyl]-1,2,3,4,4a,9a-hexahydro[1]benzofuro[2,3-c]pyridine | (DMSO-$d_6$): δ 2.15 (s, 2H), 3.44 (s, 2H), 4.96 (s, 2H), 7.32 (s, 1H), 7.52-7.75 (m, 5H), 8.78 (s, 1H), 9.52 (s, 1H) |
| 65 | 7-(1,3-benzothiazol-2-ylsulfonyl)-1,2,3,4,4a,9a-hexahydro[1]benzofuro[2,3-c]pyridine | (DMSO-$d_6$): δ 1.49-1.62 (m, 1H), 2.11-2.20 (m, 1H), 2.98 (s, 2H), 3.42 (s, 2H), 3.58-3.66 (m, 1H), 5.00 (s, 1H), 7.51 (s, 1H), 7.58-7.72 (m, 4H), 8.24 (dd, J = 11.8, 4.0, 2H), 7.78 (br s, 1H), 9.43 (br s, 1H) |
| 66 | 7-[(3-chloro-2-methylphenyl)sulfonyl]-1,2,3,4,4a,9a-hexahydro[1]benzofuro[2,3-c]pyridine | (DMSO-$d_6$): δ 1.47-1.60 (m, 1H), 2.10-2.20 (m, 1H), 2.42 (s, 3H), 2.89-3.02 (m, 2H), 3.47-3.68 (m, 3H), 4.94-5.00 (m, 1H), 7.26 (s, 1H), 7.41-7.61 (m, 3H), 7.80-7.87 (m, 1H), 8.10-8.17 (m, 1H), 8.72 (br s, 1H), 9.31 (br s, 1H) |
| 67 | 7-(2,1,3-benzothiadiazol-4-ylsulfonyl)-1,2,3,4,4a,9a-hexahydro[1]benzofuro[2,3-c]pyridine | (DMSO-$d_6$): δ 1.43-1.59 (m, 1H), 2.04-2.15 (m, 1H), 2.86-3.01 (m, 2H), 3.38-3.46 (m, 1H), 3.48-3.63 (m, 2H), 4.87-4.93 (m, 1H), 7.50-7.63 (m, 2H), 7.70-7.76 (m, 1H), 7.92-8.00 (m, 1H), 8.43-8.56 (m, 2H), 8.77 (br s, 1H), 9.43 (br s, 1H) |
| 68 | 7-[(1-methyl-1H-indol-4-yl)sulfonyl]-1,2,3,4,4a,9a-hexahydro[1]benzofuro[2,3-c]pyridine | (DMSO-$d_6$): δ 1.37-1.52 (m, 1H), 2.02-2.13 (m, 1H), 2.84-2.99 (m, 2H), 3.40-3.62 (m, 3H), 3.82 (s, 3H), 4.83-4.94 (m, 1H), 6.70 (s, 1H), 7.38-7.48 (m, 2H), 7.45 (d, J = 4.0 Hz, 1H), 7.53-7.62 (m, 2H), 7.76-7.82 (m, 2H), 8.78 (br s, 1H), 9.35 (br s, 1H) |
| 69 | 7-(1H-benzimidazol-2-ylsulfonyl)-1,2,3,4,4a,9a-hexahydro[1]benzofuro[2,3-c]pyridine | (DMSO-$d_6$): δ 1.51-1.62 (m, 1H), 2.08-2.20 (m, 1H), 2.88-2.99 (m, 2H), 3.36-3.47 (m, 1H), 3.51-3.65 (m, 2H), 4.96-5.01 (m, 1H), 7.32-7.40 (m, 2H), 7.46 (s, 1H), 7.60-7.77 (m, 5H), 8.73-8.85 (m, 1H), 9.52-9.62 (m, 1H) |
| 70 | 7-[(5-methyl-2,1,3-benzothiadiazol-4-yl)sulfonyl]-1,2,3,4,4a,9a-hexahydro[1]benzofuro[2,3-c]pyridine | (DMSO-$d_6$): δ 1.68-1.80 (m, 1H), 2.01-2.12 (m, 1H), 2.99 (s, 3H), 3.05-3.21 (m, 3H), 3.66-3.74 (m, 1H), 3.80-3.93 (m, 1H), 4.92-5.08 (m, 1H), 7.28-7.45 (m, 3H), 7.58-7.82 (m, 2H), 8.23-8.31 (m, 1H) |
| 71 | 7-[(5-methoxy-1,3-benzothiazol-2-yl)sulfonyl]-1,2,3,4,4a,9a-hexahydro[1]benzofuro[2,3-c]pyridine | (DMSO-$d_6$): δ 1.72-1.86 (m, 1H), 2.04-2.13 (m, 1H), 2.85-3.02 (m, 1H), 3.05-3.18 (m, 1H), 3.30-3.48 (m, 1H), 3.60-3.96 (m, 2H), 3.86 (s, 3H), 5.00-5.16 (m, 1H), 7.22-7.32 (m, 2H), 7.52-7.62 (m, 4H), 7.73 (s, 1H), 8.15 (m, 1H) |
| 72 | 7-(2,1,3-benzoxadiazol-4-ylsulfonyl)-1,2,3,4,4a,9a-hexahydro[1]benzofuro[2,3-c]pyridine | (DMSO-$d_6$): δ 1.72-1.84 (m, 1H), 2.01-2.12 (m, 1H), 2.83-3.02 (m, 1H), 3.03-3.15 (m, 1H), 3.33-3.46 (m, 1H), 3.69-3.78 (m, 1H), 3.82-3.94 (m, 1H), 4.98-5.12 (m, 1H), 7.36 (s, 1H), 7.50-7.57 (m, 1H), 7.62-7.69 (m, 1H), 7.78-7.85 (m, 1H), 8.33-8.48 (m, 2H) |
| 73 | N-[3-(1,2,3,4,4a,9a-hexahydro[1]benzofuro[2,3-c]pyridin-7-ylsulfonyl)phenyl]acetamide | DMSO-$d_6$: δ 1.48-1.58 (m, 1H), 2.04 (s, 3H), 2.04-2.18 (m, 1H), 2.84-2.99 (m, 2H), 3.38-3.44 (m, 1H), 3.49-3.60 (m, 1H), 4.91-4.98 (m, 1H), 7.32 (s, 1H), 7.44-7.62 (m, 4H), 7.76-7.81 (m, 1H), 8.30 (s, 1H), 8.81 (br s, 1H), 9.61 (br s, 1H), 10.49 (s, 1H) |
| 79 | (4aR,9aS)-7-{[3-methoxy-5-(propan-2-yloxy)phenyl]sulfonyl}-1,2,3,4,4a,9a-hexahydro[1]benzofuro[2,3-c]pyridine | (DMSO-$d_6$): δ 1.23 (d, J = 3.4, 6H), 1.47-1.60 (m, 1H), 2.10-2.18 (m, 1H), 2.88-2.99 (m, 2H), 3.38-3.46 (m, 1H), 3.49-3.59 (m, 2H), 3.80 (s, 3H), 4.68-4.76 (m, 1H), 4.95 (s, 1H), 6.74 (s, 1H), 6.92-7.02 (m, 2H), 7.45 (s, 1H), 7.50-7.62 (m, 2H), 9.21 (br s, 2H) |
| 80 | 7-[(5-chloro-2-methoxyphenyl)sulfonyl]-1,2,3,4-tetrahydro[1]benzofuro[2,3-c]pyridine | (DMSO-$d_6$): δ 2.96 (s, 2H), 3.42 (s, 2H), 3.72 (s, 3H), 4.48 (s, 2H), 7.18 (d, J = 4.4 Hz, 1H), 7.70-7.78 (m, 1H), 7.88 (s, 2H), 7.99 (s, 1H), 8.22 (s, 1H), 9.80 (s, 2H) |
| 81 | 7-[(3-chloro-2-fluorophenyl)sulfonyl]-1,2,3,4-tetrahydro[1]benzofuro[2,3-c]pyridine | (DMSO-$d_6$): δ 2.98 (s, 2H), 3.42 (s, 2H), 4.46 (s, 2H), 7.52 (t, J = 4.2 Hz, 1H), 7.85-8.09 (m, 4H), 8.24 (s, 1H), 10.18 (s, 2H) |

-continued

| Ex. No. | Name | $^1$H-NMR Data (400 MHz) |
|---|---|---|
| 82 | 7-[(3-chloro-2-methylphenyl)sulfonyl]-1,2,3,4-tetrahydro[1]benzofuro[2,3-c]pyridine | (DMSO-$d_6$): δ 2.46 (s, 3H), 2.94 (s, 2H), 3.52 (s, 2H), 4.47 (s, 2H), 7.44-7.60 (m, 1H), 7.66-7.93 (m, 3H), 8.08-8.28 (m, 2H), 9.90 (s, 2H) |
| 88 | 6-[(2,3-dichlorophenyl)sulfonyl]-7-methoxy-1,2,3,4,4a,9a-hexahydro[1]benzofuro[2,3-c]pyridine | (DMSO-$d_6$): δ 1.44-1.60 (m, 1H), 2.06-2.18 (m, 1H), 2.55 (s, 3H), 2.88-3.02 (m, 2H), 3.37-3.47 (m, 1H), 3.51-3.62 (m, 2H), 4.91-4.99 (m, 1H), 7.38 (s, 1H), 7.56-7.64 (m, 2H), 8.08 (s, 1H), 8.15 (d, J = 3.5 Hz, 1H), 8.71 (br s, 1H), 9.23 (br s, 1H) |
| 472 | 1-(difluoromethyl)-7-[(2,3-difluorophenyl)sulfonyl]-1-methyl-1,2,3,4-tetrahydro[1]benzofuro[2,3-c]pyridine | (DMSO-$d_6$): δ 8.28 (s, 1H), 7.96 (m, 3H), 7.84 (m, 1H), 7.53 (M, 1H), 6.62 (t, J = 52.2 Hz, 1H), 3.57 (br.s, 2H), 3.46 (m, 2H), 2.98 (m, 2H), 1.72 (s, 3H) |
| 473 | 7-[(2,3-difluorophenyl)sulfonyl]-3,4,4',5'-tetrahydro-2H-spiro[1-benzofuro[2,3-c]pyridine-1,3'-furan] | (CDCl$_3$): δ 10.23 (br.s, 1H), 8.26 (s, 1H), 7.94 (m, 3H), 7.84 (d, J = 8.9 Hz, 1H), 7.53 (m, 1H), 4.27 (d, J = 10.1 Hz, 1H), 4.15 (d, J = 7.9 Hz, 1H), 4.03 (m, 2H), 3.52 (m, 2H), 3.38 (m, 2H), 3.01 (m, 2H), 2.58 (m, 1H) |
| 476 | 2-fluoro-6-(1,2,3,4,4a,9a-hexahydro[1]benzofuro[2,3-c]pyridin-7-ylsulfonyl)-N,N-dimethylbenzamide | (DMSO-$d_6$): δ 8.82 (br.s, 1H), 7.96 (m, 1H), 7.70 (m, 2H), 7.57 (m, 2H), 7.48 (m, 1H), 4.93 (m, 1H), 3.57 (m, 2H), 3.44 (m, 1H), 3.40 (m, 1H), 3.04 (s, 3H), 2.97 (m, 2H), 2.77 (m, 3H), 2.13 (m, 1H), 1.51 (m, 1H) |
| 477 | 2-fluoro-6-(1,2,3,4,4a,9a-hexahydro[1]benzofuro[2,3-c]pyridin-7-ylsulfonyl)-N-methylbenzamide | (DMSO-$d_6$): δ 8.95 (br.s, 1H), 8.62 (d, J = 4.8 Hz, 1H), 7.91 (d, J = 7.4 Hz, 1H), 7.67 (m, 2H), 7.60 (d, J = 9.3 Hz, 1H), 7.54 (d, J = 7.7 Hz, 1H), 7.51 (s, 1H), 4.94 (m, 1H), 3.56 (m, 1H), 3.43 (m, 1H), 2.96 (m, 2H), 2.79 (d, J = 4.6 Hz, 3H), 2.12 (m, 1H), 1.51 (m, 1H) |
| 478 | N-methyl-3-(1,2,3,4-tetrahydro[1]benzofuro[2,3-c]pyridin-7-ylsulfonyl)benzamide | (DMSO-$d_6$): δ 9.66 (br.s, 2H), 8.75 (m, 1H), 8.41 (s, 1H), 8.33 (s, 1H), 8.11 (m, 2H), 7.91 (d, J = 8.3 Hz, 1H), 7.86 (d, J = 8.3 Hz, 1H), 7.71 (t, J = 7.9 Hz, 1H), 4.48 (m, 2H), 3.45 (m, 2H), 2.94 (m, 2H), 2.80 (d, J = 4.6 Hz, 3H) |
| 479 | 2-fluoro-N,N-dimethyl-6-(1,2,3,4-tetrahydro[1]benzofuro[2,3-c]pyridin-7-ylsulfonyl)benzamide | (DMSO-$d_6$): δ 9.45 (m, 2H), 8.26 (s, 1H), 8.02 (d, J = 7.2 Hz, 1H), 7.92 (d, J = 9.9 Hz, 1H), 7.86 (d, J = 8.3 Hz, 1H), 7.71 (m, 2H), 4.50 (m, 2H), 3.47 (m, 2H), 3.06 (s, 3H), 2.95 (m, 2H), 2.79 (s, 3H) |
| 549 | 7-{[3-(prop-2-yn-1-yloxy)phenyl]sulfonyl}-1,2,3,4,4a,9a-hexahydro[1]benzofuro[2,3-c]pyridine | (DMSO-$d_6$): δ 1.47-1.58 (m, 1H), 2.05-2.17 (m, 1H), 2.90-2.97 (m, 2H), 2.35-2.42 (m, 1H), 2.51-2.62 (m, 3H), 4.90-4.96 (m, 3H), 7.23-7.29 (m, 1H), 7.42-7.59 (m, 6H), 9.05 (br s, 2H) |
| 550 | 2-{[3-(1,2,3,4,4a,9a-hexahydro[1]benzofuro[2,3-c]pyridin-7-ylsulfonyl)phenoxy]methyl}benzonitrile | (DMSO-$d_6$): δ 1.71-1.82 (m, 1H), 2.02-2.14 (m, 1H), 2.91-3.02 (m, 1H), 3.08-3.20 (m, 1H), 3.31-3.44 (m, 1H), 3.63-3.71 (m, 1H), 3.67-3.73 (m, 1H), 3.84-3.90 (m, 1H), 5.34 (s, 2H), 7.25 (s, 1H), 7.31-7.36 (m, 1H), 7.40-7.61 (m, 6H), 7.78-7.83 (m, 2H), 7.89-7.94 (m, 1H) |
| 551 | 4-{[3-(1,2,3,4,4a,9a-hexahydro[1]benzofuro[2,3-c]pyridin-7-ylsulfonyl)phenoxy]methyl}benzonitrile | (DMSO-$d_6$): δ 1.71-1.79 (m, 1H), 2.03-2.14 (m, 1H), 2.88-3.00 (m, 1H), 3.05-3.20 (m, 1H), 3.32-3.43 (m, 1H), 3.68-3.75 (m, 1H), 3.82-3.90 (m, 1H), 4.99-5.10 (m, 1H), 5.32 (s, 2H), 7.21 (s, 1H), 7.38-7.43 (m, 2H), 7.48-7.55 (m, 4H), 7.61-7.68 (m, 2H), 7.82-7.89 (m, 2H) |
| 552 | 3-{[3-(1,2,3,4,4a,9a-hexahydro[1]benzofuro[2,3-c]pyridin-7-ylsulfonyl)phenoxy]methyl}benzonitrile | (DMSO-$d_6$): δ 1.71-1.79 (m, 1H), 2.03-2.13 (m, 1H), 2.88-3.02 (m, 1H), 3.05-3.21 (m, 1H), 3.32-3.46 (m, 1H), 3.64-3.74 (m, 1H), 3.86-3.92 (m, 1H), 4.97-5.10 (m, 1H), 5.27 (s, 2H), 7.26 (s, 1H), 7.30-7.36 (m, 1H), 7.42-7.66 (m, 6H), 7.79-7.86 (m, 2H), 7.92 (s, 1H) |
| 581 | 7-{[3-(tetrahydro-2H-pyran-4-ylmethoxy)phenyl]sulfonyl}-1,2,3,4,4a,9a-hexahydro[1]benzofuro[2,3-c]pyridine | (DMSO-$d_6$): δ 1.28-1.38 (m, 2H), 1.46-1.58 (m, 1H), 1.61-1.69 (m, 2H), 1.92-2.04 (m, 1H), 2.08-2.15 (m, 1H), 2.90-2.97 (m, 2H), 3.33-3.42 (m, 3H), 3.50-3.58 (m, 2H), 3.82-3.91 (m, 4H), 4.89-4.95 (m, 1H), 7.22-7.25 (m, 1H), 7.42 (s, 2H), 7.47-7.58 (m, 4H), 8.78 (br s, 1H), 9.33 (br s, 1H) |

Preparations

P01

Tert-butyl 7-iodo-3,4,4a,9a-tetrahydro[1]benzofuro[2,3-c]pyridine-2(1H)-carboxylate

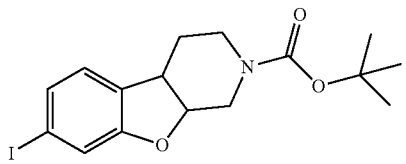 [SMILES: CC(C)(C)OC(=O)N1CCC2c3ccc(I)cc3OC2C1]

Step 1

Tert-butyl 7-methoxy-3,4,4a,9a-tetrahydro[1]benzofuro[2,3-c]pyridine-2(1H)-carboxylate

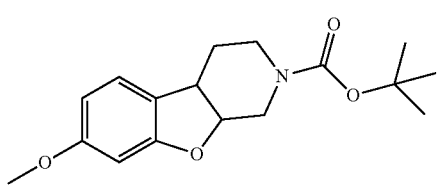 [SMILES: COc1ccc2c(c1)OC1CN(C(=O)OC(C)(C)C)CCC21]

A solution of DEAD (147 g, 0.34 mol) in toluene (40 wt %) was added over 45 min to a solution of N-boc-3-hydroxy-1,2,3,6-tetrahydropyridine (48 g, 0.24 mol) and 2-Bromo-5-methoxyphenol (49 g, 0.24 mol) in THF (800 mL). The reaction mixture was kept under 35° C. using a water bath cooling. After 1 h stirring, the solvent was evaporated, the residue suspended in 500 mL ethyl acetate:heptane (20:80) and filtered off. The combined filtrates were washed with 500 mL of 0.6N NaOH and twice with 500 mL (H$_2$O) and concentrated. Silica gel (600 g) purification eluting with ethyl acetate:heptane afforded 73 g of the bromo ether.

The bromo ether (73 g) was dissolved in toluene (3.5 L), tributyltin hydride (82 g, 0.28 mol) was added followed by AIBN (3 g, 0.02 mol). The reaction mixture was stirred at 80° C. for 5 h and DBU (48 g, 0.32 mol) was added at r.t. Methyl t-Butyl ether (1.5 L) was added, the suspension passed through silica gel and the solvent was evaporated. Crystallization using heptane (150 mL) and drying under h.v. afforded 33.8 g of tert-butyl 7-methoxy-3,4,4a,9a-tetrahydro[1]benzofuro[2,3-c]pyridine-2(1H)-carboxylate.

Step 2

Tert-butyl 7-hydroxy-3,4,4a,9a-tetrahydro[1]benzofuro[2,3-c]pyridine-2(1H)-carboxylate (P02)

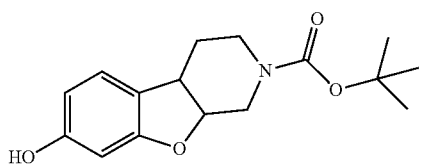 [SMILES: CC(C)(C)OC(=O)N1CCC2c3ccc(O)cc3OC2C1]

Boron tribromide (285 mL, 1 M, 0.285 mol) in DCM was added over 45 min to a solution of tert-butyl 7-methoxy-3,4,4a,9a-tetrahydro[1]benzofuro[2,3-c]pyridine-2(1H)-carboxylate (33.3 g, 0.11 mol) in DCM (1.2 L). The reaction mixture was kept at 5-8° C. using a water bath cooling. After 1 h stirring, H$_2$O (250 mL) and NaOH (350 mL, 3 M) were added, followed by di-tert-butyl dicarbonate (59.6 g, 0.27 mol). After 16 h stirring, the layers were separated, the organic layer was washed with 0.3 N HCl and H$_2$O, and concentrated. Crystallization using heptane and drying under house vacuum (h.v.) afforded 74 g of expected product. MS m/z 292 [M+H]$^+$

Step 3

Tert-butyl 7-(4,4,5,5-Tetramethyl-[1,3,2]dioxaborolan-2-yl)-3,4,4a,9a-tetrahydro[1]benzofuro[2,3-c]pyridine-2(1H)-carboxylate

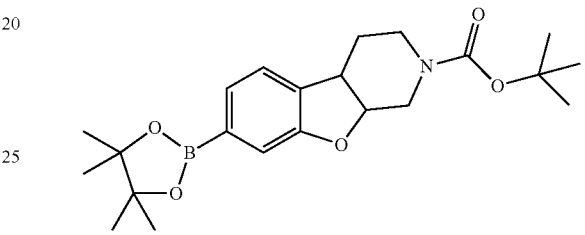

A solution of triflic anhydride (59 g) in DCM (0.2 L) was added over 30 min to a cold solution of tert-butyl 7-hydroxy-3,4,4a,9a-tetrahydro[1]benzofuro[2,3-c]pyridine-2(1H)-carboxylate (55.4 g, 0.19 mol), DMAP (11.6 g, 0.09 mol) and triethylamine (38.5 g, 0.38 mol) DCM (1.1 L). The reaction mixture was kept at 3-6° C. using a water bath cooling. After 30 min stirring, H$_2$O (250 mL) was added, the layers were separated, the organic layer was washed twice with 0.5 N HCl, and once with H$_2$O. Magnesium sulfate and DARCO G-60 were added. Filtration of the solid followed by evaporation and drying under h.v. afforded 74 g of the desired triflate.

A solution of [1,1'-bis(diphenyl-phosphino)ferrocene] dichloropalladium II in DCM (4.7 g, 0.17 mol), [1,1'-bis(diphenyl-phosphino)ferrocene] and pinacolboran (32.8 g, 0.25 mol) were added to a solution of the triflate (74 g, 0.17 mol) in absolute dioxane. Triethylamine was added, the reaction mixture was heated at 98° C. for 3 h and the solvent was evaporated. The residue was dissolved in DCM (1.5 L), washed twice with H$_2$O, once with 5% citric acid solution, diluted with ACN and passed through a silica gel plug. The solution was concentrated and cooled down to −20° C., the precipitate was collected, dried under h.v. to afford 42 g of the 7-pinacoloboronate. MS m/z 420 [M+H]$^+$

Step 4

Tert-butyl 7-iodo-3,4,4a,9a-tetrahydro[1]benzofuro[2,3-c]pyridine-2(1H)-carboxylate Tert-butyl 7-(4,4,5,5-Tetramethyl-[1,3,2]dioxaborolan-2-yl)-3,4,4a,9a-tetrahydro[1]benzofuro[2,3-c]pyridine-2(1H)-carboxylate (20 g, 0.05 mol) was dissolved in THF (0.4 L) and a solution of Chloramine T (28.1 g, 0.1 mol) in H$_2$O (0.2 L) was added, followed by a solution of sodium iodide (15 g, 0.1 mol) in H$_2$O (0.2 L) over 20 min. After 20 h stirring, of chloramine T (2.8 g, 0.01 mol) and sodium iodide (1.5 g, 0.01 mol) were added. The reaction mixture was stirred for 20 h, the solvent was evaporated, ethyl acetate and H₂O were added. The layers were separated, and the organic layer was washed with H₂O.

Silica gel (300 g) purification eluting with ethyl acetate: heptane (20:80) afforded 18 g of the crude product. Crystallization using acetonitrile and drying under h.v. afforded 16 g of the title compound (P01). MS m/z 402 [M+H]⁺

Enantiomers of tert-butyl 7-iodo-3,4,4a,9a-tetrahydro[1]benzofuro[2,3-c]pyridine-2(1H)-carboxylate

P01

Separation by SFC of tert-butyl 7-iodo-3,4,4a,9a-tetrahydro[1]benzofuro[2,3-c]pyridine-2(1H)-carboxylate P01 on a Chiralpak AD-H column (21×250 cm) at 35° C. and eluting with 30% MeOH: 0.1% diethylamine (flow: 16 mL/min) and CO₂ (36 mL/min) yielded enantiomer 1 P03 and enantiomer 2 P04 of tert-butyl 7-iodo-3,4,4a,9a-tetrahydro[1]benzofuro[2,3-c]pyridine-2(1H)-carboxylate.

P05

Tert-butyl 6-iodo-3,4,4a,9a-tetrahydro[1]benzofuro[2,3-c]pyridine-2(1H)-carboxylate

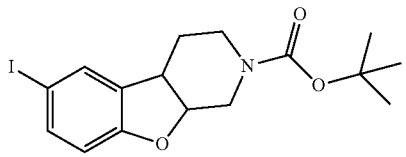 [SMILES: CC(C)(C)OC(=O)N1CCC2c3cc(I)ccc3OC2C1]

Tert-butyl 6-iodo-3,4,4a,9a-tetrahydro[1]benzofuro[2,3-c]pyridine-2(1H)-carboxylate was synthesized as described for tert-butyl 7-iodo-3,4,4a,9a-tetrahydro[1]benzofuro[2,3-c]pyridine-2(1H)-carboxylate P01 starting from N-boc-3-hydroxy-1,2,3,6-tetrahydropyridine and 2-bromo-4-methoxyphenol. MS m/z 402 [M+H]⁺

P06

Tert-butyl 6-hydroxy-3,4,4a,9a-tetrahydro[1]benzofuro[2,3-c]pyridine-2(1H)-carboxylate

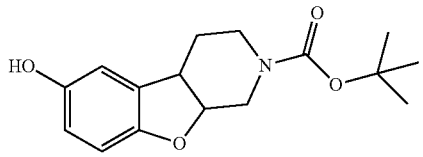 [SMILES: CC(C)(C)OC(=O)N1CCC2c3cc(O)ccc3OC2C1]

Tert-butyl 6-hydroxy-3,4,4a,9a-tetrahydro[1]benzofuro[2,3-c]pyridine-2(1H)-carboxylate was synthesized as described for tert-butyl 7-hydroxy-3,4,4a,9a-tetrahydro[1]benzofuro[2,3-c]pyridine-2(1H)-carboxylate starting N-boc-3-hydroxy-1,2,3,6-tetrahydropyridine and 2-bromo-4-methoxyphenol.

P07

Tert-butyl 8-iodo-3,4,4a,9a-tetrahydro[1]benzofuro[2,3-c]pyridine-2(1H)-carboxylate

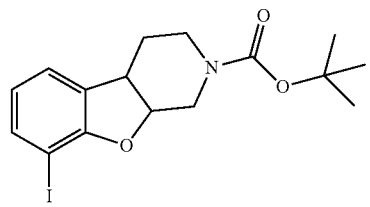 [SMILES: CC(C)(C)OC(=O)N1CCC2c3cccc(I)c3OC2C1]

Step 1

Tert-butyl 8-bromo-3,4,4a,9a-tetrahydro[1]benzofuro[2,3-c]pyridine-2(1H)-carboxylate Prepared as described for tert-butyl 7-methoxy-3,4,4a,9a-tetrahydro[1]benzofuro[2,3-c]pyridine-2(1H)-carboxylate starting from N-boc-3-hydroxy-1,2,3,6-tetrahydropyridine and 2,6-dibromo-phenol.

Step 2

8-(5,5-Dimethyl-[1,3,2]dioxaborinan-2-yl)-3,4,4a, 9a-tetrahydro-1H-benzo[4,5]furo[2,3-c]pyridine-2-carboxylic acid tert-butyl ester

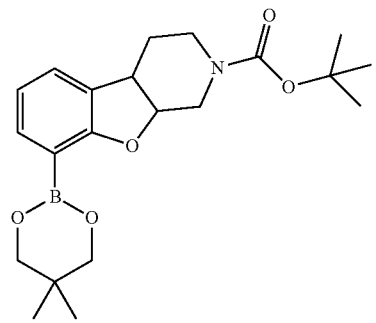 [SMILES: CC1(C)COB(c2cccc3c2OC2CN(C(=O)OC(C)(C)C)CCC32)OC1]

Anhydrous DMA (80 mL) was degassed by sparging with argon gas. [1,1'-Bis(diphenylphosphino)ferrocene]dichloropalladium(II)/DCM complex (1:1) (340 mg, 0.42 mmol), 1,1'-bis(diphenylphosphino)ferrocene (235 mg, 0.423 mmol), Potassium acetate (4.15 g, 42.3 mmol) and 5,5,5',5-Tetramethyl-2,2'-bi[1,3,2-dioxaborinanyl] (3.19 g, 14.1 mmol) were suspended in anhydrous DMA (20 mL, 200 mmol). To this suspension a solution of 8-bromo-3,4,4a,9a-tetrahydro-1H-benzo[4,5]furo[2,3-c]pyridine-2-carboxylic acid tert-butyl ester (5.00 g, 14.1 mmol) in anhydrous DMA (60 mL, 600 mmol) was added via a canula. The reaction was stirred at 80° C. overnight under argon, concentrated down. The resulting residue was dissolved in ethyl acetate, washed with H₂O (3×). After shaking, the aqueous layer was drained off. The EtOAc layer was then washed with water (3×), brine and concentrated. The resulting oil was dissolved in DCM:CH₃CN and flushed through a column of silica gel (80 g) using DCM:CH₃CN 1:1 to yield the desired product.

Step 3

Tert-butyl 8-iodo-3,4,4a,9a-tetrahydro[1]benzofuro[2,3-c]pyridine-2(1H)-carboxylate P07

Tert-butyl 8-iodo-3,4,4a,9a-tetrahydro[1]benzofuro[2,3-c]pyridine-2(1H)-carboxylate was synthesized as described for tert-butyl 7-iodo-3,4,4a,9a-tetrahydro[1]benzofuro[2,3-c]pyridine-2(1H)-carboxylate P01 starting from tert-butyl 8-(4,4,5,5-tetramethyl-[1,3,2]dioxaborolan-2-yl)-3,4,4a,9a-tetrahydro[1]benzofuro[2,3-c]pyridine-2(1H)-carboxylate. MS m/z 402 [M+H]+

P08

Tert-butyl 7-iodo-3,4-dihydro[1]benzofuro[2,3-c]pyridine-2(1H)-carboxylate

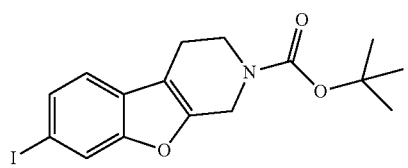 [SMILES: CC(C)(C)OC(=O)N1CCc2c(oc3cc(I)ccc23)C1]

Step 1

Methyl 2-(2-ethoxy-2-oxoethoxy)-4-iodobenzoate

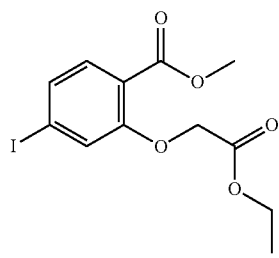 [SMILES: CCOC(=O)COc1cc(I)ccc1C(=O)OC]

Ethyl bromoacetate (80 mL; 0.72 mol, Aldrich, 98%) was added to a solution of 4-iodo-methylsalicylate (200 g, 0.72 mol; 1.0 eq), potassium carbonate (198 g, 2 eq, 1.44 mol) and potassium iodide (17.8 g 0.107 mol 0.15 eq) in acetone under nitrogen. The reaction was stirred at 50° C. for 5 h and at r.t. for 16 h. The reaction mixture was filtered and the solid was washed with acetone. The liquors were concentrated to a dark brown oil and dried under house vacuum to afford 241 g of methyl 2-(2-ethoxy-2-oxoethoxy)-4-iodobenzoate. $^1$H-NMR (400 MHz, CDCl$_3$): δ 1.31 (t, 3H), 3.89 (s, 3H), 4.28 (q, 2H), 4.70 (s, 2H), 7.22 (d, 1H), 7.41 (dd, 1H), 7.54 (d, 1H).

Step 2

6-iodo-1-benzofuran-3(2H)-one

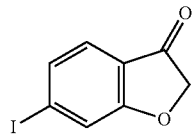 [SMILES: O=C1COc2cc(I)ccc21]

A solution of methyl 2-(2-ethoxy-2-oxoethoxy)-4-iodobenzoate (241.6 g, 0.664 mol) in toluene (500 mL) was added to a solution of LHMDS in THF (1.38 l, 1.0M; 1.33 mol; 2.0 eq) over 1 hour 35 minutes with an ice bath in place to keep the temperature at 21-25° C. After 30 min stirring, the solvent was concentrated and toluene was added. The suspension was filtered, the solids were washed with of toluene (300 mL) and dried under house vacuum to afford 256 g of brownish solid. This solid was then suspended in a mixture of H$_2$O (20 mL) and ethanol (830 mL) and sodium hydroxide pellets were added (166 g; 4.15 mol; 6.25 eq). After stirring at 80° C. for 1.5 h, 6 N HCl (885 mL; 5.31 mol; 8.0 eq) was added over 1 hour 35 minutes at 25-27° C. After 50 min stirring, the suspension was filtered, the resulting solids taken up in 495 mL of 1N HCl (495 mL), H$_2$O (165 mL) and EtOH (205 mL). This solution was heated to 60° C. for 30 min and then cooled down to 21° C. before filtration. The orange solid was washed with H$_2$O (150 mL) and dried to afford 153 g of the expected product. $^1$H-NMR (400 MHz, CDCl$_3$): δ 4.60 (s, 2H), 7.37 (d, 1H), 7.45 (d, 1H), 7.60 (s, 1H).

Step 3

6-iodo-1-benzofuran-3-carbonitrile

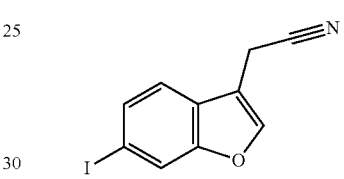

Sodium hydride (37.3 g; 0.886 mol; 1.2 eq; 60 wt % dispersion in oil) was suspended in hexanes (120 mL) under N$_2$. The sodium hydride was allowed to settle and the hexanes were syringed out of the flask and dry THF (100 mL) added. The NaH was washed again and the THF decanted. A fresh portion of dry THF (300 mL) was added and diethylcyanomethylphosphonate (0.886; 1.2 eq) was added drop wise over 35 min while keeping the temperature at 20-22° C. A solution of 6-iodo-1-benzofuran-3(2H)-one (192.0 g; 0.74 mol) in THF (1.75 L) then added over 35 min at 15-25° C. After 30 min stirring, 6N HCl (750 mL), MTBE (750 mL), and H$_2$O (500 mL) were added. The layers were separated, sodium sulfate was added to the organic layer. The organics were filtered and concentrated. The resulting red solids were suspended in MTBE (500 mL), washed four times with 1N HCl (400 mL). The solvent was evaporated to afford 214 g of the title product. $^1$H-NMR (400 MHz, CDCl$_3$): δ 3.75 (bs, 1H), 7.34 (d, 1H), 7.60 (s, 1H), 7.62 (dd, 1H), 7.91 (d, 1H).

Step 4

2-(6-iodo-1-benzofuran-3-yl)ethanamine P09

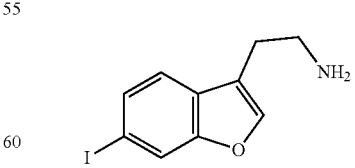

A solution of diborane (1.0 M; 806 mL; 0.806 mol; 2.4 eq) in THF was added dropwise to a solution of 6-iodo-1-benzofuran-3-carbonitrile (95 g, 0.336 mol) in THF (730 mL) over 26 min at 1.4-4.0° C. After 20 h stirring at r.t., methanol was added over 15 minutes while keeping the reaction at 18-25° C.

and the solvent was evaporated. The remaining orange liquid was taken up in 3N HCl in MeOH (417 mL; 1.25 mol; 3.72 eq), stirred for 20 h at 30° C. and 48 h at room temperature. The solvent was evaporated and the residue suspended in MTBE (450 mL). After stirring for 1.5 h, the solution was filtered. The solids were washed with MTBE (40 mL) and dried under house vacuum to provide 80.9 g of the title product as a hydrochloric acid salt. $^1$H-NMR (400 MHz, CDCl$_3$): δ 3.06 (t, 2H), 3.27 (t, 2H), 7.46 (bd, 1H), 7.61 (bd, 1H), 7.68 (bs, 1H), 7.91 (bs, 1H).

Step 5

7-iodo-1,2,3,4-tetrahydro[1]benzofuro[2,3-c]pyridine

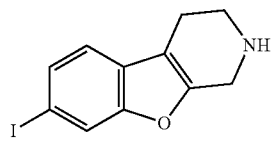 [SMILES: Ic1ccc2c3c(oc2c1)CNCC3]

Paraformaldehyde (8.9 g, 0.297 mol) was added to a solution of 2-(6-iodo-1-benzofuran-3-yl)ethanamine hydrochloride (80 g; 0.247 mol) in 1N HCl (500 mL) under N$_2$. After 2 h stirring at 70° C., another portion of paraformaldehyde (740 mg) was added. The reaction mixture was cooled down to r.t., filtered, the resulting solid was washed with 1N HCl (100 mL), dried overnight under house vacuum to afford 76.7 g of the title product as a hydrochloric acid salt. $^1$H-NMR (400 MHz, CDCl$_3$): δ 2.06 (bt, 2H), 2.92 (bt, 2H), 4.37 (s, 2H), 7.45 (d, 1H) 7.62 (dd, 1H), 8.05 (d, 1H), 10.04 (bs, 2H).

Step 6

Tert-butyl 7-iodo-3,4-dihydro[1]benzofuro[2,3-c]pyridine-2(1H)-carboxylate P08

Di-tert-butyl dicarbonate (50.4 g, 0.27 mol) was added slowly to a solution of 6-iodo-1-benzofuran-3(2H)-one hydrochloride (75 g, 0.23 mol) and triethylamine (68 mL, 0.46 mol; 2.0 eq.) in chloroform (460 mL). After 1 h stirring, the solvent was evaporated and the residue purified on silica gel eluting with hexane:ethyl acetate (95:5) and hexane:ethyl acetate (90:10). 68.7 g of the title product. MS m/z 400 [M+H]$^+$

P10

Tert-butyl[2-(6-iodo-1-benzofuran-3-yl)ethyl]carbamate

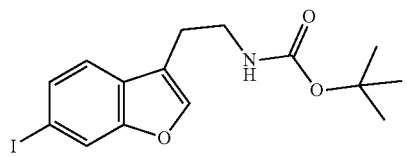 [SMILES: CC(C)(C)OC(=O)NCCc1coc2cc(I)ccc12]

Synthesized as described for tert-butyl 7-iodo-3,4-dihydro[1]benzofuro[2,3-c]pyridine-2(1H)-carboxylate starting from 2-(6-iodo-1-benzofuran-3-yl)ethanamine hydrochloride. MS m/z 332 [M+H]$^+$. $^1$H-NMR (400 MHz, CDCl$_3$): δ 1.43 (s, 9H), 2.85 (t, 2H), 3.43 (q, 2H), 4.62 (bs, 1H), 7.31 (d, 1H), 7.39 (s, 1H), 7.54 (dd, 1H), 7.84 (d, 1H).

P11

Tert-butyl 7-iodo-1-methyl-3,4-dihydro[1]benzofuro[2,3-c]pyridine-2(1H)-carboxylate

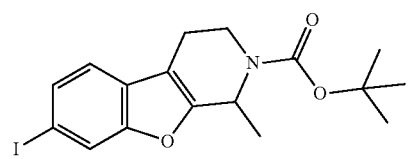 [SMILES: CC1c2oc3cc(I)ccc3c2CCN1C(=O)OC(C)(C)C]

Step 1

7-iodo-1-methyl-1,2,3,4-tetrahydro[1]benzofuro[2,3-c]pyridine

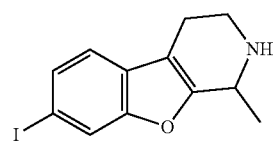

Synthesized as described for 7-iodo-1,2,3,4-tetrahydro[1]benzofuro[2,3-c]pyridine using acetaldehyde. $^1$H-NMR (400 MHz, CDCl$_3$): δ 1.60 (d, 3H), 2.92 (m, 2H), 3.37 (m, 1H), 3.59 (m, 1H), 4.77 (m, 1H), 7.46 (d, 1H), 7.64 (dd, 1H), 8.07 (d, 1H), 9.58 (bs, 1H), 10.02 (bs, 1H).

Step 2

Tert-butyl 7-iodo-1-methyl-3,4-dihydro[1]benzofuro[2,3-c]pyridine-2(1H)-carboxylate P11

Synthesized as described for 7-iodo-1,2,3,4-tetrahydro[1]benzofuro[2,3-c]pyridine starting from 7-iodo-1-methyl-1,2,3,4-tetrahydro[1]benzofuro[2,3-c]pyridine. MS m/z 414 [M+H]$^+$. $^1$H-NMR (400 MHz, CDCl$_3$): δ 1.46 (d, 3H), 1.50 (s, 9H), 2.59 (m, 1H), 2.73 (m, 1H), 3.06 (m, 1H), 4.36 (bd, 1H), 5.23 (bd, 1H), 7.18 (d, 1H), 7.52 (d, 1H), 7.79 (s, 1H).

P12

Tert-butyl 6-iodo-3,4-dihydro[1]benzofuro[2,3-c]pyridine-2(1H)-carboxylate

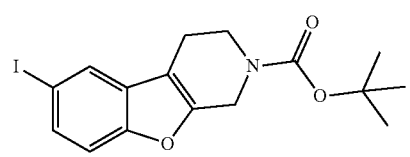 [SMILES: CC(C)(C)OC(=O)N1CCc2c(oc3ccc(I)cc23)C1]

Synthesized as described for tert-butyl 6-iodo-3,4-dihydro[1]benzofuro[2,3-c]pyridine 2(1H)-carboxylate using 2-(5-iodo-1-benzofuran-3-yl)ethanamine. MS m/z 400 [M+H]$^+$.

¹H-NMR (400 MHz, CDCl₃): δ 1.50 (s, 9H), 2.54 (m, 2H), 3.55 (m, 2H), 4.52 (m, 2H), 7.20 (d, J=8.6 Hz, 1H), 7.51 (dd, J=8.6, 1.8 Hz, 1H), 7.77 (s, 1H).

P13

2-(5-iodo-1-benzofuran-3-yl)ethanamine

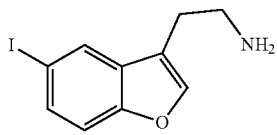 [SMILES: NCCc1coc2ccc(I)cc12]

Synthesized as described for 2-(6-iodo-1-benzofuran-3-yl)ethanamine using methyl 2-hydroxy-5-iodobenzoate. ¹H-NMR (400 MHz, DMSO-d₆): δ 2.91 (t, J=7.7 Hz, 2H), 3.11 (m, 2H), 7.45 (d, J=8.5 Hz, 1H), 7.65 (dd, J=8.5, 1.8 Hz, 1H), 7.90 (s, 1H), 8.09 (bs, 2H), 8.11 (d, J=1.7 Hz, 1H).

P14

Tert-butyl[2-(5-iodo-1-benzofuran-3-yl)ethyl]carbamate

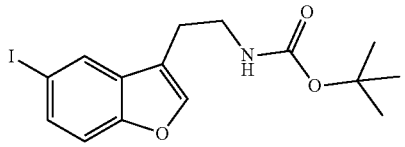 [SMILES: CC(C)(C)OC(=O)NCCc1coc2ccc(I)cc12]

Synthesized as described for tert-butyl[2-(6-iodo-1-benzofuran-3-yl)ethyl]carbamate using 2-(5-iodo-1-benzofuran-3-yl)ethanamine. ¹H-NMR (400 MHz, CDCl₃): δ 1.44 (s, 9H), 2.84 (t, 1H), 3.43 (q, 2H), 4.62 (bs, 1H), 7.25 (d, 1H), 7.43 (s, 1H), 7.56 (dd, 1H), 7.88 (d, 1H).

P15

Tert-butyl 6-iodo-1-methyl-3,4-dihydro[1]benzofuro[2,3-c]pyridine-2(1H)-carboxylate

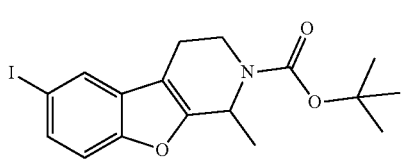 [SMILES: CC1c2oc3ccc(I)cc3c2CCN1C(=O)OC(C)(C)C]

Synthesized as described for tert-butyl 7-iodo-1-methyl-3,4-dihydro[1]benzofuro[2,3-c]pyridine-2(1H)-carboxylate starting from 6-iodo-1-methyl-1,2,3,4-tetrahydro[1]benzofuro[2,3-c]pyridine. MS m/z 414 [M+H]⁺. ¹H-NMR (400 MHz, CDCl₃): δ 1.47 (d, J=6.8 Hz, 3H), 1.51 (s, 9H), 2.57 (m, 1H), 2.71 (m, 1H), 3.05 (m, 1H), 4.38 (m, 1H), 5.21 (m, 1H), 7.20 (d, J=8.6 Hz, 1H), 7.51 (dd, J=8.6, 1.8 Hz, 1H), 7.76 (s, 1H).

P20

Tert-butyl 7-iodo-4,4-dimethyl-3,4-dihydro[1]benzofuro[2,3-c]pyridine-2(1H)-carboxylate

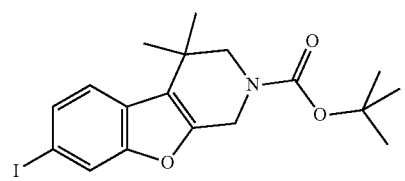 [SMILES: CC(C)(C)OC(=O)N1Cc2oc3cc(I)ccc3c2C(C)(C)C1]

Step 1

2-(6-Iodo-benzofuran-3-yl)-2-methyl-propionitrile

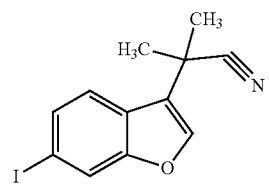

To a solution of (6-iodo-benzofuran-3-yl)-acetonitrile (1.42 g, 5.02 mmol) in tetrahydrofuran (25 mL) at −50° C. was added lithium hexamethyldisilazide (1.03M solution, 10 mL, 10.3 mmol, the mixture turned green). The mixture was stirred at −60° C. for 20 minutes and was cooled to at −78° C. Methyl iodide (2 mL, 30 mmol) was added dropwise and the mixture was slowly allowed to warm up. After 3 h (temp. was below 0° C.) the mixture was quenched with saturated ammonium chloride solution. The mixture was extracted from ethyl acetate and combine organic was washed with water and brine. After drying, solvent was evaporated and the crude product was purified by ISCO (80 g column, hexane with 7.5% ethyl acetate). 2-(6-Iodo-benzofuran-3-yl)-2-methyl-propionitrile was obtained as syrup (1.32 g).

Step 2

2-(6-Iodo-benzofuran-3-yl)-2-methyl-propylamine
P21

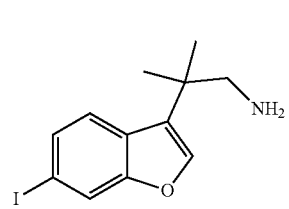

Synthesized as described for 2-(6-iodo-1-benzofuran-3-yl)ethanamine using 2-(6-iodo-benzofuran-3-yl)-2-methyl-propionitrile as the starting material.

Step 3

Tert-butyl 7-iodo-4,4-dimethyl-3,4-dihydro[1]benzo-furo[2,3-c]pyridine-2(1H)-carboxylate P20

Synthesized as described for tert-butyl 7-iodo-3,4-dihydro[1]benzofuro[2,3-c]pyridine-2(1H)-carboxylate using 2-(6-iodo-benzofuran-3-yl)-2-methyl-propylamine as the starting material. MS m/z 372 [M−tBu+H]⁺

P26

7-Iodo-4-methyl-3,4-dihydro-1H-benzo[4,5]furo[2,3-c]pyridine-2-carboxylic acid tert-butyl ester

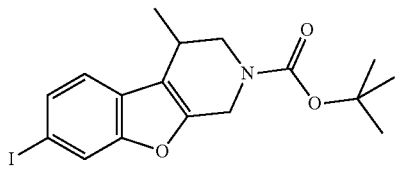 [SMILES: CC1CN(C(=O)OC(C)(C)C)Cc2oc3cc(I)ccc3c21]

Step 1

2-(6-Iodo-benzofuran-3-yl)-propionitrile

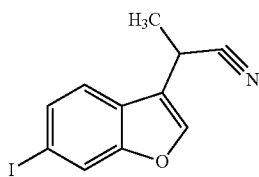

To a solution of (6-iodo-benzofuran-3-yl)-acetonitrile (1 g, 4 mmol) in tetrahydrofuran (25 mL) at −50° C. was added Lithium hexamethyldisilazide (1.03M solution, 10 mL). The mixture was stirred at −60° C. for 20 minutes and was cooled to at −78° C. Methyl iodide (0.30 mL, 4.8 mmol) was added dropwise and the mixture was slowly allowed to warm up. After 3 h the mixture was quenched with saturated ammonium chloride solution and was extracted from ethyl acetate. Combined organics were washed with water and brine. After drying, solvent was evaporated and the crude product was purified by ISCO (7.5% ethyl acetate in hexane) to afford. 2-(6-Iodo-benzofuran-3-yl)-propionitrile (547 mg, 52%). mp 71-72° C.; MS m/z: 298 [M+H]⁺

Step 2

7-Iodo-4-methyl-3,4-dihydro-1H-benzo[4,5]furo[2,3-c]pyridine-2-carboxylic acid tert-butyl ester P26

Synthesized as described for tert-butyl 7-iodo-4,4-dimethyl-3,4-dihydro[1]benzofuro[2,3-c]pyridine-2(1H)-carboxylate using 2-(6-Iodo-benzofuran-3-yl)-propionitrile 2-(6-Iodo-benzofuran-3-yl)-2-methyl-propylamine.

P22

(6-Iodo-7-methoxy-3,4,4a,9a-tetrahydro-1H-benzo[4,5]furo[2,3-c]pyridine-2-carboxylic acid tert-butyl ester

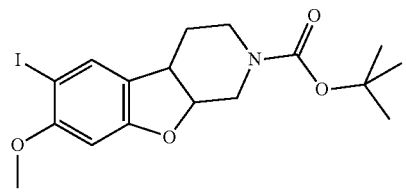 [SMILES: COc1cc2c(cc1I)C1CCN(C(=O)OC(C)(C)C)CC1O2]

To a solution of 7-methoxy-3,4,4a,9a-tetrahydro-1H-benzo[4,5]furo[2,3-c]pyridine-2-carboxylic acid tert-butyl ester (500 mg, 2 mmol) in methanol (7 mL, 200 mmol) was added dropwise a solution of iodine monochloride (340 mg, 2.1 mmol) in 5 ml of methanol at RT. The mixture was stirred overnight at RT. After 18 h, the solvent was removed and the crude reaction mixture was treated with 50 mL of acetonitrile, di-tert-butyl dicarbonate (0.5 mL) and 10 mg of DMAP (10 mg). The mixture was stirred overnight at RT. After 18 h, solvent was removed and the crude product was purified by ISCO chromatography (Hexane:EtOAc 70:30) which was obtained as a syrup (321 mg, 45%). MS m/z 454 [M+H]⁺

P23

Tert-butyl 7-iodo-4a-methyl-3,4,4a,9a-tetrahydro[1]benzofuro[2,3-c]pyridine-2(1H)-carboxylate

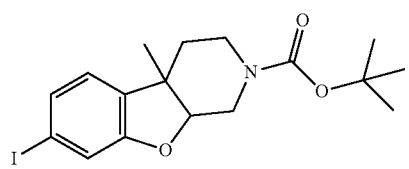 [SMILES: CC(C)(C)OC(=O)N1CCC2(C)c3ccc(I)cc3OC2C1]

Step 1

(2-Acetyl-5-methoxy-phenoxy)-acetic acid ethyl ester

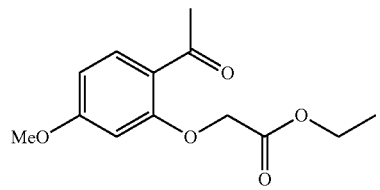 [SMILES: CCOC(=O)COc1cc(OC)ccc1C(C)=O]

Into a Round bottom flask was added Ethanone, 1-(2-hydroxy-4-methoxyphenyl)-ethanone (40.01 g, 0.241 mol), ethyl bromoacetate (28.17 mL, 0.2540 mol), potassium carbonate (69.6 g, 0.504 mol), and N,N-Dimethylformamide (200 mL, 2 mol). The reaction was heated at 90° C. for 6 h before cooling to RT overnight. The reaction was poured into ice/water and extracted with ethyl ether (twice). The combined ether extracts were dried, filtered and concentrated. The resulting solid was triturated in hexanes, filtered and dried. The product was used in the next reaction step without further purification.

Step 2

[2-(-2-Cyano-1-methyl-vinyl)-5-methoxy-phenoxy]-acetic acid ethyl ester

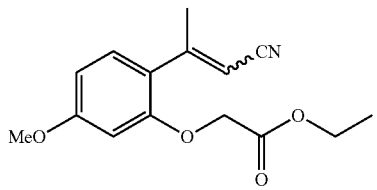 [SMILES: CCOC(=O)COc1cc(OC)ccc1C(C)=CC#N]

To a slurry of Sodium hydride, 60% disp. in mineral oil (7.44 g, 0.186 mol) in Tetrahydrofuran (200 mL, 2 mol) was added and a solution of diethyl cyanomethylphosphonate (30.0 mL, 0.186 mol) in THF (50 mL) slowly, hydrogen was released. After addition and 10 minutes at RT the reaction was cooled at 0° C. and a mixture of (2-acetyl-5-methoxy-phenoxy)-acetic acid ethyl ester (44.6 g, 0.177 mol) in tetrahydrofuran (150 mL) was added dropwise. After 2 hr at 0° C., the reaction was transferred into ice/water and extracted with diethylether. The ether layer was washed with brine, dried, filtered and concentrated. The product was used in the next reaction step without further purification.

Step 3

3-Cyano-6-methoxy-3-methyl-2,3-dihydro-benzofuran-2-carboxylic acid ethyl ester

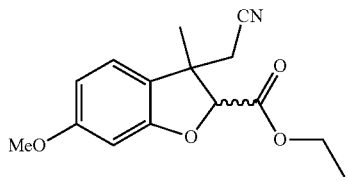 [SMILES: CCOC(=O)C1Oc2cc(OC)ccc2C1(C)CC#N]

To a mixture of [2-(2-cyano-1-methyl-vinyl)-5-methoxy-phenoxy]-acetic acid ethyl ester (39 g, 0.14 mol), separated into 6 tubes with 6.5 gm in each, was added ethanol (7 mL, 0.1 mol) and then sodium hydride (15 mg, 0.38 mmol, 60% in mineral oil) was added slowly and the reaction was heated at 80° C. for 1 h. The reaction mixtures were cooled to RT, transferred into ice and extracted with diethylether. The ether layers were washed with sat. sodium bicarbonate, brine, dried over sodium sulfate, filtered and concentrated to a brown oil. The product was used in the next reaction step without further purification.

Step 4

7-Methoxy-4a-methyl-3,4,4a,9a-tetrahydro-2Hbenzo[4,5]furo[2,3-c]pyridine-1-one

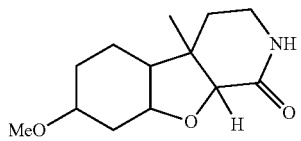 [SMILES: COC1CCC2C(C1)OC1C(=O)NCCC12C]

A mixture of 3-cyano-6-methoxy-3-methyl-2,3-dihydro-benzofuran-2-carboxylic acid ethyl ester (33.53 g, 0.1283 mol), platinum dioxide (250 mg, 0.0011 mol) and acetic acid (50 mL, 0.9 mol) were hydrogenated on a paar shaker at 55 psi for 3 h. The reaction mixture was filtered through a plug of Celite. The filtrate was concentrated, the residue was dissolved in ethyl acetate, washed with water, bicarbonate, brine, dried over sodium sulfate and filtered. The solvent was evaporated and the residue was purified on silica gel column (300 g) and eluting first with ethyl acetate and then 10% methanol/DCM. The product was used in the next reaction step without further purification.

Step 5

7-Methoxy-4a-methyl-3,4,4a,9a-tetrahydro[1]benzofuro[2,3-c]pyridine

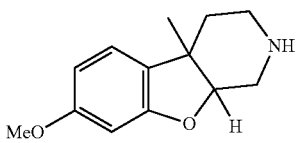 [SMILES: COc1ccc2c(c1)OC1CNCCC21C]

To a solution of 7-methoxy-4a-methyl-3,4,4a,9a-tetrahydro-2Hbenzo[4,5]furo[2,3-c]pyridine-1-one (1.0 g, 4.30 mmol) in tetrahydrofuran (3 mL) was slowly added 1.0 M of lithium tetrahydroaluminate in tetrahydrofuran (2 mL). After 30 min stirring another portion of 1.0 M of lithium tetrahydroaluminate in tetrahydrofuran (1 mL) was added and the reaction was stirred for 2 h. The reaction was transferred into ice, 6N aqueous HCl was added followed by ethyl acetate. The aqueous layer was basified by adding NaOH and the product was extracted with ethyl acetate. The organic layer was washed with brine, dried over sodium sulfate, filtered and the solvent was evaporated to provide a colorless oil. The product was used in the next reaction step without further purification.

Step 6

Tert-butyl 7-hydroxy-4a-methyl-3,4,4a,9a-tetrahydro[1]benzofuro[2,3-c]pyridine-2(1H)-carboxylate

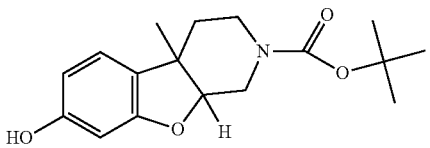 [SMILES: CC(C)(C)OC(=O)N1CCC2(C)c3ccc(O)cc3OC2C1]

Synthesized as described for tert-butyl 7-hydroxy-3,4,4a,9a-tetrahydro[1]benzofuro[2,3-c]pyridine-2(1H)-carboxylate starting from 7-Methoxy-4a-methyl-3,4,4a,9a-tetrahydro[1]benzofuro[2,3-c]pyridine.

Step 7

Tert-butyl 7-iodo-4a-methyl-3,4,4a,9a-tetrahydro[1]benzofuro[2,3-c]pyridine-2(1H)-carboxylate P23

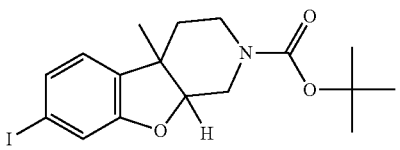 [SMILES: CC(C)(C)OC(=O)N1CCC2(C)c3ccc(I)cc3OC2C1]

Synthesized as described for tert-butyl 7-iodo-3,4,4a,9a-tetrahydro[1]benzofuro[2,3-c]pyridine-2(1H)-carboxylate starting from tert-butyl 7-hydroxy-4a-methyl-3,4,4a,9a-tetrahydro[1]benzofuro[2,3-c]pyridine-2(1H)-carboxylate. MS m/z 360 [M-tBu+H]$^+$

P24

Tert-butyl 6-iodo-4a-methyl-3,4,4a,9a-tetrahydro[1]benzofuro[2,3-c]pyridine-2(1H)-carboxylate

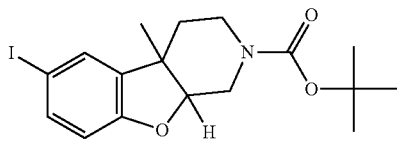 [SMILES: CC(C)(C)OC(=O)N1CCC2(C)c3cc(I)ccc3OC2C1]

Synthesized as described for tert-butyl 7-iodo-4a-methyl-3,4,4a,9a tetrahydro[1]benzofuro[2,3-c]pyridine-2(1H)-carboxylate starting from tert-butyl 6-hydroxy-4a-methyl-3,4,4a,9a-tetrahydro[1]benzofuro[2,3-c]pyridine-2(1H)-carboxylate. MS m/z 360 [M-tBu+H]$^+$

P25

Tert-butyl 6-hydroxy-4a-methyl-3,4,4a,9a-tetrahydro[1]benzofuro[2,3-c]pyridine-2(1H)-carboxylate

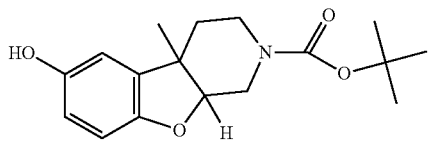 [SMILES: CC(C)(C)OC(=O)N1CCC2(C)c3cc(O)ccc3OC2C1]

Synthesized as described for tert-butyl 7-hydroxy-4a-methyl-3,4,4a,9a-tetrahydro[1]benzofuro[2,3-c]pyridine-2(1H)-carboxylate and as described in *J. Med. Chem.*, 1989, 32, 2221-2226 starting from 1-(2-hydroxy-3-methoxyphenyl)-ethanone. MS m/z 250 [M-tBu+H]$^+$

P30 tert-butyl 7-iodo-1,1-dimethyl-3,4-dihydro[1]benzofuro[2,3-c]pyridine-2(1H)-carboxylate

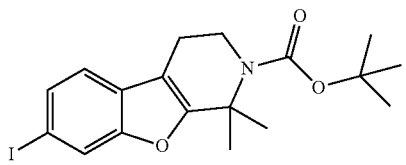 [SMILES: CC(C)(C)OC(=O)N1CCc2c(oc3cc(I)ccc23)C1(C)C]

Step 1

To a solution of 2-(6-iodo-benzofuran-3-yl)-ethylamine (4.20 g, 14.63 mmol) in methanol (60.0 mL, 1.48 mol) was added acetone (1.63 mL) and the reaction mixture was stirred at rt. After 2 days the solvent was evaporated. The residue was dissolved in a mixture of TFA (7.0 mL) and DCE (70.0 mL) and heated to reflux. After 20 h the reaction mixture was cooled down and basified with 5M aq. NaOH. The layers were separated and the aqueous phase extracted with DCM. The combined organic layers was dried (Na$_2$SO$_4$) and the solvent was evaporated. The residue was purified on a silica gel column eluting with DCM-MeOH—NH$_4$OH to afford 7-iodo-1,1-dimethyl-1,2,3,4-tetrahydro-benzo[4,5]furo[2,3-c]pyridine as an off-white solid. mp 97-98° C.; MS m/z 328 [M+H]$^+$.

Step 2

To a solution of 7-iodo-1,1-dimethyl-1,2,3,4-tetrahydro-benzo[4,5]furo[2,3-c]pyridine (0.420 g, 1.28 mmol) in THF (10.0 mL) was added water (10.0 mL), sodium bicarbonate (0.647 g, 7.70 mmol) followed by di-tert-butyldicarbonate (0.420 g, 1.92 mmol). After 16 h stirring, the solution was concentrated and extracted with DCM. The organic layer was dried over Na$_2$SO$_4$ and the solvent was evaporated to give the title product. The product was used in the next reaction step without further purification. MS m/z 449 [M+H]$^+$.

A01

7-iodo-3,4,5',6'-tetrahydro-2H,4'H-spiro[1-benzofuro[2,3-c]pyridine-1,3'-pyran]

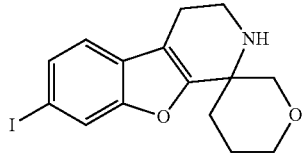 [SMILES: Ic1ccc2c3c(oc2c1)C1(CCCOC1)NCC3]

A solution of 2-(6-iodo-benzofuran-3-yl)-ethylamine (1.00 g, 3.48 mmol) and dihydro-pyran-3-one (1.05 g, 10.4 mmol) in trifluoroacetic acid (4.00 mL) was heated at 80° C. for 15 h. The reaction mixture was cooled down, 1M aqueous NaOH was added and the mixture was extracted with DCM. The solvent was evaporated and the residue was purified by silica gel chromatography eluting with DCM-MeOH—NH$_4$OH to afford the title product. mp 131-137° C. dec.; MS m/z 370 [M+H]$^+$ Chiral separation of 7-iodo-3,4,5',6'-tetrahydro-2H,4'H-spiro[1-benzofuro[2,3-c]pyridine-1,3'-pyran] A01 was performed using SFC chromatography on a chiral column as described in the general method. Enantiomer 1 A02, MS m/z 370 [M+H]$^+$ and Enantiomer 2 A03, MS m/z 370 [M+H]$^+$ were obtained.

The following examples in the table were prepared as described by the above synthetic procedure. Enantiomers were obtained using SFC chromatography on a chiral column as described in the general method and starting from the corresponding stereoisomer mixture.

| Prep | Chemical name | MS m/z [M + H]$^+$ | Stereochemistry | Scaffold | Starting material |
|---|---|---|---|---|---|
| A04 | 7-iodo-3,4-dihydro-2H-spiro[1-benzofuro[2,3-c]pyridine-1,1'-cyclobutane] | 340 | | P09 | cyclobutanone |

-continued

| Prep | Chemical name | MS m/z [M + H]+ | Stereochemistry | Scaffold | Starting material |
|---|---|---|---|---|---|
| A05 | 7-iodo-3,4-dihydro-2H-spiro[1-benzofuro[2,3-c]pyridine-1,3'-oxetane] | 342 | | P09 | oxetan-3-one |
| A06 | 1-ethyl-7-iodo-1-methyl-1,2,3,4-tetrahydro[1]benzofuro[2,3-c]pyridine | 342 | | P09 | butan-2-one |
| A07 | 7-iodo-3,4-dihydro-2H-spiro[1-benzofuro[2,3-c]pyridine-1,1'-cyclopentane] | 354 | | P09 | cyclopentanone |
| A08 | 1-cyclopropyl-7-iodo-1-methyl-1,2,3,4-tetrahydro[1]benzofuro[2,3-c]pyridine | 354 | | P09 | 1-cyclopropylethanone |
| A09 | 7-iodo-3,4,4',5'-tetrahydro-2H-spiro[1-benzofuro[2,3-c]pyridine-1,3'-furan] | 356 | racemic | P09 | dihydrofuran-3(2H)-one |
| A10 | 7-iodo-3,4,4',5'-tetrahydro-2H-spiro[1-benzofuro[2,3-c]pyridine-1,3'-furan] | 356 | enantiomer 1 | P09 | dihydrofuran-3(2H)-one |
| A11 | 7-iodo-3,4,4',5'-tetrahydro-2H-spiro[1-benzofuro[2,3-c]pyridine-1,3'-furan] | 356 | enantiomer 2 | P09 | dihydrofuran-3(2H)-one |
| A12 | 7-iodo-1-(methoxymethyl)-1-methyl-1,2,3,4-tetrahydro[1]benzofuro[2,3-c]pyridine | 358 | | P09 | 1-methoxypropan-2-one |
| A13 | 1-(ethoxymethyl)-7-iodo-1,2,3,4-tetrahydro[1]benzofuro[2,3-c]pyridine | 358 | | P09 | 1,1,2-triethoxyethane |
| A14 | 7-iodo-1-(methoxymethyl)-1-methyl-1,2,3,4-tetrahydro[1]benzofuro[2,3-c]pyridine | 358 | | P09 | 1-methoxypropan-2-one |
| A15 | 1-(difluoromethyl)-7-iodo-1-methyl-1,2,3,4-tetrahydro[1]benzofuro[2,3-c]pyridine | 364 | racemic | P09 | 1,1-difluoropropan-2-one |
| A16 | 1-(difluoromethyl)-7-iodo-1-methyl-1,2,3,4-tetrahydro[1]benzofuro[2,3-c]pyridine | 364 | enantiomer 1 | P09 | 1,1-difluoropropan-2-one |
| A17 | 1-(difluoromethyl)-7-iodo-1-methyl-1,2,3,4-tetrahydro[1]benzofuro[2,3-c]pyridine | 364 | enantiomer 2 | P09 | 1,1-difluoropropan-2-one |
| A18 | 1,1-bis(fluoromethyl)-7-iodo-1,2,3,4-tetrahydro[1]benzofuro[2,3-c]pyridine | 364 | Racemic | P09 | 1,3-difluoropropan-2-one |
| A19 | 7-iodo-1-methyl-1-(2-methylpropyl)-1,2,3,4-tetrahydro[1]benzofuro[2,3-c]pyridine | 370 | Racemic | P09 | 4-methylpentan-2-one |
| A20 | 7-iodo-1-methyl-1-(trifluoromethyl)-1,2,3,4-tetrahydro[1]benzofuro[2,3-c]pyridine | 382 | Racemic | P09 | 1,1,1-trifluoropropan-2-one |
| A21 | 7-iodo-4,4-dimethyl-3,4,4',5'-tetrahydro-2H-spiro[1-benzofuro[2,3-c]pyridine-1,3'-furan] | 384 | Racemic | P09 | dihydrofuran-3(2H)-one |
| A22 | 7-iodo-2',3,3',4,5',6'-hexahydro-2H-spiro[1-benzofuro[2,3-c]pyridine-1,4'-thiopyran] | 386 | | P09 | tetrahydro-4H-thiopyran-4-one |

-continued

| Prep | Chemical name | MS m/z [M + H]+ | Stereochemistry | Scaffold | Starting material |
|---|---|---|---|---|---|
| A23 | 7-iodo-1,1-bis(methoxymethyl)-1,2,3,4-tetrahydro[1]benzofuro[2,3-c]pyridine | 388 | | P09 | 1,3-dimethoxypropan-2-one |
| A24 | 7-iodo-4,4-dimethyl-2',3,3',4,5',6'-hexahydro-2H-spiro[1-benzofuro[2,3-c]pyridine-1,4'-pyran] | 398 | | P09 | tetrahydro-4H-pyran-4-one |
| A25 | 2-(7-iodo-1-methyl-1,2,3,4-tetrahydro[1]benzofuro[2,3-c]pyridin-1-yl)-N,N-dimethylacetamide | 399 | Racemic | P09 | N,N-dimethyl-3-oxobutanamide |
| A26 | 1-(7-iodo-3,4-dihydro-1'H,2H-spiro[1-benzofuro[2,3-c]pyridine-1,4'-piperidin]-1'-yl)ethanone | 411 | | P09 | 1-acetylpiperidin-4-one |
| A27 | 6-iodo-1,1-dimethyl-1,2,3,4-tetrahydro[1]benzofuro[2,3-c]pyridine | 328 | | P13 | propan-2-one |
| A28 | 7-iodo-2',3,3',4,5',6'-hexahydro-2H-spiro[1-benzofuro[2,3-c]pyridine-1,4'-pyran] | 370 | Racemic | P09 | tetrahydro-4H-pyran-4-one |
| A29 | 7-iodo-4,4-dimethyl-1-(tetrahydro-2H-pyran-4-yl)-1,2,3,4-tetrahydro[1]benzofuro[2,3-c]pyridine | 412 | Racemic | P21 | tetrahydro-2H-pyran-4-carbaldehyde |
| A30 | 7-iodo-4,4-dimethyl-3,4,4',5'-tetrahydro-2H-spiro[1-benzofuro[2,3-c]pyridine-1,3'-furan] | 384 | Racemic | P21 | dihydrofuran-3(2H)-one |
| A31 | 6-iodo-3,4,4',5'-tetrahydro-2H-spiro[1-benzofuro[2,3-c]pyridine-1,3'-furan] | 356 | Racemic | P13 | dihydrofuran-3(2H)-one |

A32

7-iodo-2,2',3,3',4,5',6',9-octahydrospiro[beta-carboline-1,4'-pyran]

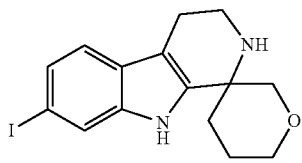 [SMILES: Ic1ccc2c3c([nH]c2c1)C1(CCCOC1)NCC3]

A solution of [2-(6-Iodo-1H-indol-3-yl)-ethyl]-carbamic acid tert-butyl ester (500.0 mg, 1.294 mmol) was stirred into a mixture of DCE (2.0 mL) and TFA (2.0 mL) for 10 min. Tetrahydro-4H-pyran-4-one (360.0 uL, 3.88 mmol) was added. The reaction mixture was stirred at 40° C. for one hour, then at 50° C. for two hours and finally at 60° C. for one hour. The reaction solution was then concentrated down and the product was used in the next step without further purification. MS m/z 369 [M+H]+.

The following examples were prepared essentially as described directly above.

| Preparation | Name | MS m/z [M + H]+ | Starting material |
|---|---|---|---|
| A32 | 7-iodo-2,2',3,3',4,5',6',9-octahydrospiro[beta-carboline-1,4'-pyran] | 369 | tetrahydro-4H-pyran-4-one |
| A33 | 7-iodo-2,3,4,5',6',9-hexahydro-4'H-spiro[beta-carboline-1,3'-pyran] | 369 | tetrahydro-4H-pyran-3-one |
| A34 | 7-iodo-2,3,4,4',5',9-hexahydrospiro[beta-carboline-1,3'-furan] | 355 | dihydrofuran-3(2H)-one |

B01

Tert-butyl-7-iodo-3,4,4',5'-tetrahydro-2H-spiro[1-benzofuro[2,3-c]pyridine-1,3'-furan]-2-carboxylate enantiomer 2

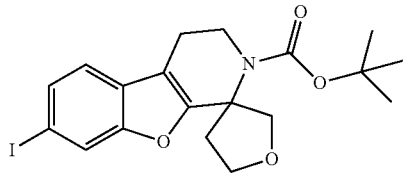 [SMILES: CC(C)(C)OC(=O)N1CCc2c(oc3cc(I)ccc23)C12CCOC2]

To a solution of 7-iodo-3,4,4',5'-tetrahydro-2H-spiro[1-benzofuro[2,3-c]pyridine-1,3'-furan] (790 mg, 2.2 mmol) in anhydrous 1,4-dioxane (12 mL), N,N-diisopropylethylamine (1.16 mL, 6.67 mmol) and di-tert-butyldicarbonate (1.28 mL, 5.56 mmol) were added. After 1 h stirring at 80° C. another portion of di-tert-butyldicarbonate (1.28 mL, 5.56 mmol) was added. After 3 h stirring at 80° C., the reaction was concentrated down. The crude product was suspended in a mixture of DCM (14 mL) and a solution of DMAP in H2O (0.05M, 10 mL). The resulting biphasic mixture was vigorously stirred for 1 h. The aqueous layer was removed, the organic layer was washed with saturated ammonium chloride (2×), water and brine, dried over anhydrous magnesium sulfate and concentrated to yield a tan solid. MS m/z 477.90 [M+Na]+.

The following examples in the table were prepared as described in the above synthetic procedure. Enantiomers B16 and B17 were obtained from preparation B15 using SFC chromatography on a chiral column according to the general method.

| Preparation | Name | MS m/z [M + H]+ | Stereochemistry | Starting material |
|---|---|---|---|---|
| B01 | tert-butyl (1R)-7-iodo-3,4,4',5'-tetrahydro-2H-spiro[1-benzofuro[2,3-c]pyridine-1,3'-furan]-2-carboxylate | 456 | enantiomer 2 | A11 |
| B02 | tert-butyl (1S)-7-iodo-3,4,4',5'-tetrahydro-2H-spiro[1-benzofuro[2,3-c]pyridine-1,3'-furan]-2-carboxylate | 456 | enantiomer 1 | A10 |
| B03 | tert-butyl 7-iodo-3,4,4',5'-tetrahydro-2H-spiro[1-benzofuro[2,3-c]pyridine-1,3'-furan]-2-carboxylate | 456 | racemic | A09 |
| B04 | tert-butyl 7-iodo-3,4,5',6'-tetrahydro-2H,4'H-spiro[1-benzofuro[2,3-c]pyridine-1,3'-pyran]-2-carboxylate | 470 | enantiomer 1 | A02 |
| B05 | tert-butyl 7-iodo-3,4,5',6'-tetrahydro-2H,4'H-spiro[1-benzofuro[2,3-c]pyridine-1,3'-pyran]-2-carboxylate | 470 | enantiomer 2 | A03 |
| B06 | tert-butyl 7-iodo-2',3,3',4,5',6'-hexahydro-2H-spiro[1-benzofuro[2,3-c]pyridine-1,4'-pyran]-2-carboxylate | 470 | | A37 |
| B07 | tert-butyl 6-iodo-3,4,4',5'-tetrahydro-2H-spiro[1-benzofuro[2,3-c]pyridine-1,3'-furan]-2-carboxylate | 456 | racemic | A31 |
| B08 | tert-butyl 7-iodo-4,4-dimethyl-2',3,3',4,5',6'-hexahydro-2H-spiro[1-benzofuro[2,3-c]pyridine-1,4'-pyran]-2-carboxylate | 498 | racemic | A24 |
| B15 | tert-butyl 7-iodo-4,5',6',9-tetrahydro-4'H-spiro[beta-carboline-1,3'-pyran]-2(3H)-carboxylate | 469 | racemic | A33 |
| B16 | tert-butyl 7-iodo-4,5',6',9-tetrahydro-4'H-spiro[beta-carboline-1,3'-pyran]-2(3H)-carboxylate | 469 | enantiomer 1 | B15 |
| B17 | tert-butyl 7-iodo-4,5',6',9-tetrahydro-4'H-spiro[beta-carboline-1,3'-pyran]-2(3H)-carboxylate | 469 | enantiomer 2 | B15 |

B09

{2-[6-(3-Fluoro-benzenesulfonyl)-benzofuran-3-yl]-ethyl}-carbamic acid tert-butyl ester

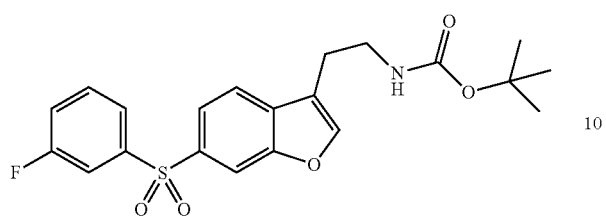

Synthesized as described for 6-(3-chloro-benzenesulfonyl)-3,4,4a,9a-tetrahydro-1H-benzo[4,5]furo[2,3-c]pyridine-2-carboxylic acid tert-butyl ester starting from tert-butyl [2-(6-iodo-1-benzofuran-3-yl)ethyl]carbamate and purified using preparative LC-MS. MS m/z 420 [M+H]+

The following examples were prepared essentially as described directly above.

| Prep | Chemical name | MS m/z [M + H]+ | Scaffold | Starting mat |
|---|---|---|---|---|
| B09 | tert-butyl (2-{6-[(3-fluorophenyl)sulfonyl]-1-benzofuran-3-yl}ethyl)carbamate | 420 | P10 | 3-fluorobenzenethiol |
| B10 | tert-butyl (2-{5-[(3-fluorophenyl)sulfonyl]-1-benzofuran-3-yl}ethyl)carbamate | 420 | P14 | 3-fluorobenzenethiol |
| B11 | tert-butyl (2-{6-[(3-chlorophenyl)sulfonyl]-1-benzofuran-3-yl}ethyl)carbamate | 436 | P10 | 3-chlorobenzenethiol |
| B12 | tert-butyl (2-{5-[(3-chlorophenyl)sulfonyl]-1-benzofuran-3-yl}ethyl)carbamate | 436 | P14 | 3-chlorobenzenethiol |
| B13 | tert-butyl {2-[6-(phenylsulfonyl)-1-benzofuran-3-yl]ethyl}carbamate | 402 | P10 | benzenethiol |
| B14 | tert-butyl (2-{6-[(3-fluorophenyl)sulfonyl]-1H-indol-3-yl}ethyl)carbamate | 419 | [2-(6-Iodo-1H-indol-3-yl)-ethyl]-carbamic acid tert-butyl ester | 3-fluorobenzenethiol |

C01

1,1-Dimethyl-7-triisopropylsilanylsulfanyl-3,4-dihydro-1H-benzo[4,5]furo[2,3-c]pyridine-2-carboxylic acid tert-butyl ester

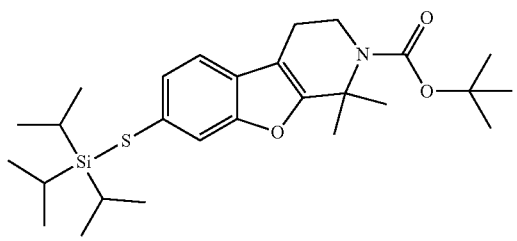 [SMILES: CC(C)[Si](Sc1ccc2c3c(oc2c1)C(C)(C)N(C(=O)OC(C)(C)C)CC3)(C(C)C)C(C)C]

Anhydrous dioxane was bubbled with Argon for 1 h before being used. Triisopropylsilanethiol (4.00 mL, 18.6 mmol) was dissolved into anhydrous 1,4-dioxane (15 mL) and a solution of lithium hexamethyldisilazide in THF (1.0 M 17.7 mL, 17.7 mmol) was added slowly. The reaction was stirred for 2.5 h. A portion of the lithium triisopropylsilanethiolate solution (15.4 mL, 7.70 mmol) was added to a suspension of 7-iodo-1,1-dimethyl-3,4-dihydro-1H-benzo[4,5]furo[2,3-c]pyridine-2-carboxylic acid tert-butyl ester (3.00 g, 7.02 mmol) and tetrakis(triphenylphosphine)palladium(0) (0.81 g, 0.70 mmol) in 1,4-dioxane (10 mL) under argon. The reaction mixture was stirred at 60° C. for 2 h and the solvent was evaporated. The residue was triturated with anhydrous hexane, filtered through a plug of Celite and the filtrate was concentrated down to yield 4.48 g of 1,1-dimethyl-7-triisopropylsilanylsulfanyl-3,4-dihydro-1H-benzo[4,5]furo[2,3-c]pyridine-2-carboxylic acid tert-butyl ester. This product was used in the next step without further purification. MS m/z 490 [M+H]+

The following examples in the table were prepared as described in the above synthetic procedure.

| Prep | Name | MS m/z | Stereochemistry | Starting material |
|---|---|---|---|---|
| C01 | tert-butyl 1,1-dimethyl-7-[(tripropan-2-ylsilyl)sulfanyl]-3,4-dihydro[1]benzofuro[2,3-c]pyridine-2(1H)-carboxylate | 434 [M − tBu + H]+ | | P30 |

| Prep | Name | MS m/z | Stereochemistry | Starting material |
|---|---|---|---|---|
| C02 | tert-butyl 7-[(tripropan-2-ylsilyl)sulfanyl]-3,4,4a,9a-tetrahydro[1]benzofuro[2,3-c]pyridine-2(1H)-carboxylate | 486 [M + Na]⁺ | racemate | P01 |
| C03 | tert-butyl 7-[(tripropan-2-ylsilyl)sulfanyl]-3,4,4a,9a-tetrahydro[1]benzofuro[2,3-c]pyridine-2(1H)-carboxylate | 464 [M + Na]⁺ | enantiomer 1 | P03 |
| C04 | tert-butyl 7-[(tripropan-2-ylsilyl)sulfanyl]-3,4,4a,9a-tetrahydro[1]benzofuro[2,3-c]pyridine-2(1H)-carboxylate | 464 [M + Na]⁺ | enantiomer 2 | P04 |
| C05 | tert-butyl 4a-methyl-7-[(tripropan-2-ylsilyl)sulfanyl]-3,4,4a,9a-tetrahydro[1]benzofuro[2,3-c]pyridine-2(1H)-carboxylate | 500 [M + Na]⁺ | | P23 |
| C06 | tert-butyl 7-[(tripropan-2-ylsilyl)sulfanyl]-3,4-dihydro[1]benzofuro[2,3-c]pyridine-2(1H)-carboxylate | 447 [M − Me + H]⁺ | | P08 |
| C07 | tert-butyl 6-[(tripropan-2-ylsilyl)sulfanyl]-3,4-dihydro[1]benzofuro[2,3-c]pyridine-2(1H)-carboxylate | 447 [M − Me + H]⁺ | | P12 |
| C08 | tert-butyl 4,4-dimethyl-7-[(tripropan-2-ylsilyl)sulfanyl]-3,4-dihydro[1]benzofuro[2,3-c]pyridine-2(1H)-carboxylate | | | P20 |
| C09 | 4,4-dimethyl-7-[(tripropan-2-ylsilyl)sulfanyl]-3,4,4',5'-tetrahydro-2H-spiro[1-benzofuro[2,3-c]pyridine-1,3'-furan] | 446 [M + H]⁺ | | A21 |

SM01

3-Trifluoromethyl-5-triisopropylsilanylsulfanyl-pyridine

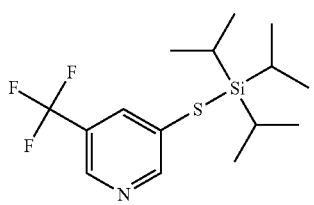 [SMILES: CC(C)[Si](Sc1cncc(C(F)(F)F)c1)(C(C)C)C(C)C]

Anhydrous toluene was bubbled with Argon for 1 h before being used. Palladium acetate (0.050 g, 0.22 mmol), triphenylphosphine (0.255 g, 0.973 mmol), cesium carbonate (1.87 g, 5.75 mmol) and 3-bromo-5-trifluoromethyl-pyridine (1.00 g, 4.42 mmol) were introduced into a 50 mL round bottom flask under argon. Toluene (10 mL) and triisopropylsilanethiol (1.23 mL, 5.75 mmol) were added. The reaction was stirred at 100° C. overnight, then cooled to room temperature and diluted with hexanes. The suspension was filtered through a plug of Celite. The filtrate was concentrated down to afford 3-trifluoromethyl-5-triisopropylsilanylsulfanyl-pyridine which was used in the next reaction step without further purification.

The following examples were prepared essentially as described immediately above.

| Preparation | Chemical name | Starting material |
|---|---|---|
| SM02 | (2,3-dihydro-1,4-benzodioxin-5-ylsulfanyl)(tripropan-2-yl)silane | 5-bromo-2,3-dihydro-1,4-benzodioxine |
| SM03 | [(3,5-difluoro-2-methoxyphenyl)sulfanyl](tripropan-2-yl)silane | 1-bromo-3,5-difluoro-2-methoxybenzene |
| SM04 | [(2,2-difluoro-1,3-benzodioxol-4-yl)sulfanyl](tripropan-2-yl)silane | 4-bromo-2,2-difluoro-1,3-benzodioxole |

SM05

(3,5-Dimethoxy-phenylsulfanyl)-triisopropyl-silane

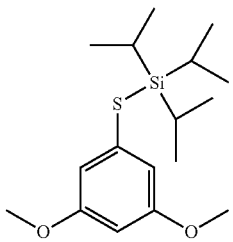

To a solution of triisopropylsilanethiol (0.49 g, 2.6 mmol) in 1,4-dioxane (5 mL, 60 mmol) was added lithium hydride (23 mg, 2.9 mmol). After 10 minutes, 1-bromo-3,5-dimethoxy-benzene (500 mg, 2 mmol) and tetrakis(triphenylphosphine)palladium(0) (270 mg, 0.23 mmol) were added and the reaction mixture was heated to 60° C. for 16 h. The reaction mixture was diluted with DCM, filtered and concentrated. The resulting residue was dissolved in DCM and purified using silica gel chromatographie (40 g silica gel column) eluting with hexanes:DCM (3:1) to afford the title product.

SM06

[(2,3-difluorophenyl)sulfanyl](tripropan-2-yl)silane

Prepared as described for (1,2-dimethoxy-phenylsulfanyl)-triisopropyl-silane starting from 1,2-difluoro-3-iodobenzene.

SM07

2-Fluoro-3-isopropoxy-phenylsulfanyl)-triisopropyl-silane

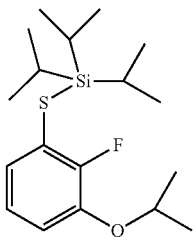 [SMILES: CC(C)Oc1cccc(S[Si](C(C)C)(C(C)C)C(C)C)c1F]

Triisopropylsilanethiol (1.10 mL, 5.15 mmol) was added to a mixture of 1-bromo-2-fluoro-3-isopropoxy-benzene (1.00 g, 4.29 mmol), tris(dibenzylideneacetone)dipalladium (0) (98.2 mg, 0.107 mmol), 9,9-dimethyl-4,5-bis(diphenylphosphino)xanthene (65 mg, 0.11 mmol) and a solution of lithium hexamethyldisilazide (1.2 equivalent) in toluene (8 mL,). The reaction mixture was stirred at 120° C. for 6 h. After cooling down to room temperature, the reaction mixture was filtered through a plug of alumina and eluted with diethylether. The solvent was evaporated and the resulting product (996 mg) was used in the next reaction step without further purification.

The following examples in the table were prepared as described in the above synthetic procedures.

| Preparation | Chemical name | Starting material |
|---|---|---|
| SM07 | {[2-fluoro-3-(propan-2-yloxy)phenyl]sulfanyl}-(tripropan-2-yl)silane | 1-Bromo-2-fluoro-3-isopropoxy-benzene |
| SM08 | {[3-(benzyloxy)-5-fluorophenyl]sulfanyl}-(tripropan-2-yl)silane | 1-(benzyloxy)-3-bromo-5-fluorobenzene |
| SM09 | {[(2E,4Z)-4-fluoro-5-(tetrahydro-2H-pyran-4-ylmethoxy)-hepta-2,4,6-trien-3-yl]sulfanyl}-(tripropan-2-yl)silane | 4-({[(3Z,5E)-5-bromo-4-fluorohepta-1,3,5-trien-3-yl]oxy}methyl)tetrahydro-2H-pyran |
| SM10 | {[(2E,4Z)-4-chloro-5-(tetrahydro-2H-pyran-4-ylmethoxy) hepta-2,4,6-trien-3-yl]sulfanyl}-(tripropan-2-yl)silane | 4-({[(3Z,5E)-5-bromo-4-chlorohepta-1,3,5-trien-3-yl]oxy}methyl)-tetrahydro-2H-pyran |

The above procedures were found in or adapted from the following references: *Adv. Synth. Catal.,* 2005, 47, 313-319 (aryl bromides); *J. Am. Chem. Soc. Comm.,* 2006, 128, 2180-2181; and WO 03/004501 A2.

SM11

1-Fluoro-3-iodo-5-ethoxybenzene

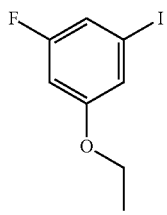

(3-Ethoxy-5-fluorophenyl)boronic acid (2.5 g, 0.014 mol) was dissolved in THF (30 mL) and a solution of sodium iodide (4.1 g, 0.028 mol) in H$_2$O (15 mL) was added followed by a solution of chloramine T (7.8 g, 0.1 mol) in H$_2$O (15 mL). After 20 h stirring, the reaction mixture was extracted with diethylether (3×50 mL). The organic layers were combined and the solvent was evaporated. The resulting residue was triturated with hexanes (3×) and the hexanes layers were combined. The solvent was evaporated to yield 1-fluoro-3-iodo-5-ethoxybenzene as an orange oil. The product was used in the next reaction step without further purification.

The following examples were prepared essentially as described immediately above.

| Preparation | Chemical name | Starting material |
|---|---|---|
| SM11 | 1-ethoxy-3-fluoro-5-iodobenzene | (3-ethoxy-5-fluorophenyl)-boronic acid |
| SM12 | 2-fluoro-1-iodo-3-methoxybenzene | (2-fluoro-3-methoxyphenyl)-boronic acid |
| SM13 | 1-iodo-2-(propan-2-yloxy)benzene | [2-(propan-2-yloxy)phenyl]-boronic acid |
| SM14 | 1-fluoro-3-iodo-5-methoxybenzene | (3-fluoro-5-methoxyphenyl)-boronic acid |
| SM15 | 1-fluoro-3-iodo-5-(propan-2-yloxy)benzene | [3-fluoro-5-(propan-2-yloxy)phenyl]boronic acid |
| SM16 | 1-fluoro-3-iodo-5-(2-methylpropoxy)benzene | [3-fluoro-5-(2-methylpropoxy)phenyl]-boronic acid |
| SM17 | 1-iodo-2-(2,2,2-trifluoroethoxy)benzene | [2-(2,2,2-trifluoroethoxy)-phenyl]boronic acid |
| SM18 | 1-fluoro-3-iodo-5-(2,2,2-trifluoroethoxy)benzene | [3-fluoro-5-(2,2,2-trifluoroethoxy)phenyl]-boronic acid |

SM19

3-Iodo-N-methylbenzamide

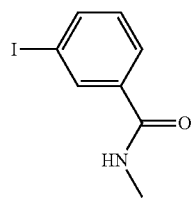

To a solution of 3-iodobenzoic acid (1.5 g, 6 mmol) in anhydrous DMF (10 mL) was added 1,1'-carbonyldiimidazole (1.2 g, 7.2 mmol). The reaction mixture was heated to 50° C. under an atmosphere of nitrogen for 1 h. Upon cooling to room temperature, a solution of methylamine in THF (2 M, 6 mL, 10 mmol) was added. The reaction was stirred at r.t. for 15 min and then transferred into a solution of cold, saturated ammonium chloride (200 mL). The resulting precipitate was collected by filtration and dried to afford the title compound as a white solid, mp 94-97° C.

SM20

3-Iodo-N,N-dimethylbenzamide

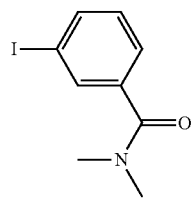

EDCI (1.3 g, 6.6 mmol) was added to a solution of dimethylamine in THF (2 M, 6 mL, 10 mmol) and 3-iodobenzoic acid (1.5 g, 6 mmol). After 18 h stirring the reaction was transferred into water, and then extracted with ethyl acetate. The organic phase was dried over sodium sulfate. The solvent was evaporated to afford the product as a viscous, clear oil. The product was used in the next reaction step without further purification. MS m/z: 276 [M+H]$^+$.

SM21

2-Fluoro-6-iodo-N,N-dimethylbenzamide

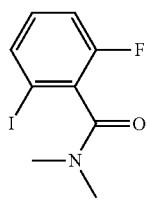

2-Fluoro-6-iodobenzoylchloride 1.0 mL, 6.9 mmol was added dropwise to a solution of dimethylamine in THF (2.0 M 7.0 mL, 10 mmol). The reaction mixture was stirred for 16 h and then transferred into water. The resulting suspension was collected by filtration and dried to afford the title compound as a pale yellow solid. The product was used in the next reaction step without further purification. mp 86-89° C.

SM22

2-Fluoro-6-iodo-N-methylbenzamide

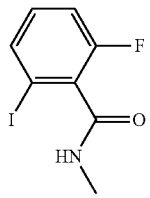

As described for 2-Fluoro-6-iodo-N,N-dimethylbenzamide SM21, mp 190-193° C.

SM23

1-Bromo-2-fluoro-3-isopropoxy-benzene

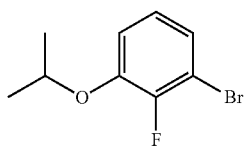

To a mixture of 3-bromo-2-fluoro-phenol (2 g, 10 mmol) and cesium carbonate (10 g, 40 mmol) in acetonitrile (20 mL) was added 2-bromopropane (4 mL, 50 mmol). The reaction mixture was stirred at 80° C. for 4 h. The mixture was filtered through a plug of Celite and eluted with ethyl acetate. The resulting solution was evaporated. The residue was purified by flash chromatography on silica gel and eluting with hexanes:EtOAc (1:1) to afford the title product (1.7 g).

SM 24

1-(Benzyloxy)-3-bromo-5-fluorobenzene

Prepared as described for 1-bromo-2-fluoro-3-isopropoxy-benzene SM23 using 3-bromo-5-fluorophenol and benzylbromide.

SM25

4-(3-Bromo-2-fluoro-phenoxymethyl)tetrahydropyran

Prepared as described for 1-bromo-2-fluoro-3-isopropoxy-benzene SM23 starting from 3-bromo-2-fluorophenol and 4-bromomethyltetrahydropyran. MS m/z: 290 [M+H]$^+$.

SM26

4-(3-Bromo-2-chloro-phenoxymethyl)tetrahydropyran

Prepared as described for 4-(3-bromo-2-fluoro-phenoxymethyl)tetrahydropyran SM25 using 3-bromo-2-chlorophenol

SM27

1-Benzyloxy-3-iodo-5-isopropoxy-benzene

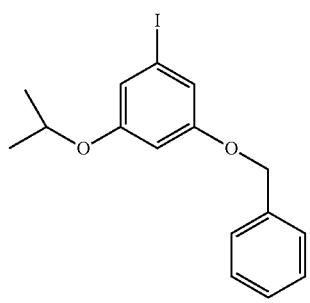 [SMILES: CC(C)Oc1cc(I)cc(OCc2ccccc2)c1]

Step 1

3-Iodo-5-isopropoxy phenol

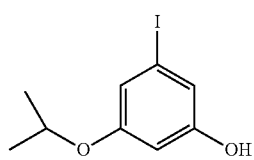

A mixture of 5-Iodo-benzene-1,3-diol (2 g, 8 mmol), 2-bromopropane (0.88 mL, 9.3 mmol) and potassium carbonate (1.3 g, 9.3 mmol) in DMF (15 mL, 190 mmol) was stirred at 65° C. After 18 h, the mixture was cooled to RT and the solvent was evaporated. The residue was dissolved in DCM, washed with water and brine. The solvent was evaporated and the residue was purified on silica gel using an ISCO instrument and eluting with hexanes:EtOAc (4:1) to afford the title product (841 mg). MS m/z: 279 [M+H]$^+$.

Step 2

1-Benzyloxy-3-iodo-5-isopropoxy-benzene

A solution of 3-iodo-5-isopropoxy-phenol (840 mg, 3.0 mmol), benzyl bromide (0.4 mL, 3.3 mmol) and potassium carbonate (830 mg, 6.0 mmol) in DMF (15 mL, 190 mmol) was stirred at 65° C. for 18 h. The reaction mixture was cooled to RT, the solvent was removed and the residue was dissolved in DCM. The organic layer was washed with water and brine. The solvent was evaporated and the residue was purified on silica gel using an ISCO instrument and eluting with hexanes: EtOAc (4:1) to afford the title product SM27 (895 mg). MS m/z: 369 [M+H]$^+$.

SM28

3-Benzyloxy-benzenethiol

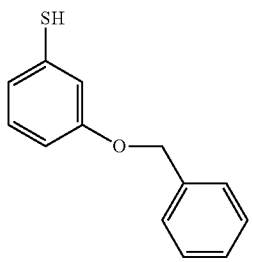 [SMILES: Sc1cccc(OCc2ccccc2)c1]

3-Benzyloxyaniline (2.06 g, 10.3 mmol) was dissolved in water (40 ml) and concentrated HCl (8 ml). The solution was cooled to 0° C. and solution of sodium nitrite (778 mg, 11.3 mmol) in water (10 ml) was added. After 15 min stirring at 0° C., the mixture was added to a solution of potassium ethyl xanthate (3.1 g, 20 mmol) in water (10 ml), and heated to 65° C. for 30 min. After cooling to room temperature, the reaction mixture was extracted twice with ethyl acetate. The combined organic layers were washed with 1N NaOH and water, and dried over MgSO$_4$. The solvent was evaporated and the residue was dissolved in ethanol (50 ml). Potassium hydroxide (2 g, 40 mmol) was added and the mixture was heated to reflux for 16 h. The reaction mixture was cooled to room temperature, concentrated, and partitioned between diethylether and water. The aqueous layer was acidified to pH 1 with concentrated HCl, and then extracted twice with methylene chloride. The combined organic layers were dried over MgSO$_4$ and the solvent was evaporated. The product was used in the next reaction step without further purification.

The following examples were prepared essentially as described immediately above.

| Preparation | Chemical name | Starting mat |
|---|---|---|
| SM29 | 3-(benzyloxy)-5-methoxybenzenethiol | 3-(benzyloxy)-5-methoxyaniline |
| SM30 | 3-(benzyloxy)-2-methylbenzenethiol | 3-(benzyloxy)-2-methylaniline |

SM31

5-Chloro-2-methoxy-benzenethiol

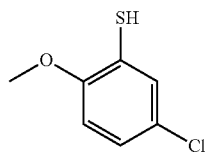

5-Chloro-2-methoxy-benzenesulfonyl chloride (1.0 g, 4.1 mmol) and triphenylphosphine (3.81 g, 14.5 mmol) were dissolved in THF (10 ml). Water (1.3 ml) was added and the mixture was stirred for 2 h at room temperature. The mixture was partitioned between 2N aqueous NaOH and diethylether. The aqueous phase was acidified to pH 1 with concentrated HCl and then extracted twice with methylene chloride. The combined organic layers were dried over MgSO$_4$ and the solvent was evaporated to afford the desired product (690 mg), which was used in the next reaction step without further purification. MS m/z: 175 [M+H]$^+$ The following examples were prepared essentially as described directly above.

| Preparation | Chemical name | Starting mat |
|---|---|---|
| SM32 | 2,1,3-benzoxadiazole-4-thiol | 2,1,3-benzoxadiazole-4-sulfonyl chloride |
| SM33 | 3-chloro-2-fluorobenzenethiol | 3-chloro-2-fluorobenzene-sulfonyl chloride |
| SM34 | 1-methyl-1H-indole-7-thiol | 1-methyl-1H-indole-7-sulfonyl chloride |
| SM35 | N-(3-sulfanylphenyl)acetamide | 3-(acetylamino)benzene-sulfonyl chloride |
| SM36 | 2,1,3-benzothiadiazole-4-thiol | 2,1,3-benzothiadiazole-4--sulfonyl chloride |
| SM37 | 3-(1H-tetrazol-1-yl)benzenethiol | 3-(1H-tetrazol-1-yl)benzene-sulfonyl chloride |
| SM38 | 5-methyl-2,1,3-benzothiadiazole-4-thiol | 5-methyl-2,1,3-benzothiadiazole- 4-sulfonyl chloride |

SM39

3-Isopropoxy-5-methoxy-benzenethiol

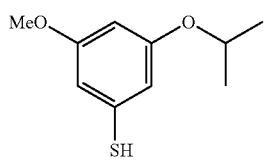

Step 1

3-Amino-5-methoxyphenol

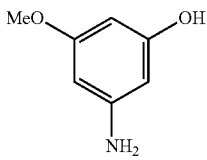

3,5-Dimethoxyaniline (9.97 g, 65.1 mmol) and sodium methyl mercaptide (9.1 g, 130 mmol) were dissolved in N-methylpyrrolidinone (60 ml). The reaction mixture was stirred at 140° C. for 1 h. After cooling to room temperature, the reaction mixture was partitioned between ethyl acetate and saturated aqueous $Na_2HPO_4$. The layers were separated and the organic layer was washed with water, dried over $MgSO_4$ and the solvent was evaporated. The residue was purified by flash chromatography on silica gel eluting with 50% EtOAc/hexanes to afford 3-amino-5-methoxyphenol (5.44 g). MS m/z: 140 [M+H]$^+$ Step 2

3-Isopropoxy-5-methoxyaniline

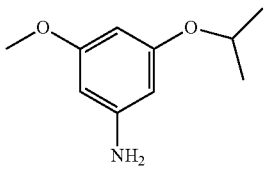

To a solution of 3-amino-5-methoxyphenol (5.44 g, 39.1 mmol), isopropyl alcohol (3.6 ml, 47 mmol) and triphenylphosphine (12.0 g, 47 mmol) in THF, was added diethyl azodicarboxylate (7.4 ml, 47 mmol). The reaction mixture was stirred for 16 h and the solvent was removed. The residue was purified by flash chromatography on silica gel eluting with 20% EtOAc/hexanes to afford the title compound (4.13 g). MS m/z: 182 [M+H]$^+$ Step 3

3-Isopropoxy-5-methoxy-benzenethiol SM39

Prepared as described for 3-benzyloxy-benzenethiol SM28 starting from 3-isopropoxy-5-methoxyaniline. MS m/z: 199 [M+H]$^+$

D01

7-(3-Hydroxy-benzenesulfonyl)-3,4,4a,9a-tetrahydro-1H-benzo[4,5]furo[2,3-c]pyridine-2-carboxylic acid tert-butyl ester

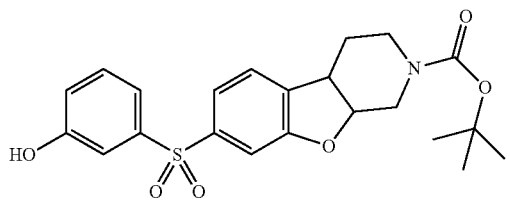 [SMILES: CC(C)(C)OC(=O)N1CCC2c3ccc(S(=O)(=O)c4cccc(O)c4)cc3OC2C1]

Step 1

7-(3-Benzyloxy-benzenesulfonyl)-3,4,4a,9a-tetrahydro-1H-benzo[4,5]furo[2,3-c]pyridine-2-carboxylic acid tert-butyl ester

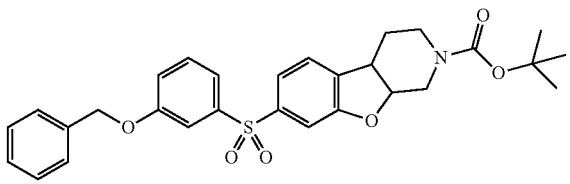 [SMILES: CC(C)(C)OC(=O)N1CCC2c3ccc(S(=O)(=O)c4cccc(OCc5ccccc5)c4)cc3OC2C1]

As described for 6-(3-chloro-benzenesulfonyl)-3,4,4a,9a-tetrahydro-1H-benzo[4,5]furo[2,3-c]pyridine-2-carboxylic acid tert-butyl ester starting from 3-benzyloxy-benzenethiol and 7-iodo-3,4,4a,9a-tetrahydro-1H-benzo[4,5]furo[2,3-c]pyridine-2-carboxylic acid tert-butyl ester and 3-(benzyloxy)benzenethiol. MS m/z: 422 [M-Boc+H]$^+$ Step 2

7-(3-Hydroxy-benzenesulfonyl)-3,4,4a,9a-tetrahydro-1H-benzo[4,5]furo[2,3-c]pyridine-2-carboxylic acid tert-butyl ester 7-(3-Benzyloxy-benzenesulfonyl)-3,4,4a,9a-tetrahydro-1H-benzo[4,5]furo[2,3c]pyridine-2-carboxylic acid tert-butyl ester (1.76 g, 3.37 mmol) was dissolved in a mixture of ethyl acetate (200 ml) and methanol (100 ml). Palladium hydroxide on carbon (20% by weight, 50% wet; 200 mg, 0.1 mmol) was added and the suspension was hydrogenated at 55 psi using a Parr apparatus for 16 h. The reaction mixture was then filtered through a plug of Celite and the solvent was evaporated. The residue was purified by flash chromatography on silica gel and eluting with 50% EtOAc/hexanes to afford the title compound D01 (1.39 g). MS m/z: 332 [M-Boc+H]$^+$ The following examples were prepared essentially as described immediately above.

| Preparation | Chemical name | MS m/z [M + H]+ | Stereo chemistry | Scaffold | Starting mat |
|---|---|---|---|---|---|
| D01 | tert-butyl 7-[(3-hydroxyphenyl)sulfonyl]-3,4,4a,9a-tetrahydro[1]benzofuro[2,3-c]pyridine-2(1H)-carboxylate | 432.1 | racemic | P01 | 3-(benzyloxy)benzenethiol |
| D02 | tert-butyl 7-[(3-hydroxyphenyl)sulfonyl]-3,4,4a,9a-tetrahydro[1]benzofuro[2,3-c]pyridine-2(1H)-carboxylate | 432.1 | enantiomer 1 | P03 | 3-(benzyloxy)benzenethiol |
| D03 | tert-butyl 7-[(3-hydroxyphenyl)sulfonyl]-3,4,4a,9a-tetrahydro[1]benzofuro[2,3-c]pyridine-2(1H)-carboxylate | 432.1 | enantiomer 2 | P04 | 3-(benzyloxy)benzenethiol |
| D04 | tert-butyl 7-[(3-hydroxy-2-methylphenyl)sulfonyl]-3,4,4a,9a-tetrahydro[1]benzofuro[2,3-c]pyridine-2(1H)-carboxylate | 446.2 | racemic | P01 | 3-(benzyloxy)-2-methylbenzenethiol |
| D05 | tert-butyl 7-[(3-hydroxy-2-methylphenyl)sulfonyl]-3,4,4a,9a-tetrahydro[1]benzofuro[2,3-c]pyridine-2(1H)-carboxylate | 446.2 | enantiomer 1 | P03 | 3-(benzyloxy)-2-methylbenzenethiol |
| D06 | tert-butyl 7-+(3-hydroxy-2-methylphenyl)sulfonyl]-3,4,4a,9a-tetrahydro[1]benzofuro[2,3-c]pyridine-2(1H)-carboxylate | 446.2 | enantiomer 2 | P04 | 3-(benzyloxy)-2-methylbenzenethiol |
| D07 | tert-butyl 7-[(3-hydroxy-5-methoxyphenyl )sulfonyl]-3,4,4a,9a-tetrahydro[1]benzofuro[2,3-c]pyridine-2(1H)-carboxylate | 462.2 | racemic | P01 | 3-(benzyloxy)-5-methoxybenzenethiol |
| D08 | tert-butyl 7-[(3-hydroxy-5-methoxyphenyl )sulfonyl]-3,4,4a,9a-tetrahydro[1]benzofuro[2,3-c]pyridine-2(1H)-carboxylate | 462.2 | enantiomer 1 | P03 | 3-(benzyloxy)-5-methoxybenzenethiol |
| D09 | tert-butyl 7-[(3-hydroxy-5-methoxyphenyl )sulfonyl]-3,4,4a,9a-tetrahydro[1]benzofuro[2,3-c]pyridine-2(1H)-carboxylate | 462.2 | enantiomer 2 | P04 | 3-(benzyloxy)-5-methoxybenzenethiol |

D10

7-(3-Hydroxy-5-isopropoxy-benzenesulfonyl)-3,4,4a,9a-tetrahydro-1H benzo[4,5]furo[2,3-c]pyridine-2-carboxylic acid tert-butyl ester

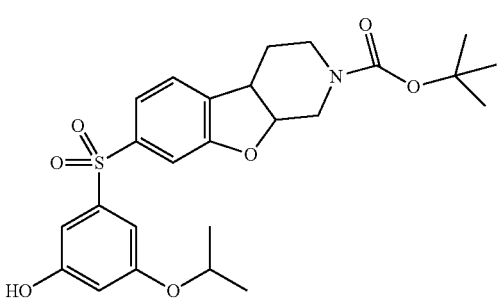 [SMILES: CC(C)Oc1cc(O)cc(S(=O)(=O)c2ccc3c(c2)OC2CN(C(=O)OC(C)(C)C)CCC32)c1]

Step 1

7-(3-benzyloxy-5-isopropoxy-benzenesulfonyl)-3,4,4a,9a-tetrahydro-1H-benzo[4,5]furo[2,3-c]pyridine-2-carboxylic acid tert-butyl ester

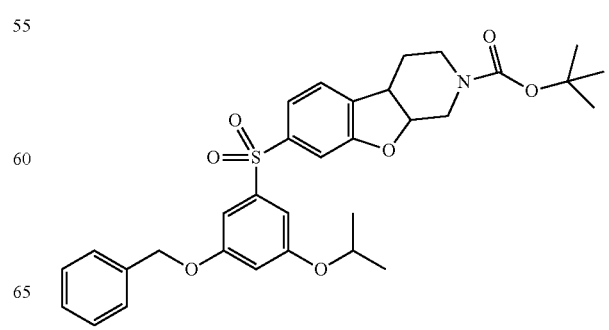

Prepared as described for 7-(3-Fluoro-5-isopropoxy-benzenesulfonyl)-1,2,3,4,4a,9a-hexahydro-benzo[4,5]furo[2,3-c]pyridine hydrochloride starting from 1-(benzyloxy)-3-iodo-5-(propan-2-yloxy)benzene and tert-butyl 7-[(tripropan-2-ylsilyl)sulfanyl]-3,4,4a,9a-tetrahydro[1]benzofuro[2,3-c]pyridine-2(1H)-carboxylate C02. Sulfur oxidation was performed with mCPBA as described for 6-(3-chloro-benzenesulfonyl)-3,4,4a,9a-tetrahydro-1H-benzo[4,5]furo[2,3-c]pyridine-2-carboxylic acid tert-butyl ester.

Step 2

7-(3-Hydroxy-5-isopropoxy-benzenesulfonyl)-3,4,4a,9a-tetrahydro-1H-benzo[4,5]furo[2,3-c]pyridine-2-carboxylic acid tert-butyl ester D10

Synthesized as described for 7-(3-Hydroxy-benzenesulfonyl)-3,4,4a,9a-tetrahydro-1H-benzo[4,5]furo[2,3-c]pyridine-2-carboxylic acid tert-butyl ester D01 starting from 7-(3-benzyloxy-5-isopropoxy-benzenesulfonyl)-3,4,4a,9a-tetrahydro-1H-benzo[4,5]furo[2,3-c]pyridine-2-carboxylic acid tert-butyl ester.

The following examples were prepared essentially as described immediately above.

| Prep | Chemical name | MS m/z $[M + H]^+$ | Stereochemistry | Scaffold | Starting mat |
|---|---|---|---|---|---|
| D10 | tert-butyl 7-{[3-hydroxy-5-(propan-2-yloxy)phenyl]sulfonyl}-3,4,4a,9a-tetrahydro[1]benzofuro[2,3-c]pyridine-2(1H)-carboxylate | 490 | racemic | C02 | 1-(benzyloxy)-3-iodo-5-(propan-2-yloxy)benzene |
| D11 | tert-butyl 7-{[3-hydroxy-5-(propan-2-yloxy)phenyl]sulfonyl}-3,4,4a,9a-tetrahydro[1]benzofuro[2,3-c]pyridine-2(1H)-carboxylate | 490 | enantiomer 1 | C03 | 1-(benzyloxy)-3-iodo-5-(propan-2-yloxy)benzene |
| D12 | tert-butyl 7-{[3-hydroxy-5-(propan-2-yloxy)phenyl]sulfonyl}-3,4,4a,9a-tetrahydro[1]benzofuro[2,3-c]pyridine-2(1H)-carboxylate | 490 | enantiomer 2 | C04 | 1-(benzyloxy)-3-iodo-5-(propan-2-yloxy)benzene |
| D13 | tert-butyl 7-[(3-fluoro-5-hydroxyphenyl)sulfonyl]-3,4,4a,9a-tetrahydro[1]benzofuro[2,3-c]pyridine-2(1H)-carboxylate | 450 | racemic | P01 | {[3-(benzyloxy)-5-fluorophenyl]sulfanyl}(tripropan-2-yl)silane |
| D14 | tert-butyl 7-[(3-fluoro-5-hydroxyphenyl)sulfonyl]-3,4,4a,9a-tetrahydro[1]benzofuro[2,3-c]pyridine-2(1H)-carboxylate | 450 | enantiomer 1 | P02 | {[3-(benzyloxy)-5-fluorophenyl]sulfanyl}(tripropan-2-yl)silane |
| D15 | tert-butyl 7-[(3-fluoro-5-hydroxyphenyl)sulfonyl]-3,4,4a,9a-tetrahydro[1]benzofuro[2,3-c]pyridine-2(1H)-carboxylate | 450 | enantiomer 2 | P03 | {[3-(benzyloxy)-5-fluorophenyl]sulfanyl}(tripropan-2-yl)silane |

The invention claimed is:

1. A compound having the structure of Formula III-B

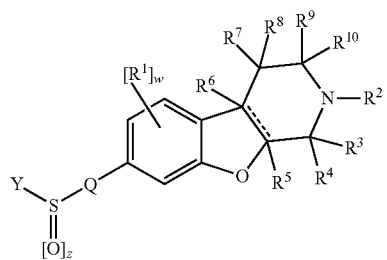

III-B or a salt thereof, wherein:

$R^2$ is selected from H, $C_1$-$C_6$alkyl, $(C_3$-$C_{10})$cycloalkyl, $(C_6$-$C_{10})$aryl, and $(C_1$-$C_6)$alkyl$(C_6$-$C_{10})$aryl;

$R^3$ and $R^4$ are each H;

"- - - -" is either a bond or is absent;

$R^5$ and $R^6$ are each independently selected from H and $(C_1$-$C_6)$alkyl, provided that "- - - -" is absent;

$R^7$, $R^8$, $R^9$, and $R^{10}$ are each H;

Q is —O—;

Z is 2; and

Y is selected from $(C_6$-$C_{10})$aryl, $(C_1$-$C_6)$alkyl$(C_6$-$C_{10})$aryl, $(C_4$-$C_9)$heteroaryl and $C_1$-$C_6)$alkyl$(C_3$-$C_{10})$cycloalkyl wherein any of the foregoing is optionally substituted with one or more substituents selected from $(C_1$-$C_6)$alkyl, halogen, $(C_1$-$C_6)$alkoxy, $NR^{13}$CO—$(C_1$-$C_6)$alkyl, $(C_4$-$C_9)$heteroaryl, $(C_1$-$C_6)$haloalkyl, $(C_6$-$C_{10})$aryl, $(C_1$-$C_6)$haloalkoxy, $(C_2$-$C_9)$heterocycloalkyl, $(C_6$-$C_{10})$aryloxy, and $NO_2$.

2. A compound according to claim 1 or a salt thereof, wherein:

W is 0;

$R^2$ is H;

"- - - -" is absent;

$R^5$ and $R^6$ are each H.

3. A compound according to claim 1 or a salt thereof, wherein:

W is 0;

$R^2$ is selected from $(C_1$-$C_6)$alkyl, $(C_3$-$C_{10})$cycloalkyl, and $(C_1$-$C_6)$alkyl$(C_6$-$C_{10})$aryl;

"- - - -" is absent; and $R^5$ and $R^6$ are each H; and

Y is $(C_6$-$C_{10})$aryl optionally substituted with one or more substituents selected from $(C_1$-$C_6)$alkyl, halogen, $(C_1$-$C_6)$alkoxy, $NR^{13}$CO—$(C_1$-$C_6)$alkyl, $(C_4$-$C_9)$heteroaryl, $(C_1$-$C_6)$haloalkyl, $(C_6$-$C_{10})$aryl, $(C_1$-$C_6)$haloalkoxy, $(C_2$-$C_9)$heterocycloalkyl, $(C_6$-$C_{10})$aryloxy, and $NO_2$.

4. A compound according to claim 1 or a salt thereof, wherein:

W is O;

"- - - -" is a bond; and

Y is $(C_4-C_9)$heteroaryl optionally substituted with one or more substituents selected from $(C_1-C_6)$alkyl, halogen, $(C_1-C_6)$alkoxy, $NR^{13}CO—(C_1-C_6)$alkyl, $(C_4-C_9)$heteroaryl, $(C_1-C_6)$haloalkyl, $(C_6-C_{10})$aryl, $(C_1-C_6)$haloalkoxy, $(C_2-C_9)$heterocycloalkyl, $(C_6-C_{10})$aryloxy, and $NO_2$.

5. A compound having the structure of Formula III-C:

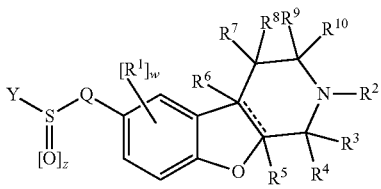

or a salt thereof, wherein:

W is O;

$R^2$ is H;

$R^3$, $R^4$, $R^7$, $R^8$, $R^9$, and $R^{10}$ are each H;

"- - - -" is a bond;

Q is absent; and

Y is selected from $(C_6-C_{10})$aryl, $(C_5-C_9)$heteroaryl, and $(C_3-C_{10})$cycloalkyl wherein any of the foregoing is optionally substituted with one or more substituents selected from halogen, $(C_1-C_6)$alkyl, $(C_1-C_6)$alkoxy, $(C_1-C_6)$haloalkyl, $(C_6-C_{10})$aryloxy, $NO_2$, $CO_2(C_1-C_6)$alkyl, CN, $NR^{13}CO—(C_1-C_6)$alkyl, $(C_1-C_6)$haloalkoxy, $(C_6-C_{10})$aryl, $N(R^{13})_2$, and oxo.

6. A compound having the structure of Formula III-C:

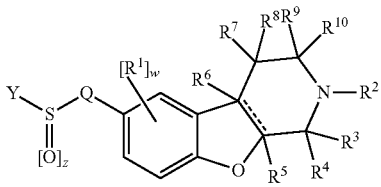

or a salt thereof, wherein:

W is O;

$R^2$ is H;

$R^3$, $R^4$, $R^7$, $R^8$, $R^9$, and $R^{10}$ are each H;

"- - - -" is absent;

$R^5$ and $R^6$ are each independently selected from H and $(C_1-C_6)$alkyl;

Q is absent; and

Y is selected from $(C_6-C_{10})$aryl and $(C_5-C_9)$heteroaryl wherein either of the foregoing is optionally substituted with one or more substituents selected from halogen, $(C_1-C_6)$alkoxy, $(C_1-C_6)$alkyl, $NO_2$, $(C_6-C_{10})$aryloxy, oxo, $NR^{13}CO—(C_1-C_6)$alkyl, and $(C_1-C_6)$hydroxyalkyl.

7. A compound having the structure of Formula III-C:

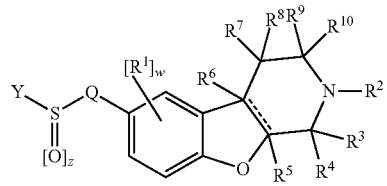

or a salt thereof, wherein:

W is O;

$R^2$ is H;

$R^3$ and $R^4$ are each independently selected from H, $(C_1-C_6)$alkyl, $(C_1-C_6)$haloalkyl, $(C_3-C_{10})$cycloalkyl, $(C_1-C_6)$alkyl$(C_1-C_6)$alkoxy, $(C_2-C_9)$heterocycloalkyl, and $(C_1-C_6)$alkyl-$NR^{13}CO—(C_1-C_6)$alkyl; or $R^3$ and $R^4$ are taken together to form a $(C_3-C_9)$heterocycloalkyl spirocyclic ring;

$R^7$, $R^8$, $R^9$, and $R^{10}$ are each H;

"- - - -" is a bond;

Z is 2;

Q is absent; and

Y is selected from $(C_6-C_{10})$aryl optionally substituted with one or more substituents selected from halogen, $(C_1-C_6)$haloalkyl, and $(C_1-C_6)$alkoxy.

8. A compound having the structure of Formula III-C:

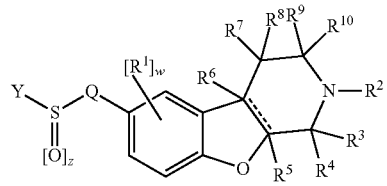

or a salt thereof, wherein:

W is O;

$R^2$ and one of $R^3$ and $R^4$ are taken together to form a $(C_3-C_9)$heterocycloalkyl ring and the other of $R^3$ and $R^4$ is H;

"- - - -" is a bond;

Z is 2;

Q is absent; and

Y is $(C_6-C_{10})$aryl optionally substituted with one or more substituents selected from halogen, $(C_1-C_6)$alkoxy, $(C_1-C_6)$alkyl, $(C_1-C_6)$haloalkyl, $(C_1-C_6)$haloalkoxy, $(C_3-C_9)$heteroaryl, $(C_1-C_6)$haloalkyl, $(C_6-C_{10})$aryloxy, $NR^{13}CO—(C_1-C_6)$alkyl, $(C_6-C_{10})$aryl, and $NO_2$.

9. A compound having the structure of Formula III-C:

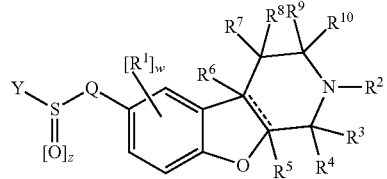

or a salt thereof, wherein:
- $R^2$ is selected from H, $(C_1-C_6)$alkyl, $(C_3-C_{10})$cycloalkyl, and $(C_1-C_6)$alkyl$(C_6-C_{10})$aryl;
- $R^3$, $R^4$, $R^7$, $R^8$, $R^9$, and $R^{10}$ are each H;
- "- - - -" is absent;
- $R^5$ and $R^6$ are each independently selected from H and $(C_1-C_6)$alkyl;
- Q is —O—;
- Z is 2; and
- Y is selected from $(C_6-C_{10})$aryl, $(C_1-C_6)$alkyl$(C_6-C_{10})$aryl, and $(C_3-C_9)$heteroaryl wherein any of the foregoing is optionally substituted with one or more substituents selected from halogen, $(C_1-C_6)$alkoxy, $(C_1-C_6)$alkyl, $(C_1-C_6)$haloalkyl, $(C_1-C_6)$haloalkoxy, $(C_3-C_9)$heteroaryl, $(C_1-C_6)$haloalkyl, $(C_6-C_{10})$aryloxy, $NR^{13}CO$—$(C_1-C_6)$alkyl, $(C_6-C_{10})$aryl, and $NO_2$.

10. A compound according to claim 9 or a salt thereof, wherein:
- W is 0; and
- $R^2$ is H.

11. A compound according to claim 9 or a salt thereof, wherein:
- W is 0; and
- $R^2$ is selected from $(C_1-C_6)$alkyl, $(C_3-C_{10})$cycloalkyl, and $(C_1-C_6)$alkyl$(C_6-C_{10})$aryl.

12. A compound having the structure of Formula III-C:

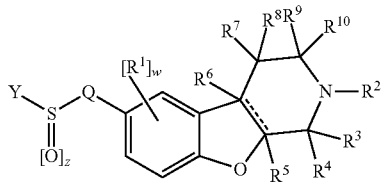

or a salt thereof, wherein:
- $R^2$ is selected from H and $CO(C_1-C_6)$alkyl;
- $R^3$, $R^4$, $R^7$, $R^8$, $R^9$, and $R^{10}$ are each H;
- "- - - -" is absent;
- $R^5$ and $R^6$ are each H;
- Q is —NH—;
- Z is 2; and
- Y is selected from $(C_6-C_{10})$aryl, $(C_3-C_9)$heteroaryl, and $(C_1-C_6)$alkyl$(C_6-C_{10})$aryl wherein any of the foregoing may be optionally substituted with one or more substituents selected from halogen, $(C_1-C_6)$alkoxy, $(C_1-C_6)$alkyl, $(C_1-C_6)$haloalkyl, $(C_1-C_6)$haloalkoxy, $(C_3-C_9)$heteroaryl, $(C_1-C_6)$haloalkyl, $(C_6-C_{10})$aryloxy, $NR^{13}CO$—$(C_1-C_6)$alkyl, $(C_6-C_{10})$aryl, and $NO_2$.

13. A compound according to claim 12 or a salt thereof, wherein:
- $R^2$ is H; and
- Y is selected from $(C_6-C_{10})$aryl, $(C_3-C_9)$heteroaryl, and $(C_1-C_6)$alkyl$(C_6-C_{10})$aryl wherein any of the foregoing may be optionally substituted with one or more substituents selected from $(C_1-C_6)$alkyl, halogen, and $(C_1-C_6)$alkoxy.

14. A compound having the structure of Formula III-C:

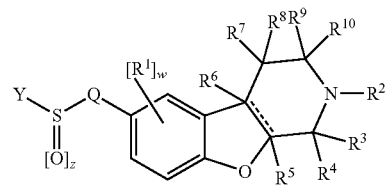

or a salt thereof, wherein:
- W is 0;
- $R^2$ is H;
- $R^3$, $R^4$, $R^7$, $R^8$, $R^9$, $R^{10}$ are each H;
- "- - - -" is absent;
- $R^5$ and $R^6$ are each H;
- $R^{13}$ is H or methyl;
- Z is 2; and
- Y is selected from $(C_6-C_{10})$aryl, $(C_1-C_6)$alkyl$(C_6-C_{10})$aryl, or $(C_3-C_{10})$cycloalkyl wherein any of the foregoing is optionally substituted with one or more substituents selected from $(C_1-C_6)$alkyl, $(C_1-C_6)$alkoxy, and halogen.

15. A compound according to claim 14 or a salt thereof, wherein:
- W is 0;
- $R^2$ is H;
- $R^3$, $R^4$, $R^7$, $R^8$, $R^9$, $R^{10}$ are each H;
- "- - - -" is absent;
- $R^5$ and $R^6$ are each H;
- Q is absent;
- Z is 2; and
- Y is $NR^{14}R^{15}$ wherein $R^{14}$ and $R^{15}$ are taken together to form a $(C_2-C_9)$heterocycloalkyl ring which is optionally substituted with one or more substituents selected from $(C_6-C_{10})$aryl or $(C_2-C_9)$heterocycloalkyl.

16. A composition comprising a compound according to any of claims 1 to 4 and 5 to 15, or a salt thereof, and at least one pharmaceutically acceptable excipient.

* * * * *